US009629843B2

(12) United States Patent
Shokat et al.

(10) Patent No.: US 9,629,843 B2
(45) Date of Patent: Apr. 25, 2017

(54) MTOR MODULATORS AND USES THEREOF

(71) Applicants: The Regents of the University of California, Oakland, CA (US); Intellikine, Inc., La Jolla, CA (US)

(72) Inventors: Kevan M. Shokat, San Francisco, CA (US); David Fruman, Irvine, CA (US); Pingda Ren, San Diego, CA (US); Troy Edward Wilson, San Marino, CA (US); Liansheng Li, San Diego, CA (US); Andrew Hsieh, San Francisco, CA (US); Morris Feldman, San Francisco, CA (US); Beth Apsel, San Francisco, CA (US); Yi Liu, San Diego, CA (US); Christian Rommel, La Jolla, CA (US); Katrina Chan, San Diego, CA (US); Davide Ruggero, San Francisco, CA (US); David Pearce, San Francisco, CA (US); Matthew Janes, Altadena, CA (US)

(73) Assignees: THE REGENTS OF THE UNIVERSITY OF CALIFORNIA, Oakland, CA (US); INTELLIKINE, INC., La Jolla, CA (US)

( * ) Notice: Subject to any disclaimer, the term of this patent is extended or adjusted under 35 U.S.C. 154(b) by 0 days.

(21) Appl. No.: 14/731,778

(22) Filed: Jun. 5, 2015

(65) Prior Publication Data

US 2016/0000789 A1    Jan. 7, 2016

Related U.S. Application Data

(63) Continuation of application No. 13/003,562, filed as application No. PCT/US2009/049969 on Jul. 8, 2009, now abandoned.

(Continued)

(51) Int. Cl.
 *A61K 31/519* (2006.01)
 *C12Q 1/48* (2006.01)

(52) U.S. Cl.
 CPC ............ *A61K 31/519* (2013.01); *C12Q 1/485* (2013.01); *G01N 2500/04* (2013.01); *G01N 2510/00* (2013.01)

(58) Field of Classification Search
 None
 See application file for complete search history.

(56) References Cited

U.S. PATENT DOCUMENTS 4,001,230 A    1/1977   Friedman
4,044,130 A    8/1977   Howarth et al.
(Continued)

FOREIGN PATENT DOCUMENTS

CA        1338379 C      6/1996
CN      101602768 A     12/2009
(Continued)

OTHER PUBLICATIONS

Ji Johnson et al. Relationships between drug activity in NCI prelinical in vitro and in vivo models and early clinical trials. British Journal of Cancer, 2001, 9 sheets.*
(Continued)

*Primary Examiner* — Anna Pagonakis
(74) *Attorney, Agent, or Firm* — Anson M. Nomura; Mintz, Levin, Cohn, Ferris, Glovsky and Popeo, P.C.

(57) ABSTRACT

The present invention provides methods and compositions for selective modulation of certain protein kinases, and especially mTor complexes. The methods and compositions are particularly useful in inhibiting mTor selectively for therapeutic applications.

1 Claim, 37 Drawing Sheets

Related U.S. Application Data

(60) Provisional application No. 61/079,103, filed on Jul. 8, 2008.

(56) References Cited

U.S. PATENT DOCUMENTS

| | | |
|---|---|---|
| 4,704,381 A | 11/1987 | Schaumann et al. |
| 4,861,760 A | 8/1989 | Mazuel et al. |
| 4,911,920 A | 3/1990 | Jani et al. |
| 4,992,445 A | 2/1991 | Lawter et al. |
| 5,001,139 A | 3/1991 | Lawter et al. |
| 5,023,252 A | 6/1991 | Hseih |
| 5,212,162 A | 5/1993 | Missel et al. |
| 5,240,941 A | 8/1993 | Bruneau |
| 5,310,731 A | 5/1994 | Olsson et al. |
| 5,364,862 A | 11/1994 | Spada et al. |
| 5,403,841 A | 4/1995 | Lang et al. |
| 5,420,419 A | 5/1995 | Wood |
| 5,428,125 A | 6/1995 | Hefner, Jr. et al. |
| 5,442,039 A | 8/1995 | Hefner, Jr. et al. |
| 5,506,347 A | 4/1996 | Erion et al. |
| 5,561,134 A | 10/1996 | Spada et al. |
| 5,563,257 A | 10/1996 | Zilch et al. |
| 5,593,997 A | 1/1997 | Dow et al. |
| 5,646,128 A | 7/1997 | Firestein et al. |
| 5,652,366 A | 7/1997 | Spada et al. |
| 5,654,307 A | 8/1997 | Bridges et al. |
| 5,665,721 A | 9/1997 | Bhagwat et al. |
| 5,674,998 A | 10/1997 | Boyer et al. |
| 5,686,455 A | 11/1997 | Adams et al. |
| 5,736,554 A | 4/1998 | Spada et al. |
| 5,747,235 A | 5/1998 | Farid et al. |
| 5,756,711 A | 5/1998 | Zilch et al. |
| 5,759,787 A | 6/1998 | Strulovici |
| 5,763,596 A | 6/1998 | Boyer et al. |
| 5,763,597 A | 6/1998 | Ugarkar et al. |
| 5,763,885 A | 6/1998 | Murphy et al. |
| 5,795,977 A | 8/1998 | Ugarkar et al. |
| 5,824,492 A | 10/1998 | Hiles et al. |
| 5,858,753 A | 1/1999 | Chantry et al. |
| 5,914,488 A | 6/1999 | Sone |
| 5,919,808 A | 7/1999 | Petrie et al. |
| 5,922,753 A | 7/1999 | Petrie et al. |
| 5,948,776 A | 9/1999 | Petrie et al. |
| 5,965,573 A | 10/1999 | Petrie et al. |
| 5,977,061 A | 11/1999 | Holy et al. |
| 5,981,533 A | 11/1999 | Traxler et al. |
| 5,985,589 A | 11/1999 | Chantry et al. |
| 5,990,169 A | 11/1999 | Petrie et al. |
| 5,994,358 A | 11/1999 | Petrie et al. |
| 6,001,839 A | 12/1999 | Calderwood et al. |
| 6,057,305 A | 5/2000 | Holy et al. |
| 6,084,095 A | 7/2000 | Bridges et al. |
| 6,093,737 A | 7/2000 | Anthony et al. |
| 6,127,121 A | 10/2000 | Meyer, Jr. et al. |
| 6,153,631 A | 11/2000 | Petrie et al. |
| 6,191,170 B1 | 2/2001 | Medina |
| 6,251,901 B1 | 6/2001 | Petrie et al. |
| 6,265,410 B1 | 7/2001 | Bridges et al. |
| 6,268,370 B1 | 7/2001 | Adams et al. |
| 6,312,894 B1 | 11/2001 | Hedgpeth et al. |
| 6,323,201 B1 | 11/2001 | Carson et al. |
| 6,342,514 B1 | 1/2002 | Petrie et al. |
| 6,350,741 B1 | 2/2002 | Golec et al. |
| 6,383,790 B1 | 5/2002 | Shokat |
| 6,384,039 B1 | 5/2002 | Fossa |
| 6,387,894 B1 | 5/2002 | Fossa |
| 6,390,821 B1 | 5/2002 | Shokat |
| 6,455,534 B2 | 9/2002 | Bridges et al. |
| 6,472,153 B1 | 10/2002 | Dempcy et al. |
| 6,482,623 B1 | 11/2002 | Vanhaesebroeck et al. |
| 6,485,906 B2 | 11/2002 | Meyer, Jr. et al. |
| 6,492,346 B1 | 12/2002 | Hedgpeth et al. |
| 6,506,769 B2 | 1/2003 | Snow et al. |
| 6,518,277 B1 | 2/2003 | Sadhu et al. |
| 6,521,417 B1 | 2/2003 | Shokat |
| 6,521,620 B1 | 2/2003 | Bridges et al. |
| 6,531,491 B1 | 3/2003 | Kania et al. |
| 6,534,524 B1 | 3/2003 | Kania et al. |
| 6,545,005 B1 | 4/2003 | Baxter et al. |
| 6,552,192 B1 | 4/2003 | Hanus et al. |
| 6,562,819 B2 | 5/2003 | Carson et al. |
| 6,583,161 B1 | 6/2003 | Medina |
| 6,613,798 B1 | 9/2003 | Porter et al. |
| 6,630,495 B1 | 10/2003 | Cooke et al. |
| 6,632,789 B1 | 10/2003 | June |
| 6,645,989 B1 | 11/2003 | Adams et al. |
| 6,649,631 B1 | 11/2003 | Orme et al. |
| 6,653,296 B1 | 11/2003 | Holy et al. |
| 6,653,306 B1 | 11/2003 | Alexander et al. |
| 6,660,744 B1 | 12/2003 | Hirst et al. |
| 6,660,845 B1 | 12/2003 | Gall et al. |
| 6,664,269 B2 | 12/2003 | Martin et al. |
| 6,667,300 B2 | 12/2003 | Sadhu et al. |
| 6,690,583 B1 | 2/2004 | Bergstedt et al. |
| 6,713,484 B2 | 3/2004 | Bridges et al. |
| 6,720,344 B2 | 4/2004 | Kerwin et al. |
| 6,734,187 B1 | 5/2004 | Tanaka et al. |
| 6,770,639 B2 | 8/2004 | Snow et al. |
| 6,777,425 B2 | 8/2004 | Burli et al. |
| 6,777,439 B2 | 8/2004 | Durden |
| 6,790,844 B2 | 9/2004 | Ueno et al. |
| 6,800,620 B2 | 10/2004 | Sadhu et al. |
| 6,849,420 B2 | 2/2005 | Vanhasebroeck et al. |
| 6,849,713 B2 | 2/2005 | Zhang et al. |
| 6,852,727 B2 | 2/2005 | Goulet et al. |
| 6,906,103 B2 | 6/2005 | Zhang et al. |
| 6,919,332 B2 | 7/2005 | Noe et al. |
| 6,921,763 B2 | 7/2005 | Hirst et al. |
| 6,949,535 B2 | 9/2005 | Sadhu et al. |
| 7,026,461 B1 | 4/2006 | Shokat |
| 7,041,676 B2 | 5/2006 | McDonald et al. |
| 7,049,116 B2 | 5/2006 | Shokat |
| 7,049,312 B1 | 5/2006 | Rafferty et al. |
| 7,064,218 B2 | 6/2006 | Dyatkina et al. |
| 7,071,355 B2 | 7/2006 | Leban et al. |
| 7,115,627 B2 | 10/2006 | Pinto et al. |
| 7,115,653 B2 | 10/2006 | Baxter et al. |
| 7,144,903 B2 | 12/2006 | Collins et al. |
| 7,157,487 B2 | 1/2007 | Nakayama et al. |
| 7,166,293 B2 | 1/2007 | Teng et al. |
| 7,208,601 B2 | 4/2007 | Mjalli et al. |
| 7,217,794 B2 | 5/2007 | Abdel-Meguid et al. |
| 7,244,741 B2 | 7/2007 | Simon et al. |
| 7,247,736 B2 | 7/2007 | Leban et al. |
| 7,262,204 B2 | 8/2007 | Collins et al. |
| 7,265,111 B2 | 9/2007 | Bigot et al. |
| 7,265,131 B2 | 9/2007 | Johnson et al. |
| 7,329,765 B2 | 2/2008 | Burli et al. |
| 7,332,497 B2 | 2/2008 | Hirst et al. |
| 7,348,427 B2 | 3/2008 | Burli et al. |
| 7,365,094 B2 | 4/2008 | Leban et al. |
| 7,384,967 B2 | 6/2008 | Polisetti et al. |
| 7,396,836 B2 | 7/2008 | Harada et al. |
| 7,414,036 B2 | 8/2008 | Sevillano et al. |
| 7,429,596 B2 | 9/2008 | Tanaka et al. |
| 7,439,254 B2 | 10/2008 | Bergnes |
| 7,459,462 B2 | 12/2008 | Simon et al. |
| 7,459,472 B2 | 12/2008 | Mjalli et al. |
| 7,470,721 B2 | 12/2008 | Durden |
| 7,501,538 B2 | 3/2009 | Mjalli et al. |
| 7,534,797 B2 | 5/2009 | Arnold et al. |
| 7,541,373 B2 | 6/2009 | Polisetti et al. |
| 7,569,571 B2 | 8/2009 | Dong et al. |
| 7,572,913 B2 | 8/2009 | McKerracher et al. |
| 7,579,348 B2 | 8/2009 | Wang et al. |
| 7,585,868 B2 | 9/2009 | Knight et al. |
| 7,608,594 B2 | 10/2009 | Blagg et al. |
| 7,615,552 B2 | 11/2009 | Ono et al. |
| 7,622,451 B2 | 11/2009 | Blagg et al. |
| 7,678,803 B2 | 3/2010 | Huang et al. |
| 7,700,607 B2 | 4/2010 | Hu et al. |
| 7,745,485 B2 | 6/2010 | Durden |
| 7,932,260 B2 | 4/2011 | Fowler et al. |
| 8,642,604 B2 | 2/2014 | Knight et al. |

(56) References Cited

U.S. PATENT DOCUMENTS

| | | |
|---|---|---|
| 8,901,134 B2 | 12/2014 | Bloomfield et al. |
| 2001/0019829 A1 | 9/2001 | Nelson et al. |
| 2001/0027197 A1 | 10/2001 | Bridges et al. |
| 2002/0016460 A1 | 2/2002 | Snow et al. |
| 2002/0016976 A1 | 2/2002 | Shokat |
| 2002/0037856 A1 | 3/2002 | Zhang et al. |
| 2002/0102590 A1 | 8/2002 | Taing et al. |
| 2002/0146690 A1 | 10/2002 | Meyer et al. |
| 2002/0147160 A1 | 10/2002 | Bhat et al. |
| 2002/0156081 A1 | 10/2002 | Hirst et al. |
| 2002/0161014 A1 | 10/2002 | Sadhu et al. |
| 2002/0173524 A1 | 11/2002 | Collins et al. |
| 2003/0001141 A1 | 1/2003 | Sun et al. |
| 2003/0008896 A1 | 1/2003 | Martin et al. |
| 2003/0018022 A1 | 1/2003 | Collins et al. |
| 2003/0022344 A1 | 1/2003 | Williams et al. |
| 2003/0064997 A1 | 4/2003 | Adams et al. |
| 2003/0073218 A1 | 4/2003 | Shokat |
| 2003/0083268 A1 | 5/2003 | Burli et al. |
| 2003/0109248 A1 | 6/2003 | Lewis |
| 2003/0113765 A1 | 6/2003 | Dempcy et al. |
| 2003/0119479 A1 | 6/2003 | Arima et al. |
| 2003/0119791 A1 | 6/2003 | Kerwin et al. |
| 2003/0139427 A1 | 7/2003 | Castelhano et al. |
| 2003/0143602 A1 | 7/2003 | Meyer et al. |
| 2003/0166929 A1 | 9/2003 | Snow et al. |
| 2003/0180924 A1 | 9/2003 | DeSimone |
| 2003/0186987 A1 | 10/2003 | Bridges et al. |
| 2003/0187001 A1 | 10/2003 | Calderwood et al. |
| 2003/0195211 A1 | 10/2003 | Sadhu et al. |
| 2003/0199516 A1 | 10/2003 | Moser et al. |
| 2003/0208800 A1 | 11/2003 | Eby et al. |
| 2003/0212113 A1 | 11/2003 | Dyatkina et al. |
| 2003/0232849 A1 | 12/2003 | Noe et al. |
| 2003/0235822 A1 | 12/2003 | Lokhov et al. |
| 2004/0039035 A1 | 2/2004 | Collins et al. |
| 2004/0043983 A1 | 3/2004 | Li |
| 2004/0067901 A1 | 4/2004 | Bhat et al. |
| 2004/0067915 A1 | 4/2004 | McMahon et al. |
| 2004/0072766 A1 | 4/2004 | June |
| 2004/0072788 A1 | 4/2004 | Bhat et al. |
| 2004/0102423 A1 | 5/2004 | MacLaughlan et al. |
| 2004/0102437 A1 | 5/2004 | Takami et al. |
| 2004/0110717 A1 | 6/2004 | Carroll et al. |
| 2004/0110945 A1 | 6/2004 | Nakayama et al. |
| 2004/0116689 A1 | 6/2004 | Gall et al. |
| 2004/0122235 A1 | 6/2004 | Polisetti et al. |
| 2004/0127434 A1 | 7/2004 | Bigot et al. |
| 2004/0176458 A1 | 9/2004 | Leban et al. |
| 2004/0176601 A1 | 9/2004 | Goulet et al. |
| 2004/0192758 A1 | 9/2004 | Leban et al. |
| 2004/0266780 A1 | 12/2004 | Sadhu et al. |
| 2005/0004149 A1 | 1/2005 | Harada et al. |
| 2005/0008472 A1 | 1/2005 | Iizuka |
| 2005/0043239 A1 | 2/2005 | Douangpanya et al. |
| 2005/0049310 A1 | 3/2005 | Mjalli et al. |
| 2005/0054614 A1 | 3/2005 | Diacovo et al. |
| 2005/0059713 A1 | 3/2005 | Mjalli et al. |
| 2005/0085472 A1 | 4/2005 | Tanaka et al. |
| 2005/0101551 A1 | 5/2005 | Sevillano et al. |
| 2005/0124637 A1 | 6/2005 | Cheng et al. |
| 2005/0143317 A1 | 6/2005 | Abdel-Meguid et al. |
| 2005/0153997 A1 | 7/2005 | Simon et al. |
| 2005/0171148 A1 | 8/2005 | Mjalli et al. |
| 2005/0182045 A1 | 8/2005 | Nagase et al. |
| 2005/0187418 A1 | 8/2005 | Small et al. |
| 2005/0197340 A1 | 9/2005 | Arora et al. |
| 2005/0215579 A1 | 9/2005 | Simon et al. |
| 2005/0239809 A1 | 10/2005 | Watts et al. |
| 2005/0250770 A1 | 11/2005 | Ono et al. |
| 2005/0256066 A1 | 11/2005 | Abel et al. |
| 2005/0261317 A1 | 11/2005 | Sadhu et al. |
| 2005/0272751 A1 | 12/2005 | McKerracher et al. |
| 2006/0019988 A1 | 1/2006 | McDonald et al. |
| 2006/0069034 A1 | 3/2006 | Burli et al. |
| 2006/0079538 A1 | 4/2006 | Hallahan et al. |
| 2006/0106038 A1 | 5/2006 | Bouscary et al. |
| 2006/0116326 A1 | 6/2006 | Burli et al. |
| 2006/0135790 A1 | 6/2006 | Hyett et al. |
| 2006/0156485 A1 | 7/2006 | Lim |
| 2006/0183783 A1 | 8/2006 | Polisetti et al. |
| 2006/0199776 A1 | 9/2006 | Blagg et al. |
| 2006/0235031 A1 | 10/2006 | Arnold et al. |
| 2006/0276470 A1 | 12/2006 | Jackson et al. |
| 2006/0287295 A1 | 12/2006 | Barlaam et al. |
| 2007/0015773 A1 | 1/2007 | Bergeron et al. |
| 2007/0027193 A1 | 2/2007 | Leban et al. |
| 2007/0032640 A1 | 2/2007 | Varghese et al. |
| 2007/0054915 A1 | 3/2007 | Arora et al. |
| 2007/0072897 A1 | 3/2007 | Mahaney et al. |
| 2007/0099871 A1 | 5/2007 | Davis et al. |
| 2007/0142405 A1 | 6/2007 | Dong et al. |
| 2007/0224672 A1 | 9/2007 | Leban et al. |
| 2007/0249598 A1 | 10/2007 | Wang et al. |
| 2007/0270452 A1 | 11/2007 | Blagg et al. |
| 2008/0032960 A1 | 2/2008 | Knight et al. |
| 2008/0058521 A1 | 3/2008 | Krishnan et al. |
| 2008/0070935 A1 | 3/2008 | Huang et al. |
| 2008/0119454 A1 | 5/2008 | Polisetti et al. |
| 2008/0119455 A1 | 5/2008 | Polisetti et al. |
| 2008/0119461 A1 | 5/2008 | Sin et al. |
| 2008/0200465 A1 | 8/2008 | Burli et al. |
| 2008/0249090 A1 | 10/2008 | Hu et al. |
| 2008/0261956 A1 | 10/2008 | Choi et al. |
| 2008/0287469 A1 | 11/2008 | Diacovo et al. |
| 2008/0292626 A1 | 11/2008 | Wang et al. |
| 2008/0293674 A1 | 11/2008 | Schwarz et al. |
| 2008/0306053 A1 | 12/2008 | Tachdjian et al. |
| 2008/0306093 A1 | 12/2008 | Servant et al. |
| 2008/0312180 A1 | 12/2008 | Liang et al. |
| 2008/0318942 A1 | 12/2008 | Simon et al. |
| 2009/0030023 A1 | 1/2009 | Harada et al. |
| 2009/0053192 A1 | 2/2009 | Millan et al. |
| 2009/0088452 A1 | 4/2009 | Coleman et al. |
| 2009/0099214 A1 | 4/2009 | Fairhurst et al. |
| 2009/0105233 A1 | 4/2009 | Chua et al. |
| 2009/0118283 A1 | 5/2009 | Defert et al. |
| 2009/0124638 A1 | 5/2009 | Shokat et al. |
| 2009/0124654 A1 | 5/2009 | Mjalli et al. |
| 2009/0163481 A1 | 6/2009 | Murphy et al. |
| 2009/0163709 A1 | 6/2009 | Blagg |
| 2009/0170879 A1 | 7/2009 | Szucova et al. |
| 2009/0181920 A1 | 7/2009 | Watkins et al. |
| 2009/0181988 A1 | 7/2009 | Tanaka et al. |
| 2009/0187014 A1 | 7/2009 | Blagg |
| 2009/0203689 A1 | 8/2009 | Dhalla et al. |
| 2009/0232768 A1 | 9/2009 | Birkus et al. |
| 2009/0247513 A1 | 10/2009 | Burli et al. |
| 2009/0253694 A1 | 10/2009 | Ono et al. |
| 2009/0264409 A1 | 10/2009 | Dong et al. |
| 2009/0264423 A2 | 10/2009 | Chua et al. |
| 2009/0270426 A1 | 10/2009 | Knight et al. |
| 2009/0270567 A1 | 10/2009 | Small et al. |
| 2009/0312319 A1 | 12/2009 | Ren et al. |
| 2009/0312406 A1 | 12/2009 | Hsieh et al. |
| 2009/0325967 A1 | 12/2009 | Fairhurst et al. |
| 2010/0009963 A1 | 1/2010 | Knight et al. |
| 2010/0022585 A1 | 1/2010 | deLong et al. |
| 2010/0029658 A1 | 2/2010 | Gavish et al. |
| 2010/0029693 A1 | 2/2010 | Douangpanya et al. |
| 2010/0048540 A1 | 2/2010 | Boyle et al. |
| 2010/0048882 A1 | 2/2010 | Blagg et al. |
| 2010/0056494 A1 | 3/2010 | Winzeler et al. |
| 2010/0105630 A1 | 4/2010 | Blagg |
| 2010/0190749 A1 | 7/2010 | Ren et al. |
| 2011/0046165 A1 | 2/2011 | Ren et al. |
| 2011/0124641 A1 | 5/2011 | Ren et al. |
| 2011/0144134 A1 | 6/2011 | Shokat et al. |
| 2011/0172228 A1 | 7/2011 | Ren et al. |
| 2011/0224223 A1 | 9/2011 | Shokat et al. |
| 2011/0269779 A1 | 11/2011 | Wilson et al. |
| 2011/0281866 A1 | 11/2011 | Ren et al. |
| 2011/0301144 A1 | 12/2011 | Knight et al. |
| 2012/0059000 A1 | 3/2012 | Ren et al. |

(56) References Cited

U.S. PATENT DOCUMENTS

| | | |
|---|---|---|
| 2012/0065154 A1 | 3/2012 | Tanaka et al. |
| 2012/0294930 A1 | 11/2012 | Ren et al. |
| 2012/0322814 A1 | 12/2012 | Korennykh et al. |
| 2012/0329776 A1 | 12/2012 | Ren et al. |
| 2014/0066462 A1 | 3/2014 | Pearce et al. |
| 2014/0288096 A1 | 9/2014 | Knight et al. |
| 2015/0031881 A1 | 1/2015 | Tanaka et al. |
| 2016/0168151 A1 | 6/2016 | Tanaka et al. |

FOREIGN PATENT DOCUMENTS

| | | |
|---|---|---|
| EP | 0 496 61 B1 | 7/1992 |
| EP | 0 496 617 A1 | 7/1992 |
| EP | 773023 A1 | 5/1997 |
| EP | 1020445 A1 | 7/2000 |
| GB | 812366 A | 4/1959 |
| GB | 937725 A | 9/1963 |
| JP | 61109797 | 5/1986 |
| JP | 05-112595 A | 5/1993 |
| JP | 8295667 | 11/1996 |
| JP | 9143163 | 6/1997 |
| JP | 10206995 | 8/1998 |
| JP | 11-502859 A | 3/1999 |
| JP | 11-507390 A | 6/1999 |
| JP | 2000072773 A | 3/2000 |
| JP | 2002037787 A | 2/2002 |
| JP | 2002131859 A | 5/2002 |
| JP | 2003073357 A | 3/2003 |
| JP | 2004161716 A | 6/2004 |
| JP | 5256693 B2 | 8/2013 |
| WO | WO-83/01446 A1 | 4/1983 |
| WO | WO-91/17161 A1 | 11/1991 |
| WO | WO-92/14733 A1 | 9/1992 |
| WO | WO-93/16091 A1 | 8/1993 |
| WO | WO-93/16092 A1 | 8/1993 |
| WO | WO-93/18035 A1 | 9/1993 |
| WO | WO-93/22443 A1 | 11/1993 |
| WO | WO-94/13677 A1 | 6/1994 |
| WO | WO-94/17803 A1 | 8/1994 |
| WO | WO-95/12588 A1 | 5/1995 |
| WO | WO-95/29673 A1 | 11/1995 |
| WO | WO-95/32984 A1 | 12/1995 |
| WO | WO-96/31510 A1 | 10/1996 |
| WO | WO-96/40706 A1 | 12/1996 |
| WO | WO-97/15658 A1 | 5/1997 |
| WO | WO-97/28133 A1 | 8/1997 |
| WO | WO-97/28161 A1 | 8/1997 |
| WO | WO-98/41525 A1 | 9/1998 |
| WO | WO-98/52611 A1 | 11/1998 |
| WO | WO-98/57952 A1 | 12/1998 |
| WO | WO-00/17202 A1 | 3/2000 |
| WO | WO-00/04204 A3 | 7/2000 |
| WO | WO-00/042042 A2 | 7/2000 |
| WO | WO-01/02369 A2 | 1/2001 |
| WO | WO-01/02369 A3 | 1/2001 |
| WO | WO-01/16114 A2 | 3/2001 |
| WO | WO-01/16114 A3 | 3/2001 |
| WO | WO-01/19829 A2 | 3/2001 |
| WO | WO-01/19829 A3 | 3/2001 |
| WO | WO-01/25238 A2 | 4/2001 |
| WO | WO-01/25238 A3 | 4/2001 |
| WO | WO-01/31063 A1 | 5/2001 |
| WO | WO-0138584 A2 | 5/2001 |
| WO | WO-0138584 A3 | 5/2001 |
| WO | WO-01/55140 A1 | 8/2001 |
| WO | WO-01/56988 A1 | 8/2001 |
| WO | WO-01/81346 A2 | 11/2001 |
| WO | WO-01/81346 A3 | 11/2001 |
| WO | WO-02/06192 A1 | 1/2002 |
| WO | WO-02/30944 A2 | 4/2002 |
| WO | WO-02/30944 A3 | 4/2002 |
| WO | WO-02/057425 A2 | 7/2002 |
| WO | WO-02/057425 A3 | 7/2002 |
| WO | WO-02/076986 A1 | 10/2002 |
| WO | WO-02/083143 A1 | 10/2002 |
| WO | WO-02080926 A1 | 10/2002 |
| WO | WO-02/088025 A1 | 11/2002 |
| WO | WO-02/090334 A1 | 11/2002 |
| WO | WO-03/000187 A2 | 1/2003 |
| WO | WO-03/000187 A3 | 1/2003 |
| WO | WO-03/016275 A1 | 2/2003 |
| WO | WO-03/020880 A2 | 3/2003 |
| WO | WO-03/024969 A1 | 3/2003 |
| WO | WO-03/029209 A2 | 4/2003 |
| WO | WO-03/029209 A3 | 4/2003 |
| WO | WO-03/035075 A1 | 5/2003 |
| WO | WO-03/059884 A1 | 7/2003 |
| WO | WO-03/082341 A1 | 10/2003 |
| WO | WO-03/106426 A1 | 12/2003 |
| WO | WO-2004/006906 A2 | 1/2004 |
| WO | WO-2004/006906 A3 | 1/2004 |
| WO | WO-2004/018058 A2 | 3/2004 |
| WO | WO-2004/018058 A3 | 3/2004 |
| WO | WO-2004/031177 A1 | 4/2004 |
| WO | WO-2004/039774 A2 | 5/2004 |
| WO | WO-2004/039774 A3 | 5/2004 |
| WO | WO-2004/087053 A2 | 10/2004 |
| WO | WO-2004/087053 A3 | 10/2004 |
| WO | WO-2004/111014 A1 | 12/2004 |
| WO | WO-2005/002585 A1 | 1/2005 |
| WO | WO-2005/007085 A2 | 1/2005 |
| WO | WO-2005/007085 A3 | 1/2005 |
| WO | WO-2005/012323 A2 | 2/2005 |
| WO | WO-2005/012323 A3 | 2/2005 |
| WO | WO-2005/016348 A1 | 2/2005 |
| WO | WO-2005/016349 A1 | 2/2005 |
| WO | WO-2005/016528 A2 | 2/2005 |
| WO | WO-2005/016528 A3 | 2/2005 |
| WO | WO-2005/021533 A1 | 3/2005 |
| WO | WO-2005/044181 A2 | 5/2005 |
| WO | WO-2005/044181 A3 | 5/2005 |
| WO | WO-2005/047289 A1 | 5/2005 |
| WO | WO-2005/061460 A1 | 7/2005 |
| WO | WO-2005/063258 A1 | 7/2005 |
| WO | WO-2005/067901 A2 | 7/2005 |
| WO | WO-2005/067901 A3 | 7/2005 |
| WO | WO-2005/074603 A2 | 8/2005 |
| WO | WO-2005/074603 A3 | 8/2005 |
| WO | WO-2005/097800 A1 | 10/2005 |
| WO | WO-2005/105760 A1 | 11/2005 |
| WO | WO-2005/112935 A1 | 12/2005 |
| WO | WO-2005/113556 A1 | 12/2005 |
| WO | WO-2005/117889 A1 | 12/2005 |
| WO | WO-2005/120511 A1 | 12/2005 |
| WO | WO-2006/030032 A1 | 3/2006 |
| WO | WO-2006/038865 A1 | 4/2006 |
| WO | WO-2006/050501 A2 | 5/2006 |
| WO | WO-2006/050501 A3 | 5/2006 |
| WO | WO-2006/050946 A1 | 5/2006 |
| WO | WO-2006/068760 A2 | 6/2006 |
| WO | WO-2006/068760 A3 | 6/2006 |
| WO | WO-2006/089106 A2 | 8/2006 |
| WO | WO-2006/089106 A3 | 8/2006 |
| WO | WO-2006/108107 A1 | 10/2006 |
| WO | WO-2006/112666 A1 | 10/2006 |
| WO | WO-2006/114064 A2 | 11/2006 |
| WO | WO-2006/114064 A3 | 11/2006 |
| WO | WO-2006/114065 A2 | 11/2006 |
| WO | WO-2006/114065 A3 | 11/2006 |
| WO | WO-2006/114180 A1 | 11/2006 |
| WO | WO-2007/002293 A2 | 1/2007 |
| WO | WO-2007/002293 A3 | 1/2007 |
| WO | WO-2007/006547 A1 | 1/2007 |
| WO | WO-2007/020046 A1 | 2/2007 |
| WO | WO-2007025090 A2 | 3/2007 |
| WO | WO-2007025090 A3 | 3/2007 |
| WO | WO-2007/057466 A1 | 5/2007 |
| WO | WO-2007/061737 A2 | 5/2007 |
| WO | WO-2007/061737 A3 | 5/2007 |
| WO | WO-2007/075554 A2 | 7/2007 |
| WO | WO-2007/075554 A3 | 7/2007 |
| WO | WO-2007/079164 A2 | 7/2007 |
| WO | WO-2007/079164 A3 | 7/2007 |
| WO | WO-2007/095223 A2 | 8/2007 |

(56) References Cited

FOREIGN PATENT DOCUMENTS

| | | |
|---|---|---|
| WO | WO-2007/095223 A3 | 8/2007 |
| WO | WO-2007/103308 A2 | 9/2007 |
| WO | WO-2007/103308 A3 | 9/2007 |
| WO | WO-2007/106503 A2 | 9/2007 |
| WO | WO-2007/106503 A3 | 9/2007 |
| WO | WO-2007/112005 A2 | 10/2007 |
| WO | WO-2007/112005 A3 | 10/2007 |
| WO | WO-2007/114926 A2 | 10/2007 |
| WO | WO-2007/114926 A3 | 10/2007 |
| WO | WO-2007/121453 A2 | 10/2007 |
| WO | WO-2007/121453 A3 | 10/2007 |
| WO | WO-2007/121920 A2 | 11/2007 |
| WO | WO-2007/121920 A3 | 11/2007 |
| WO | WO-2007/121924 A2 | 11/2007 |
| WO | WO-2007/121924 A3 | 11/2007 |
| WO | WO-2007/124854 A1 | 11/2007 |
| WO | WO-2007/125310 A2 | 11/2007 |
| WO | WO-2007/125310 A3 | 11/2007 |
| WO | WO-2007/125315 A2 | 11/2007 |
| WO | WO-2007/125315 A3 | 11/2007 |
| WO | WO-2007/135380 A2 | 11/2007 |
| WO | WO-2007/135380 A3 | 11/2007 |
| WO | WO-2007/135398 A1 | 11/2007 |
| WO | WO-2007126841 A2 | 11/2007 |
| WO | WO-2007126841 A3 | 11/2007 |
| WO | WO-2007134828 A1 | 11/2007 |
| WO | WO-2008/025755 A1 | 3/2008 |
| WO | WO 2008/037477 * | 4/2008 |
| WO | WO-2008/037477 A1 | 4/2008 |
| WO | WO-2008/047821 A1 | 4/2008 |
| WO | WO-2008/063625 A2 | 5/2008 |
| WO | WO-2008/063625 A3 | 5/2008 |
| WO | WO-2008/064018 A1 | 5/2008 |
| WO | WO-2008/079028 A1 | 7/2008 |
| WO | WO-2008/082487 A2 | 7/2008 |
| WO | WO-2008/082487 A3 | 7/2008 |
| WO | WO-2008/094737 A2 | 8/2008 |
| WO | WO-2008/094737 A3 | 8/2008 |
| WO | WO-2008/112715 A2 | 9/2008 |
| WO | WO-2008/112715 A3 | 9/2008 |
| WO | WO-2008/118454 A2 | 10/2008 |
| WO | WO-2008/118454 A3 | 10/2008 |
| WO | WO-2008/118455 A1 | 10/2008 |
| WO | WO-2008/118468 A1 | 10/2008 |
| WO | WO-2008/125014 A1 | 10/2008 |
| WO | WO-2008/125207 A1 | 10/2008 |
| WO | WO-2008/127226 A2 | 10/2008 |
| WO | WO-2008/127226 A3 | 10/2008 |
| WO | WO-2008/136457 A1 | 11/2008 |
| WO | WO-2009/004621 A1 | 1/2009 |
| WO | WO-2009/010925 A2 | 1/2009 |
| WO | WO-2009/010925 A3 | 1/2009 |
| WO | WO-2009/023718 A2 | 2/2009 |
| WO | WO-2009/023718 A3 | 2/2009 |
| WO | WO-2009/044707 A1 | 4/2009 |
| WO | WO-2009/050506 A2 | 4/2009 |
| WO | WO-2009/050506 A3 | 4/2009 |
| WO | WO-2009/062118 A2 | 5/2009 |
| WO | WO-2009/062118 A3 | 5/2009 |
| WO | WO-2009/064802 A2 | 5/2009 |
| WO | WO-2009/064802 A3 | 5/2009 |
| WO | WO-2009/088986 A1 | 7/2009 |
| WO | WO-2009/088990 A1 | 7/2009 |
| WO | WO-2009/100406 A2 | 8/2009 |
| WO | WO-2009/100406 A3 | 8/2009 |
| WO | WO-2009/117157 A1 | 9/2009 |
| WO | WO-2009000412 A1 | 12/2009 |
| WO | WO-2010/006072 A2 | 1/2010 |
| WO | WO-2010/006072 A3 | 1/2010 |
| WO | WO-2010/006086 A2 | 1/2010 |
| WO | WO-2010/006086 A3 | 1/2010 |
| WO | WO-2010/009207 A1 | 1/2010 |
| WO | WO-2010/019210 A2 | 2/2010 |
| WO | WO-2010/019210 A3 | 2/2010 |
| WO | WO-2010/036380 A1 | 4/2010 |
| WO | WO-2010/039534 A2 | 4/2010 |
| WO | WO-2010/039534 A3 | 4/2010 |
| WO | WO-2010/045542 A2 | 4/2010 |
| WO | WO-2010/045542 A3 | 4/2010 |
| WO | WO-2010/051042 A1 | 5/2010 |
| WO | WO-2010/051043 A1 | 5/2010 |
| WO | WO-2011/022439 A1 | 2/2011 |
| WO | WO-2012/151562 A1 | 11/2012 |
| WO | WO-2012/154695 A2 | 11/2012 |
| WO | WO-2012/154695 A3 | 11/2012 |

OTHER PUBLICATIONS

Sausville et al. (Cancer Research, 2006, vol. 66, pp. 3351-3354).*
U.S. Appl. No. 13/862,348, filed Apr. 12, 2013, Tanaka et al.
U.S. Appl. No. 14/458,641, filed Aug. 13, 2014, Knight et al.
U.S. Appl. No. 14/668,797, filed Mar. 25, 2015, Knight et al.
U.S. Appl. No. 14/523,581, filed Oct. 24, 2014, Tanaka et al.
U.S. Appl. No. 14/738,169, filed Jun. 12, 2015, Tanaka et al.
U.S. Appl. No. 14/934,187, filed Nov. 6, 2015, Knight et al.
U.S. Appl. No. 15/159,689, filed May 19, 2016, Knight et al.
"Report of the Expert Committee on the Diagnosis and Classification of Diabetes Mellitus", Diabetes Care (1992) 2(Suppl 1):S5-S19.
Abdel-Mohsen, S.A., "Synthesis, reactions and antimicrobial activity of 2-amino-4-(8-quinolinol-5-yl)-1-(p-tolyl)-pyrrole-3-carbonitrile", Bull. Korean Chem. Soc. 2005 26(5):719-728.
Ames et al., "Heterocyclic Synthesis from o-Halogen-acids. Part II. Thienopyridinones and Thienopyranones from 3-bromothiophene-2- and 4-Bromothiophene-3-Carboxylic Acids", Journal of the Chemical Society, Perkin Transactions 1, Jan. 14:1390-1395 (1975).
Andrews, R.C., et al. "Effects of the 11 beta-Hydroxysteroid Dehydrogenase Inhibitor Carbenoxolone on Insulin Sensitivity in Men with Type 2 Diabetes", J. Clin. Endocrinol. Metab. (2003) 88(1):285-291.
Arnold, et al. "Pyrrolo[2,3-d]pyrimidines containing an extended 5-substituent as potent and selective inhibitors of Ick I", Bioorg. & Med. Chem. Lett (2000) 10:2167-70.
Banker, G.S., et al. Modem Pharmaceutics, 3ed, Marcel Dekker, New York, 1996, pp. 451-596.
Barf, T. et al. "Arylsulfonamidothiazoles as a New Class of Potential Antidiabetic Drugs. Discovery of Potent and Selective Inhibitors of the 1113-Hydroxysteroid Dehydrogenase Type 1", J. Med. Chem. (2002) 45(18):3813-3815.
Barnes, P.J., et al. "Efficacy and Safety of Inhaled Corticosteroids in Asthma", Am. Rev. Respir. Dis. (1993) 148:S1-26.
BASOTEST®, "Test Kit for the Quantitative Determination of the Degranulation of Basophilic Granulocytes in Heparinized Human Whole Blood", [www.biocarta.comiTDS/10-0500.pdf], Retreived from the Internet Nov. 29, 2011, 10 pages.
Beeram, M. et al., "Akt-induced endocrine therapy resistance is reversed by inhibition of mTOR signaling", Annals of Oncology 18:1323-1328, 2007.
Bell, G., et al. "Glucokinase Mutations Insulin Secretion, and Diabetes Mellitus", Annu. Rev. Physiol., (1996) 58:171-186.
Bhat, G. A., et al., "Pyrazolopyrimidine nucleosides. 12. Synthesis and biological activity of certain pyrazolo[3,4-d]pyrimidine nucleosides related to adenosine," J. Med. Chem. vol. 24, No. 10, (1981), pp. 1165-1172.
Bishop, A.C. et al. "Generation of monospecific nanomolar tyrosine kinase inhibitors via a chemical genetic approach", Journal of the American Chemical Society, American Chemical Society, Washington, DC, US, vol. 121, No. 4, 1999, pp. 627-631.
Bohren, K.M., et al. "Expression, Crystallization and Preliminary Crystallographic Analysis of Human Carbonyl Reductase", J. MoL Biol. (1994) 224:659-664.
Campora, et al. Binuclear complexes of nickel bridged by hydrocarbon ligands. Isocyanide insertion chemistry and amide formation by intramolecular coupling of acyl and imidoyl functionalities. Organometallics. Jan. 1992;11(1):11-13.
Campora, et al. Isocyanide insertion chemistry. Synthesis and structural characterization of bridging imidoyl complexes of nickel

(56) References Cited

OTHER PUBLICATIONS and amide formation by intramolecular coupling of acyl and imidoyl functionalities. Organometallics. Oct. 1993;12(10):4025-31.

Chaisuparat, et al. Dual Inhibition of PI3K(alpha) and mTOR as an Alternative Treatment for Kaposi's Sarcoma. Cancer Research. 2008;68:8361.

Chappelow, et al. Neovascular Age-Related Macular Degeneration: Potential Therapies. Drugs. 2008;68(8):1029-1036.

Cox, B., et al. "Human Colorectal Cancer Cells Efficiently Conjugate the Cyclopentenone; Prostaglandin, Prostaglandin J2 to Glutathione", Biochim. Biophys. Acta (2002) 1584:37-45;.

Davis, et al. The Preparation of Substituted 1(2H)-Isoquinolinones from Dilithiated 2-Methyl-N-arylbenzamides, 2-Methyl-N-(arylmethyl)-benzamides, or 2-Methylbenzoic Acid, 2,2-Dimethylhydrazide. Synthetic Communications. Sep. 1997;27(17):2961-9.

Diederich, S., et al. "In the Search for Specific Inhibitors of Human 11β-Hydroxysteroid-Dehydrogenases (11β-HSDs): Chenodeoxycholic Acid Selectively Inhibits 11β-HSD-I", Eur. J. Endocrinol. (2000) 142:200-207.

Dijksman, et al. 271. 1 : 2-Dihydro-2-thianaphthalene derivatives. Part I. Preparation and reactions of 1 : 2-dihydro-1-keto-2-thianaphthalenes. J. Chem. Soc. 1951:1213-18.

Ding, S., et al. "A Combinatorial Scaffold Approach Toward Kinase-Directed Heterocycle Libraries", J. Am. Chem. Soc. (2002) 124(8):1594-1596.

Ding, S., et al. "A Concise and Traceless Linker Strategy Toward Combinatorial Libraries of 2,6,9-Substituted Purines", J. Org. Chem. (2001) 66:8273-8276.

Ding, S., et al. "Resin-Capture and Release Strategy Toward Combinatorial Libraries of 2,6,9-Substituted Purines", J. Comb. Chem.(2002) 4:183-186.

Donati. Emerging Therapies for Neovascular Age-Related Macular Degeneration: State of the Art. Ophthalmologica. 2007;221:366-377.

Fajans, S., et al."Maturity Onset Diabetes of the Young (MODY)", Diabet. Med. (1996) 13:S90-S95.

Feinstein, M.B., et al. "Regulation of the Action of Hydrocotisone in Airway Epithelial Cells by 11β-Hydroxysteroid Dehydrogenase", Am. J. Respir. Cell. Mol. Biol. (1999) 21:403-408.

Feldman, M.E. et al. , "Active site inhibitors of mTOR target rapamycin-resistant outputs of mTORC1 and mTORC2", PLOS Biology 7(2):371-383, Feb. 2009.

Fingl, E., et al. "General Principles", The Pharmacological Basis of Therapeutics, Fifth Edition (1975), Ch. 1, 1-46.

Forrest, G.L., et al. "Carbonyl Reductase", Chem. Biol. Interact. (2000) 129:21-40.

Forrest, G.L., et al. "Induction of a Human Carbonyl Reductase Gene Located on Chromosome 21", Biochim. Biophys. Acta. (1990) 1048:149-155.

Franzen, R. "The Suzuki, the Heck, and the Stille reaction—three versatile methods for the introduction of new C—C bonds on solid support", Can J. Chem. (2000) 78:957-962.

Funder, J.W., et al. "Mineralocorticoid Action: Target Tissue Specificity Is Enzyme, Not Receptor, Mediated", Science (1998) 242:583-585.

Garber, M.E., et al. "Diversity of Gene Expression in Adenocarcinoma of the Lung", Proc. Nat. Acad. Sci. USA (2001) 98(24):13784-13789.

Gonzalez, B., et al. "Protection against Daunorubicin Cytotoxicity by Expression of a Cloned Human Carbonyl Reductase cDNA in K562 Leukemia Cells", Cancer Res. (1995) 55:4646-4650.

Graupera, et al. Angiogenesis selectively requires the p110 isoform of PI3K to control endothelial cell migration. Nature. 2008;453:662-666.

Haase, A.,et al. "Detection of Viral Nucleic Acids by in Situ Hybridization", Methods in Virology (1984) VII:189-226.

Hanefeld, U., et al. "One-pot Synthesis of Tetrasubstituted Pyrazoles Proof of Regiochemistry", J. Chem. Soc. Perkin Trans. (1996) 1:1545-1552.

Hellwinkel, et al. Heterocyclensynthesen mit MF/A1203-Basensystemen: 2-Arylbenzofurane and 2,3-Diarylisochinolin-1(2H)-one. Synthesis. 1995;1995(9):1135-41.

Ishiyama, T., et al. "A Stoichiometric Aromatic C—H Borylation Catalyzed by Iridium(I)/2,2'-Bipyridine Complexes at Room Temperature", Angew. Chem. IInt.Ed. (2002) 41(16):3056-3058.

Ishiyama, T., et al. "Mild Iridium-Catalyzed Borylation of Arenes. High Turnover Numbers, Room Temperature Reactions, and Isolation of a Potential Intermediate", J. Am. Chem. Soc. (2002) 124(3):390-391.

Kajita, et al. Nickel-catalyzed decarbonylative addition of phthalimides to alkynes. J Am Chem Soc. May 14, 2008;130(19):6058-9.

Kallberg, Y., et al. "Short-Chain Dehydrogenase/Reductase (SDR) Relationships: a Large Family with Eight Clusters Common to Human, Animal, and Plant Genomes", Protein Sci. (2002) 11:636-641.

Kallberg, Y., et al. "Short-Chain Dehydrogenases/Reductases (SDRs)", Eur. J. Biochem. (2002) 269:4409-4417.

Kim, M. et al. , "Activation and function of the mTORC1 pathway in mast cells", The Journal of Immunology 180:4586-4595, Apr. 2008.

Knight, et al. "A Pharmacological Map of the PI3-K Family Defines a Role for p110a in Insulin Signaling", Cell (2006) 125:733-747.

Kost et al., "Recyclization of 3-Alkyl- and 1,3-Dialkylisoquinolinium Salts to Naphthylamines", Chemistry of Heterocyclic Compounds, Jan. 16(9):965-970 (1981).

Kraybill, B.C. et al. "Inhibitor scaffolds as new allele specific kinase substrates", Journal of the American Chemical Society, American Chemical Society, Washington, DC, US, vol. 124, No. 41, Oct. 16, 2002, pp. 12118-12128.

Kreutzberger, A. et al. , "5-substituierte 4-aminopyrimidine durch aminomethinylierung von acetonitrilen", Justus Liebigs Annalen der Chemie 4:537-544, 1977.

Kumar et al., "Keten Dithioacetals. Part II. Reaction of 3-Cyano-4-Methylthio-2(1 H)-pyridones with Hydazine and Guanidine: Synthesis of Novel Substituted and Fused Pyrazolo[4,3-c]pyridone and Pyrido[4,3-d]pyrimidine Derivatives", Journal of the Chemical Society, Perkin Transactions 1, Chemical Society, Letchworth, Jan. 8:857-862 (1978).

Kundu, et al. Palladium-Catalysed Heteroannulation with Terminal Alkynes: a Highly Regio- and Stereoselective Synthesis of (Z)-3-Aryl(alkyl)idene Isoindolin-1-ones1. Tetrahedron. Jun. 30, 2000;56(27):4777-92.

Kwok, B.H., et al. "The Anti-Inflammatory Natural Product Parthenolide from the Medicinal Herb Feverfew Directly Binds to and Inhibits IkB Kinase", Chem. Biol. (2001) 8:759-766.

Lee, et al. All roads lead to mTOR: integrating inflammation and tumor angiogenesis.. Cell Cycle. 2007;6(24):3011-3014.

Majumder, et al. mTOR inhibition reverses Akt-dependent prostate intraepithelial neoplasia through regulation of apoptotic and HIF-1-dependent pathways. Nature Medicine. 2004;10:594-601.

Mayer, T.U., et al. "Small Molecule Inhibitor of Mitotic Spindle Bipolarity Identified in a Pheontype-Based Screen", Science (1999) 286:971-974.

Mellinghoff, et al. TORward AKTually useful mouse models. Nature Medicine. 2004;10:579-580.

Miyaura, N., et al., "Palladium-Catalyzed Cross-Coupling Reactions of Organoboron Compounds," Chem. Rev. (1995) 95(7):2457-2483.

Modi, et at. Isoquinolones: Part IV-Synthesis of 3-Methyl, 3-Formyl & Other 3-Substituted N-Arylisoquinolones, Indian J. Chem. 1979; 186:304-306.

Moon, H.S., et al. "A Novel Microtubule Destabilizing Entity from Orthogonal Synthesis of Triazine Library and Zebrafish Embryo Screening", J. Am. Chem. Soc. (2002) 124:11608-11609.

Nakanishi, M., et al. "Cloning and Sequence Analysis of a cDNA Encoding Tetrameric Carbonyl Reductase of Pig Lung", Biochem. Biophys. Acta (1993) 194(3):1311-1316.

(56) References Cited

OTHER PUBLICATIONS

Nemazanyi, et al. 3-Amino-4-aryl-1(2H)-isoquinolones. Chemistry of Heterocyclic Compounds. Mar. 1991;27(3):307-8.
Niswender, C.M., et al. "Protein Engineering of Protein Kinase A Catalytic Subunits Results in the Acquisition of Novel Inhibitor Sensitivity", The Journal of Biological Chemistry (2002) 277(32):28916-28922.
Nobel, C.S.I., et al. "Purification of Full-Length Recombinant Human and Rat Type 1 11 beta-hydroxysteroid Dehydrogenases with Retained Oxidoreductase Activities", Protein Expr. Purif. (2002) 26:349-356.
Oda, et al. PIK3CA Cooperates with Other Phosphatidylinositol 3'-Kinase Pathway Mutations to Effect Oncogenic Transformation. Cancer Research. 2008;68:8127.
Oppermann, U.C., et al. "Forms and Functions of Human SDR Enzymes", Chem. Biol. Interact. (2001) 130-132(1-3):699-705.
Ozaki, et al. Studies on 4 (1H)-Quinazolinones. IV. Convenient Syntheses of 12-Methyl-6H-isoquino [2,1-a] quinazolin-6-one and 6-Methyl-13H-quinazolino [3,4-a] quinazolin-13-one. Chem. Pharm. Bull. Jun. 25, 1984;32(6):2160-4.
Ozol, et al. Autoxidative transformations of 2-substituted 3-alkyl-4-hydroxy-1-oxo-1, 2-dihydroisoquinolines. Chemistry of Heterocyclic Compounds. Jun. 1978;14(6):644-8.
Patel, et al. Immunopathological aspects of age-related macular degeneration. Seminars in Immunopathology. 2008;30(2):97-110.
Persson, C.G. "Glucocorticoids for Asthma—Early Contributions", Pulm. Pharmacol. (1989) 2:163-166.
Pietrie et al., "novel biotinylated adenylate analogue derived from pyrazolo[3,4-d]pyrimidine for labeling DNA probes," Bioconj. Chem. vol. 2, No. 6, (1991), pp. 441-446.
Pudlo, J.S., et al. "Synthesis, Antiproliferative, and Antiviral Activity of Certain 4-Substituted and 4,5 Disubstituted 7[1,3-Dihydroxy-2-propoxy)methylipyrrolo[2,3-d]pyrimidines", J. Med. Chem. (1990) 33:1984-1992.
Robertson, R.P. "Eicosandoids and Human Disease", Harrison's Principles of Internal Medicine, Isselbacher K.J., et al. (eds.), McGraw-Hill, New York City (1994) 1:431-435.
Romero, D.G., et al. "Cloning and Expression of the Bovine 1113-hydroxysteroid Dehydrogenase Type-2", J. Steroid Biochm. Mol. Biol. (2000) 72:231-237.
Singer, R.H., et al. "Optimization of in situ Hybridization Using Isotopic and Non-Isotopic Detection Methods", Biotechniques (1986) 4(3):230-250.
Soldan, M., et al. "Induction of Daunorubicin Carbonyl Reducing Enzymes by Daunorubicin in Sensitive and Resistant Pancreas Carcinoma Cells", Biochem. Pharmacol. (1996) 51:117-123.
Stanoeva et al. Homophthalic anhydrides and their application to the synthesis of heterocyclic compounds (review). Chemistry of Heterocyclic Compounds. Dec. 1984;20(12);1305-15.
Takeuchi, H. et al. , "Synergistic augmentation of reapamycin-induced autophagy in malignant glioma cells by phosphatidylinositol 3-kinase/protein kinase B inhibitors", Cancer Research 65(8):3336-3346, Apr. 15, 2005.
Tanaka, M., et al. "An Unbiased Cell Morphology-Based Screen for New, Biologically Active Small Molecules", PLoS Biology (2005) 3(5):0764-0776.
Ugarkar, B.G., et al. "Adenosine Kinase Inhibitors. 2. Synthesis, Enzyme Inhibition, and Antiseizure Activity of Diaryltubercidin Analogues", J. Med. Chem. (2000) 43:2894-2905.
Vasilevsky et al., "Study of the Heterocyclization of vic-Substituted Hydrazides of Acetylenylpyrazolecarboxylic Acids into N-Amino Pyrazolopyridinones", Journal of Heterocyclic Chemistry, Nov., 39(6):1229-1233 (2002).
Vasilevsky et al., "Unexpected results in the heterocyclization of 5-acetylenylpyrazole-4-carboxylic acid hydrazides under the influence of CuCl: formatin of a diazepinone and dehydrodimerization into the corresponding bis(pyrazolo [4,3-d] [1,2] diazepinone)", Tetrahedron Letters, Jan., 46(26): 4457-4459 (2005).

White, P.C., et al. "11 beta-Hydroxysteroid Dehydrogenase and the Syndrome of Apparent Mineralocorticoid Excess", Endocr. Rev. (1997) 18(1):135-156.
Widler, L., et al. "7-Alkyl- and 7-Cycloalkyl-5-aryl-pyrrolo[2,3-cipyrimidines-Potent Inhibitors of the Tyrosine Kinase c-Src," Bioorganic & Medicinal Chemistry Letters (2001) 11(6):849-852.
Wolff, M. E. Burger's Medicinal Chemistry, 5ed, Part 1, John Wiley & Sons, 1995, pp. 975-977.
Yaguchi, et al. Antitumor activity of ZSTK474, a new phosphatidylinositol 3-kinase inhibitor. J. Natl. Cancer. Inst. 2006; 98(8): 545-556. Abstract only.
Abdul-Majeed, S., "Polycystic diseases in visceral organs." Obstetrics and gynecology international (2011) Article ID 609370: 1-7.
Apsel, Beth et al., "Targeted polypharmacology: discovery of dual inhibitors of tyrosine and phosphoinositide kinases", Nature Chemical Biology 4(11):691-699, 2008.
Aragon, Anthony D. et al., "Characterization of Differentiated Quiescent and Nonquiescent Cells in Yeast Stationary-Phase Cultures", Molecular Biology of the Cell 19:1271-1280, 2008.
Aragon, Anthony D. et al., Microarray based analysis of temperature and oxidative stress induced messenger RNA in Schistosoma mansoni', Molecular & Biochemical Parasitology 162:134-141, 2008.
Aragon, Tomas et al., "Messenger RNA targeting to endoplasmic reticulum stress signaling sites", Nature 457(7230):736-740, 2009.
Berge, Stephen M. et al., "Pharmaceutical Salts", Journal of Pharmaceutical Sciences Berge et al., "Pharmaceutical Salts", Journal of Pharmaceutical Sciences 66(1):1-19, 1977.
Bishop, Anthony C. et al., "Design of allele-specific inhibitors to probe protein kinase signalling", Current Biology 8:257-266, 1998.
Blethrow, Justin et al., "Design and Use of Analog-Sensitive Protein Kinases", Current Protocols in Molecular Biology 18.11.1-18.11.19, 2004.
Braun, M., "Ovarian toxicity from sirolimus." New England Journal of Medicine 366.11 (2012): 1062-1064.
Cannon, J.G., "Analog Design", Burger's Medicinal Chemistry and Drug Discovery, Fifth Edition, vol. 1: Principles and Practice, 1995, pp. 783-802.
Carrasco, Daniel R. et al., "The Differentiation and Stress Response Factor XBP-1 Drives Multiple Myeloma Pathogenesis", Cancer Cell 11:349-360, 2007.
Chapin, H.C. & Caplan, M.J., "The cell biology of polycystic kidney disease", The Journal of Cell Biology 2010, 191(4):701-710.
Cox, Jeffery S. et al., "A Novel Mechanism for Regulating Activity of a Transcription Factor That Controls the Unfolded Protein Response", Cell 87:391-404, 1996.
Credle, Joel J. et al., "On the mechanism of sensing unfolded protein in the endoplasmic reticulum", Proceedings of the National Academy of Sciences 102(52):18773-18784, 2005.
Dar, Arvin C. et al., "Small Molecule Recognition of c-Src via the Imatinib-Binding Conformation", Chemistry & Biology 15:1015-1022, 2008.
Doody, Gina M. et al., "BLIMP-1 is a target of cellular stress and downstream of the unfolded protein response", European Journal of Immunology 36:1572-1582, 2006.
Funder; J.W., et al. "Mineralocorticoid Action: Target Tissue Specificity Is Enzyme, Not Receptor, Mediated", Science (1998) 242:583-585.
Gonzalez, Tania N. et al., "Ire1p: A Kinase and Site-Specific Endoribonuclease", Methods in Molecular Biology 160:25-36, 2001.
Grantham et al., "mTOR Inhibitors and Autosomal Dominant Polycystic Kidney Disease", The New England journal of medicine 2011, 364(3):286-287.
Kimata, Yukio et al., "Two regulatory steps of ER-stress sensor Ire 1 involving its cluster formation and interaction with unfolded proteins", The Journal of Cell Biology 179(1):75-86, 2007.
Koong, Albert C. et al., "Targeting XBP-1 as a Novel Anti-Cancer Strategy", Cancer Biology & Therapy 5(7):756-759, 2006.
Koulen et al., "Polycystin-2 is an intracellular calcium release channel", Nature Cell Biolgy 2002, 4:191-197.

(56) References Cited

OTHER PUBLICATIONS

Kudo, Takashi et al., "The Unfolded Protein Response Is Involved in the Pathology of Alzheimer's Disease", New York Academy of Sciences 977:349-355, 2002.
Lee, Kenneth P.K. et al., "Structure of the Dual Enzyme Ire1 Reveals the Basis for the Catalysis and Regulation in Nonconventional RNA Splicing", Cell 132:89-100, 2008.
Lin, Jonathan H. et al., "IRE1 Signaling Affects Cell Fate During the Unfolded Protein Response", Science 318:944 (2007).
Ma, Yanjun et al., "The role of the unfolded protein response in tumour development: friend or foe?", Nature Reviews Cancer 4:966-977, 2004.
McKee, B. et al. (2005). "Rapamycin-Induced Amelioration of Murine Polycystic Kidney Disease," Experimental Biology IUPS 2005: Meeting Abstracts A244, Abstract 197.18, 2 pages.
Mostov, K. E., "mTOR is out of control in polycystic kidney disease", Proc. Natl. Acad. Sci. USA, Apr. 4, 2006, 103(14):5247-5248.
Naidoo, Nirinjini et al., "Sleep deprivation induces the unfolded protein response in mouse cerebral cortex", Journal of Neurochemistry 92:1150-1157, 2005.
Papa, Feroz R. et al., "Bypassing a Kinase Activity with an ATP-Competitive Drug", Science 302:1533-1537, 2003.
Piontek et aL, "A Functional Flexed Allele of Pfd that Can Be Conditionally inactivated In Vivo", J Arn Soo Nephrof 2004. 15:3035-3043.
Shamu, Caroline E. et al., "Oligomerization and phosphorylation of the Ire1p kinase during intracellular signaling from the endoplasmic reticulum to the nucleus", The EMBO Journal 15(12):3028-3039, 1996.
Sheridan, R.P., "The Most Common Chemical Replacements in Drug-Like Compounds". J. Chem. Inf. Comput. Sci. 2002, 42:103-108.
Shiilingford, J.M. et al. (Apr. 4, 2006, e-published Mar. 27, 2006). "The mTOR pathway is regulated by polycystin-1, and its inhibition reverses renal cystogenesis in polycystic kidney disease," 103(14):5466-5471.
Tseng, Ping-Hui et al., "Synergistic interactions between imatinib mesylate and the novel phosphoinositide-dependent kinase-1 inhibitor OSU-03012 in overcoming imatinib mesylate resistance", Blood 105:4021-4027, 2005.
Wahl, P.R. et al. (Mar. 2006, e-published Oct. 12, 2005). "Inhibition of mTOR with sirolimus slows disease progression in Han:SPRD rats with autosomal dominant polycystic kidney disease (ADPKD)," Nephrol Dial Transplant 21(3):598-604.
Walker et al., "Structural Determinants of Phosphoinositide 3-Kinase Inhibition by Wortmannin, LY294002, Quercetin, Myricetin, and Staurosporine", Molecular Cell 2000, 6(4):909-919.
Wüthrich, R.P. et al. (Jun. 2014, e-published Mar. 28, 2014). "Pharmacological management of polycystic kidney disease," Expert Opin Pharmacother 15(8):1085-1095.
West et al., "Activation of the PI3K/Akt pathway and chemotherapeutic resistance," Drug Resistance Updates, 5, 2002, 234-248.
Wymann, et al., "Wortmannin Inactivates Phosphoinositide 3-Kinase by Covalent Modification of Lys-802, a Residue Involved in the Phosphate Transfer Reaction", Molecular and Cellular Biology 1996, 16(4):1722-1733.
Yaguchi, et al., "A novel phosphatidylinositol 3-kinase inhibitor, ZSTK474 exterted antitumor activity against human tumor xenografts by oral administration", Proc. Amer. Assoc. Cancer Res. 2005, 46:1691 (Abstract).
Yoshida, Hiderou et al., "XBP1 mRNA Is Induced by ATF6 and Spliced by IRE1 in Response to ER Stress to Produce a Highly Active Transcription Factor", Cell 107:881-891, 2001.
Yu et al., "Essential rove of deavage of Polycysth-:-1 at G protein-coupled receptor protedytic site for kidney tubular structure", Proc. Natl. Acad. Sci. U. S. A. 2007, 104(47):18688-18693.
Zhang, Xuewu et al., "An Allosteric Mechanism for Activation of the Kinase Domain of Epidermal Growth Factor Receptor", *Cell* 125:1137-1149, 2006.
Zheng, Yi et al., "Hepatitis C Virus Non-structural Protein NS4B Can Modulate an Unfolded Protein Response", The Journal of Microbiology 43(6):529-536, 2005.
Balram Dhawan et al., "4-Aminopyrazolo[3,4-d]pyrimidines" Organic Preparations and Procedures Intl 13(5):379-382, 1981.
Zachary A. Knight et al., "A Pharmacological Man of the PI3-K Family Defines a Role of p110 (alpha) in Insulin Signaling" Cell 125:733-747, May 2006.
Philip L. Southwick et al., "Preparation of 4,6-Diaminopyrazolo[3-4d]pyrimidines with Variations in Substitution at the 1- and 3-Positions" J. Heterocyclic Chem. 12(6):1199-1205, Dec. 1975.
Knox et al., Thorax, 2005, BMJ Publishing Group 60:88-89.
Vippagunta et al., Advanced Drug Delivery Reviews, 2001 Elsevier 48:3-26.
Johnson, J.I. et al. (May 18, 2001). "Relationships between drug activity in NCI preclinical in vitro and in vivo models and early clinical trials," Br J Cancer 84(10):1424-1431.
Sausville, E.A. et al. (Apr. 1, 2006). "Contributions of human tumor xenografts to anticancer drug development," Cancer Res 66(7):3351-33514.
STN RN 180903-16-6, entered STN Sep. 18, 1996.
Wu, T.Y. H. et al. (Oct. 2, 2003). "One-pot two-step microwave-assisted reaction in constructing 4,5-disubstituted pyrazolopyrimidines," Org Lett. 5(20):3587-3590.

\* cited by examiner

| | TORKinib (PP242) | TORKinib2 (PP30) |
|---|---|---|
| mTOR | 0.008 | 0.080 |
| p110α | 1.96 | 3 |
| p110b | 2.2 | 5.8 |
| p110γ | 0.102 | 0.68 |
| p110δ | 1.27 | 0.99 |
| PI4Kβ | 22 | 5.7 |
| DNA-PK | 0.408 | 0.339 |
| PKCα | 0.049 | 10 |
| PKCβI | 0.198 | >10 |
| PKCβII | 0.185 | >10 |
| RET | 0.224 | ND |
| JAK2 | 0.11 | ND |

$IC_{50}$ μM

Rictor mTOR

Raptor

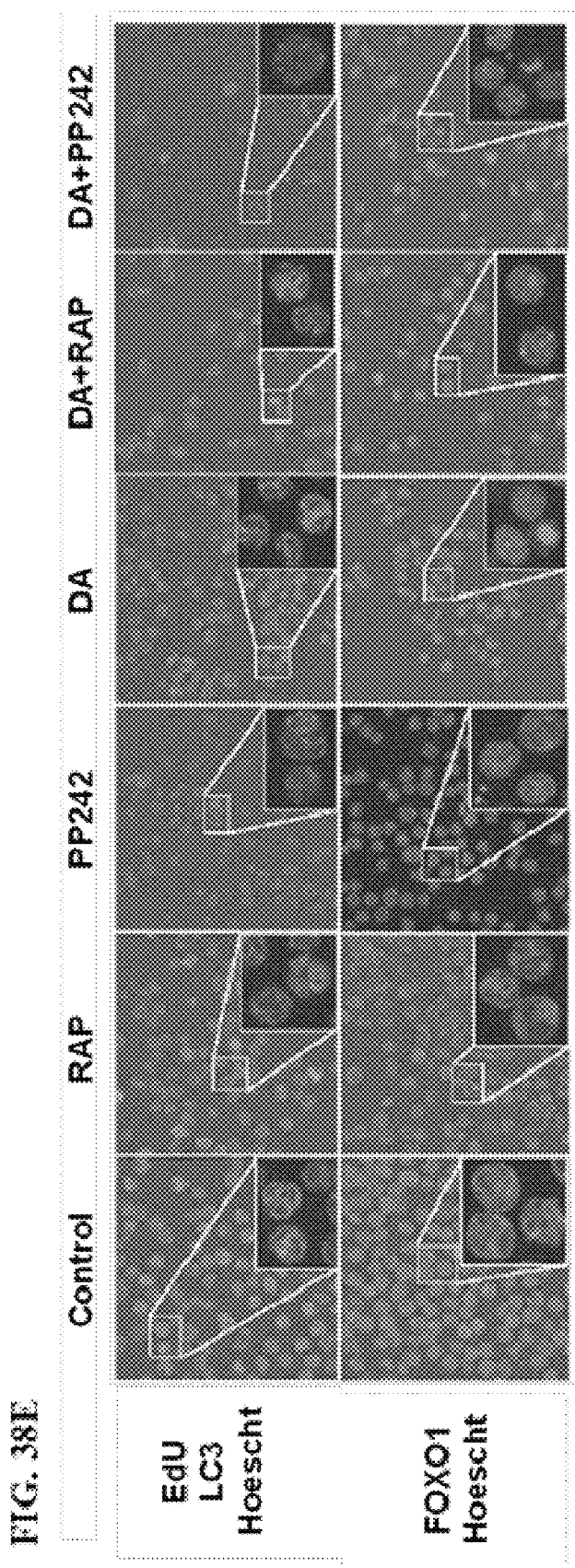

MTOR MODULATORS AND USES THEREOF

CROSS-REFERENCES TO RELATED APPLICATIONS

This application is a continuation of U.S. patent application Ser. No. 13/003,562, filed Jan. 10, 2011, which is a U.S. National Phase application under 35 U.S.C. §371 of International Application No. PCT/US2009/049969, filed Jul. 8, 2009, which in turn claims the benefit of U.S. Provisional Application No. 61/079,103, filed Jul. 8, 2008, all of which are hereby incorporated by reference in their entirety and for all purposes.

STATEMENT AS TO RIGHTS TO INVENTIONS MADE UNDER FEDERALLY SPONSORED RESEARCH OR DEVELOPMENT

This invention was made with government support under grant nos. R01-DK056695, AI044009, and DK007636, awarded by the National Institutes of Health. The Government has certain rights in the invention.

BACKGROUND OF THE INVENTION

Abnormal cellular proliferation, a hallmark of cancer, can result from a wide range of cellular phenomena. Proliferative signals are transmitted into and within a cell via a process known as signal transduction. Over the past decades, cascades of signal transduction pathways have been elucidated and found to play a central role in a variety of biological responses. Defects in various components of signal transduction pathways have been found to account for a vast number of diseases, including numerous forms of cancer, inflammatory disorders, metabolic disorders, vascular and neuronal diseases (Gaestel et al. *Current Medicinal Chemistry* (2007) 14:2214-2234).

Kinases constitute a large family of important signaling molecules. Kinases can generally be classified into protein kinases and lipid kinases, and certain kinases exhibit dual specificities. Protein kinases are enzymes that phosphorylate other proteins and/or themselves (i.e., autophosphorylation). Protein kinases can be generally classified into three major groups based upon their substrate utilization: tyrosine kinases which predominantly phosphorylate substrates on tyrosine residues (e.g., erb2, PDGF receptor, EGF receptor, VEGF receptor, src, abl), serine/threonine kinases which predominantly phosphorylate substrates on serine and/or threonine residues (e.g., mTorC1, mTorC2, ATM, ATR, DNA-PK), and dual-specificity kinases which phosphorylate substrates on tyrosine, serine and/or threonine residues.

The mammalian target of rapamycin (mTor) is a serine-threonine kinase related to the lipid kinases of the phosphatidylinositol 3 kinase (PI3K) family. mTor has been implicated in a wide range of biological processes including cell growth/proliferation, cell motility and survival. Dysregulation of the mTor pathway has been reported in various types of cancer. mTor is a multifunctional kinase that integrates growth factor and nutrient signals to regulate protein translation, nutrient uptake, autophagy and mitochondrial function.

mTor exists in two complexes, mTorC1 and mTorC2. mTorC1 contains the raptor subunit and mTorC2 contains rictor. These complexes are differentially regulated, and have distinct substrate specificities and rapamycin sensitivity. For example, mTorC1 phosphorylates S6 kinase (S6K) and 4EBP1 (eIF4E-binding protein 1, also known as also known as EIF4EBP1), promoting increased translation and ribosome biogenesis to facilitate cell growth and cell cycle progression. S6K also acts in a feedback pathway to attenuate PI3K/Akt activation. mTorC2 is generally insensitive to rapamycin. mTorC2 is thought to modulate growth factor signaling by phosphorylating the C-terminal hydrophobic motif of some AGC kinases such as Akt. In many cellular contexts, mTorC2 is required for phosphorylation of the S473 site of Akt.

The serine/threonine kinase Akt (also known as protein kinase B) possesses a pleckstrin homology (PH) domain that binds PIP3, leading to Akt kinase activation. Akt phosphorylates many substrates and is a central downstream effector of PI3K for diverse cellular responses (FIG. 1). Full activation of Akt typically requires phosphorylation of T308 in the activation loop and S473 in a hydrophobic motif. One important function of Akt is to augment the activity of mTor, through phosphorylation of TSC2 and other mechanisms.

Phosphoinositide 3-kinases (PI3Ks) are a family of lipid kinase enzymes whose products mediate reversible membrane localization of cytoplasmic proteins. PI3K activation in most cells correlates with proliferation and suppression of apoptosis. PI3K and its downstream effectors also control cell polarity, motility, metabolism and other physiological processes. This signaling pathway also plays a prominent role in cancer: the PI3K pathway activity is enhanced in nearly all human tumors. This can occur by gain-of-function mutations or amplifications of PI3K genes, loss of the tumor suppressor PTEN (the major lipid phosphatase that opposes PI3K signaling), or expression of oncogenes that activate PI3K (FIG. 1). In mouse models, enhanced PI3K signaling in lymphocytes leads to lymphoproliferation, susceptibility to leukemia, and spontaneous autoimmunity. Conversely, deletion of PI3K genes causes immunodeficiency and resistance to malignant transformation. Pharmacological suppression of immune responses and cancer cell proliferation can also be achieved using rapamycin, which inhibits mTor (mammalian target of rapamycin) downstream of PI3K (FIG. 1).

The PI3K/Akt/mTor signaling axis has been extensively studied with small molecule inhibitors. Wortmannin and LY294002 are two broad-spectrum PI3K inhibitors that have potent anti-proliferative effects; however, these agents have broad inhibition activity towards most PI3K isozymes as well as other cellular targets. A key example of these off-target effects is the direct inhibition of mTor by LY294002 (and wortmannin at high concentrations).

Conventional mTor selective inhibitors also suffer from several profound drawbacks. For example, the mTor inhibitors, namely rapamycin and analogs, also termed "rapalogs" are potent immunosuppressants. They have also been used in clinical trials for various types of cancer. Unfortunately, the results of these clinical trials to date have been mixed, with few malignancies showing consistent response to rapalogs. Rapamycin (RAP) has a mechanistic limitation: it is an allosteric, noncompetitive inhibitor of mTorC1 that does not acutely inhibit mTorC2 in most cells. Hence, cells treated with RAP usually display increased Akt phosphorylation on both T308 and S473, due to loss of the feedback inhibitory circuit mediated by S6K (FIG. 1). This can lead to chemoresistance of cancer cells treated with rapalogs. Although RAP does inhibit mTorC2 in some cell types by disrupting assembly of the complex, the phenomenon of rapamycin-induced stimulation of Akt has been observed in many settings. It is also worth noting that mTorC2 might have additional functions in tumor cells, other than Akt-S473 phosphorylation, which remain unaffected by RAP.

BRIEF SUMMARY OF THE INVENTION

Given these concerns as well as the emerging evidence for PI3K-independent mTorC1 activity, there exists a considerable need for alternative methods and biological agents that can selectively inhibit mTorC1 and/or mTorC2. In some embodiments, the methods and compositions disclosed herein yield selective inhibition of mTor-mediated signal transduction without affecting upstream PI3K. In some other embodiments, the methods and compositions provided herein can inhibit mTor-mediated activity more effectively than rapamycin, hence providing an alternative treatment for rapamycin-resistant conditions.

In one embodiment, the present invention provides a method for inhibiting cell proliferation comprising contacting a cell with a biologically active agent that selectively inhibits mTorC1 and/or mTorC2 activity relative to one or more type I phosphatidylinositol 3-kinases (PI3-kinase), wherein the one or more type I PI3-kinase is selected from the group consisting of PI3-kinase α, PI3-kinase β, PI3-kinase γ, and PI3-kinase δ. In some embodiment, the selective inhibition is ascertained by an in vitro kinase assay. In some aspect, the in vitro kinase assay is a cell-based assay.

In separate embodiment, the present invention provides a method of inhibiting phosphorylation of both Akt (S473) and Akt (T308) in a cell, comprising contacting a cell with an effective amount of biologically active agent that selectively inhibits both mTorC1 and mTorC2 activity relative to one or more type I phosphatidylinositol 3-kinases (PI3-kinase), thereby Akt phosphorylation at residues S473 and T308 is simultaneously inhibited. In some embodiments, the selective inhibition is ascertained by an in vitro kinase including but not limited to a cell-based assay The subject inhibition methods can take place in vitro or in vitro. The inhibition methods can cause apoptosis or cell cycle arrest.

In one aspect, the biologically active agent used in the subject methods selectively inhibits both mTorC1 and mTORC2 activity relative to all type I phosphatidylinositol 3-kinases (PI3-kinase). In another aspect, the biologically active agent inhibits mTor activity with an $IC_{50}$ value of about 100 nM or less, preferably about 50 nM, about 25 nM, about 10 nM, 5 nM, about 1 nM, 100 pM, 50 pM, 25 pM, 10 pM, 1 pM, or less, as ascertained in an in vitro kinase or a cell based assay. In another aspect, the biologically active agent inhibits mTor activity with an $IC_{50}$ value of about 10 nM or less as ascertained in an in vitro cell proliferation assay. Preferably, the biologically active agent is substantially ineffective in inhibiting a type I PI3-kinase at a concentration of 100 nM, 150 nM, 250 nM, 500 nM, 1 uM, 5 uM, 10 uM, 100 uM or even higher, when assayed in an in vitro kinase or a cell-based assay. In yet another aspect, the biologically active agent is substantially ineffective in inhibiting one or more enzymes of the group consisting of PI4Kβ, DNA-PK, and JAK2 at a concentration of 100 nM, 150 nM, 250 nM, 500 nM, 1 uM, 5 uM, 10 uM, 100 uM or even higher, when assayed in an in vitro kinase assay including but not limited to a cell-based assay. In still yet another aspect, the biologically active agent inhibits phosphorylation of Akt (S473) and Akt (T308) more effectively than rapamycin when tested at a comparable molar concentration in vitro kinase assay including but not limited to a cell-based assay. Where desired, a biologically active agent that inhibits phosphorylation of Akt (S473) and Akt (T308) with an ED50 value of 1 uM or less can be employed in practicing the subject methods. In some aspects, the biological active agent competes with ATP for binding to the ATP-binding site on mTorC1 and/or mTorC2

The subject inhibitory methods apply to any cell types, preferably eukaryotic cells such as mammalian cells (e.g., human cells) and especially those that exhibit neoplastic phenotype or propensity.

The present invention further provides a method of inhibiting proliferation of a neoplastic cell. The method comprises the step of contacting the cell with an effective amount of an antagonist that inhibits full activation of Akt in a cell and an anti-cancer agent, wherein said inhibition of cell proliferation is enhanced through a synergistic effect of said antagonist and said anti-cancer agent.

Also provided is a method of ameliorating a medical condition mediated by mTorC1 and/or mTorC2. The method involves the step of administering to a subject in need thereof a therapeutically effective amount of a compound that selectively inhibits mTorC1 and/or mTorC2 activity relative to one or more type I phosphatidylinositol 3-kinases (PI3-kinase) as ascertained in an in vitro kinase including but not limited to a cell-based assay, wherein the one or more type I PI3-kinase is selected from the group consisting of PI3-kinase α, PI3-kinase β, PI3-kinase γ, and PI3-kinase δ. In some embodiments, the selective inhibition of mTorC1 and/or mTorC2 activity relative to one or more type I PI3-kinases is ascertained by an in vitro kinase assay including but not limited to a cell-based assay.

Further provided is another combination treatment for a subject diagnosed with or at risk of a neoplastic condition. The method involves the step of administering to said subject a therapeutically effective amount of an antagonist that inhibits full activation of Akt in a cell and an anti-cancer agent, wherein the efficacy of said treatment is enhanced through a synergistic effect of said antagonist and said anti-cancer agent.

In one aspect, the antagonist used in the subject treatment methods selectively inhibits both mTorC1 and mTORC2 activity relative to all type I phosphatidylinositol 3-kinases (PI3-kinase) consisting of PI3-kinase α, PI3-kinase β, PI3-kinase γ, and PI3-kinase δ. The anti-cancer agent is selected from the group consisting of rapamycin, Gleevac, or derivative thereof that inhibits a mammalian target of rapamycin or Gleevac. The antagonist and/or the anti-cancer agent is administered parenterally, orally, intraperitoneally, intravenously, intraarterially, transdermally, intramuscularly, liposomally, via local delivery by catheter or stent, subcutaneously, intraadiposally, or intrathecally. A variety of conditions can be treated by the subject methods. They include but are not limited to neoplastic condition such as restenosis, various types of cancer.

The present invention further provides a method of developing a biologically active agent that inhibits cell proliferation. The method comprises: (a) contacting a candidate agent with a cell of interest; (b) detecting a selective inhibition of mTorC1 and/or mTorC2 activity relative to one or more type I phosphatidylinositol 3-kinases (PI3-kinase), wherein the one or more type I PI3-kinase is selected from the group consisting of PI3-kinase α, PI3-kinase β, PI3-kinase γ, and PI3-kinase δ, wherein said selective inhibition is ascertained by an in vitro kinase or a cell-based assay.

In another aspect, there is provided a method of treating a condition caused by aberrant ion transport across epithelial cells in a patient in need thereof. The method includes administering to the patient a therapeutically effective amount of a biologically active agent that selectively inhibits mTorC1 and/or mTorC2 activity relative to one or more type I phosphatidylinositol 3-kinases (PI3-kinase) ascertained by an in vitro kinase assay. The one or more type I PI3-kinase is selected from the group consisting of PI3-kinase α, PI3-kinase β, PI3-kinase γ, and PI3-kinase δ.

In another aspect, there is provided a method of treating T cell lymphoma in a patient in need thereof. The method includes administering to the patient a therapeutically effective amount of a biologically active agent that selectively inhibits mTorC1 and/or mTorC2 activity relative to one or more type I phosphatidylinositol 3-kinases (PI3-kinase) ascertained by an in vitro kinase assay, wherein the one or more type I PI3-kinase is selected from the group consisting of PI3-kinase α, PI3-kinase β, PI3-kinase γ, and PI3-kinase δ.

In another aspect, there is provided a method of inhibiting phosphorylation of 4EBP1 in a cell. The method includes contacting a cell with an effective amount of biologically active agent that selectively inhibits both mTorC1 and mTorC2 activity relative to one or more type I phosphatidylinositol 3-kinases (PI3-kinase) as ascertained by a cell-based assay or an in vitro kinase assay, wherein the one or more type I PI3-kinase is selected from the group consisting of PI3-kinase α, PI3-kinase β, PI3-kinase γ, and PI3-kinase δ, thereby Akt phosphorylation at residues S473 and T308 is simultaneously inhibited.

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 15A shows mean $IC_{50}$ values and the 95% confidence interval. FIG. 15B shows the results of a representative experiment.

FIG. 26A: $2 \times 10^6$ Akt transgenic thymocytes were injected subcutaneously and allowed to form tumors for 20 days. 45 tumor bearing mice were randomized into three groups of 15: vehicle, rapamycin 5 mg/kg and PP242 100 mg/kg. Treatments were given by gavage once daily, seven days a week for 20 days. FIG. 26B: Representative mice from each cohort after 20 days of therapy. Dotted lines about the midsection indicate primary tumor; dotted distal lines indicate multiple sites of lymph node metastasis; arrows (inset) indicate areas of significant cervical lymphadenopathy. FIG. 26C: Tumors areas: square=vehicle, triangle tip up=rapamycin, triangle tip down=PP242. FIG. 26D: Mouse weights in grams during the course of treatment; legend as in FIG. 26C.

FIG. 27A: Percent live cells by PI/Annexin exclusion (n=10 mice/cohort), * p<0.01, ** p<0.05, ANOVA with Bonferroni's post test. FIG. 27B: Percent annexin+ cells (n=10 mice/cohort), * p=0.002, ** p=0.03, non-paired t-test. FIG. 27C: In vivo analysis of tumor proliferation by BrDU incorporation (n=5 mice/cohort), * p<0.01, ** p<0.05, ANOVA with Bonferroni's post test. FIG. 27D: Cell cycle analysis of post-treatment tumor samples (n=10 mice/cohort). FIG. 27E: Pharmacodynamic analysis of mTOR targets through western blot analysis. Each lane represents 1 post-treatment tumor 20 days after initiation of therapy. β-actin=loading control. FIG. 27F: G1 inhibition induced by rapamycin versus PP242 in wild type (WT) and 4EBP1/2 double knockout (DKO) mouse embryonic fibroblasts.

FIG. 28A: Immunoblots of mpkCCD cell lysates detected by holo-SGK1, anti-phosphohydrophobic motif (pHM), anti-Akt p-S473 and anti-phospho-p70S6K antibodies. Cells were grown on TRANSWELL™ filters and treated with aldosterone and insulin for 4 h, followed by treatment with inhibitors as shown for 1 h. α-tubulin is shown as loading control. FIG. 28B: For phosphatase treatment, cells were grown on TRANSWELL™ filters and treated with aldosterone and insulin as above. Whole cell lysates were treated with λ-phosphatase (lambda-PPase) prior to Western blotting analysis with antibodies. FIG. 28C: Immunodetection of HM phosphorylated SGK1. HEK293 cells were transfected with a flag-tagged SGK1 or vector control, incubated with insulin and treated with inhibitors.

FIG. 29A: Inhibition of ENaC-dependent Na+ current by PP242. mpkCCD cells were grown on TRANSWELL™ filters, incubated with aldosterone and insulin for 4 h, and treated with PP242 at various concentrations for 1 h. FIG. 29B: A time course showing the effects of PP242 on ENaC-dependent Na+ current in mpkCCD cells. The cells were grown on TRANSWELL™ filters, incubated with aldosterone (Aldo) and insulin, and treated with inhibitors at various concentrations. Legend: LY, LY294002; Rap, rapamycin.

FIG. 30A: A flag-tagged SGK1 plasmid was transfected into HEK 293 cells. 24 hrs. after transfection, recombinant lentiviruses harboring the rictor shRNA or an irrelevant shRNA were used to infect the transfected cells. After another 24 hrs., cells were lysed and analyzed by Western blotting using antibodies against rictor to assay for expression knockdown. FIG. 30B: Quantitative analysis of knockdown of rictor expression. FIG. 30C: The cell lysates were incubated with an anti-flag antibody cross-linked to beads. After washing, SGK1 protein bound to the beads was recovered and analyzed by immunoblotting using antibodies against phosphorylated SGK1. FIG. 3D: Quantitative analysis of inhibition of SGK1 phosphorylation by rictor shRNA. Legend: LY, LY294002.

FIG. 31A: Recombinant lentiviruses harboring the rictor shRNA or an irrelevant shRNA were used to infect mpkCCD cells. The infected cells were plated on collagen-coated TRANSWELL™ polycarbonate membranes. ENaC-dependent Na+ currents were measured and quantified. FIG. 31B: The infected cells were lysed on the TRANSWELL™ membranes. Cell lysates were recovered and analyzed by Western blotting using antibodies against rictor to assay for expression knockdown. FIG. 31C: Quantitative analysis of knockdown of rictor expression in mpkCCD cells.

FIG. 32A: The flag-tagged SGK1 plasmid was transfected into HEK 293 cells. 24 hrs. after transfection, recombinant lentiviruses harboring the raptor shRNA or an irrelevant shRNA were used to infect the transfected cells. After another 24 hrs., cells were lysed and analyzed by Western blotting using antibodies against raptor to assay for expression knockdown. FIG. 32B: Quantitative analysis of knockdown of raptor expression. FIG. 32C: The cell lysates were incubated with an anti-flag antibody cross-linked to beads. After washing, SGK1 protein bound to the beads was recovered and analyzed by immunoblotting using antibodies against phosphorylated SGK1. FIG. 32D: Quantitative analysis of SGK1 phosphorylation in cells expressing raptor shRNA.

FIG. 33A: Recombinant lentiviruses harboring the raptor shRNA or an irrelevant shRNA were used to infect mpkCCD cells. The infected cells were plated on collagen-coated TRANSWELL™ polycarbonate membranes. ENaC-dependent Na+ currents were measured and quantified. FIG. 33B: The infected cells were lysed on the TRANSWELL™ membranes. Cell lysates were recovered and analyzed by Western blotting using antibodies against pS6K. FIG. 33C: The lysates were analyzed by Western blotting using antibodies against raptor to assay for expression knockdown. FIG. 33D: Quantitative analysis of knockdown of raptor expression in mpkCCD cells.

FIG. 34A: A flag-tagged SGK1 plasmid was transfected into HEK293 cells. 48 hrs. post-transfection, the cells were lysed and incubated with anti-flag antibody cross-linked to beads. After washing, SGK1 protein bound to the beads was recovered and analyzed by Western blotting using an antibody against rictor. FIG. 34B: The same blot of SGK1 immunoprecipitates was stripped and analyzed by Western blotting using an antibody against mTOR. Note that a residual rictor band was detected due to incomplete stripping of the blot. FIG. 34C: The same SGK1 immunoprecipitates were analyzed by Western blotting using an antibody against raptor. Note that a residual rictor band was detected due to incomplete stripping of the blot.

FIG. 37A: Mouse p190 cells (upper) and human SUP-B15 cells (lower) were cultured with inhibitors at the concentrations indicated for 48 hr. FIG. 37B: p190 cells were cultured for 24 hr with the inhibitors indicated, then DNA content was measured by flow cytometry. FIG. 37C: p190 cells were cultured for 48 hr with the indicated combinations of compounds and assessed for survival using the median effect method. FIG. 37D: CD19+CD34+ magnetically sorted cells from five different patients were assessed for colony formation potential in cultures with DAD (5 nM) alone or in combination with increasing concentrations [10 or 100 nM] of RAP, PP242, or BEZ-235 (*P<0.05, **P<0.01, #P<0.001. FIG. 37E: Schematic model of BCR-ABL driven mechanisms of oncogenic survival (left) and a new model of incomplete mTOR inhibition (middle) versus complete mTOR inhibition (right) in B-ALL.

FIGS. 38A-38E illustrate that PP242 completely inhibits mTORC2/AKT and mTORC1 signaling in B-ALL whereas rapamycin suppresses mTORC1 driving a PI3K/AKT surge. FIGS. 38A-38B: Western blots of p190 cells treated for 1.5 hr (FIG. 38A) or 3 hr (FIG. 38B) with indicated inhibitors. FIG. 38C: Activation of PI3K was quantified in cells by signal pixel intensity and localized area of PIP3 accumulation by confocal microscopy. FIG. 38D: PP242 and high concentrations of IM (5 µM) both inhibit cap-dependent translation whereas RAP does not. FIG. 38E: p190 cells expressing LC3-GFP were cultured for 8 hr in chamber wells with DA (10 nM), PP242 (250 nM), BEZ-235 (250 nM), RAP (250 nM), and pulsed with EdU 1 hr prior to fixation. Autophagy (LC3 puncta accumulation), loss of proliferation (EdU accumulation), and distinct localization patterns of Foxo1 were assessed by confocal microscopy and representative cells were magnified for clarity.

FIG. 39A: Mice injected with p190 cells (i.v.), were treated daily (q24) starting on D7 post-transplant. Imatinib ("IM," 150 mg kg$^{-1}$, i.p.), rapamycin ("RAP," 7 mg kg$^{-1}$, i.p.) and PP242 (30 and 60 mg kg$^{-1}$, p.o.) were administered to mice as the mice were followed daily for overall survival (median±interquartile range) in groups of 5 mice. FIG. 39B: Schematic of treatment design. FIG. 39C: Leukemic burden (mean %±s.d.) was assessed by flow cytometry in the corresponding bone marrow and peripheral blood of treated mice. FIG. 39D: The abundance of leukemic cells actively cycling (EdU+) following treatment was measured by flow cytometry (mean %±s.d.). FIG. 39E: Pharmacodynamic activity of PP242 using intracellular phospho-staining of bone marrow and peripheral blood cells. FIG. 39F: Schematic of treatment design for primary human Ph+B-ALL whole bone marrow xenografts. FIG. 39G: Leukemic burden and cells actively cycling (mean %±s.d.) was assessed by flow cytometry in the corresponding bone marrow of treated mice.

FIG. 40A: Western blot analysis of SUP-B15 cells treated with the PI3K/mTOR inhibitor BEZ-235 [600 nM], RAP [20 nM], in comparison to a low dose titration of PP242 [5, 15, 45, 135, 405 nM] for 3 hours. FIG. 40B: Western blot of SUP-B15 cells treated with PI3K/mTOR inhibitor PI-103 [2000 nM] and the ABL/Src kinase inhibitor dasatinib [DA; 10, 100 nM] alone, or in combination [DA at 100 nM] with RAP [RAP 50, 400 nM], PP242 [50, 400 nM], or BEZ-235 [50, 400 nM] as indicated.

DETAILED DESCRIPTION OF THE INVENTION

I. Definitions

Compounds Designations

Figure 1:
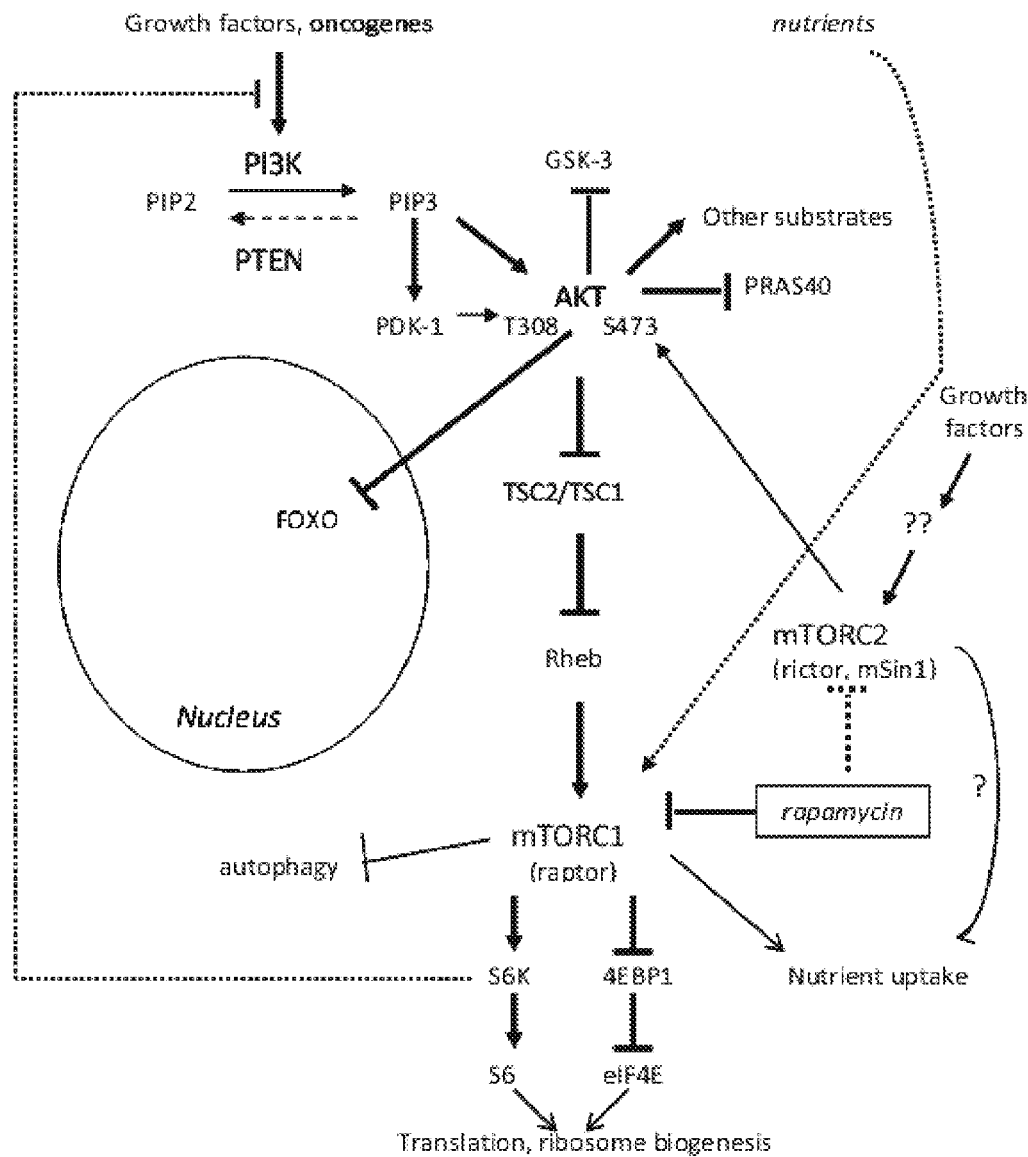
FIG. 1 is a schematic overview of the PI3K/Akt/mTor signaling pathway. Oncongenes are underlined.

The terms "PP242" and "TORKinib" refer to the same pyrazolopyrimidine compound and are interchangeable.

The terms "TORKinib2" and "PP30" refer to the same compound, and are interchangeable.

The terms "IC87114" (ICOS corporation) and IC refer to the same compound and are interchangeable.

The terms "DAS" and dasatinib, refer to the same compound and are interchangeable.

The terms "IM" and "imatinib", refer to the same compound and are interchangeable.

The terms and "RAP" and "rapamycin", refer to the same compound and are interchangeable.

The term "B-ALL" as used herein refers to B-cell Acute Lymphoblastic Leukemia.

The term "AML" as used herein refers to Acute Myelogenous Leukemia.

The term "IP" or "i.p." as used herein refers to intraperitoneal administration.

The term "p.o." as used herein refers to oral administration or oral lavage.

As used herein, "agent" or "biologically active agent" refers to a biological, pharmaceutical, or chemical compound or other moiety. Non-limiting examples include simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present invention.

The term "antagonist" or "inhibitor" as used herein refers to a molecule having the ability to inhibit a biological function of a target polypeptide. Accordingly, the term "antagonist" is defined in the context of the biological role of the target polypeptide. While preferred antagonists herein specifically interact with (e.g. bind to) the target, molecules that inhibit a biological activity of the target polypeptide by interacting with other members of the signal transduction pathway of which the target polypeptide is a member are also specifically included within this definition. A preferred biological activity inhibited by an antagonist is associated with the development, growth, or spread of a tumor. Antagonists, as defined herein, without limitation, include antibodies and immunoglobulin variants, peptides, peptidomimetics, non-peptide small molecules, antisense molecules, and oligonucleotide decoys.

The term "agonist" as used herein refers to a molecule having the ability to initiate or enhance a biological function of a target polypeptide. Accordingly, the term "agonist" is defined in the context of the biological role of the target polypeptide. While preferred agonists herein specifically interact with (e.g. bind to) the target, molecules that inhibit a biological activity of the target polypeptide by interacting with other members of the signal transduction pathway of which the target polypeptide is a member are also specifically included within this definition. A preferred biological activity inhibited by an agonist is associated with the prevention or inhibition of the development, growth, or spread of a tumor or other diseased or damaged cell or tissue. For example, agonist ligand binding can stimulate the expression of a biological response modifier such as a phosphatase that inhibits cell growth or accumulation of a factor useful for the development of a tumor, such as by way of example and without limitation, phosphorylated 4EBP1. Agonists, as defined herein, without limitation, include antibodies and immunoglobulin variants, peptides, peptidomimetics, non-peptide small molecules, antisense molecules, and oligonucleotide decoys.

The term "effective amount" or "therapeutically effective amount" refers to that amount of an antagonist or biological agent that is sufficient to effect the intended applications, including with out limitation, clinical results as shrinking the size of the tumor (in the cancer context, for example, B-ALL), retardation of cancerous cell growth, delaying the development of metastasis, inducing apoptosis or cell cycle arrest of cancer cells, decreasing symptoms resulting from the disease, increasing the quality of life of those suffering from the disease, decreasing the dose of other medications required to treat the disease, enhancing the effect of another medication, delaying the progression of the disease, and/or prolonging survival of individuals. The therapeutically effective amount will vary depending upon the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose will vary depending on the particular antagonist chosen, the dosing regimen to be followed, whether is administered in combination with other compounds, timing of administration, the tissue to be imaged, and the physical delivery system in which it is carried.

As used herein, "treatment" or "treating," or "palliating" or "ameliorating" are used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. For purposes of this invention, beneficial or desired clinical results include, but are not limited to, one or more of the following: reducing the proliferation of (or destroying) cancerous cells or other diseased, reducing metastasis of cancerous cells found in cancers, shrinking the size of the tumor, decreasing symptoms resulting from the disease, increasing the quality of life of those suffering from the disease, palliating the pain resulting from the disease, decreasing the dose of other medications required to treat the disease, delaying the progression of the disease, and/or prolonging survival of individuals. Treatment includes preventing the disease, that is, causing the clinical symptoms of the disease not to develop by administration of a protective composition prior to the induction of the disease; suppressing the disease, that is, causing the clinical symptoms of the disease not to develop by administration of a protective composition after the inductive event but prior to the clinical appearance or reappearance of the disease; inhibiting the disease, that is, arresting the development of clinical symptoms by administration of a protective composition after their initial appearance; preventing re-occurring of the disease and/or relieving the disease, that is, causing the regression of clinical symptoms by administration of a protective composition after their initial appearance.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

"Radiation therapy" means exposing a patient, using routine methods and compositions known to the practitioner, to radiation emitters such as alpha-particle emitting radionuclides (e.g., actinium and thorium radionuclides), low linear energy transfer (LET) radiation emitters (i.e. beta emitters), conversion electron emitters (e.g. strontium-89 and samarium-153-EDTMP, or high-energy radiation, including without limitation x-rays, gamma rays, and neutrons.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

A "subject," "individual" or "patient" is used interchangeably herein, which refers to a vertebrate, preferably a mammal, more preferably a human. Mammals include, but are not limited to, murines, simians, humans, farm animals, sport animals, and pets. Tissues, cells and their progeny of a biological entity obtained in vitro or cultured in vitro are also encompassed.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

The term "cell proliferation" refers to a phenomenon by which the cell number has changed as a result of division. This term also encompasses cell growth by which the cell morphology has changed (e.g., increased in size) consistent with a proliferative signal.

The term "selective inhibition" or "selectively inhibit" as referred to a biologically active agent refers to the agent's ability to preferentially reduce the target signaling activity as compared to off-target signaling activity, via direct or interact interaction with the target.

"mTorC1 and/or mTorC2 activity" as applied to a biologically active agent refers to the agent's ability to modulate signal transduction mediated by mTorC1 and/or mTorC2. For example, modulation of mTorC1 and/or mTorC2 activity is evidenced by alteration in signaling output from the PI3K/Akt/mTor pathway.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with," and their grammatical equivalents, as used herein, encompasses administration of two or more agents to an animal so that both agents and/or their metabolites are present in the animal at the same time. Co-administration includes simultaneous administration in separate compositions, administration at different times in separate compositions, or administration in a composition in which both agents are present.

The term "in vivo" refers to an event that takes place in a subject's body.

The term "in vitro" refers to an event that takes places outside of a subject's body. For example, an in vitro assay encompasses any assay run outside of a subject assay. In vitro assays encompass cell-based assays in which cells alive or dead are employed. In vitro assays also encompass a cell-free assay in which no intact cells are employed.

Unless indicated differently, the abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched chain, or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or combinations thereof, consisting of at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—CH$_3$, —O—CH$_2$—CH$_3$, and —CN. Up to two heteroatoms may be consecutive, such as, for example, —CH$_2$—NH—OCH$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo," as used herein, means an oxygen that is double bonded to a carbon atom.

The term "alkylsulfonyl," as used herein, means a moiety having the formula —S(O$_2$)—R', where R' is an alkyl group as defined above. R' may have a specified number of carbons (e.g., "C$_1$-C$_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN, and —NO$_2$ in a number ranging from zero to (2m'+1), where m' is the total number of carbon atoms in such radical. R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R''', and R'''' groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR)$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described herein for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_4$-C$_8$ cycloalkyl, and each substituted or unsubstituted heterocycloalkyl is a substituted or unsubstituted 4 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_5$-C$_7$ cycloalkyl, and each substituted or unsubstituted heterocycloalkyl is a substituted or unsubstituted 5 to 7 membered heterocycloalkyl.

Where a substituent is "R-substituted", it is to be understood that the substituent is substituted with one or more of the recited R groups and that each R group attached to the substituent is optionally different. For example, an $R^7$-substituted alkyl is substituted with one or more $R^7$ groups wherein each of the $R^7$ groups are optionally different.

I. Embodiments of the Invention

This invention pertains to the discovery of a distinct class of biologically active agents that exhibit selective inhibition of certain protein kinases, and the uses of these agents for treatment of diseases mediated by such protein kinases. In one embodiment, the present invention provides a method for inhibiting cell proliferation comprising contacting a cell with a biologically active agent that selectively inhibits mTorC1 and/or mTorC2 activity relative to one or more type I phosphatidylinositol 3-kinases (PI3-kinase), wherein the one or more type I PI3-kinase is selected from the group consisting of PI3-kinase α, PI3-kinase β, PI3-kinase γ, and PI3-kinase δ.

It is generally recognized that there are four types of PI3K: IA, IB, II and III. Type IA enzymes act downstream of tyrosine kinases to generate phosphatidylinositol-3,4,5-trisphosphate (PIP3), a crucial second messenger that promotes proliferation and transformation. Class IA enzymes typically exist as dimers of a 110 kDa catalytic subunit (p110α, p110β or p110δ) and a regulatory subunit of varying size. The single class IB PI3K enzyme, p110γ, is activated downstream of G protein-coupled receptors.

Any agents that selectively and negatively regulate mTorC1 and/or mTor2C expression or activity can be used as selective mTor inhibitors in the methods of the invention. The relative efficacies of agents as inhibitors of mTorC1 or mTorC2 can be established by determining the concentrations at which each agent inhibits the activity to a predefined extent.

In one aspect, a determination is the concentration that inhibits 50% of the activity in a cell-based assay or in an in vitro kinase assay. $IC_{50}$ determinations can be accomplished using any conventional techniques known in the art. In general, an $IC_{50}$ can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the "$IC_{50}$" value. Analogously, other inhibitory concentrations can be defined through appropriate determinations of activity. For example, in some settings it can be desirable to establish a 90% inhibitory concentration, i.e., $IC_{90}$, etc.

Alternatively, $IC_{50}$ determinations can be accomplished by measuring the phosphorylation level of substrate proteins of the target in a cell-based assay. For example, one substrate of mTOR is AKT, which may be phosphorylated at T308 or S473. Cells, for example, may be contacted with the inhibitor under study under conditions, such as 100 nM insulin, which would normally yield phosphorylation of mTOR substrates including but not limited to AKT at S473 and T308. Cells may then be prepared by various methods known to the art including fixation or lysis, and analyzed for the phosphorylation levels of mTOR substrates. Optionally, specificity or selectivity may be determined by examining the effect of the inhibitor under study on the phosphorylation of substrates of other kinases. Phosphorylation levels may be analyzed using any methods known to the art including but not limited to the use of antibodies specific for the phosphorylated forms of the substrates to be assayed via immunoblot or flow cytometry.

In another aspect, a selective mTor inhibitor alternatively can be understood to refer to an agent that exhibits a 50% inhibitory concentration ($IC_{50}$) with respect to mTorC1 and/or mTorC2, that is at least at least 10-fold, at least 20-fold, at least 50-fold, at least 100-fold, at least 1000-fold, at least 10,100-fold, or more, lower than the inhibitor's $IC_{50}$ with respect to one, two, three, or more type I PI3-kinases. In some embodiment, a selective mTor inhibitor alternatively can be understood to refer to an agent that exhibits a 50% inhibitory concentration ($IC_{50}$) with respect to mTorC1 and/or mTorC2, that is at least at least 10-fold, at least 20-fold, at least 50-fold, at least 100-fold, at least 1000-fold, at least 10,100-fold, or more, lower than the inhibitor's $IC_{50}$ with respect to all of type I PI3-kinases.

In yet another aspect, a selective mTor inhibitor, or an inhibitor that selectively inhibits mTor mediated signaling, alternatively can be understood to refer to a compound that exhibits a 50% inhibitory concentration ($IC_{50}$) with respect to mTor, that is at least at least 10-fold, at least 20-fold, at least 50-fold, at least 100-fold, at least 1000-fold, at least 10,100-fold, or lower, than the inhibitor's $IC_{50}$ with respect to one or more protein kinases selected from the group consisting of PKCβI, PKCβII, and RET, PI4Kβ, DNA-PK, and JAK2.

The subject biologically active agent may inhibit both mTorC1 and mTorC2 activity with an $IC_{50}$ value of about 100 nM or less, preferably about 50 nM, about 25 nM, about 10 nM, about 5 nM, about 1 nM, 100 pM, 50 pM, 25 pM, 10 pM, 1 pM, or less, as ascertained in a cell-based assay or an in vitro kinase assay.

Inhibition of mTorC1 and/or mTorC2 activity can be determined by a reduction in signal transduction of the PI3K/Akt/mTor pathway. A wide variety of readouts can be utilized to establish a reduction of the output of such signaling pathway. Some non-limiting exemplary readouts include (1) a decrease in phosphorylation of Akt at residues, including but not limited to S473 and T308; (2) a decrease in activation of Akt as evidenced by a reduction of phosphorylation of Akt substrates including but not limited to FoxO1/O3α T24/32, GSK3α/β S21/9, and TSC2 T1462; (3) a decrease in phosphorylation of signaling molecules downstream of mTor, including but not limited to ribosomal S6 S240/244, 70S6K T389, and 4EBP1 T37/46; (4) inhibition of proliferation of cells including but not limited to normal or neoplastic cells, mouse embryonic fibroblasts, leukemic blast cells, cancer stem cells, and cells that mediate autoimmune reactions; (5) induction of apoptosis of cells or cell cycle arrest; (6) reduction of cell chemotaxis; and (7) an increase in binding of 4EBP1 to eIF4E. The term "eIF4E" refers to a 24-kD eukaryotic translation initiation factor involved in directing ribosomes to the cap structure of mRNAs, having human gene locus 4q21-q25.

mTor exists in two types of complexes, mTorC1 containing the raptor subunit and mTorC2 containing rictor. As known in the art, "rictor" refers to a cell growth regulatory protein having human gene locus 5p13.1. These complexes are regulated differently and have a different spectrum of substrates. For instance, mTorC1 phosphorylates S6 kinase (S6K) and 4EBP1, promoting increased translation and ribosome biogenesis to facilitate cell growth and cell cycle progression. S6K also acts in a feedback pathway to attenuate PI3K/Akt activation. Thus, inhibition of mTorC1 (e.g. by a biologically active agent as discussed herein) results in activation of 4EBP1, resulting in inhibition of (e.g. a decrease in) RNA translation.

mTorC2 is generally insensitive to rapamycin and selective inhibitors. mTorC2 is thought to modulate growth factor signaling by phosphorylating the C-terminal hydrophobic motif of some AGC kinases such as Akt. In many cellular contexts, mTorC2 is required for phosphorylation of the S473 site of Akt. Thus, mTorC1 activity is partly controlled by Akt whereas Akt itself is partly controlled by mTorC2.

Growth factor stimulation of PI3K causes activation of Akt by phosphorylation at the two key sites, S473 and T308. It has been reported that full activation of Akt requires phosphorylation of both S473 and T308Active. Akt promotes cell survival and proliferation in many ways including suppressing apoptosis, promoting glucose uptake, and modifying cellular metabolism. Of the two phosphorylation sites on Akt, activation loop phosphorylation at T308, mediated by PDK1, is believed to be indispensable for kinase activity, while hydrophobic motif phosphorylation at S473 enhances Akt kinase activity.

Selective mTor inhibition may also be determined by expression levels of the mTor genes, its downstream signaling genes (for example by RT-PCR), or expression levels of the proteins (for example by immunocytochemistry, immunohistochemistry, Western blots) as compared to other PI3-Kinases or protein kinases.

Cell-based assays for establishing selective inhibition of mTorC1 and/or mTorC2 can take a variety of formats. This generally will depend on the biological activity and/or the signal transduction readout that is under investigation. For example, the ability of the agent to inhibit mTorC1 and/or mTorC2 to phosphorylate the downstream substrate(s) can be determined by various types of kinase assays known in the art. Representative assays include but are not limited to immunoblotting and immunoprecipitation with antibodies such as anti-phosphotyrosine, anti-phosphoserine or anti-phosphothreonine antibodies that recognize phosphorylated proteins. Alternatively, antibodies that specifically recognize a particular phosphorylated form of a kinase substrate (e.g. anti-phospho AKT S473 or anti-phospho AKT T308) can be used. In addition, kinase activity can be detected by high throughput chemiluminescent assays such as AlphaScreen™ (available from Perkin Elmer) and eTag™ assay (Chan-Hui, et al. (2003) *Clinical Immunology* 111: 162-174). In another aspect, single cell assays such as flow cytometry as described in the phosflow experiment can be used to measure phosphorylation of multiple downstream mTOR substrates in mixed cell populations.

One advantage of the immunoblotting and phosflow methods is that the phosphorylation of multiple kinase substrates can be measured simultaneously. This provides the advantage that efficacy and selectivity can be measured at the same time. For example, cells may be contacted with an mTOR inhibitor at various concentrations and the phosphorylation levels of substrates of both mTOR and other kinases can be measured. In one aspect, a large number of kinase substrates are assayed in what is termed a "comprehensive kinase survey." Selective mTOR inhibitors are expected to inhibit phosphorylation of mTOR substrates without inhibiting phosphorylation of the substrates of other kinases. Alternatively, selective mTOR inhibitors may inhibit phosphorylation of substrates of other kinases through anticipated or unanticipated mechanisms such as feedback loops or redundancy.

Effect of inhibition of mTorC1 and/or mTorC2 can be established by cell colony formation assay or other forms of cell proliferation assay. A wide range of cell proliferation assays are available in the art, and many of which are available as kits. Non-limiting examples of cell proliferation assays include testing for tritiated thymidine uptake assays, BrdU (5'-bromo-2'-deoxyuridine) uptake (kit marketed by Calibochem), MTS uptake (kit marketed by Promega), MTT uptake (kit marketed by Cayman Chemical), CyQUANT® dye uptake (marketed by INVITROGEN™).

Apoptosis and cell cycle arrest analysis can be performed with any methods exemplified herein as well other methods known in the art. Many different methods have been devised to detect apoptosis. Exemplary assays include but are not limited to the TUNEL (TdT-mediated dUTP Nick-End Labeling) analysis, ISEL (in situ end labeling), and DNA laddering analysis for the detection of fragmentation of DNA in populations of cells or in individual cells, Annexin-V analysis that measures alterations in plasma membranes, detection of apoptosis related proteins such p53 and Fas.

A cell-based assay typically proceeds with exposing the target cells (e.g., in a culture medium) to a candidate mTorC1 and/or mTorC2 selective inhibitor, and then assaying for readout under investigation. Depending on the nature of the candidate mTor inhibitors, they can directly be added to the cells or in conjunction with carriers. For instance, when the agent is nucleic acid, it can be added to the cell culture by methods well known in the art, which include without limitation calcium phosphate precipitation, microinjection or electroporation. Alternatively, the nucleic acid can be incorporated into an expression or insertion vector for incorporation into the cells. Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression. Examples of vectors are viruses, such as baculovirus and retrovirus, bacteriophage, adenovirus, adeno-associated virus, cosmid, plasmid, fungal vectors and other recombination vehicles typically used in the art which have been described for expression in a variety of eukaryotic and prokaryotic hosts, and may be used for gene therapy as well as for simple protein expression. Among these are several non-viral vectors, including DNA/liposome complexes, and targeted viral protein DNA complexes. To enhance delivery to a cell, the nucleic acid or proteins of this invention can be conjugated to antibodies or binding fragments thereof which bind cell surface antigens. Liposomes that also comprise a targeting antibody or fragment thereof can be used in the methods of this invention. Other biologically acceptable carriers can be utilized, including those described in, for example, REMINGTON'S PHARMACEUTICAL SCIENCES, 19th Ed. (2000), in conjunction with the subject compounds.

The subject agents can also be utilized to inhibit phosphorylation of both Akt (S473) and Akt (T308) in a cell. Accordingly, the present invention provides a method comprises the step of contacting a cell with an effective amount of such biologically active agent such that Akt phosphorylation at residues S473 and T308 is simultaneously inhibited. In one aspect, the biologically active agent inhibits phosphorylation of S473 of Akt more effectively than phosphorylation of T308 of Akt when tested at a comparable molar concentration, preferably at an identical molar concentration.

Inhibition of Akt phosphorylation can be determined using any methods known in the art or described herein. Representative assays include but are not limited to immunoblotting and immunoprecipitation with antibodies such as anti-phosphotyrosine antibodies that recognize the specific phosphorylated proteins. Cell-based ELISA kit quantifies the amount of activated (phosphorylated at S473) Akt relative to total Akt protein is also available (SuperArray Biosciences).

In practicing the subject methods, any cells that express mTorC1, mTorC2 and/or Akt can be utilized. Non-limiting examples of specific cell types whose proliferation can be inhibited include fibroblast, cells of skeletal tissue (bone and cartilage), cells of epithelial tissues (e.g. liver, lung, breast, skin, bladder and kidney), cardiac and smooth muscle cells, neural cells (glia and neurones), endocrine cells (adrenal, pituitary, pancreatic islet cells), melanocytes, and many different types of haemopoietic cells (e.g., cells of B-cell or T-cell lineage, and their corresponding stem cells, lymphoblasts). Also of interest are cells exhibiting a neoplastic propensity or phenotype. Of particular interest is the type of cells that differentially expresses (over-expresses or underexpresses) a disease-causing gene. The types of diseases involving abnormal functioning of genes include but are not limited to autoimmune diseases, cancer, obesity, hypertension, diabetes, neuronal and/or muscular degenerative diseases, cardiac diseases, endocrine disorders, and any combinations thereof.

A. Active Agents

The subject methods can employ any biologically active agents that exhibit selective inhibitory activities towards mTorC1 and/or mTorC2 described herein. One class of biologically active agent for use in the subject methods encompasses compounds, e.g., pyrazolopyrimidine derivatives, including but not limited to compounds having a structure of the following Formula (I) and Formula (II).

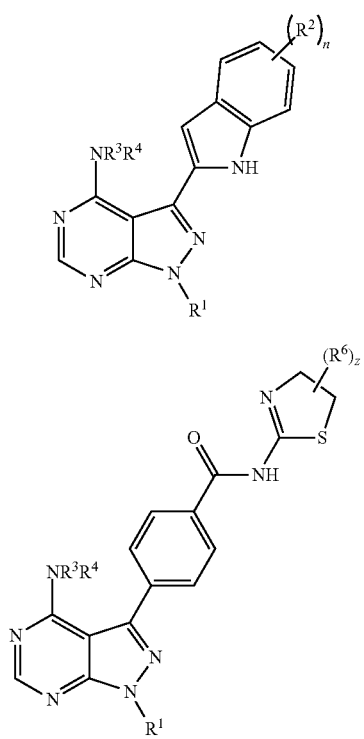

In some embodiments of the compounds of Formulae (I) or (II), $R^1$, $R^3$, and $R^4$ are independently hydrogen, halogen, —CN, —CF$_3$, —OH, —NH$_2$, —SO$_2$, —COOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, at least one of $R^3$ or $R^4$ is hydrogen. In some embodiments, $R^1$, $R^3$, and $R^4$ are independently hydrogen or substituted or unsubstituted $C_1$-$C_{10}$ alkyl (e.g. $C_1$-$C_5$ alkyl or $C_1$-$C_3$ alkyl). $R^1$, $R^3$, and $R^4$ may also independently be hydrogen or unsubstituted $C_1$-$C_{10}$ alkyl (e.g. $C_1$-$C_5$ alkyl or $C_1$-$C_3$ alkyl).

In some embodiments of Formulae (I) or (II), $R^1$, $R^3$, and $R^4$ are independently hydrogen, halogen, —CN, —CF$_3$, —OH, —NH$_2$, —SO$_2$, —COOH, $R^7$-substituted or unsubstituted alkyl, $R^7$-substituted or unsubstituted heteroalkyl, $R^7$-substituted or unsubstituted cycloalkyl, $R^7$-substituted or unsubstituted heterocycloalkyl, $R^7$-substituted or unsubstituted aryl, or $R^7$-substituted or unsubstituted heteroaryl. $R^7$ is independently oxo, halogen, —CN, —CF$_3$, —OH, —NH$_2$, —SO$_2$, —COOH, $R^8$-substituted or unsubstituted alkyl, $R^8$-substituted or unsubstituted heteroalkyl, $R^8$-substituted or unsubstituted cycloalkyl, $R^8$-substituted or unsubstituted heterocycloalkyl, $R^8$-substituted or unsubstituted aryl, or $R^8$-substituted or unsubstituted heteroaryl. $R^8$ is independently halogen, oxo, —CN, —CF$_3$, —OH, —NH$_2$, —SO$_2$, —COOH, unsubstituted alkyl, unsubstituted heteroalkyl, unsubstituted cycloalkyl, unsubstituted heterocycloalkyl, unsubstituted aryl or unsubstituted heteroaryl. In some embodiments, $R^1$ is substituted or unsubstituted alkyl or substituted or unsubstituted heterocycloalkyl (e.g. morpholino). In some embodiments, $R^1$ is substituted with —C(O)$R^{8A}$, wherein $R^{8A}$ is unsubstituted alkyl.

In some embodiments of Formula (I), $R^2$ is independently hydrogen, halogen, —CN, —CF$_3$, —OR$^5$, —NH$_2$, —SO$_2$, —COOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^2$ is independently hydrogen, —OR$^5$, —CN, —NH$_2$, —SH, —CN, —CF$_3$, —NO$_2$, or substituted or unsubstituted alkyl. $R^5$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^5$ is hydrogen or substituted or unsubstituted alkyl (e.g. unsubstituted $C_1$-$C_5$ alkyl).

$R^2$ may independently be hydrogen, halogen, —OR$^5$, —CN, —NH$_2$, —SH, —CN, —CF$_3$, —NO$_2$, $R^9$-substituted or unsubstituted alkyl, $R^9$-substituted or unsubstituted heteroalkyl, $R^9$-substituted or unsubstituted cycloalkyl, $R^9$-substituted or unsubstituted heterocycloalkyl, $R^9$-substituted or unsubstituted aryl, or $R^9$-substituted or unsubstituted heteroaryl. $R^9$ is independently halogen, oxo, —CN, —CF$_3$, —OH, —NH$_2$, —SO$_2$, —COOH, $R^{10}$-substituted or unsubstituted alkyl, $R^{10}$-substituted or unsubstituted heteroalkyl, $R^{10}$-substituted or unsubstituted cycloalkyl, $R^{10}$-substituted or unsubstituted heterocycloalkyl, $R^{10}$-substituted or unsubstituted aryl, or $R^{10}$-substituted or unsubstituted heteroaryl. $R^{10}$ is independently halogen, oxo, —CN, —CF$_3$, —OH, —NH$_2$, —SO$_2$, —COOH, unsubstituted alkyl, unsubstituted heteroalkyl, unsubstituted cycloalkyl, unsubstituted heterocycloalkyl, unsubstituted aryl or unsubstituted heteroaryl. In other embodiments, $R^2$ is —OR$^5$. In some related embodiments, $R^5$ is hydrogen or unsubstituted $C_1$-$C_5$ alkyl (e.g. hydrogen).

In some embodiments of Formulae (I) or (II), $R^5$ is independently hydrogen, $R^{11}$-substituted or unsubstituted alkyl, $R^{11}$-substituted or unsubstituted heteroalkyl, $R^{11}$-substituted or unsubstituted cycloalkyl, $R^{11}$-substituted or unsubstituted heterocycloalkyl, $R^{11}$-substituted or unsubstituted aryl, or $R^{11}$-substituted or unsubstituted heteroaryl. $R^{11}$ is independently halogen, oxo, —CN, —CF$_3$, —OH, —NH$_2$, —SO$_2$, —COOH, $R^{12}$-substituted or unsubstituted alkyl, $R^{12}$-substituted or unsubstituted heteroalkyl, $R^{12}$-substituted or unsubstituted cycloalkyl, $R^{12}$-substituted or unsubstituted heterocycloalkyl, $R^{12}$-substituted or unsubstituted aryl, or $R^{12}$-substituted or unsubstituted heteroaryl. $R^{12}$ is independently halogen, oxo, —CN, —CF$_3$, —OH, —NH$_2$, —SO$_2$, —COOH, unsubstituted alkyl, unsubstituted heteroalkyl, unsubstituted cycloalkyl, unsubstituted heterocycloalkyl, unsubstituted aryl or unsubstituted heteroaryl.

In some embodiments of Formula (II), $R^6$ is independently hydrogen, halogen, —CN, —CF$_3$, —OR$^5$, —NH$_2$, —SO$_2$, —COOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^6$ may also independently be hydrogen, —OR$^5$, —CN, halogen, —NH$_2$, —SH, —CN, —CF$_3$, —NO$_2$, halogen, or substituted or unsubstituted alkyl (e.g. unsubstituted $C_1$-$C_5$ alkyl). $R^5$ is as defined above in the description of Formula (I). In some embodiments, $R^6$ is independently hydrogen, —OR$^5$, —CN, —NH$_2$, —SH, —CN, —CF$_3$, —NO$_2$, $R^{13}$-substituted or unsubstituted alkyl, $R^{13}$-substituted or unsubstituted heteroalkyl, $R^{13}$-substituted or unsubstituted cycloalkyl, $R^{13}$-substituted or unsubstituted heterocycloalkyl, $R^{13}$-substituted or unsubstituted aryl, or $R^{13}$-substituted or unsubstituted heteroaryl. $R^{13}$ is independently halogen, oxo, —CN, —CF$_3$, —OH, —NH$_2$, —SO$_2$, —COOH, $R^{14}$-substituted or unsubstituted alkyl, $R^{13}$-substituted or unsubstituted heteroalkyl, $R^{14}$-substituted or unsubstituted cycloalkyl, $R^{14}$-substituted or unsubstituted heterocycloalkyl, $R^{14}$-substituted or unsubstituted aryl, or $R^{14}$-substituted or unsubstituted heteroaryl. $R^{14}$ is independently halogen, oxo, —CN, —CF$_3$, —OH, —NH$_2$, —SO$_2$, —COOH, unsubstituted alkyl, unsubstituted heteroalkyl, unsubstituted cycloalkyl, unsubstituted heterocycloalkyl, unsubstituted aryl or unsubstituted heteroaryl. $R^6$ may also independently be hydrogen, —OR$^5$, —CN, halogen, —NH$_2$, —SH, —CN, —CF$_3$, —NO$_2$, halogen, or unsubstituted $C_1$-$C_5$ alkyl. In some embodiments, $R^6$ is hydrogen.

In some embodiments of Formula (I) or (II), $R^3$ and $R^4$ are hydrogen. In some embodiments of Formula (I), n is 1 or 2. In some related embodiments of Formula (I), n is 1. In other related embodiments, $R^2$ is —OR$^5$ and n is 1. In still other related embodiments, $R^5$ is hydrogen. In some embodiments of Formula (II), z is an integer from 1 to 2. In some embodiments, z is 1.

In some embodiments, $R^1$, $R^2$, $R^3$, $R^4$, $R^5$, $R^6$, $R^7$, $R^8$, $R^9$, $R^{10}$, $R^{11}$, $R^{12}$, $R^{13}$ and/or $R^{14}$ are size-limited substituents. In some embodiments $R^1$, $R^2$, $R^3$, $R^4$, $R^5$, $R^6$, $R^7$, $R^8$, $R^9$, $R^{10}$, $R^{11}$, $R^{12}$, $R^{13}$ and/or $R^{14}$ are $C_1$-$C_{10}$, $C_1$-$C_5$ alkyl or $C_1$-$C_3$ alkyl, for example methyl, ethyl, propyl, isopropyl, butyl and the like, optionally substituted as described herein. In some embodiments, $R^1$, $R^2$, $R^3$, $R^4$, $R^5$, $R^6$, $R^7$, $R^8$, $R^9$, $R^{10}$, $R^{11}$, $R^{12}$, $R^{13}$ and/or $R^{14}$ are 2-10 membered, 2-5 membered, or 2-3-membered heteroalkyl, optionally substituted as described herein. In some embodiments, $R^1$, $R^2$, $R^3$, $R^4$, $R^5$, $R^6$, $R^7$, $R^8$, $R^9$, $R^{10}$, $R^{11}$, $R^{12}$, $R^{13}$ and/or $R^{14}$ are $C_3$-$C_{10}$, $C_3$-$C_8$, $C_3$-$C_6$ or $C_3$-$C_5$ cycloalkyl, including but not limited to cyclopropyl, cyclobutyl, cyclopentyl, cyclohexyl, cycloheptyl, cyclooctyl and the like, optionally substituted as described herein. In some embodiments, $R^1$, $R^2$, $R^3$, $R^4$, $R^5$, $R^6$, $R^7$, $R^8$, $R^9$, $R^{10}$, $R^{11}$, $R^{12}$, $R^{13}$ and/or $R^{14}$ are 3-membered, 4-membered, 5-membered, 6-membered, 7-membered, 8-membered, 9-membered or 10-membered heterocycloalkyl, including but not limited to aziridine, oxirane, thiirane, azetidine, oxetane, thietane, pyrrolidine, dihydrofuran, tetrahydrofuran, dihydrothiophene, tetrahydrothiophene, piperidine, dihydropyran, tetrahydropyran, dihydrothiopyran, tetrahydrothiopyran, optionally substituted as described herein. In some embodiments, $R^1$, $R^2$, $R^3$, $R^4$, $R^5$, $R^6$, $R^7$, $R^8$, $R^9$, $R^{10}$, $R^{11}$, $R^{12}$, $R^{13}$ and/or $R^{14}$ are $C_6$-$C_{10}$ aryl, including but not limited to phenyl or naphthyl, optionally substituted as described herein. In some embodiments $R^1$, $R^2$, $R^3$, $R^4$, $R^5$, $R^6$, $R^7$, $R^8$, $R^9$, $R^{10}$, $R^{11}$, $R^{12}$, $R^{13}$ and/or $R^{14}$ are 5-10-membered, 5-6-membered heteroaryl as described herein, optionally substituted as described herein.

In other embodiments, the biologically active agent (e.g. the compounds of Formula (I) or (II)) is selected from the following compounds:

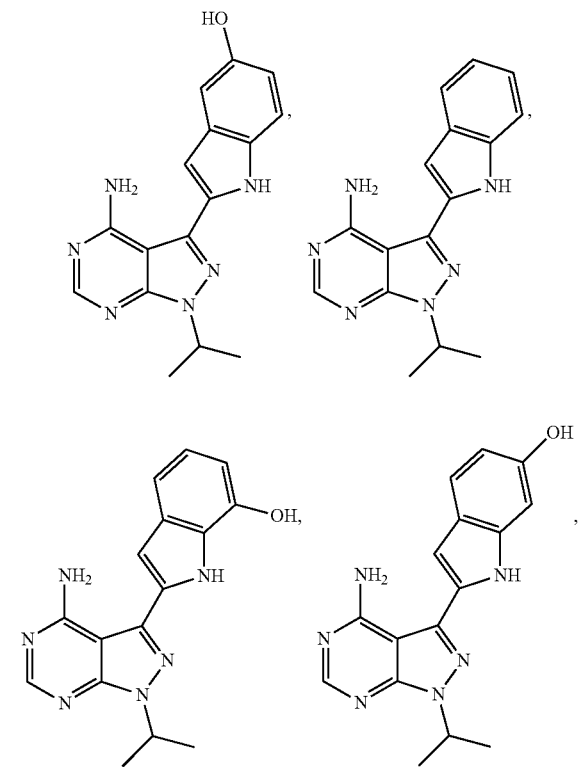

27
-continued
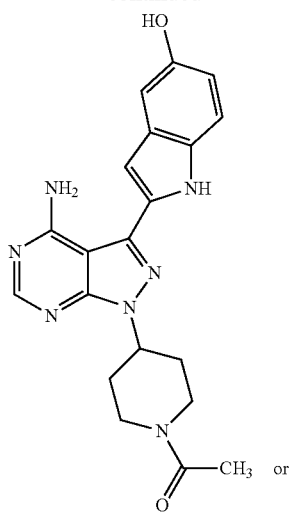
or
28
-continued
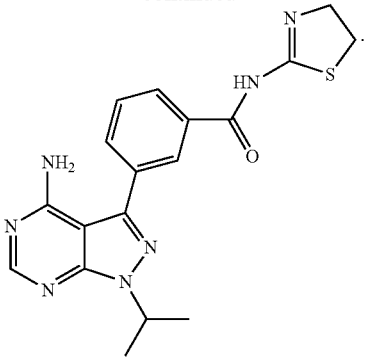
The table below summarizes the IC$_{50}$ values of these compounds when tested against mTor complexes and type I PI3-kinases. The ability of these compounds to inhibit proliferation of PC3 cells is also indicated.
| Compound Structure | mTor IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|
| 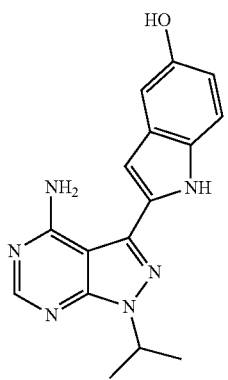 [SMILES: CC(C)n1nc(-c2cc3cc(O)ccc3[nH]2)c2c(N)ncnc21] | 6.7 | 22500 | 18400 | 400 | 120 | 100 |
| 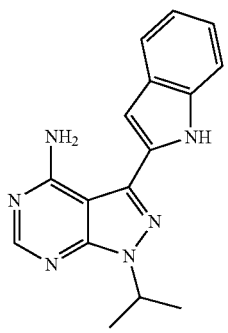 [SMILES: CC(C)n1nc(-c2cc3ccccc3[nH]2)c2c(N)ncnc21] | 79 | | | | 11189 | 2062 |

-continued

| Compound Structure | mTor IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|
| (structure) | 0.7 | 3465 | 3580 | 450 | 330 | 38 |
| (structure) | 26 | 279 | 2160 | 115 | 395 | 1000 |
| (structure) | 80 | 3000 | 5800 | 680 | 990 | — |
| (structure) | 14 | 5750 | 25000 | — | 9800 | 11800 |

Additional anti-cell proliferation agents can be screened based on the ability of selective inhibition of mTorC1 and/or mTorC2. Accordingly, the present invention provides, in one embodiment, a method of developing a biologically active agent that inhibits cell proliferation. The method comprises: (a) contacting a candidate agent with a population of cells of interest; (b) detecting selective inhibition of mTorC1 and/or mTorC2 activity relative to one or more type I phosphatidylinositol 3-kinases (PI3-kinase), wherein the one or more type I PI3-kinase is selected from the group consisting of PI3-kinase α, PI3-kinase β, PI3-kinase γ, and PI3-kinase δ.

For the purposes of this invention, a candidate agent effective to selectively inhibit mTorC1 and/or mTorC2 activity is intended to include, but not be limited to a biological or chemical compound such as a simple or complex organic or inorganic compounds, peptide, peptide mimetic, protein (e.g. antibody), liposome, small interfering RNA, or a polynucleotide (e.g. anti-sense). A class of preferred agents include those that block the downstream signaling effect of mTorC1 and/or mTorC2. Any of the methods and assays disclosed herein that evidence modulation of mTorC1 and/or mTorC2 activity can be employed in developing such agent.

In some embodiments, the biologically active agent (e.g. compound) is capable of selectively inhibiting mTorC2 activity (or mTorC2 mediated effects) relative to mTorC1 activity (or mTorC2 mediated effects). The biologically active agent may be capable of decreasing phosphorylation of Akt at residues, including but not limited to, S473 and T308 relative to the amount of phosphorylation in the absence of the biologically active agent. In other embodiments, the biologically active agent is capable of decreasing phosphorylation of Akt substrates including but not limited to FoxO1/O3α T24/32, GSK3α/β S21/9, and TSC2 T1462 relative to the amount of phosphorylation in the absence of the biologically active agent.

In some embodiments, the biologically active agent (e.g. compound) is capable of selectively inhibiting mTorC1 activity (or mTorC2 mediated effects) relative to mTorC2 activity (or mTorC2 mediated effects). In some embodiments, the biologically active agent is capable of decreasing phosphorylation of signaling molecules downstream of mTor, including but not limited to ribosomal S6 S240/244, 70S6K T389, and/or 4EBP1 (e.g. 4EBP1 T37/46) relative to the amount of phosphorylation in the absence of the biologically active agent. The biologically active agent may also be capable of increasing binding of 4EPB1 to eIF4E relative to the amount of binding in the absence of the biologically active agent. This increased binding results in a decrease in RNA translation. Therefore, in some embodiments, where the biologically active agent (e.g. compound) is capable of selectively inhibiting mTorC1 activity (or mTorC2 mediated effects) relative to mTorC2 activity (or mTorC2 mediated effects), the biologically active agent is useful in treating cancer (e.g. solid tumors, lymphomas and leukemia).

In other embodiments, the biologically active agent may increase inhibition of proliferation of cells including but not limited to normal or neoplastic cells, mouse embryonic fibroblasts, leukemic blast cells, cancer stem cells, and cells that mediate autoimmune reactions and/or increase induction of apoptosis of cells or cell cycle arrest relative to the amount of increase in the absence of the biologically active agent.

A vast array of compounds can be synthesized, for example polymers, such as polypeptides and polynucleotides, and synthetic inorganic and organic compounds based on various core structures, all of which are also contemplated herein. In addition, various natural sources can provide compounds for screening, such as plant or animal extracts, and the like. It should be understood, although not always explicitly stated that the active agent can be used alone or in combination with another modulator, having the same or different biological activity as the agents identified by the subject screening method. A subject agent can assert its selective inhibitory effect by directly binding to or directly interacting with the target. An agent can also assert its inhibitory effect indirectly by first interacting with a molecule in the same signaling pathway. The mTor selective inhibitors of the present invention encompasses simple or complex organic or inorganic molecule, peptide, peptide mimetic, protein (e.g. antibody), liposome, small interfering RNA, or a polynucleotide (e.g. anti-sense) that can reduce the deleterious effect of mTor in vitro.

The compounds described above, including the compounds of Formula (I) or (II), or pharmaceutically acceptable salts thereof, may be used in the methods of the present invention.

B. Methods

The invention also relates to a method of ameliorating a medical condition mediated by mTorC1 and/or mTorC2. In one aspect, the present invention encompasses a method of treating a hyperproliferative disorder in a mammal that comprises administering to said mammal a therapeutically effective amount of a biologically active agent of the present invention, or a pharmaceutically acceptable salt, ester, prodrug, solvate, hydrate or derivative thereof. In some embodiments, said method relates to the treatment of cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS related AIDS-related (e.g. Lymphoma and Kaposi's Sarcoma) or viral-induced cancer. In some embodiments, said method relates to the treatment of a non-cancerous hyperproliferative disorder such as benign hyperplasia of the skin (e. g., psoriasis), restenosis, or prostate (e. g., benign prostatic hypertrophy (BPH)).

In some embodiments, the medical condition mediated by mTorC1 and/or mTorC2 is polycystic kidney disease (PKD), such as autosomal dominant PKD. In other embodiments, the medical condition mediated by mTorC1 and/or mTorC2 is organ rejection derived from an organ transplantation procedure, such as kidney transplantation. Thus, in some embodiments methods are provided for prophylaxis of organ rejection an organ transplant recipient patient (e.g. kidney transplant). The method includes administering to the organ transplant recipient patient a prophylactic amount of a biologically active agent that selectively inhibits mTorC1 and/or mTorC2 activity relative to one or more type I phosphatidylinositol 3-kinases (PI3-kinase), wherein the one or more type I PI3-kinase is selected from the group consisting of PI3-kinase α, PI3-kinase β, PI3-kinase γ, and PI3-kinase δ. In some related embodiments, the biologically active agent is a compound of Formula (I) or (II).

The invention also relates to a method for the treatment of a hyperproliferative disorder in a mammal that comprises administering to said mammal a therapeutically effective amount of a biologically active agent of the present invention, or a pharmaceutically acceptable salt, ester, prodrug, solvate, hydrate or derivative thereof, in combination with an anti-tumor agent. In some embodiments, the anti-tumor agent is selected from the group consisting of mitotic inhibitors, alkylating agents, anti-metabolites, intercalating antibiotics, growth factor inhibitors, cell cycle inhibitors, enzyme inhibitors, topoisomerase inhibitors, biological response modifiers, anti-hormones, angiogenesis inhibitors, and anti-androgens.

The invention also relates to a method of treating diseases related to vasculogenesis or angiogenesis in a mammal that comprises administering to said mammal a therapeutically effective amount of a biologically active agent of the present invention, or a pharmaceutically acceptable salt, ester, prodrug, solvate, hydrate or derivative thereof. In some embodiments, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

Patients that can be treated with biologically active agents of the present invention, or pharmaceutically acceptable salt, ester, prodrug, solvate, hydrate or derivative of said biologically active agents, according to the methods of this invention include, for example, patients that have been diagnosed as having psoriasis; restenosis; atherosclerosis; BPH; breast cancer such as a ductal carcinoma in duct tissue in a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarcinoma that has migrated to the bone; pancreatic cancer such as epithelioid carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer; thyroid cancer such as papillary, follicular, medullary and anaplastic; AIDS-related lymphoma such as diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Müllerian tumor; oral cavity and oropharyngeal cancer such as, hypopharyngeal cancer, laryngeal cancer, nasopharyngeal cancer, and oropharyngeal cancer; stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer.

The invention also relates to a method of treating diabetes in a mammal that comprises administering to said mammal a therapeutically effective amount of a biologically active agent of the present invention, or a pharmaceutically acceptable salt, ester, prodrug, solvate, hydrate or derivative thereof.

The invention also relates to a method of treating an inflammation disorder, including autoimmune diseases, in a mammal that comprises administering to said mammal a therapeutically effective amount of a biologically active agent of the present invention, or a pharmaceutically acceptable salt, ester, prodrug, solvate, hydrate or derivative thereof. Examples of autoimmune diseases includes but is not limited to acute disseminated encephalomyelitis (ADEM), Addison's disease, antiphospholipid antibody syndrome (APS), aplastic anemia, autoimmune hepatitis, coeliac disease, Crohn's disease, Diabetes mellitus (type 1), Goodpasture's syndrome, Graves' disease, Guillain-Barré syndrome (GBS), Hashimoto's disease, lupus erythematosus, multiple sclerosis, myasthenia gravis, opsoclonus myoclonus syndrome (OMS), optic neuritis, Ord's thyroiditis, oemphigus, polyarthritis, primary biliary cirrhosis, psoriasis, rheumatoid arthritis, Reiter's syndrome, Takayasu's arteritis, temporal arteritis (also known as "giant cell arteritis"), warm autoimmune hemolytic anemia, Wegener's granulomatosis, alopecia universalis, Chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, and vulvodynia. Other disorders include bone-resorption disorders and thrombosis.

For instance, the biologically active agents described herein can be used to treat encephalomyelitis. In other embodiments the biologically active agents described herein are used for the treatment of obstructive pulmonary disease. Chronic obstructive pulmonary disease (COPD) is an umbrella term for a group of respiratory tract diseases that are characterized by airflow obstruction or limitation. Conditions included in this umbrella term are: chronic bronchitis, emphysema, and bronchiectasis.

In another embodiment, the biologically active agents described herein are used for the treatment of asthma. Also, the biologically active agents described herein may be used for the treatment of endotoxemia and sepsis. In one embodiment, the biologically active agents described herein are used to for the treatment of rheumatoid arthritis (RA). In yet another embodiment, the biologically active agents described herein is used for the treatment of contact or atopic dermatitis. Contact dermatitis includes irritant dermatitis, phototoxic dermatitis, allergic dermatitis, photoallergic dermatitis, contact urticaria, systemic contact-type dermatitis and the like. Irritant dermatitis can occur when too much of a substance is used on the skin of when the skin is sensitive to certain substance. Atopic dermatitis, sometimes called eczema, is a kind of dermatitis, an atopic skin disease.

In addition, the biologically active agents described herein may be used to treat acne.

In addition, the biologically active agents described herein may be used for the treatment of arteriosclerosis, including atherosclerosis. Arteriosclerosis is a general term describing any hardening of medium or large arteries. Atherosclerosis is a hardening of an artery specifically due to an atheromatous plaque.

Further the biologically active agents described herein may be used for the treatment of glomerulonephritis. Glomerulonephritis is a primary or secondary autoimmune renal disease characterized by inflammation of the glomeruli. It may be asymptomatic, or present with hematuria and/or proteinuria. There are many recognized types, divided in acute, subacute or chronic glomerulonephritis. Causes are infectious (bacterial, viral or parasitic pathogens), autoimmune or paraneoplastic.

Additionally, the biologically active agents described herein may be used for the treatment of bursitis, lupus, acute disseminated encephalomyelitis (ADEM), Addison's disease, antiphospholipid antibody syndrome (APS), aplastic anemia, autoimmune hepatitis, coeliac disease, Crohn's disease, diabetes mellitus (type 1), Goodpasture's syndrome, graves' disease, Guillain-Barré syndrome (GBS), Hashimoto's disease, inflammatory bowel disease, lupus erythematosus, myasthenia gravis, opsoclonus myoclonus syndrome (OMS), optic neuritis, Ord's thyroiditis, ostheoarthritis, uveoretinitis, pemphigus, polyarthritis, primary biliary cirrhosis, Reiter's syndrome, Takayasu's arteritis, temporal arteritis, warm autoimmune hemolytic anemia, Wegener's granulomatosis, alopecia universalis, Chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, vulvodynia, appendicitis, arteritis, arthritis, blepharitis, bronchiolitis, bronchitis, cervicitis, cholangitis, cholecystitis, chorioamnionitis, colitis, conjunctivitis, cystitis, dacryoadenitis, dermatomyositis, endocarditis, endometritis, enteritis, enterocolitis, epicondylitis, epididymitis, fasciitis, fibrositis, gastritis, gastroenteritis, gingivitis, hepatitis, hidradenitis, ileitis, iritis, laryngitis, mastitis, meningitis, myelitis, myocarditis, myositis, nephritis, omphalitis, oophoritis, orchitis, osteitis, otitis, pancreatitis, parotitis, pericarditis, peritonitis, pharyngitis, pleuritis, phlebitis, pneumonitis, proctitis, prostatitis, pyelonephritis, rhinitis, salpingitis, sinusitis, stomatitis, synovitis, tendonitis, tonsillitis, uveitis, vaginitis, vasculitis, or vulvitis.

The invention also relates to a method of treating a cardiovascular disease in a mammal that comprises administering to said mammal a therapeutically effective amount of a biologically active agent of the present invention, or a pharmaceutically acceptable salt, ester, prodrug, solvate, hydrate or derivative thereof. Examples of cardiovascular conditions include, but are not limited to, atherosclerosis, restenosis, vascular occlusion and carotid obstructive disease.

In another aspect, the present invention provides methods of disrupting the function of a leukocyte or disrupting a function of an osteoclast. The method includes contacting the leukocyte or the osteoclast with a function disrupting amount of a biologically active agent of the invention.

In some embodiments, a method of treating a condition caused by aberrant ion transport across epithelial cells in a patient in need thereof is provided. The method includes administering to the patient a therapeutically effective amount of a biologically active agent that selectively inhibits mTorC1 and/or mTorC2 activity relative to one or more type I phosphatidylinositol 3-kinases (PI3-kinase) ascertained by an in vitro kinase assay. The one or more type I PI3-kinase is selected from the group consisting of PI3-kinase α, PI3-kinase β, PI3-kinase γ, and PI3-kinase δ.

A condition caused by aberrant ion (e.g. sodium ion, proton, lithium ion, potassium ion) transport across epithelial cells is a condition that would not occur but for the presence of aberrant ion transport across at least some epithelial cells in the patient. The epithelial cells typically form at least part of glands, connective tissue (e.g. the outer layer of connective tissues) and/or tissues lining the cavities of surfaces of structures (e.g. organs) throughout the body. In some embodiments, the epithelial cells are renal, lung, or colon epithelial cells.

The epithelial cells may include an epithelial sodium channel (ENaC) (also commonly referred to as sodium channel non-neuronal 1 (SCNN1) or amiloride sensitive sodium channel (ASSC)), a membrane-bound ion-channel that is permeable to $Li^+$-ions, protons and Nations. Thus, in some embodiments, the condition caused by aberrant ion transport across epithelial cells is a condition caused by aberrant ion transport across ENaC channels, including for example, cystic fibrosis and Liddle's syndrome.

In other embodiments, the condition caused by aberrant ion transport across epithelial cells is a condition caused by aberrant ion transport across kidney epithelial cells, such as kidney collecting duct cells.

The condition caused by aberrant ion transport across epithelial cells may also be a disease caused by aberrant sodium ion transport across epithelial cells, such as ENaC-dependent Na+ transport in renal epithelial cells. The collecting duct is the major site for cyst generation in the autosomal dominant and autosomal recessive forms of human polycystic kidney disease (PKD). Cysts may form due to abnormal cellular proliferation, and abnormal ion and fluid transport, which fills the cysts. Therefore, in some embodiments, the condition caused by aberrant ion transport across epithelial cells is PKD, a disease of collecting duct cell proliferation kidney (e.g. cyst formation), a blood pressure disease, a kidney electrolyte disorders, hypertension, congestive heart failure, nephrotic syndrome and/or cirrhosis of the liver.

In some embodiments, the biologically active agent useful in methods of treating a condition caused by aberrant ion transport across epithelial cells is an active agent capable of selectively inhibiting mTorC2 activity (or mTorC2 mediated effects) relative to mTorC1 activity (or mTorC2 mediated effects). In other embodiments, the biologically active agent is capable of inhibiting cyst progression in animal models of PKD to a greater degree than rapamycin. In other embodiments, the biologically active agent inhibits (e.g. decreases) ion transport processes in kidney tubule cells relative to the amount of ion transport in the absence of the biologically active agent. In other embodiments, the biologically active agent is excreted in the kidney. In other embodiments, the biologically active agent inhibits (e.g. decreases) phosphorylation and/or activation of SGK1, a key mediator of hormone-regulated Na+ transport, relative to the amount of phosphorylation and/or activation of SGK1 in the absence of the biologically active agent. In other embodiments, the biologically active agent is a compound of Formula (I) or (II) as described above. In some embodiments, the biologically active agent is PP242.

In another embodiment, a method of treating T cell lymphoma, or a cancer arising out of thymocyte proliferation such as thymic lymphoma, in a patient in need thereof is provided. The method includes administering to the patient a therapeutically effective amount of a biologically active agent that selectively inhibits mTorC1 and/or mTorC2 activity relative to one or more type I phosphatidylinositol 3-kinases (PI3-kinase) ascertained by an in vitro kinase assay, wherein the one or more type I PI3-kinase is selected from the group consisting of PI3-kinase α, PI3-kinase β, PI3-kinase γ, and PI3-kinase δ. In some embodiments, the biologically active agent is a compound of Formula (I) or (II) as described above. In some embodiments, the biologically active agent is PP242.

In another embodiment, a method of treating a tumor arising from oncogenic Akt-mTOR signaling in a patient in need thereof is provided. The method includes administering to the patient a therapeutically effective amount of a biologically active agent that selectively inhibits mTorC1 and/or mTorC2 activity relative to one or more type I phosphatidylinositol 3-kinases (PI3-kinase) ascertained by an in vitro kinase assay, wherein the one or more type I PI3-kinase is selected from the group consisting of PI3-kinase α, PI3-kinase β, PI3-kinase γ, and PI3-kinase δ. In some embodiments, the biologically active agent is a compound of Formula (I) or (II) as described above. In some embodiments, the biologically active agent is PP242.

C. Combination Treatments

The present invention also provides methods for combination therapies in which an agent known to modulate other pathways, or other components of the same pathway, or even overlapping sets of target enzymes are used in combination with a biologically active agent of the present invention, or a pharmaceutically acceptable salt, ester, prodrug, solvate, hydrate or derivative thereof.

In one embodiment, the present invention provides a method of inhibiting proliferation of a neoplastic cell comprising contacting the cell with an effective amount of an antagonist that inhibits full activation of Akt in a cell and an anti-cancer agent, wherein said inhibition of cell proliferation is enhanced through a synergistic effect of said antagonist and said anti-cancer agent.

In another embodiment, provided is a combination treatment for a subject diagnosed with or at risk of a neoplastic condition. The combination treatment involves administering to said subject a therapeutically effective amount of an antagonist that inhibits full activation of Akt in a cell and an anti-cancer agent, wherein the efficacy of said treatment is enhanced through a synergistic effect of said antagonist and said anti-cancer agent.

In one aspect, such therapy includes but is not limited to the combination of the subject biologically active agent with chemotherapeutic agents, therapeutic antibodies, and radiation treatment, to provide a synergistic therapeutic effect.

Specifically, in one aspect, this invention also relates to a pharmaceutical composition for inhibiting abnormal cell growth in a mammal which comprises an amount of a biologically active agent of the present invention, or a pharmaceutically acceptable salt, ester, prodrug, solvate, hydrate or derivative thereof, in combination with an amount of an anti-cancer agent (e.g. a chemotherapeutic agent), wherein the amounts of the biologically active agent, salt, ester, prodrug, solvate, hydrate or derivative, and of the chemotherapeutic are together effective in inhibiting abnormal cell growth. Many chemotherapeutics are presently known in the art and can be used in combination with the biologically active agents of the invention.

In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

A wide variety of anti-cancer agents can be employed in combination. Of particular interest is the combination of the subject mTor selective inhibitors with PI3kinase inhibitors, other non-Tor protein kinase inhibitors, and dual kinase inhibitors (e.g., those that inhibit both protein kinase and lipid kinases). Non limiting examples of other kinase inhibitors that can be combined with the subject agent include rapamycin, TORKinhibs, PI-103, BEZ235, Akt i, IC87114, and PIK-90.

Additional examples of therapeutic agents for a combined treatment are chemotherapeutic agents, cytotoxic agents, and non-peptide small molecules such as Gleevec (Imatinib Mesylate), Velcade (bortezomib), Casodex (bicalutamide), Iressa (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.R™; razoxane; sizofiran; spirogermanium; tenuazonic acid; triaziquone; 2,2',2"-trichlorotriethyla-mine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO).

This invention further relates to a method for inhibiting abnormal cell growth in a mammal or treating a hyperproliferative disorder which method comprises administering to the mammal an amount of a biologically active agent of the present invention, or a pharmaceutically acceptable salt, ester, prodrug, solvate, hydrate or derivative thereof, in combination with radiation therapy, wherein the amounts of the biologically active agent, salt, ester, prodrug, solvate, hydrate or derivative, is in combination with the radiation therapy effective in inhibiting abnormal cell growth or treating the hyperproliferative disorder in the mammal. Techniques for administering radiation therapy are known in the art, and these techniques can be used in the combination therapy described herein. The administration of the biologically active agent of the invention in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g. At-211, I-131, I-125, Y-90, Re-186, Re-188, Sm-153, Bi-212, P-32, and radioactive isotopes of Lu), Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without be limiting to any theory, the biologically active agents of the present invention can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a biologically active agent of the present invention or pharmaceutically acceptable salt, ester, prodrug, solvate, hydrate or derivative thereof, which amount is effective is sensitizing abnormal cells to treatment with radiation. The amount of the biologically active agent, salt, or solvate in this method can be determined according to the means for ascertaining effective amounts of such biologically active agents described herein.

The invention also relates to a method of and to a pharmaceutical composition of inhibiting abnormal cell growth in a mammal which comprises an amount of a biologically active agent of the present invention, or a pharmaceutically acceptable salt, ester, prodrug, solvate, hydrate or derivative thereof, or an isotopically-labeled derivative thereof, and an amount of one or more substances selected from anti-angiogenesis agents, signal transduction inhibitors, and antiproliferative agents.

Anti-angiogenesis agents, such as MMP-2 (matrix-metalloproteinase 2) inhibitors, MMP-9 (matrix-metalloproteinase 9) inhibitors, and COX-11 (cyclooxygenase 11) inhibitors, can be used in conjunction with a biologically active agent of the present invention and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (i. e., MAP-1, MMP-3, MMP-4, MMP-5, MMP-6, MMP-7, MMP-8, MMP-10, MMP-11, MMP-12, andMMP-13). Some specific examples of MMP inhibitors useful in the present invention are AG-3340, RO 32-3555, and RS 13-0830.

The invention also relates to a method of and to a pharmaceutical composition of treating a cardiovascular disease in a mammal which comprises an amount of a biologically active agent of the present invention, or a pharmaceutically acceptable salt, ester, prodrug, solvate, hydrate or derivative thereof, or an isotopically-labeled derivative thereof, and an amount of one or more therapeutic agents use for the treatment of cardiovascular diseases.

Examples for use in cardiovascular disease applications are anti-thrombotic agents, e.g., prostacyclin and salicylates, thrombolytic agents, e.g., streptokinase, urokinase, tissue plasminogen activator (TPA) and anisoylated plasminogen-streptokinase activator complex (APSAC), anti-platelets agents, e.g., acetyl-salicylic acid (ASA) and clopidrogel, vasodilating agents, e.g., nitrates, calcium channel blocking drugs, anti-proliferative agents, e.g., colchicine and alkylating agents, intercalating agents, growth modulating factors such as interleukins, transformation growth factor-beta and congeners of platelet derived growth factor, monoclonal antibodies directed against growth factors, anti-inflammatory agents, both steroidal and nonsteroidal, and other agents that can modulate vessel tone, function, arteriosclerosis, and the healing response to vessel or organ injury post intervention. Antibiotics can also be included in combinations or coatings comprised by the invention. Moreover, a coating can be used to effect therapeutic delivery focally within the vessel wall. By incorporation of the active agent in a swellable polymer, the active agent will be released upon swelling of the polymer.

The biologically active agents of the invention may be formulated or administered in conjunction with other agents that act to relieve the symptoms of inflammatory conditions such as encephalomyelitis, asthma, and the other diseases described herein. These agents include nonsteroidal anti-inflammatory drugs (NSAIDs), e.g. acetylsalicylic acid; ibuprofen; naproxen; indomethacin; nabumetone; tolmetin; etc. Corticosteroids are used to reduce inflammation and suppress activity of the immune system. The most commonly prescribed drug of this type is Prednisone. Chloroquine (Aralen) or hydroxychloroquine (Plaquenil) may also be very useful in some individuals with lupus. They are most often prescribed for skin and joint symptoms of lupus. Azathioprine (Imuran) and cyclophosphamide (Cytoxan) suppress inflammation and tend to suppress the immune system. Other agents, e.g. methotrexate and cyclosporin are used to control the symptoms of lupus. Anticoagulants are employed to prevent blood from clotting rapidly. They range from aspirin at very low dose which prevents platelets from sticking, to heparin/coumadin.

The biologically active agents describe herein may be formulated or administered in conjunction with liquid or solid tissue barriers also known as lubricants. Examples of tissue barriers include, but are not limited to, polysaccharides, polyglycans, seprafilm, interceed and hyaluronic acid.

Medicaments which may be administered in conjunction with the biologically active agents described herein include any suitable drugs usefully delivered by inhalation for example, analgesics, e.g. codeine, dihydromorphine, ergotamine, fentanyl or morphine; anginal preparations, e.g. diltiazem; antiallergics, e.g. cromoglycate, ketotifen or nedocromil; anti-infectives, e.g. cephalosporins, penicillins, streptomycin, sulphonamides, tetracyclines or pentamidine; antihistamines, e.g. methapyrilene; anti-inflammatories, e.g. beclomethasone, flunisolide, budesonide, tipredane, triamcinolone acetonide or fluticasone; antitussives, e.g. noscapine; bronchodilators, e.g. ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]methyl]benzenemethanol; diuretics, e.g. amiloride; anticholinergics e.g. ipratropium, atropine or oxitropium; hormones, e.g. cortisone, hydrocortisone or prednisolone; xanthines e.g. aminophylline, choline theophyllinate, lysine theophyllinate or theophylline; and therapeutic proteins and peptides, e.g. insulin or glucagon. It will be clear to a person skilled in the art that, where appropriate, the medicaments may be used in the form of salts (e.g. as alkali metal or amine salts or as acid addition salts) or as esters (e.g. lower alkyl esters) or as solvates (e.g. hydrates) to optimize the activity and/or stability of the medicament.

Other exemplary therapeutic agents useful for a combination therapy include but are not limited to agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Other therapeutic agents contemplated include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include antimicrobial agents, sulfonamides, trimethoprim-sulfamethoxazole quinolones, and agents for urinary tract infections, penicillins, cephalosporins, and other, β-Lactam antibiotics, an agent comprising an aminoglycoside, protein synthesis inhibitors, drugs used in the chemotherapy of tuberculosis, *mycobacterium avium* complex disease, and leprosy, antifungal agents, antiviral agents including nonretroviral agents and antiretroviral agents.

Examples of therapeutic antibodies that can be combined with a subject biologically active agent include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

Further therapeutic agents that can be combined with a subject biologically active agent may be found in Goodman and Gilman's "*The Pharmacological Basis of Therapeutics*" Tenth Edition edited by Hardman, Limbird and Gilman or the Physician's Desk Reference, both of which are incorporated herein by reference in their entirety.

The biologically active agents described herein can be used in combination with the agents disclosed herein or other suitable agents, depending on the condition being treated. Hence, in some embodiments the biologically active agents of the invention will be co-administered with other agents as described above. When used in combination therapy, the biologically active agents described herein may be administered with the second agent simultaneously or separately. This administration in combination can include simultaneous administration of the two agents in the same dosage form, simultaneous administration in separate dosage forms, and separate administration. That is, a biologically active agent described herein and any of the agents described above can be formulated together in the same dosage form and administered simultaneously. Alternatively, a biologically active agent of the present invention and any of the agents described above can be simultaneously administered, wherein both the agents are present in separate formulations. In another alternative, a biologically active agent of the present invention can be administered just followed by and any of the agents described above, or vice versa. In the separate administration protocol, a biologically active agent of the present invention and any of the agents described above may be administered a few minutes apart, or a few hours apart, or a few days apart.

Administration

Administration of the biologically active agents of the present invention can be effected by any method that enables delivery of the biologically active agents to the site of action. These methods include oral routes, intraduodenal routes, parenteral injection (including intravenous, intraarterial, subcutaneous, intramuscular, intravascular, intraperitoneal or infusion), topical (e.g. transdermal application), rectal administration, via local delivery by catheter or stent. Biologically active agents can also be administered intraadiposally or intrathecally.

The amount of the biologically active agent administered will be dependent on the mammal being treated, the severity of the disorder or condition, the rate of administration, the disposition of the biologically active agent and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g. by dividing such larger doses into several small doses for administration throughout the day.

The biologically active agent may be applied as a sole therapy or may involve one or more other anti-tumor substances, for example those selected from, mitotic inhibitors, for example vinblastine; alkylating agents, for example cis-platin, carboplatin and cyclophosphamide; anti-metabolites, for example 5-fluorouracil, cytosine arabinside and hydroxyurea, or, for example, one of the preferred antimetabolites disclosed in European Patent Application No. 239362 such as N-(5-[N-(3,4-dihydro-2-methyl-4-oxoquinazolin-6-yhnethyl)-N-methylamino]-2-thenoyl)-L-glutamic acid; growth factor inhibitors; cell cycle inhibitors; intercalating antibiotics, for example adriamycin and bleomycin; enzymes, for example, interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl) propionanilide). Such conjoint treatment may be achieved by way of the simultaneous, sequential or separate dosing of the individual components of treatment.

In some embodiments, a biologically active agent of the invention is administered in a single dose. Typically, such administration will be by injection, e.g., intravenous injection, in order to introduce the agent quickly. However, other routes may be used as appropriate. A single dose of a biologically active agent of the invention may also be used for treatment of an acute condition.

In some embodiments, a biologically active agent of the invention is administered in multiple doses. Dosing may be about once, twice, three times, four times, five times, six times, or more than six times per day. Dosing may be about once a month, once every two weeks, once a week, or once every other day. In another embodiment a biologically active agent of the invention and another agent are administered together about once per day to about 6 times per day. In another embodiment the administration of a biologically active agent of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the agents of the invention may continue as long as necessary. In some embodiments, an agent of the invention is administered for more than 1, 2, 3, 4, 5, 6, 7, 14, or 28 days. In some embodiments, an agent of the invention is administered for less than 28, 14, 7, 6, 5, 4, 3, 2, or 1 day. In some embodiments, an agent of the invention is administered chronically on an ongoing basis, e.g., for the treatment of chronic effects.

An effective amount of a biologically active agent of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, as an inhalant.

The compositions of the invention may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, biologically active agents of the invention may slow or inhibit the migration and proliferation of smooth muscle cells in the arterial wall which contribute to restenosis. A biologically active agent of the invention may be administered, for example, by local delivery from the struts of a stent, from a stent graft, from grafts, or from the cover or sheath of a stent. In some embodiments, a biologically active agent of the invention is admixed with a matrix. Such a matrix may be a polymeric matrix, and may serve to bond the biologically active agent to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly (ether-ester) copolymers (e.g. PEO-PLLA); polydimethylsiloxane, poly(ethylene-vinylacetate), acrylate-based polymers or copolymers (e.g. polyhydroxyethyl methylmethacrylate, polyvinyl pyrrolidinone), fluorinated polymers such as polytetrafluoroethylene and cellulose esters. Suitable matrices may be nondegrading or may degrade with time, releasing the biologically active agent or biologically active agents. Biologically active agents of the invention may be applied to the surface of the stent by various methods such as dip/spin coating, spray coating, dip-coating, and/or brush-coating. The biologically active agents may be applied in a solvent and the solvent may be allowed to evaporate, thus forming a layer of biologically active agent onto the stent. Alternatively, the biologically active agent may be located in the body of the stent or graft, for example in microchannels or micropores. When implanted, the biologically active agent diffuses out of the body of the stent to contact the arterial wall. Such stents may be prepared by dipping a stent manufactured to contain such micropores or microchannels into a solution of the biologically active agent of the invention in a suitable solvent, followed by evaporation of the solvent. Excess drug on the surface of the stent may be removed via an additional brief solvent wash. In yet other embodiments, biologically active agents of the invention may be covalently linked to a stent or graft. A covalent linker may be used which degrades in vitro, leading to the release of the biologically active agent of the invention. Any biolabile linkage may be used for such a purpose, such as ester, amide or anhydride linkages. Biologically active agents of the invention may additionally be administered intravascularly from a balloon used during angioplasty. Extravascular administration of the biologically active agents via the pericard or via advential application of formulations of the invention may also be performed to decrease restenosis.

A variety of stent devices which may be used as described are disclosed, for example, in the following references, all of which are hereby incorporated by reference: U.S. Pat. Nos. 5,451,233; 5,040,548; 5,061,273; 5,496,346; 5,292,331; 5,674,278; 3,657,744; 4,739,762; 5,195,984; 5,292,331; 5,674,278; 5,879,382; 6,344,053; 4,762,129; 6,152,946; 6,663,652; 6,027,520 6,676,682; 6,663,652; 6,872,216; 6,027,520; 6,114,653; 5,852,277; 5,843,120; 5,643,312; 5,733,303; 5,597,378; 5,653,727; 4,762,129; 5,922,021; 3,657,744; 4,739,762; 5,195,984; 5,451,233; 3,657,744; 4,739,762; 5,195,984; 4,739,762; 3,657,744; 4,739,762; 5,195,984; 5,292,331; 5,674,278; 5,643,312; 5,879,370; 5,421,955; 5,514,154; 5,603,721; 5,421,955; 5,514,154; 5,603,721; 5,292,331; 5,674,278; 5,879,382; 6,344,053; 5,728,067; 5,980,486; 6,129,708; 5,733,303; 5,843,120; 5,972,018; 5,972,018; 5,733,303; 5,843,120; 4,739,762; 5,195,984; 5,902,332; 5,156,594; 5,395,334; 6,090,083; 5,639,278; 6,051,020; 6,117,167; 5,632,772; 6,165,213; 4,762,129; 5,156,594; 5,217,482; 5,395,334; 4,641,653; 4,739,762; 5,922,021; 5,895,406; 6,251,920; 6,120,536; 5,292,331; 5,674,278; 5,879,382; 6,344,053; 5,609,627; 6,251,920; 5,733,303; 5,843,120; 5,972,018; 6,344,053; 5,292,331; 5,674,278; 5,879,382; 5,653,760; 6,190,358; 6,210,364; 6,283,939; 6,605,057; 5,292,331; 5,674,278; 5,879,382; 6,344,053; 5,423,851; 6,007,575; 5,501,759; 5,674,208; 5,843,032; 5,961,765; 6,027,477; 6,319,228; 6,471,673; 6,190,358; 6,605,057; 6,858,037; 7,001,358; 5,156,594; 5,217,482; 5,395,334; 5,702,439; 5,501,759; 5,674,208; 5,843,032; 5,961,765; 6,027,477; 6,319,228; 6,471,673; 5,759,192; 6,527,789; 5,147,302; 5,342,307; 6,290,485; 6,352,551; 6,402,778; 6,488,694; 6,511,505; 6,613,073; 6,582,458; 5,820,594; 5,824,173; 5,538,510; 4,323,071; 4,762,129; 4,846,186; 5,156,594; 5,217,482; 5,395,334; 5,156,594; 4,323,071; 5,040,548; 5,061,273; 5,451,233; 5,496,346; 5,496,275; 5,496,346; 5,040,548; 5,061,273; 5,451,233; 5,496,346; 4,596,563; 5,040,548; 5,061,273; 5,350,395; 5,451,233; 5,445,625; 6,083,213; 6,475,195; 5,421,955; 5,514,154; 5,603,721; 5,292,331; 5,674,278; 5,879,382; 6,344,053; 6,238,415; 5,421,955; 5,514,154; and 5,603,721.

The biologically active agents of the invention may be administered in dosages as described herein. It is known in the art that due to intersubject variability in biologically active agent pharmacokinetics, individualization of dosing regimen is necessary for optimal therapy. Dosing for a biologically active agent of the invention may be found by routine experimentation.

When a biologically active agent of the invention, is administered in a composition that comprises one or more agents, and the agent has a shorter half-life than the biologically active agent of the invention unit dose forms of the agent and the biologically active agent of the invention may be adjusted accordingly.

The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a biologically active agent according to the invention as an active ingredient. In addition, it may include other medicinal or pharmaceutical agents, carriers, adjuvants, etc.

Exemplary parenteral administration forms include solutions or suspensions of active biologically active agent in sterile aqueous solutions, for example, aqueous propylene glycol or dextrose solutions. Such dosage forms can be suitably buffered, if desired.

The activity of the biologically active agents of the present invention may be determined by the following procedure, as well as the procedure described in the examples below. N-terminal 6 His-tagged, constitutively active kinase is expressed in $E.$ $coli$ and protein is purified by conventional methods (Ahn et al. Science 1994, 265, 966-970). The activity of the kinase is assessed by measuring the incorporation of $\gamma$-$^{33}$P-phosphate from $\gamma$-$^{33}$P-ATP onto N-terminal His tagged substrate, which is expressed in $E.$ $coli$ and is purified by conventional methods, in the presence of the kinase. The assay is carried out in 96-well polypropylene plate. The incubation mixture (100, μL) comprises of 25 mM HEPES, pH 7.4, 10 mM MgCl$_2$, 5 mM β-glycerolphosphate, 100 μM Na-orthovanadate, 5 mM DTT, 5 nM kinase, and 1 μM substrate. Inhibitors are suspended in DMSO, and all reactions, including controls are performed at a final concentration of 1% DMSO. Reactions are initiated by the addition of 10 μM ATP (with 0.5 μCi γ-$^{33}$P-ATP/well) and incubated at ambient temperature for 45 minutes. Equal volume of 25% TCA is added to stop the reaction and precipitate the proteins. Precipitated proteins are trapped onto glass fiber B filterplates, and excess labeled ATP washed off using a Tomtec MACH III harvestor. Plates are allowed to air-dry prior to adding 30 μL/well of Packard Microscint 20, and plates are counted using a Packard TopCount.

The examples and preparations provided below further illustrate and exemplify the biologically active agents of the present invention and methods of preparing such biologically active agents. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

EXAMPLES

Example 1

Kinase Inhibition Assay

Purified kinase domains (e.g. mTor, P110α, P110β, P110γ, P110δ, PI4Kβ, DNA-PK, PKCα, PKCβ1, PKCβII, RET, and JAK2) were incubated with inhibitors at 2- or 4-fold dilutions over a concentration range of 50-0.001 μM or with vehicle (0.1% DMSO) in the presence of 10 μM ATP, 2.5 μCi of γ-$^{32}$P-ATP and substrate. Reactions were terminated by spotting onto nitrocellulose or phosphocellulose membranes, depending on the substrate; this membrane was then washed 5-6 times to remove unbound radioactivity and dried. Transferred radioactivity was quantitated by phosphorimaging and IC$_{50}$ values were calculated by fitting the data to a sigmoidal dose-response using Prism software.

Figure 2:
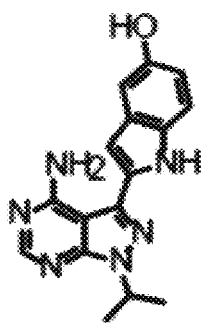
FIG. 2 is a table of in vitro $IC_{50}$ values in micromolar for inhibition of mTor or PI3K family members by PP242 (Torkinib) and PP30 (TORKinib2). The results suggest that PP242 and PP30 can selectively inhibit mTor as compared to type I PI3-kinases and other protein kinases.

The results as shown in FIG. 2 demonstrate that TORKinib is a potent and specific inhibitor of mTor with an IC$_{50}$ of about 8 nM. TORKinib was also relatively inactive against PKCβ, RET, and JAK2 (V617F), but inhibited PKCα with an IC$_{50}$ of about 50 nM. TORKinib2 likewise is an extremely potent and specific inhibitor of mTor with an IC$_{50}$ of about 80 nM. Furthermore, TORKinib2 does not inhibit PKCα significantly at about 1 μM or less. Therefore, TORKinib2 can be used to confirm that the effects of TORKinib are due to inhibition of mTor and not PKCα.

Example 2

Effect of mTor Inhibitors on Kinase Substrate Phosphorylation

L6 myoblasts were grown typically grown in DMEM supplemented with about 10% FBS, glutamine and penicillin/streptomycin. Confluent L6 myoblasts were differentiated into mytubes by culturing them for approximately 5 days in media containing about 2% FBS. L6 myotubes were maintained in media containing approximately 2% FBS until use.

In order to compare the effect of TORKinibs and PIK-90 on Akt phosphorylation, L6 myotubes were serum starved overnight and incubated with inhibitors or about 0.1% DMSO for approximately 30 minutes prior to stimulation with insulin (e.g. 100 nM) for about 10 minutes. Cells were lysed by scraping into ice cold lysis buffer (generally: 300 mM NaCl, 50 mM Tris pH 7.5, 5 mM EDTA, 1% TRITON™ X-100, 0.02% NaN3, 20 nM microcystin, Sigma phosphatase inhibitor cocktails 1 and 2, Roche protease inhibitor cocktail and 2 mM PMSF). After contacting cells with lysis buffer, the solution was briefly sonicated. Lysates were cleared by centrifugation, resolved by SDS-PAGE, transferred to nitrocellulose and immunoblotted using antibodies to phospho-Akt S473, phospho-Akt T308, Akt, and β-actin (Cell Signaling Technologies).

Figure 3:
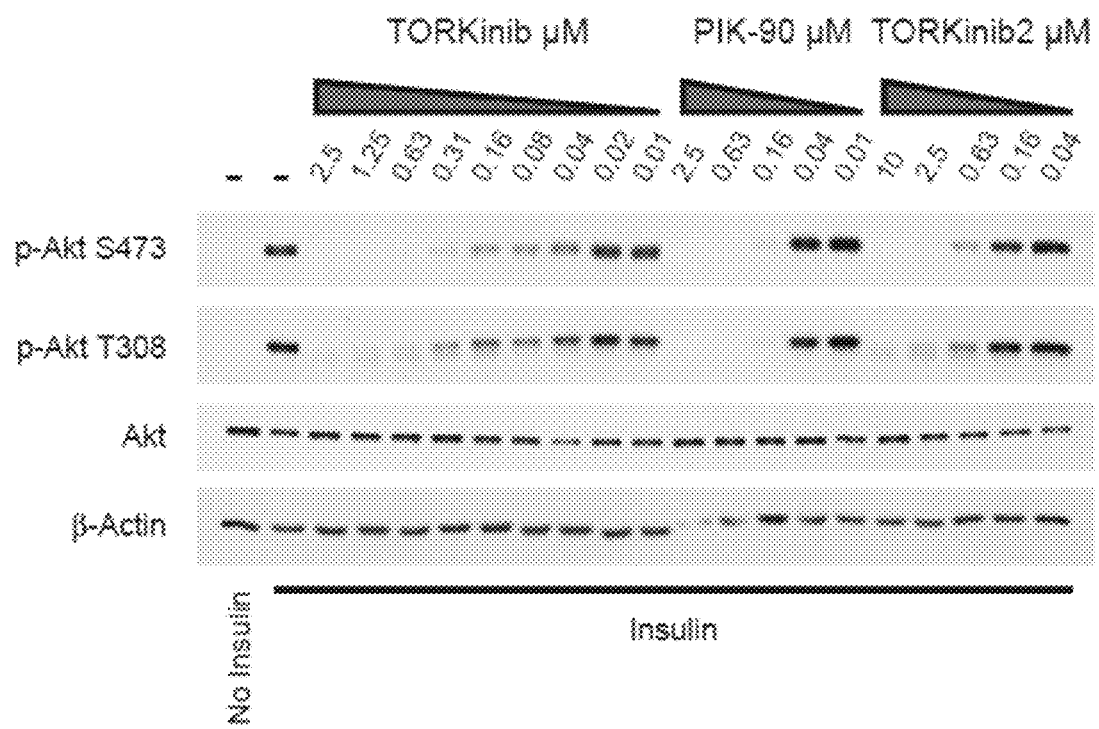
FIG. 3 is a western blot illustrating the dose dependent effect of treatment with TORKinibs on Akt phosphorylation of insulin stimulated L6 myotubes. The TORKinibs demonstrate a differential ability to inhibit phosphorylation of Akt S473 at lower concentrations than Akt T308. The differential effect is not seen in the control treatment with the PI3K inhibitor PIK-90.

The results as shown in FIG. 3 demonstrate that TOR-Kinib and TORKinib2 inhibit insulin stimulated phosphorylation of Akt at S473, confirming that mTor kinase activity is required for hydrophobic motif phosphorylation under the conditions tested Inhibition of mTor by TORKinibs also may result in loss of Akt phosphorylation at T308, but higher doses of the TORKinibs may be required to inhibit T308 phosphorylation as compared to S473 phosphorylation. In contrast, the PI3K inhibitor PIK-90 may inhibit the phosphorylation of both Akt sites equipotently under the conditions tested.

Example 3

Kinetics of Kinase Substrate Phosphorylation

Figure 4:
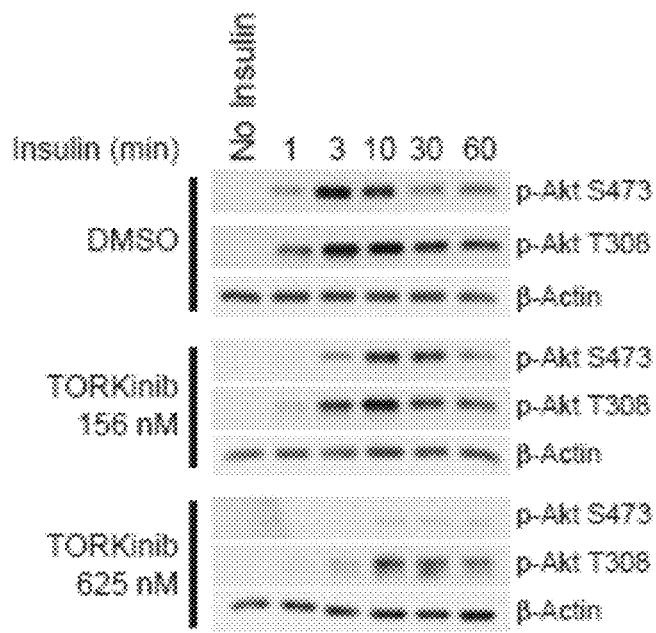
FIG. 4 is a western blot depicting a time course for Akt phosphorylation of insulin stimulated L6 myotubes treated with TORKinib at high (156 nM) and low (625 nM) concentration. The enhanced effect of TORKinib on Akt S473 phosphorylation is not likely due to kinetic differences between S473 and T308 phosphorylation.

L6 myotubes were serum starved overnight and incubated with TORKinib or 0.1% DMSO for about 30 minutes prior to stimulation with insulin (e.g. 100 nM) for about 1, 3, 10, 30 and 60 minutes. Cells were lysed by scraping into ice cold lysis buffer (generally 300 mM NaCl, 50 mM Tris pH 7.5, 5 mM EDTA, 1% TRITON™ X-100, 0.02% NaN3, 20 nM microcystin, Sigma phosphatase inhibitor cocktails 1 and 2, Roche protease inhibitor cocktail and 2 mM PMSF). After contacting cells with lysis buffer, the solution was briefly sonicated. Lysates were cleared by centrifugation, resolved by SDS-PAGE, transferred to nitrocellulose and immunoblotted using antibodies to phospho-Akt S473, phospho-Akt T308, and actin. The results as shown in FIG. 4 demonstrate that differential sensitivity of S473 and T308 to inhibition of phosphorylation by TORKinibs may not reflect differing kinetics of phosophorylation.

Example 4

Effect of Kinase Inhibitors on Mouse Embryonic Fibroblasts

Wild-type and SIN1−/− primary mouse embryonic fibroblasts (MEFs) were were grown in DMEM supplemented with about 10% FBS, glutamine and penicillin/streptomycin. MEFs were treated with TORKinib at about 2.5, 0.63, and 0.16 uM; rapamycin at approximately 15 nM; or PIK-90 at 625 nM for 30 minutes prior to insulin stimulation (e.g. 100 nM) for 10 minutes. Cells were lysed by scraping into ice cold lysis buffer (typically 300 mM NaCl, 50 mM Tris pH 7.5, 5 mM EDTA, 1% TRITON™ X-100, 0.02% NaN3, 20 nM microcystin, Sigma phosphatase inhibitor cocktails 1 and 2, Roche protease inhibitor cocktail and 2 mM PMSF).

Figure 5:
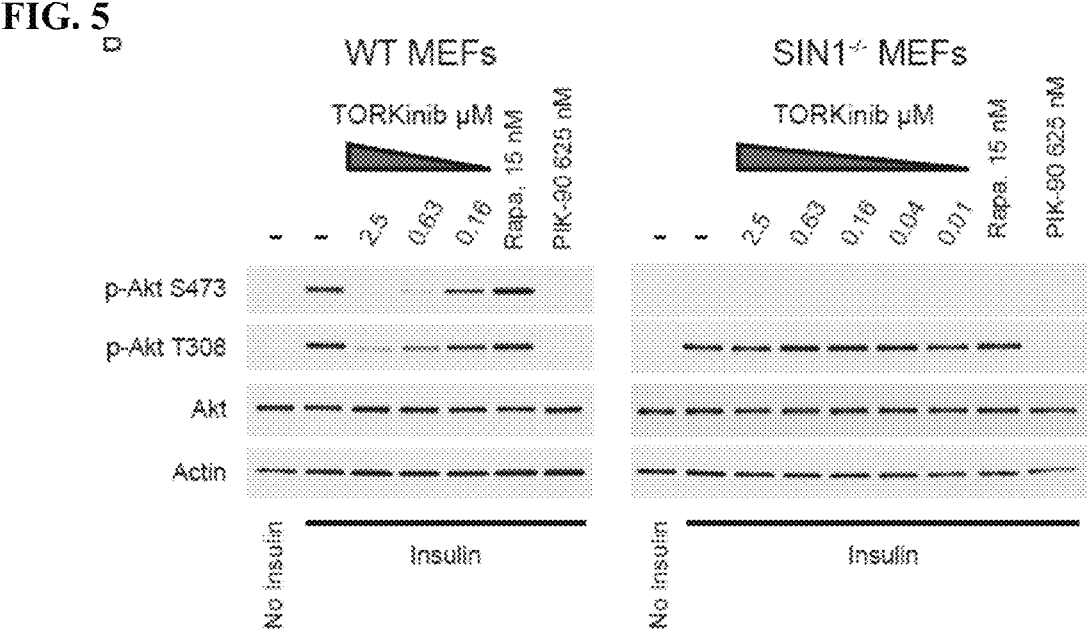
FIG. 5 is a western blot illustrating the effect of treatment of wild-type and SIN1−/− mouse embryonic fibroblasts (MEFs) with kinase inhibitors. The differential effect of TORKinib treatment on Akt S473 and T308 phosphorylation seen in wild-type MEFs is compared to rapamycin and PIK-90 which do not show a differential effect under the conditions tested. In contrast TORKinib has no significant effect on Akt phosphorylation in SIN1−/− MEFs. This suggests that TORKinib may block T308 phosphorylation of Akt indirectly by directly inhibiting mTor-dependent phosphorylation at S473.

After contacting cells with lysis buffer, the solution was briefly sonicated. Lysates were cleared by centrifugation, resolved by SDS-PAGE, transferred to nitrocellulose and immunoblotted using antibodies to phospho-Akt S473, phospho-Akt T308, Akt, and β-actin (Cell Signaling Technologies). The results are shown in FIG. 5.

SIN1 is a component of mTorC2, and knockout of SIN1 compromises the physical integrity of mTorC2 leading to a complete loss of Akt phosphorylation at S473 without affecting its phosphorylation at T308. Consistent with the results of FIG. 3 and FIG. 4, FIG. 5 shows that TORKinib inhibits the phosphorylation of Akt at both S473 and T308 in wild-type MEFs, but has no effect on the phosphorylation of T308 in SIN1−/− MEFs that lack mTorC2 under the conditions tested. Furthermore, the PI3K inhibitor PIK-90 blocks phosphorylation of T308 in SIN1−/− MEFs, indicating that the failure of TORKinib to block T308 in SIN1−/− MEFs may not reflect a general resistance of T308 to dephosphorylation in cells that lack mTorC2. This suggests that T308 phosphorylation caused by the TORKinibs results from inhibition of mTor mediated phosphorylation of S473, rather than inhibition of an unknown or off-target kinase. Further, this indicates that TORKinib blocks T308 phosphorylation indirectly by directly inhibiting mTor-dependent phosphorylation at S473.

Example 5

Phosphorylation of AKT, GSK3, TSC2, FoxO1/O3a, and S6

L6 myotubes were serum starved overnight and pre-treated with TORKinib at approximately 2.5, 0.63, 0.16, 0.04, and 0.01 μM; PIK-90 at about 625 nM; Akt-allo (AKTi Calbiochem) at about 10 μM; or rapamycin at approximately 15 nM followed by insulin stimulation (e.g. 100 nM). Cells were lysed by scraping into ice cold lysis buffer (generally: 300 mM NaCl, 50 mM Tris pH 7.5, 5 mM EDTA, 1% TRITON™ X-100, 0.02% NaN3, 20 nM microcystin, Sigma phosphatase inhibitor cocktails 1 and 2, Roche protease inhibitor cocktail and 2 mM PMSF). After contacting cells with lysis buffer, the solution was briefly sonicated. Lysates were cleared by centrifugation, resolved by SDS-PAGE, transferred to nitrocellulose and immunoblotted using antibodies to phospho-Akt S473, phospho-Akt T308, phospho GSK3α/β S21/9, phospho TSC2 T1462, phospho FoxO1/O3a T24/32, FoxO3a, phospho-S6 S240/244, and β-actin (Cell Signaling Technologies).

Figure 6:
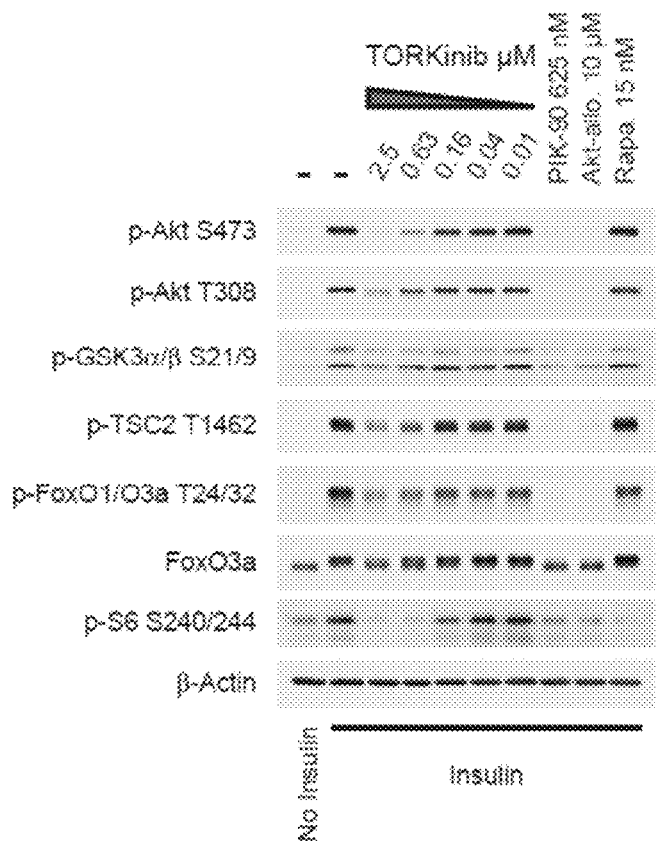
FIG. 6 is a western blot depicting the dose dependent effect of treatment of insulin stimulated L6 myotubes with the indicated kinase inhibitors on downstream kinase substrates. For all affected substrates, the extent of inhibition parallels the loss of phosphorylation at Akt T308. This indicates that loss of S473 phosphorylation alone may be unable to prevent phosphorylation of Akt substrates under the condition tested. In contrast, inhibition of PI3K or Akt inhibited the phosphorylation of the tested substrates under the conditions tested.

Low concentrations of TORKinib inhibit the phosphorylation of Akt S473 and higher concentrations inhibit Akt T308 phosphorylation under the conditions tested. Thus TORKinib may be used as in this experiment to determine if any substrates of Akt are especially sensitive to loss of phosphorylated S473. The results as shown in FIG. 6 suggest that kinase substrates downstream of mTor signaling are not sensitive to loss of phosphorylated Akt S473 alone. TORKinib partially inhibited the phosphorylation of both cytoplasmic and nuclear substrates of Akt and for all substrates tested the extent of inhibition parallels the phosphorylation of Akt at T308 under the concentrations used. This indicates that loss of phospho-S473 alone may be unable to prevent the phosphorylation of any of the Akt substrates tested. In contrast upstream inhibition of PI3K with PIK-90, and direct inhibition of Akt with Akt-allo completely inhibited the phosphorylation of Akt and its substrates under the conditions tested.

Example 6

Effect of Kinase Inhibitors on Cellular Proliferation

Figure 7:
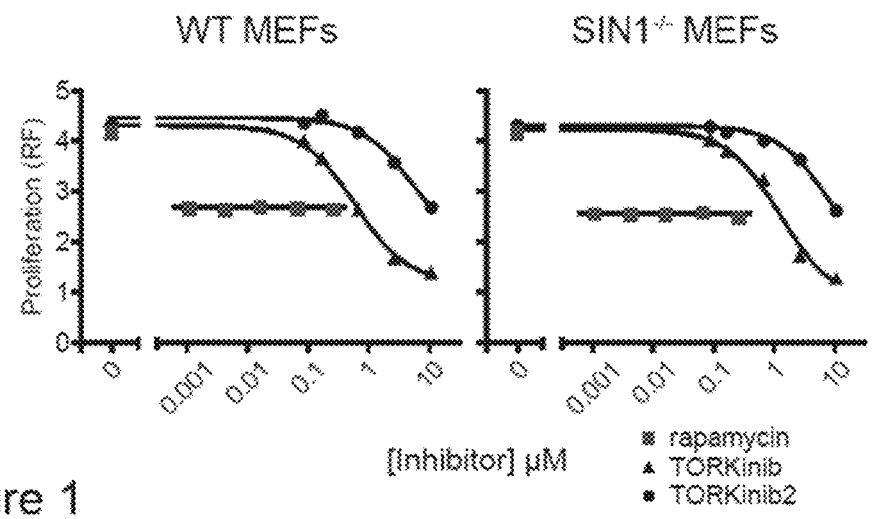
FIG. 7 illustrates the dose dependent inhibition of proliferation of wild-type and SIN1−/− mouse embryonic fibroblast by TORKinibs in comparison to rapamycin. TORKinib exhibits a more complete inhibition of proliferation than rapamycin under the conditions tested.

Wild-type and SIN1−/− MEFs were plated in 96 well tissue culture plates in DMEM supplemented with approximately 10% FBS, glutamine and penicillin/streptomycin at about 30% confluence and left overnight at about 37° C. in a humidified incubator to adhere. The following day, cells were treated with TORKinib, rapamycin, or vehicle (e.g. 0.1% DMSO). After 72 hours of treatment about 10 μl of approximately 440 μM Resazurin sodium salt (Sigma) was added to each well, and after about 18 hours the fluorescence intensity in each well was measured using a top-reading fluorescent plate reader with excitation at about 530 nM and emission at approximately 590 nM. The results are shown in FIG. 7.

Rapamycin was tested at concentrations above its mTor $IC_{50}$ and at all concentrations tested it inhibited cell growth to the same extent. In contrast, TORKinib had a dose dependent effect on proliferation and at higher doses was more effective than rapamycin at blocking cell proliferation under the conditions tested. In SIN1−/− MEFs, rapamycin was also typically less effective at blocking cell proliferation than TORKinib. That TORKinib and rapamycin exhibit very different anti-proliferative effects in SIN1−/− suggests that the two compounds may differentially affect mTorC1. Alternatively, the ability of TORKinib to more effectively bock MEF cellular proliferation than rapamycin may be a result of its ability to inhibit rapamycin resistant mTorC2.

Example 7

Phosphorylation of AKT, 70S6K, S6, 4EBP1, and MAPK

L6 myotubes were serum starved overnight and pre-treated with TORKinib at about 2.5, 0.63, 0.16, 0.04, and 0.01 μM; or rapamycin at approximately 62, 15, 4, 1, and 0.63 nM followed by insulin stimulation (at for example 100 nM). Cells were lysed by scraping into ice cold lysis buffer (typically 140 mM KCl, 10 mM Tris pH 7.5, 1 mM EDTA, 4 mM MgCl2, 1 mM DTT, 1% NP-40, 20 nM microcystin, Sigma phosphatase inhibitor cocktails 1 and 2, Roche protease inhibitor cocktail without EDTA and 2 mM PMSF). After contacting cells with lysis buffer, the solution was briefly sonicated. Lysates were cleared by centrifugation, resolved by SDS-PAGE, transferred to nitrocellulose and immunoblotted using antibodies to phospho-Akt S473, phospho-Akt T308, phospho p70S6K T389, phospho S6 S235/238, phospho S6 S240/244, phospho 4EBP1 T37/46, phospho 4EBP1 S65, 4EBP1, phospho-MAPK (p44/p42), and β-actin (Cell Signaling Technologies).

Figure 8:
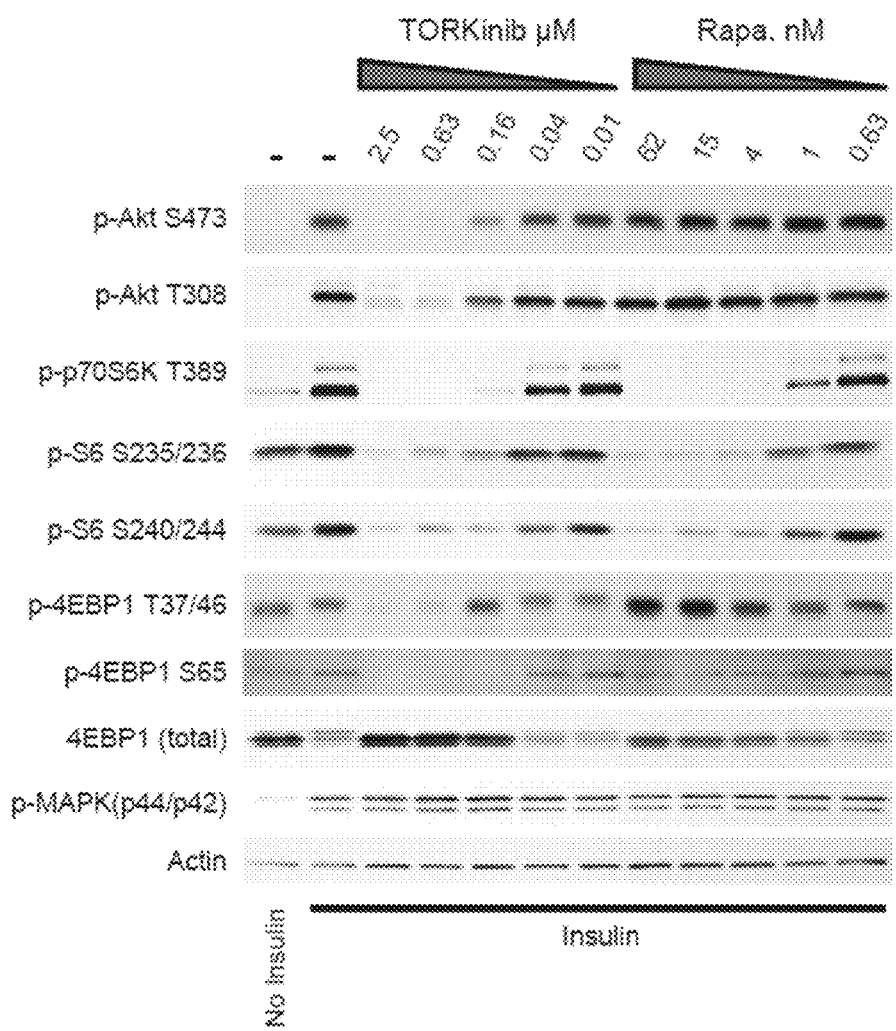
FIG. 8 is a western blot depicting a comparison of Akt, 70S6K, S6, 4EBP1, and MAPK phosphorylation in insulin treated L6 myotubes in response to TORKinib or rapamycin treatments. TORKinib is a more effective inhibitor of phosphorylation of Akt and 4EBP1 than rapamycin under the conditions tested.

The results as shown in FIG. 8 demonstrate that both rapamycin and TORKinib may inhibit phosphorylation of S6 kinase (S6K) and its substrate S6, and neither rapamycin nor TORKinib affect the phosphorylation of 4EBP1 at T70 under the conditions tested. In contrast, rapamycin weakly enhances the phosphorylation of 4EBP1 at T37/46 and weakly inhibits phosphorylation of 4EBP1 at S65, while TORKinib fully inhibits the phosphorylation at both sites at the concentrations examined.

Example 8

Phosphorylation of 70S6K and 4EBP1

Figure 9:
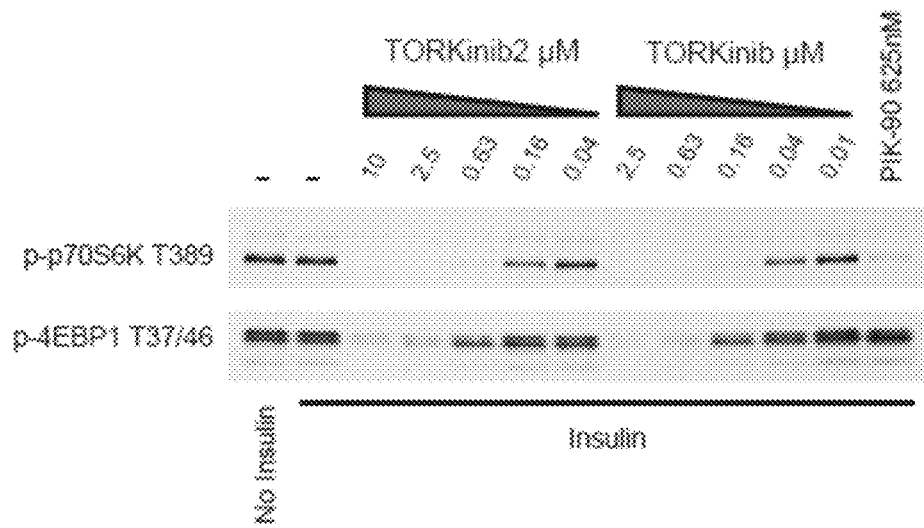
FIG. 9 is a western blot illustrating inhibition of rapamycin resistant phosphorylation of 4EBP1 by TORKinibs but not PIK-90 in insulin treated L6 myotubes.

L6 myotubes were serum starved overnight and pre-treated with TORKinib2 at about 10, 2.5, 0.63, 0.16, and 0.04 µM; TORKinib at approximately 2.5, 0.63, 0.16, 0.04, and 0.01 µM; or PIK-90 at about 625 nM followed by insulin stimulation (with for example 100 nM insulin). Cells were lysed by scraping into ice cold lysis buffer (typically 140 mM KCl, 10 mM Tris pH 7.5, 1 mM EDTA, 4 mM MgCl2, 1 mM DTT, 1% NP-40, 20 nM microcystin, Sigma phosphatase inhibitor cocktails 1 and 2, Roche protease inhibitor cocktail without EDTA and 2 mM PMSF). After contacting cells with lysis buffer, the solution was briefly sonicated. Lysates were cleared by centrifugation, resolved by SDS-PAGE, transferred to nitrocellulose and immunoblotted using antibodies to phospho p70S6K T389, and phospho 4EBP1 T37/46 (Cell Signaling Technologies). The results are shown in FIG. 9.

The results show that PIK-90 does not reduce the phosphorylation of 4EBP1 at T37/46, wherease both TORKinib and TORKinib2 are able to inhibit 4EBP1 phosphorylation at T37/46 under the conditions tested. This demonstrates that inhibition of PI3K and Akt activation alone may not be sufficient to block the phosphorylation of 4EBP1 at T37/46. This further supports the mechanism whereby TORKinibs are able to more fully inhibit mTor activity than rapamycin, or PI3K/Akt inhibitors.

Example 9

Method of m7GTP Cap Pull-Down Assay

Figure 10:
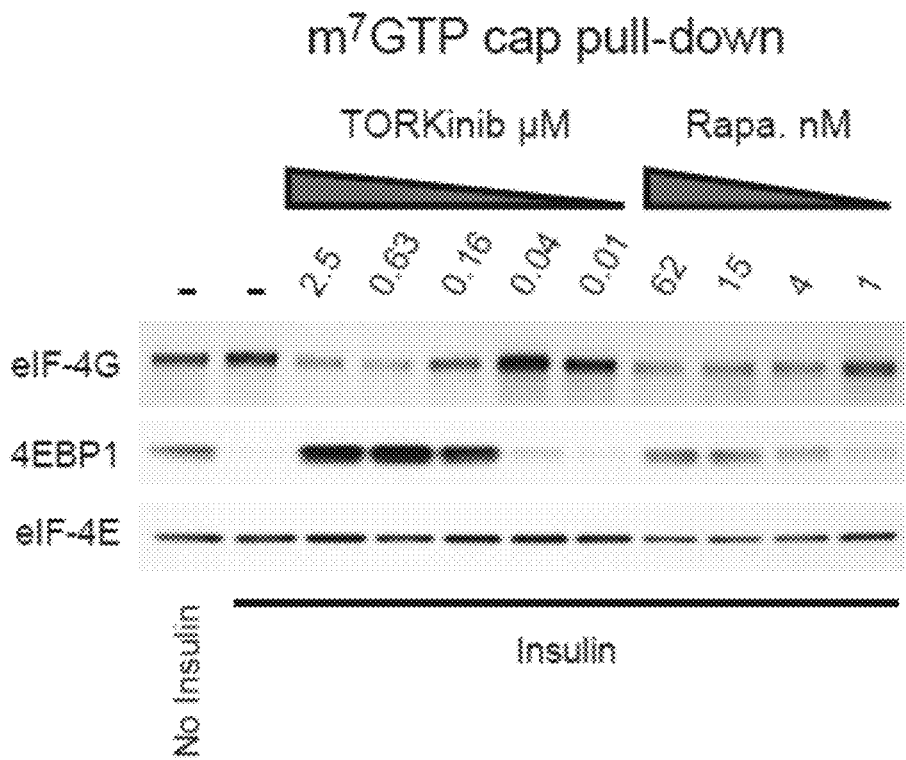
FIG. 10 is a western blot of co-precipitated proteins bound to m7GTP SEPHAROSE™ beads. TORKinib demonstrates increased efficacy over rapamycin in inducing 4EBP1 dephosphorylation and binding to the m7GTP binding protein eIF-4E in insulin treated L6 myotubes. Binding of 4EBP1 to eIF-4E results in release of eIF-4G bound to eIF-4E.

L6 myotubes were serum starved overnight and pretreated with TORKinib at about 2.5, 0.63, 0.16, 0.04, and 0.01 µM; or rapamycin at approximately 62, 15, 4, and 1 nM followed by insulin stimulation (100 nM). Cells were lysed by scraping into ice cold lysis buffer (generally 140 mM KCl, 10 mM Tris pH 7.5, 1 mM EDTA, 4 mM MgCl2, 1 mM DTT, 1% NP-40, 20 nM microcystin, Sigma phosphatase inhibitor cocktails 1 and 2, Roche protease inhibitor cocktail without EDTA and 2 mM PMSF). After contacting cells with lysis buffer, the solution was briefly sonicated. Lysates were cleared by centrifugation, about 50 µl of detergent free cap lysis buffer and about 20 µl of prewashed m7GTP SEPHAROSE™ beads were added to approximately 150 µl of cleared lysate and incubated at 4° C. overnight with spinning. The beads were washed twice with about 400 µl of cap wash buffer (typically cap lysis buffer with 0.5% NP-40 instead of 1% NP-40) and twice with about 500 µl PBS. The beads were boiled in SDS-PAGE sample buffer and the retained proteins were resolved by SDS-PAGE, transferred to nitrocellulose and immunoblotted using antibodies to eIF-4E, 4EBP1 (Cell Signaling Technologies) and eIF-4E (BD Biosciences). The results are shown in FIG. 10.

Mammalian translation initiation factor 4F (eIF-4F) consists of three subunits, eIF-4A, eIF-4E, and eIF-4G. eIF-4E binds tightly to m7GTP, and the subunit eIF-4G binds tightly to the m7GTP bound eIF-4E during translation initiation. In response to anti-proliferative signals, PTEN activation, or kinase inhibition, the mTor substrate 4EBP1 can become dephosphorylated. Upon dephosphorylation, 4EBP1 binds to eIF-4E and displaces eIF-4G inhibiting translation initiation. The phosphorylation of 4EBP1 by mTor is complicated in that it occurs at multiple sites and not all sites are equally effective at causing disssociation of 4EBP1 from eIF-4E. Furthermore, a hierarchy is thought to exist whereby T37/46 require phosphorylation prior to S65/T70. Phosphorylation at S65 may cause the greatest degree of disassociation of 4EBP1 from eIF-4E and is probably the most important site in cells, but other phosphorylation sites of 4EBP1 play a role in regulating translation initiation as well. eIF-4E also binds tightly to m7GTP SEPHAROSE™ beads. This allows the examination of proteins bound to eIF-4E by pull-down or co-precipitation assay, which is a proxy for protein translation activity.

The results show that, under the conditions tested, rapamycin causes partial inhibition of the insulin stimulated release of 4EBP1 from eIF-4E consistent with the partial inhibition of S65 phosphorylation seen in FIG. 8. The rapamycin induced retention of 4EBP1 was accompanied by a loss of recovery of eIF-4G because the binding of 4EBP1 and eIF-4G to eIF-4E are mutually exclusive. In contrast, treatment with TORKinib caused a greater retention of 4EBP1, raising the retention of 4EBP1 above the level seen in unstimulated serum-starved cells which are known to have extremely low levels of protein translation.

Example 10

Phosphorylation of 70S6K and 4EBP1 in Mouse Embryonic Fibroblasts

Figure 11:
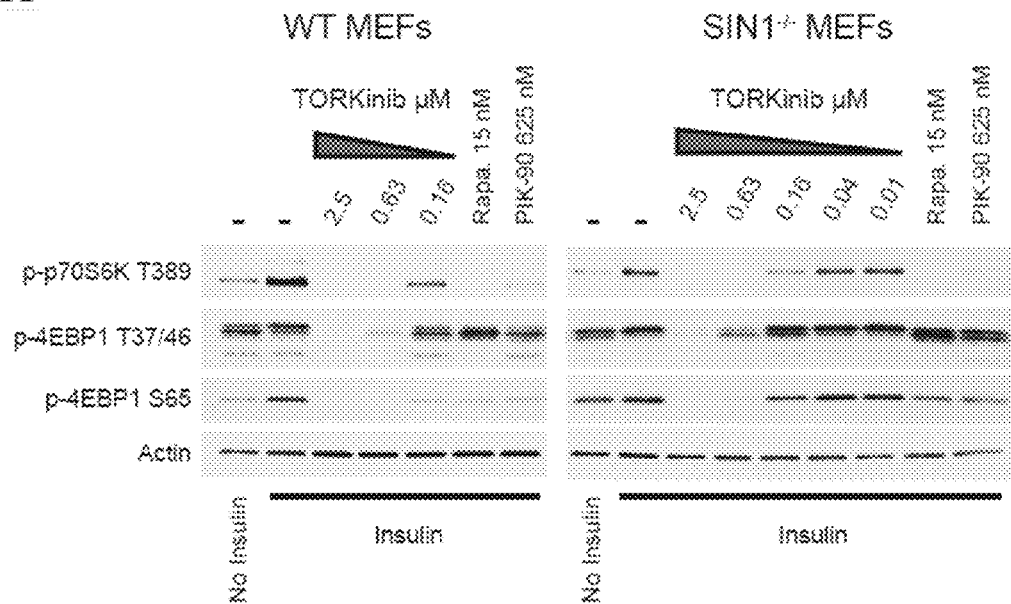
FIG. 11 is a western blot illustrating the effect of TORKinib treatment of wild-type and SIN1−/− MEFs on phosphorylation of the indicated kinase substrates. TORKinib is a more complete inhibitor of 4EBP1 phosphorylation than rapamycin on both wild-type and SIN1−/− MEFs.

Wild-type and SIN1-/- primary mouse embryonic fibroblasts (MEFs) were were grown in DMEM supplemented with about 10% FBS, glutamine and penicillin/streptomycin. MEFs were treated with TORKinib at approximately 2.5, 0.63, and 0.16 uM; rapamycin at about 15 nM; or PIK-90 at about 625 nM for approximately 30 minutes prior to insulin stimulation (e.g. 100 nM) for about 10 minutes. Cells were lysed by scraping into ice cold lysis buffer (generally: 300 mM NaCl, 50 mM Tris pH 7.5, 5 mM EDTA, 1% TRITON™ X-100, 0.02% NaN3, 20 nM microcystin, Sigma phosphatase inhibitor cocktails 1 and 2, Roche protease inhibitor cocktail and 2 mM PMSF). After contacting cells with lysis buffer, the solution was briefly sonicated. Lysates were cleared by centrifugation, resolved by SDS-PAGE, transferred to nitrocellulose and immunoblotted using antibodies to phospho-p70S6K T389, phospho-4EBP1 T37/46, phospho-4EBP1 S65, and β-actin (Cell Signaling Technologies). The results are shown in FIG. 11.

TORKinib is a more complete inhibitor of 4EBP1 phosphorylation under the conditions tested than rapamycin in wild-type and SIN1-/- cells as well, indicating that the presence of mTorC2 may not be required for rapamycin and TORKinib to have distinct effects on 4EBP1 phosphorylation, and demonstrating that TORKinib is a more complete inhibitor of mTorC1 than rapamycin under the conditions tested.

Rapamycin appears to be a substrate selective inhibitor of mTorC1 as shown by its ability to completely block the phosphorylation of p70S6K but not 4EBP1 at the concentrations examined. Consistent with this finding, experiments with purified proteins have shown that rapamycin/FKBP12 only partially inhibits the in vitro phosphorylation of 4EBP1 at Ser 65 by mTor but can fully inhibit the in vitro phosphorylation of S6K. By contrast, LY294002, a direct inhibitor of many PI3K family members including mTor, was equally effective at inhibiting the phosphorylation of S6K and 4EBP1 by mTor in vitro. These results show that TORKinib, in addition to being useful for investigating mTorC2, reveal rapamycin-resistant components of mTorC1 function. Indeed, proliferation of SIN1-/- MEFs is more sensitive to TORKinib than rapamycin (FIG. 7), suggesting that rapamycin-resistant functions of mTorC1, including aspects of translation initiation, may be key to the antiproliferative effects of TORKinib.

Example 11

In Vivo Effect of mTor Inhibitors on Kinase Substrate Phosphorylation

To explore the tissue specific roles of mTorC1 and mTorC2 and confirm the pathway analysis from cell culture experiments, mice were treated with TORKinib or rapamycin, and the acute effect of these drugs on insulin signaling in fat, skeletal muscle and liver tissue were examined.

Figure 12:
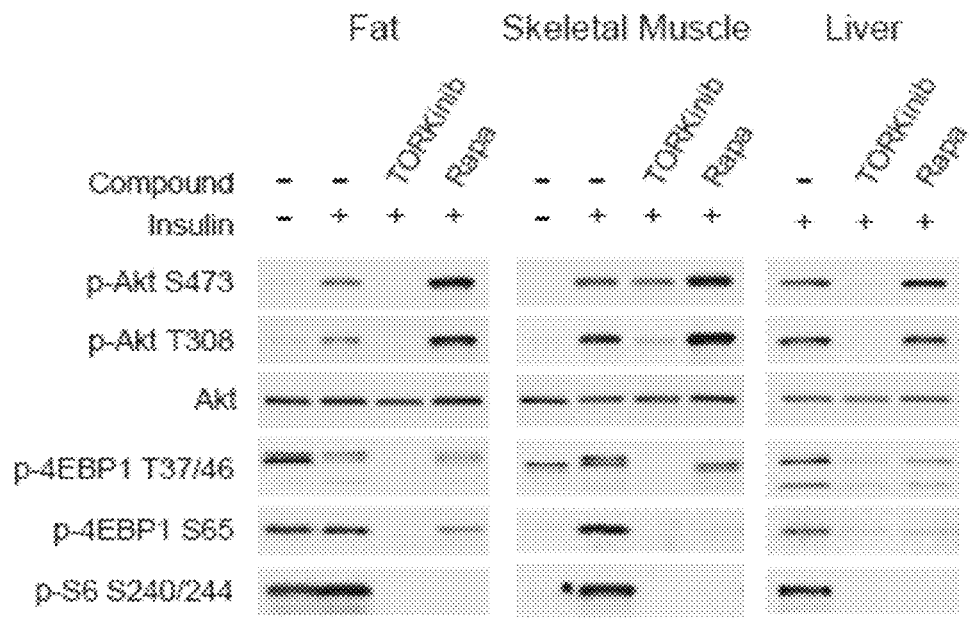
FIG. 12 is a western blot illustrating the in vitro effect of TORKinib treatment of insulin stimulated mice on PI3K signaling in fat, skeletal muscle, and liver. Under the conditions tested, in fat and liver TORKinib completely inhibits Akt S473 and T308 phosphorylation. In skeletal muscle, TORKinib partially inhibits Akt phosphorylation at the concentration tested.

Approximately 6 week old male C57BL/6 mice were starved of food overnight. Drugs were prepared in about 100 µl of vehicle containing approximately 20% DMSO, 40% PEG-400 and 40% Saline; TORKinib (e.g. 0.4 mg), rapamycin (e.g. 0.1 mg) or vehicle alone was injected intraperitoneally. After about 30 minutes for the rapamycin-treated mouse or about 10 min for the TORKinib and vehicle treated mice, approximately 250 mU of insulin in about 100 µl of saline was injected intraperitoneally. Typically 15 minutes after the insulin injection, the mice were sacrificed by $CO_2$ asphyxiation followed by cervical dislocation. Tissues were harvested and frozen on liquid nitrogen in about 200 µl of cap lysis buffer. The frozen tissue was thawed on ice, manually disrupted with a mortar and pestle, and then further processed with a micro tissue-homogenizer (Fisher PowerGen 125 with Omni-Tip probe). Protein concentration of the cleared lysate was measured by Bradford assay and 5-10 µg of protein was analyzed by western blot. The results are shown in FIG. 12.

In fat and liver, TORKinib was able to completely inhibit the phosphorylation of Akt at S473 and T308, under the conditions tested, which is consistent with its effect on these phosphorylation sites observed in cell culture. TORKinib was only partially able to inhibit the phosphorylation of Akt in skeletal muscle. Consistent with this finding, a muscle specific knockout of the integral mTorC2 component rictor also resulted in only a partial loss of Akt phosphorylation at S473. These results suggest that a kinase other than mTor may contribute to phosphorylation of Akt in muscle.

Rapamycin often stimulates the phosphorylation of Akt, probably by relieving feedback inhibition from S6K to the insulin receptor substrate 1 (IRS1), a key signaling molecule that links activation of the insulin receptor to PI3K activation. In all tissues examined, and especially in fat and muscle, acute rapamycin treatment activated the phosphorylation of Akt at S473 and T308 (FIG. 12). In contrast to rapamycin, by inhibiting both mTorC2 and mTorC1, TORKinib suppresses rather than enhances Akt activation under the conditions tested.

As was seen in cell culture, rapamycin and TORKinib differentially affect the mTorC1 substrates S6K and 4EBP1 in vitro. S6 phosphorylation was equally inhibited by rapamycin and TORKinib in all tissues examined. TORKinib was effective at blocking the phosphorylation of 4EBP1 on both T37/46 and S65 in all tissues examined. While rapamycin was more effective at inhibiting the phosphorylation of 4EBP1 in vitro than in cell culture experiments, rapamycin did not block 4EBP1 phosphorylation as completely as TORKinib under the conditions tested.

Rapamycin has been a powerful pharmacological tool allowing the discovery of mTor's central role in the control of protein synthesis. Since the discovery of a rapamycin-insensitive mTor complex there has been a significant effort to develop pharmacological tools for studying this complex. Here two structurally distinct compounds were used to chemically dissect the effects of mTor kinase inhibition toward mTorC1 and mTorC2 activity. The results of the present invention has shown through the use of these inhibitors that the inhibition of mTor kinase activity is sufficient to prevent the phosphorylation of Akt at S473, under the conditions tested, providing further evidence that mTorC2 may be the kinase responsible for Akt hydrophobic motif phosphorylation. The results disclosed herein further provide that phosphorylation at T308 is probably linked to phosphorylation at S473, as had been observed in experiments where mTorC2 was disabled by RNAi, but not homologous recombination. However, inhibition of mTorC2 does not result in a complete block of Akt signaling, as T308P is partially maintained and Akt substrate phosphorylation is only modestly affected when S473 is not phosphorylated under the conditions tested. Despite its modest effect on Akt substrates, TORKinib was a more effective anti-proliferative agent than rapamycin. These results were reproduced even in cells lacking mTorC2 (SIN1−/−), suggesting that downstream mTorC1 substrates might be responsible for TORKinib's strong anti-proliferative effects. The results disclosed herein provide that phosphorylation of the mTorC1 substrate 4EBP1 was partially resistant to rapamycin treatment at concentrations that fully inhibit p70S6K while TORKinib completely inhibits both p70S6K and 4EBP1. Consequently, the enhanced block of cell proliferation by TORKinib compared with rapamycin may reflect in part its ability to more efficiently inhibit eIF4E-dependent translation control.

Example 12

Kinase Signaling in Blood

PI3K/Akt/mTor signaling was measured in blood cells using the phosflow method. The advantage of this method is that it is by nature a single cell assay so that cellular heterogeneity can be detected rather than population averages. This allows concurrent dinstinction of signaling states in different populations defined by other markers. Phosflow is also highly quantitative. To test the effects of PP242 (TORKinib), unfractionated murine splenocytes were stimulated with anti-CD3 to initiate T-cell receptor signaling. The cells were then fixed and stained for surface markers and intracellular phosphoproteins. The results showed that PP242 inhibits anti-CD3 mediated phosphorylation of Akt-S473 and S6, whereas rapamycin inhibits S6 phosphorylation and enhances Akt phosphorylation under the conditions tested.

Figure 13:
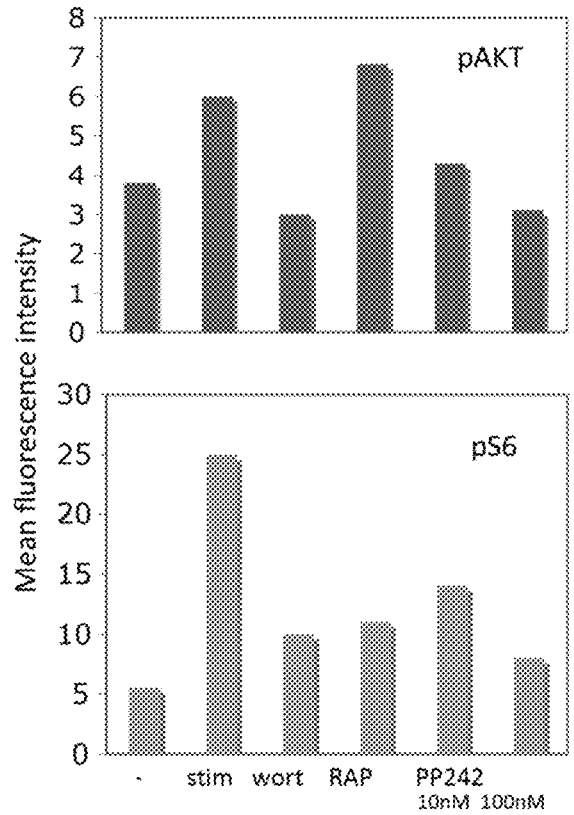
FIG. 13 illustrates the relative phosphorylation levels of Akt and S6 in T cells stimulated with anti-CD3 antibody and treated with the indicated kinase inhibitors. TORKinib (PP242) is a potent inhibitor of S6 and Akt phosphorylation in stimulated T-cells.

Aliquots of whole blood were incubated for 15 minutes with vehicle (e.g. 0.1% DMSO) or kinase inhibitors at various concentrations, before addition of stimuli to cross-link the T cell receptor (TCR) (anti-CD3 with secondary antibody) or the B cell receptor (BCR) using anti-kappa light chain antibody (Fab'2 fragments). After approximately 5 and 15 minutes, samples were fixed (e.g. with cold 4% paraformaldehyde) and used for phosflow. Surface staining was used to distinguish T and B cells using antibodies directed to cell surface markers that are known to the art. Akt and S6 phosphorylation levels were then measured by incubating the fixed cells with alexa fluor labeled antibodies specific to the phosphorylated isoforms of these proteins. The population of cells was then analyzed by flow cytometery. The results are shown on FIG. 13.

Example 13

Effect of Kinase Inhibitors on Lymphocyte Proliferation

Figure 14:
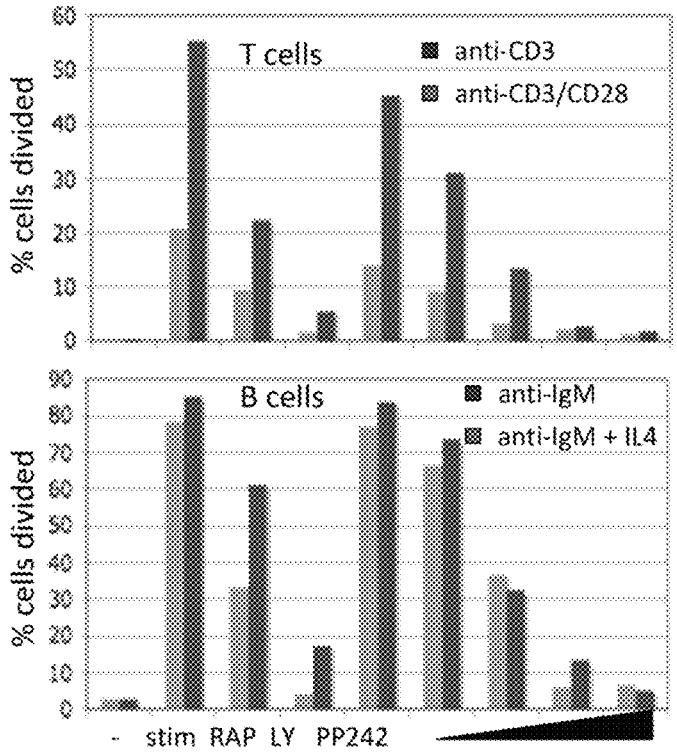
FIG. 14 illustrates the effect of the indicated kinase inhibitors on cellular division of T cells and B cells stimulated with antibodies to cell-surface markers (anti CD3/anti CD3+anti CD28 for T cells and anti IgM/anti IgM+anti IL-4 for B cells). TORKinib (PP242) is a potent inhibitor of division of stimulated T and B-cells.

To determine the effects of PP242 on lymphocyte function, purified murine T cells from lymph nodes and B cells from spleen were measured for their proliferative response to antigen receptor engagement in the presence or absence of various inhibitors. The results are shown in FIG. 14.

Compared to rapamycin, TORKinib caused a more complete suppression of lymphocyte proliferation under all conditions tested, with $IC_{50}$ values of approximately 100-300 nM. These effects were similar to treatment with LY294002 (10 µM), a non specific PI3K/mTor inhibitor.

Example 14

Effect of Kinase Inhibitors on Leukemic Cell Viability

Figure 15A:
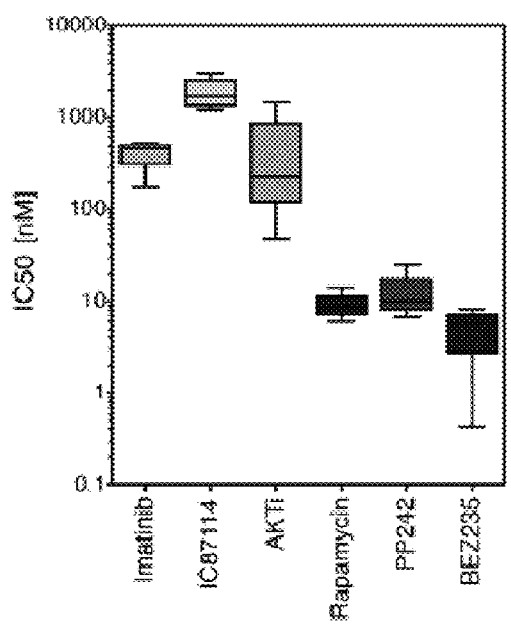
FIGS. 15A-15B illustrate the in vitro effect of the indicated inhibitors on cellular proliferation of p190 transduced cells (bone marrow cells expressing the p190 isoform of the oncoprotein BCR-ABL, also known as p190-transduced cells) as measured by reduction of 3-(4,5-dimethylthiazol-2-yl)-5-(3-carboxymethoxyphenyl)-2-(4-sulfophenyl)-2H-tetrazolium salt (MTS assay).
Figure 15B:
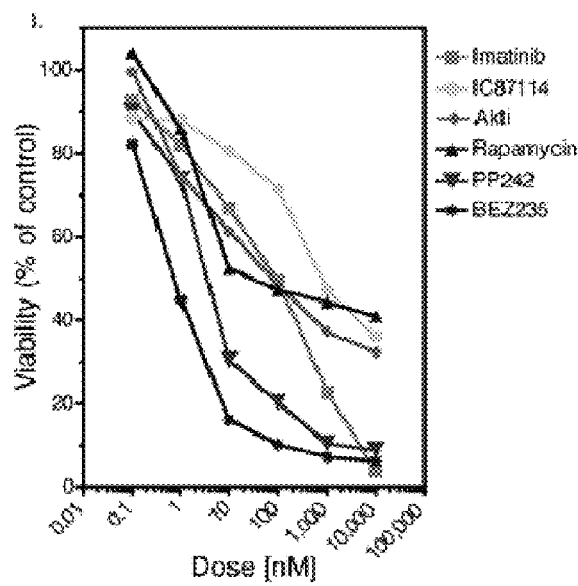

Murine B lymphoid progenitor cells transformed by a retrovirus encoding human p190-BCR-ABL (p190 transduced cells) were used to study the effect of kinase inhibitors on cell viability, proliferation, and colony forming activity. P190 transduced cells were cultured in duplicate for about 48 hrs in the presence of the indicated drugs, and reduction of 3-(4,5-dimethylthiazol-2-yl)-5-(3-carboxymethoxyphenyl)-2-(4-sulfophenyl)-2H-tetrazolium salt (MTS) was measured over the approximately the last 2 hr. FIG. 15A shows mean $IC_{50}$ values and the 95% confidence interval. FIG. 15B shows the results of a representative experiment.

FIGS. 15A-15B illustrate the effect of kinase inhibitors on p190 transduced cells on cell viability. The plateau effect seen at high concentrations of IC87114 and rapamycin is due to the fact that under the conditions tested, these two inhibitors are primarily cytostatic, while the others tested appear to induce both cell cycle arrest and apoptosis. These findings show that single inhibition of PI3K or mTorC1 signaling nodes may be insufficient to eradicate leukemia cells, whereas dual inhibition of both nodes is sufficient to cause massive cell death.

Example 15

Effect of Combination Therapy

Figure 16:
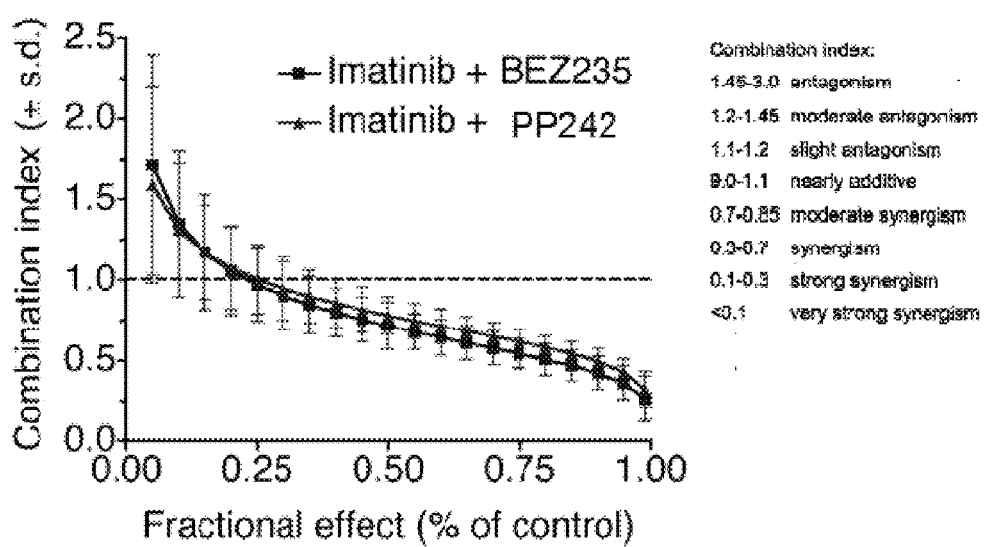
FIG. 16 illustrates the synergistic activity of treatment with the inhibitors PP242 and BEZ235 in combination with imatinib on p190 transduced cells as determined by MTS assay.

P190 transduced cells are highly sensitive to imatinib and dasatinib. To test for drug synergism at submaximal doses of imatinib, p190 transduced cells were treated with a range of drug concentrations alone and in combination at fixed rations. Calcusyn software was then used to determine the combination index according to the method of Chou 2006 Pharmacological reviews 58:621-681. The results as shown in FIG. 16 show that PP242 and BEZ235 both display a moderate to strong synergy with imatinib over a broad dose range.

Example 16

Method of Colony Forming Assay on Kinase Inhibitors with Mouse Cells

Figure 17:
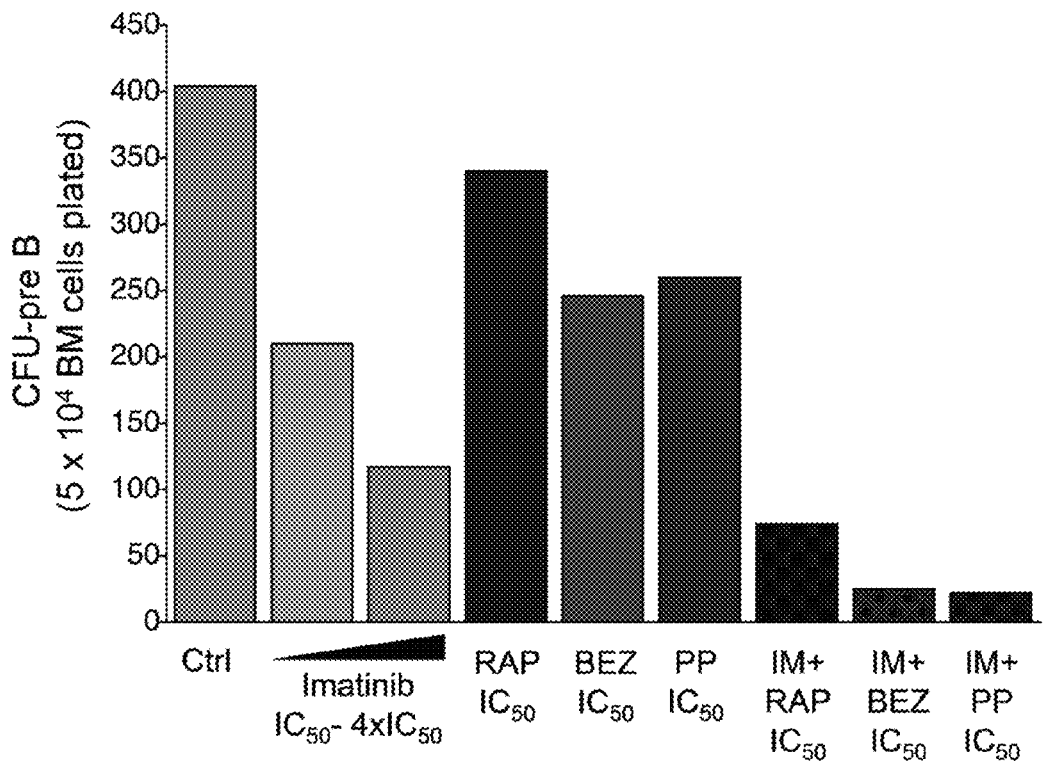
FIG. 17 illustrates the effect of the indicated kinase inhibitors alone or in combination with imatinib on the colony forming activity of p190 transduced bone marrow cells. Combination therapy shows increased efficacy in inhibiting colony forming activity at the $IC_{50}$ of the individual compounds under the conditions tested.

Murine bone marrow cells freshly transformed with p190 BCR-Abl were plated in the presence of various drug combinations in M3630 methylcellulose media for about 7 days with recombinant human IL-7 in about 30% serum, and the number of colonies formed was counted by visual examination under a microscope. The results as shown in FIG. 17 show that, compared to rapamycin, PP242 and BEZ235 potentiate the effects of a half maximal concentration of imatinib at the concentrations examined.

Example 17

Colony Forming Assay on Kinase Inhibitors with Human Cells

Figure 18:
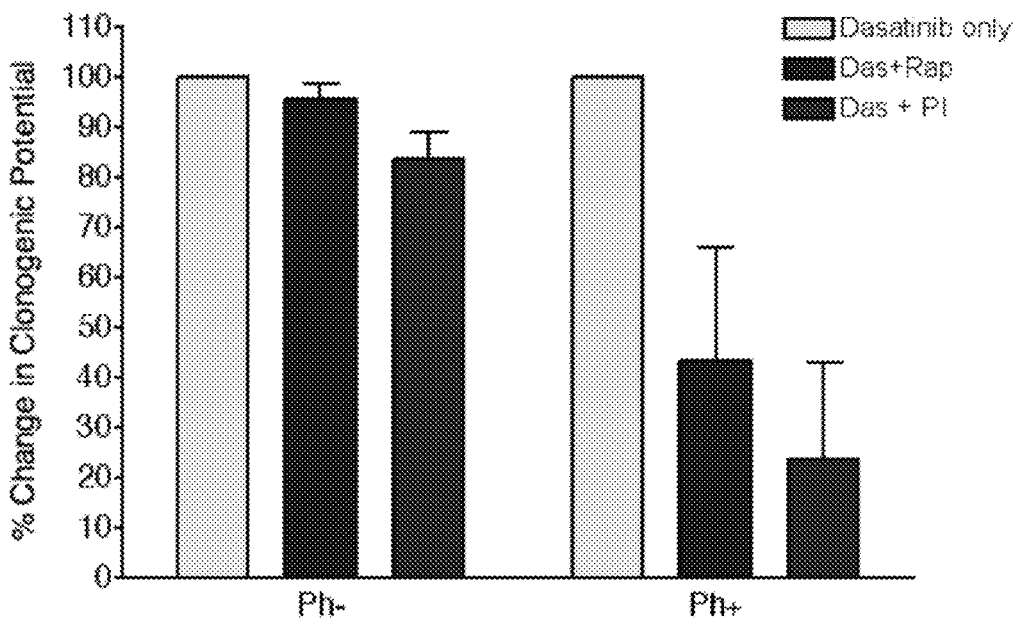
FIG. 18 illustrates the differential effect of the indicated kinase inhibitors alone or in combination with dasatinib on the colony forming activity of primary human B-cell acute lymphoblastic leukemia cells that are positive (Ph+) or negative (Ph−) for the philladelphia chromosome. Combination treatment shows increased efficacy against Ph+ acute lymphoblastic leukemia cells under the conditions tested.

Human peripheral blood mononuclear cells were obtained from philladelphia chromosome positive (Ph+) and negative (Ph−) patients upon initial diagnosis or relapse. Live cells were isolated and enriched for CD19+ CD34+ B cell progenitors. After overnight liquid culture, cells were plated in methocult GF+ H4435, Stem Cell Tehcnologies) suplemented with cytokines (IL-3, IL-6, IL-7, G-CSF, GM-CSF, CF, Flt3 ligand, and erythropoietin) and about 50 nM dasatinib in combination with either rapamycin or PI-103. Colonies were counted by microscopy 12-14 days later. The results as shown in FIG. 18 show a stronger effect of dasatinib-PI-103 combination as compared to dasatinib-rapamycin combination, although both combinations show evidence of additive or synergistic activity.

Example 18

Effect of Combination Therapy

Figure 19:
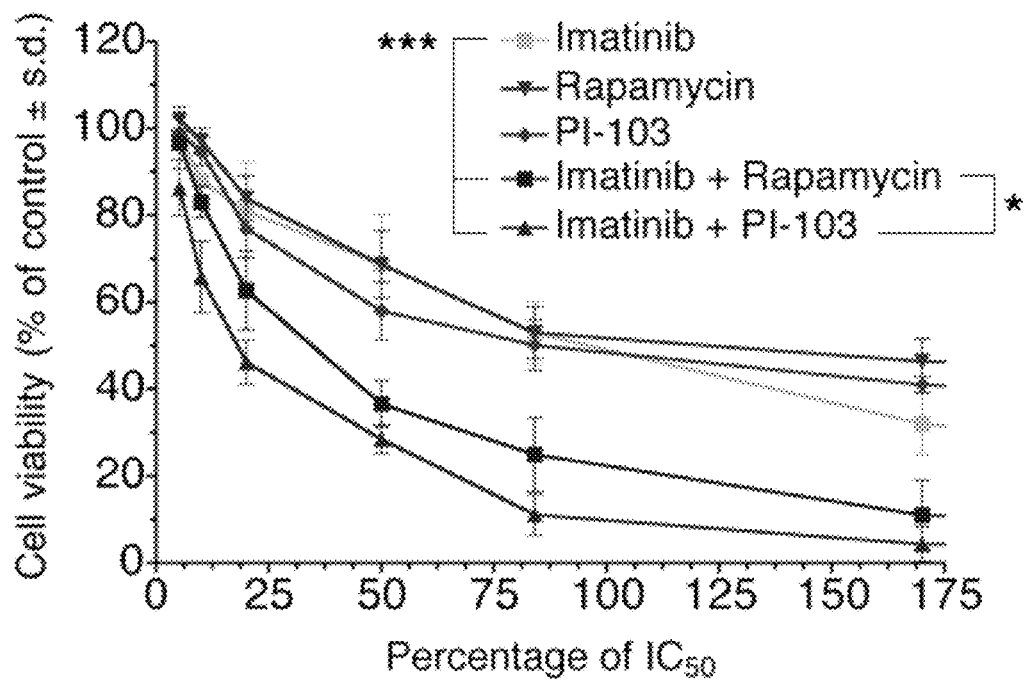
FIG. 19 illustrates the effect of 48 hr treatment with the indicated inhibitors on viability of cells as measured by MTS assay. Combination treatment with imatinib and either rapamycin or PI-103 shows increased inhibition of cellular viability in comparison to treatment with a single inhibitor under the conditions tested.
Figure 20:
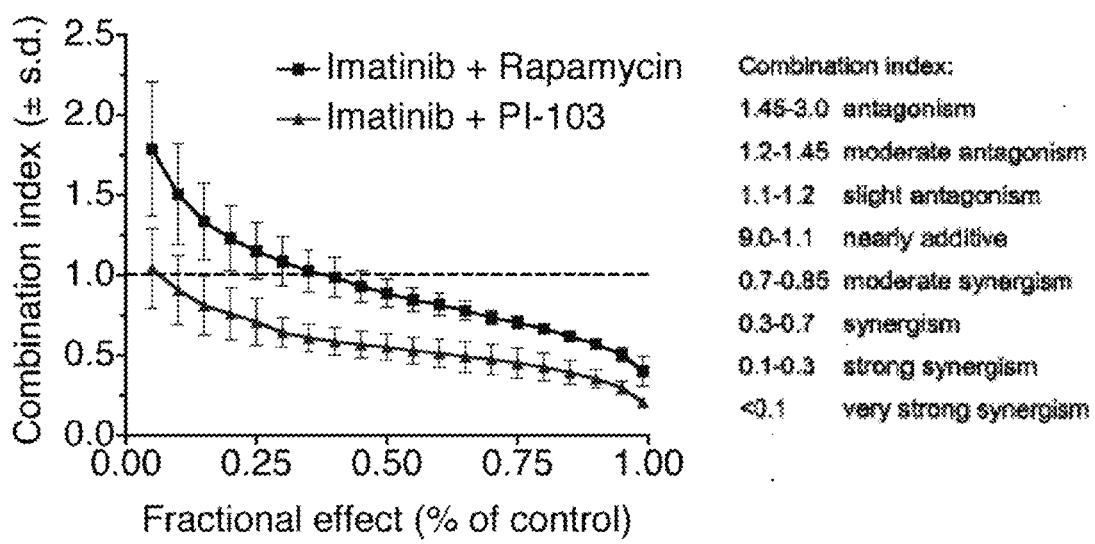
FIG. 20 illustrates the synergistic or additive effect of rapamycin and PI-103 in combination with imatinib on viability of cells as measured by MTS assay.

P190 Transduced cells were treated with various concentrations of the drugs or drug combinations as indicated for approximately 48 hrs, and reduction of MTS was measured over about the last two hours. The results as shown in FIG. 19 show that both rapamycin and PI-103 potentiate the anti-proliferative effects of imatinib under the conditions tested. FIG. 20 shows that combination index of imatinib in combination with rapamycin or PI-103. This suggests that in combination with rapamycin, PI-103 is more synergistic than rapamycin over a broad dose range under the conditions tested.

Example 19

In Vivo Effect of Kinase Inhibitors, Spleen

The murine bone marrow infection/transplantation method was used to determine the effect of kinase inhibitors on disregulated cellular proliferation in vitro. The MSCV-p190-BCR-Abl-Ires-GFP (MIG-p190) or MSCV-p190-BCR-Abl-Ires-hCD4Δtail (MIC-p190) retroviral vectors were assembled in 293T cells and used to transduce bone marrow cells. The GFP and CD4Δtail markers allow quantitation by FACS analysis and/or enrichment by magnetic sorting of transduced cells.

Female Balb/c recipient mice were lethally irradiated from a γ source in two doses about 4 hr apart, with approximately 5Gy each. About 1 hr after the second radiation dose, mice were injected i.v. with about $1\times10^6$ leukemic cells from early passage MIG-p190 or MIC p190 cultures. These cells were administered together with a radioprotective dose of about $5\times10^6$ normal bone marrow cells from 3-5 week old donor Balb/c mice. Recipients were given antibiotics in the water and monitored daily. Mice who became sick after about 14 days were euthanized and lymphoid organs were harvested for analysis. Kinase inhibitor treatment began about 10 days after leukemic cell injection and continued daily until the mice became sick or a maximum of approximately 35 days post-transplant. Inhibitors were given by oral lavage.

Figure 21:
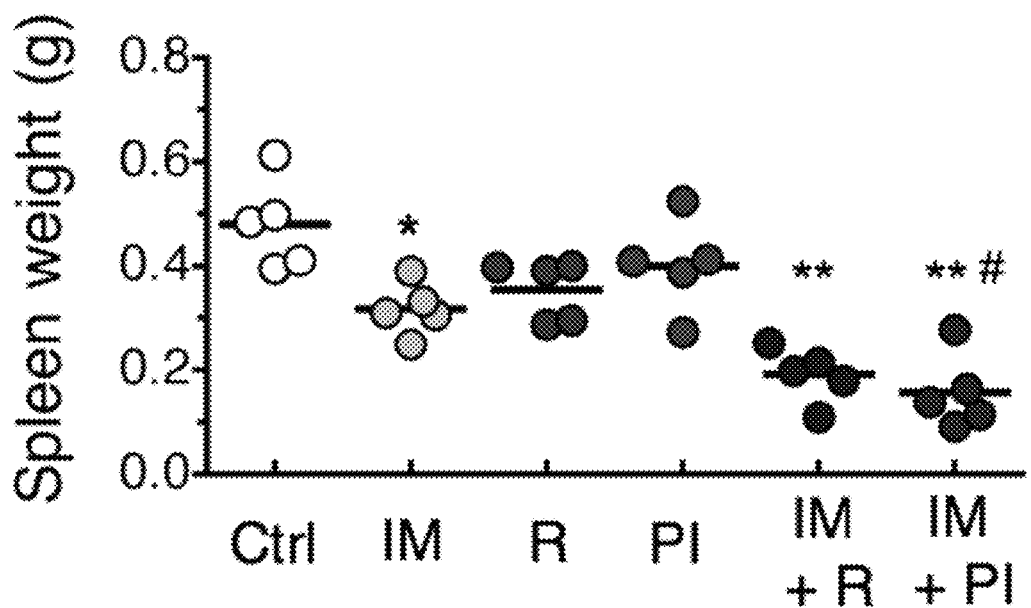
FIG. 21 illustrates the effect of the indicated inhibitors on splenomegaly in a syngenic mouse leukemia transplant model.

FIG. 21 shows the results of treatment with imatinib, rapamycin, imatinib in combination with rapamycin and imatinib in combination with PI-103. The results show a significant decrease in splenomegaly with kinase inhibitor. The results also show the enhanced beneficial effect of combination therapy under the conditions tested.

Example 20

In Vivo Effect of Kinase Inhibitors, Peripheral Blood

Female Balb/c recipient mice were lethally irradiated from a γ source in two doses about 4 hr apart, with approximately 5Gy each. About 1 hr after the second radiation dose, mice were injected i.v. with about $1 \times 10^6$ leukemic cells from early passage MIG-p190 or MIC p190 cultures. These cells were administered together with a radioprotective dose of about $5 \times 10^6$ normal bone marrow cells from 3-5 week old donor Balb/c mice. Recipients were given antibiotics in the water and monitored daily. Mice who became sick after about 14 days were euthanized and lymphoid organs were harvested for analysis. Kinase inhibitor treatment began about 10 days after leukemic cell injection and continued daily until the mice became sick or a maximum of approximately 35 days post-transplant. Inhibitors were given by oral lavage.

Figure 22:
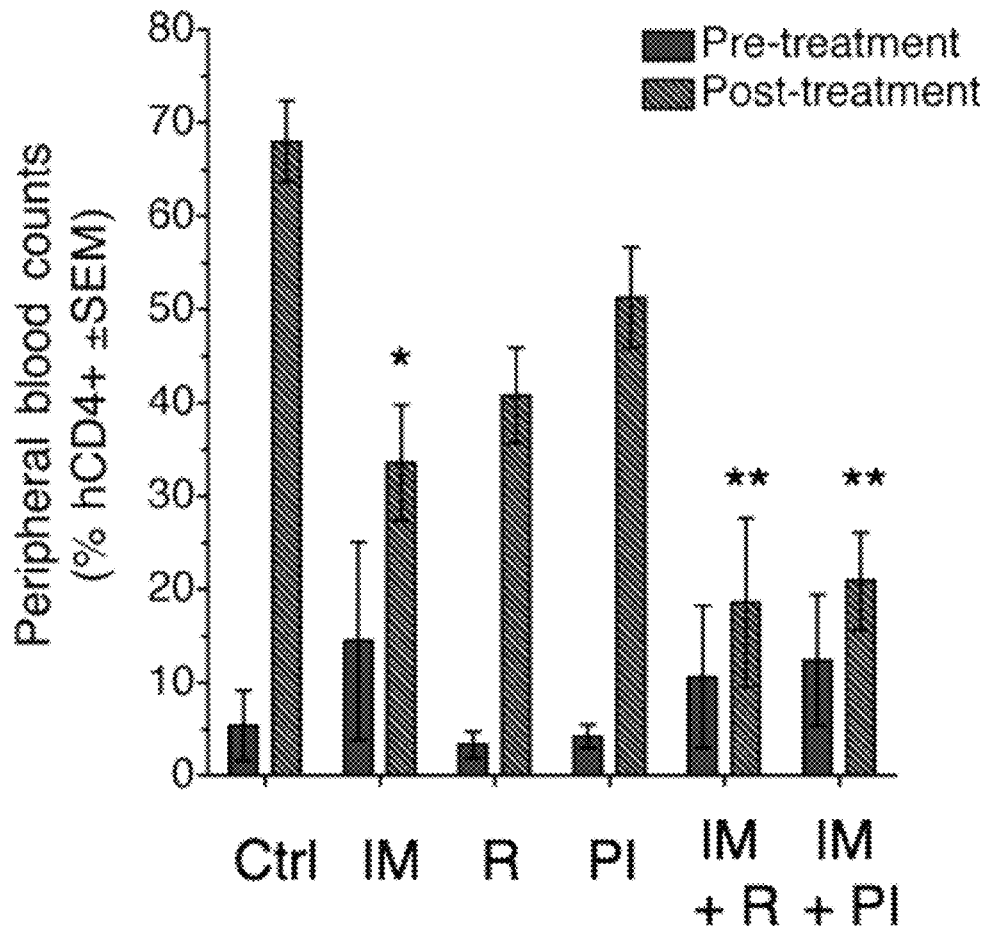
FIG. 22 illustrates the reduction of leukemic blood cell counts in mice treated with imatinib in combination with rapamycin or PI-103 in a syngenic mouse leukemia transplant model.

Peripheral blood cells were collected approximately on day 10 (pre-treatment) and upon euthanization (post treatment), contacted with labeled anti-hCD4 antibodies and counted by flow cytometry. The results as shown in FIG. 22 show that combination therapy significantly reduced leukemic blood cell counts as compared to treatment with rapamycin, imatinib, or PI-103 alone under the conditions tested.

Example 21

In Vivo Effect of Kinase Inhibitors, Bone Marrow and Spleen

Female Balb/c recipient mice were lethally irradiated from a γ source in two doses about 4 hr apart, with approximately 5Gy each. About 1 hr after the second radiation dose, mice were injected i.v. with about $1 \times 10^6$ leukemic cells from early passage MIG-p190 or MIC p190 cultures. These cells were administered together with a radioprotective dose of about $5 \times 10^6$ normal bone marrow cells from 3-5 week old donor Balb/c mice. Recipients were given antibiotics in the water and monitored daily. Mice who became sick after about 14 days were euthanized and lymphoid organs were harvested for analysis. Kinase inhibitor treatment began about 10 days after leukemic cell injection and continued daily until the mice became sick or a maximum of approximately 35 days post-transplant. Inhibitors were given by oral lavage.

Figure 23:
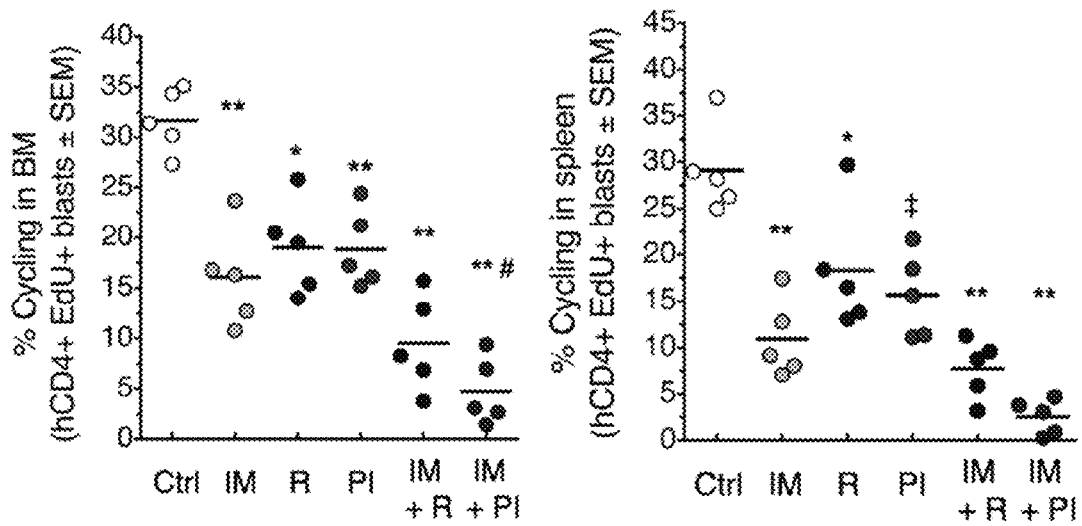
FIG. 23 illustrates a significant reduction of cycling leukemic blast cells in bone marrow (BM) and spleen in a syngenic mouse leukemia transplant model using combination therapy.

Mice were injected with the BrdU analogue EdU and sacrificed. Bone marrow and spleen were collected, blast cells were harvested from the tissue, and stained with antibodies to hCD4, and analyzed by flow cytomtery. The results as shown in FIG. 23 show that under the conditions tested in both bone marrow and spleen, imatinib, rapamycin, and PI-103 significantly reduced the number of cycling leukemic blasts as compared to control. Furthermore, combination therapy of imatinib plus rapamycin or PI-103 significantly reduced the number of cycling leukemic blasts as compared to single drug inhibition at the concentrations examined.

Example 22

In Vivo Effect of Kinase Inhibitors on Apoptosis of Leukemic Cells

Female Balb/c recipient mice were lethally irradiated from a γ source in two doses about 4 hr apart, with approximately 5Gy each. About 1 hr after the second radiation dose, mice were injected i.v. with about $1 \times 10^6$ leukemic cells from early passage MIG-p190 or MIC p190 cultures. These cells were administered together with a radioprotective dose of about $5 \times 10^6$ normal bone marrow cells from 3-5 week old donor Balb/c mice. Recipients were given antibiotics in the water and monitored daily. Mice who became sick after about 14 days were euthanized and lymphoid organs were harvested for analysis. Kinase inhibitor treatment began about 10 days after leukemic cell injection and continued daily until the mice became sick or a maximum of approximately 35 days post-transplant. Inhibitors were given by oral lavage.

Figure 24:
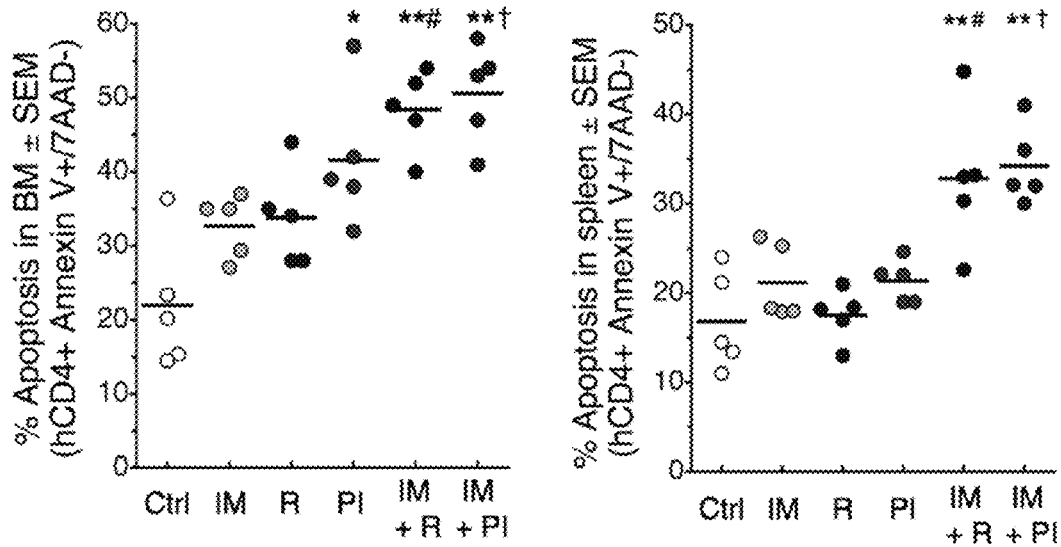
FIG. 24 illustrates significant increase in induction of apoptosis in leukemic blast cells in the bone marrow (BM) and spleen of a syngenic mouse leukemia transplant model in response to combination therapy.

Bone marrow and spleen were collected, blast cells were harvested from the tissue, and stained with antibodies to hCD4, Annexin V, and 7AAD, and analyzed by flow cytometry. The results as shown in FIG. 24 show induction of apoptosis in leukemic blast cells of the bone marrow and spleen by imatinib, rapamycin, and PI-103 under the conditions tested. The results also show significant increase at the concentrations examined in induction of apoptosis at the concentrations examined of imatinib in combination with rapamycin or PI-103.

Example 23

Measurement of CD98 Surface Expression

Figure 25:
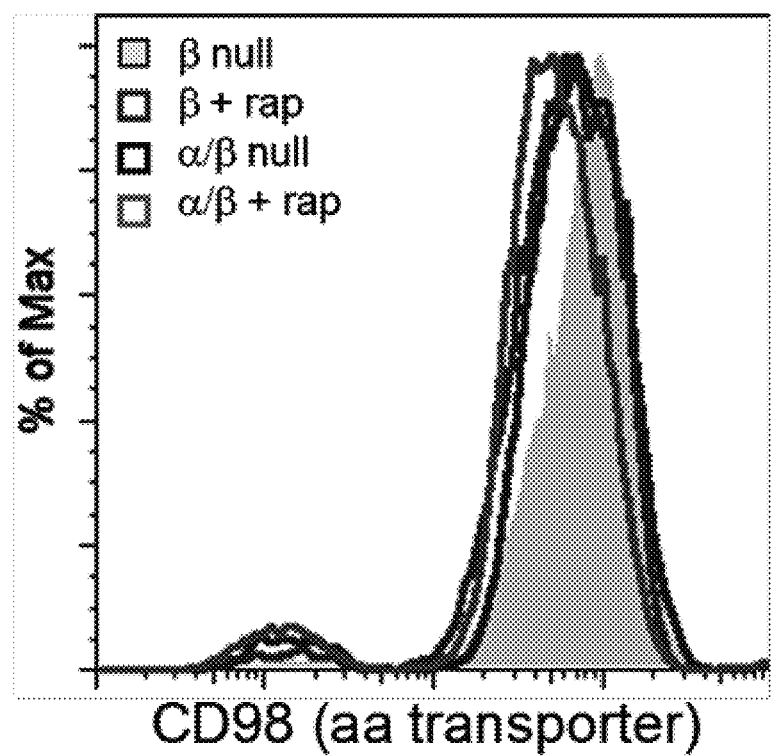
FIG. 25 illustrates the effect of rapamycin and PI3K deletion mutations on CD98 expression.

Flow cytometry was used to measure the surface expression of CD98, a component of an essential amino acid transporter. Rapamycin treatment, or genetic deletion of class IA PI3K, each reduced CD98 expression and these effects were additive FIG. 25. Although the effects were quantitatively modest, small changes in nutrient availability can have a major impact on cellular bioenergetics (imagine reducing your food intake by 20-25%). The observation that PI3K and mTorC1 contribute independently to CD98 expression provides strong rationale for studying further the regulation of nutrient uptake by PI3K and different mTor complexes.

Example 24

Treatment of Leukemic Mice with Kinase Inhibitors

Female Balb/c recipient mice are lethally irradiated from a γ source in two doses about 4 hr apart, with approximately 5Gy each. About 1 hr after the second radiation dose, mice are injected i.v. with about $1 \times 10^6$ leukemic cells from early passage MIG-p190 or MIC p190 cultures. Alternatively, NOG mice (Jackson labs) are irradiated and injected with human Ph+ acute lymphocytic leukemia cells. These cells are administered together with a radioprotective dose of about $5 \times 10^6$ normal bone marrow cells from 3-5 week old donor Balb/c mice. Recipients are given antibiotics in the water and monitored daily. Mice that become sick after about 14 days are euthanized and lymphoid organs are harvested for analysis. Kinase inhibitor (e.g. mTor inhibitor, dasatinib, imatinib etc.) or chemotherapeutic agent treatment begins about 10 days after leukemic cell injection and continues daily until the mice become sick or a maximum of approximately 35 days post-transplant. Inhibitors are given by oral lavage.

Mice are optionally injected with EdU, and sacrificed. Peripheral blood, bone marrow and spleen are harvested for analysis and hCD4+ cells are optionally enriched for. Analysis includes phosflow analysis, western blot, flow cytometry, analysis of CD98 expression, or Annexin V or 7-AAD staining. It is expected that the results of treatment of the leukemic mice with mTor inhibitors show decreased leukemic cell counts in peripheral blood and lymphoid tissues, decreased CD98 expression, increased Annexin V or 7-AAD staining, decreased phosphorylation of PI3K pathway targets, and increased apoptosis of leukemic cells in response to the drugs administered. It is also expected that the results of treatment of the leukemic mice with a combination of mTor inhibitors and other therapeutic agents provide increased efficacy above that achieved with a single agent.

Example 25

Treatment of Lupus Disease Model Mice

Mice lacking the inhibitory receptor FcγRIIb that opposes PI3K signaling in B cells develop lupus with high penetrance. FcγRIIb knockout mice (R2KO, Jackson Labs) are considered a valid model of the human disease as some lupus patients show decreased expression or function of FcγRIIb.

The R2KO mice develop lupus-like disease with antinuclear antibodies, glomerulonephritis and proteinurea within about 4-6 months of age. For these experiments, the rapamycin analogue RAD001 (available from LC Laboratories) is used as a benchmark compound, and administered p.o. This compound has been shown to ameliorate lupus symptoms in the B6.Sle1z.Sle3z model.

Lupus disease model mice such as R2KO, BXSB or MLR/lpr are treated (groups of 10) at about 2 months old, approximately 4 times per week for a period of about two months. Mice are given p.o. doses of: (1) vehicle (2) RAD001, about 10 mg/kg (3) PP242 (or analog), approximately 10 mg/kg (4) PP242, about 50 mg/kg. Blood and urine samples are obtained at approximately day 0, 30 and 60, and tested for antinuclear antibodies (in dilutions of serum) or protein concentration (in urine) as described. Serum is also tested for anti-ssDNA and anti-dsDNA antibodies by ELISA. One set of about 5 animals is euthanized at day 60 and tissues harvested for measuring spleen weight and kidney disease. Glomerulonephritis is assessed in kidney sections stained with H&E, scoring on a scale of 1-4. Another set of about 5 mice from each group is studied at 6 months of age, 60 days after cessation of treatment, using the same endpoints.

The results of this experiment demonstrate that mTor inhibitors can suppress or delay the onset of lupus symptoms in lupus disease model mice. In comparison to RAD001, it is expected that kinase inhibitors disclosed herein (e.g. PP242, PP30, PI-103, PIK-90) perform as well or better to suppress autoimmunity than an established mTorC1 inhibitor.

Example 26

Effect of mTor Inhibitors on In Vivo T and B Cell Function

Groups of about 5 WT mice (generally 6 wk old) are given daily i.p. injections of rapamycin (about 7 mg/kg) or vehicle, or daily oral administration of kinase inhibitors disclosed herein (e.g. PP242, PP30, PI-103, PIK-90, or an analogue of the compounds herein) or vehicle. Lymphoid tissues (BM, thymus, LN, spleen) are analyzed with standard panels of antibodies to quantify percentages of different B and T cell progenitor and mature subsets. Typically 2 hr before euthanasia, mice are given an i.p. injection of EdU to allow measurement of DNA synthesis rates in different subsets by FACS.

The same drug treatment regime is used to analyze effects on the following model immune responses. For B cell function, mice are immunized with a T-independent antigen (NP-Ficoll) and serum collected about 7 days later for quantification of NP-specific antibodies by ELISA. For T and B cell collaboration, mice are immunized with NP-ovalbumin and serum tested for NP-specific antibodies on about day 14, with germinal center formation analyzed in spleen sections by immunofluorescence. For CD4 T cell function, D011.10 TCR-Tg cells are purified, labeled with CFSE, and approximately 2.5×106 cells injected into wild-type recipients before immunization with about 100 μg ovalbumin protein in adjuvant. About 3 days later (+/−drug treatment), spleen and LN are harvested and in vitro expansion assessed by CFSE dilution. It is expected that the results of this experiment provide a reasonably comprehensive survey of drug effects on lymphocyte development, proliferation, signaling and immune responsiveness.

Example 27

Treatment of Leukemic Cells with Kinase Inhibitors p190 cells in 96-well plates are treated with 2-fold dilutions of dasatinib or imatinib over a range above and below its $IC_{50}$ (e.g. 0, 5, 10, 20, 40, 80, 160, 320 nM) with one concentration per row. Columns of the plates contain 2-fold dilutions of either rapamycin, PP242, IC or BEZ235 around their respective $IC_{50}$ values. Controls include wells with untreated cells, or with vehicle. MTS reagent is added to all wells during about the last 2 hr of an approximately 48 hr incubation, then absorbance quantified using a microplate reader. Synergy studies are also done using both wild-type (WT) p190 and the mutants p190-Y253F, p190-E255K and p190-T3151. Calcusyn software is used to calculate $IC_{50}$ values for individual compounds and to compute combination indeces to distinguish synergy, additivity or antagonism.

The results of the synergy experiments are expected to provide a limited set of single drug and combination treatments to measure cell proliferation and apoptosis by flow cytometry (FACS).

Example 28

Effect of mTor Inhibitors on BCR-Abl+Cells

WT p190 cells are treated with about $IC_{50}$ or approximately $5 \times IC_{50}$ concentrations of individual drugs or vehicle for about 18 hr, with or without $IC_{50}$ concentration of dasatinib, imatinib, or other chemotherapeutic agent (e.g. PP242, PI-103, PIK-90, or analogue of the compounds herein). DNA content analysis is used to quantify the fraction of cells in G0/G1 vs. S and G2/M phases, and to estimate apoptotic fraction using the sub-diploid peak. As a more precise and temporal measurement of apoptosis, caspase-3 cleavage at about 6 hr and about 18 hr using intracellular staining and FACS is assayed. Immunoblots are also used to measure expression of selected proteins as correlates of cell cycle progression vs. arrest. p190 cells are treated for about 2, 6 and 18 hrs and then lysates prepared and probed for expression of c-Myc (known mitogenic function in BCR-ABL-transformed cells), D-type cyclins (whose expression is regulated by PI3K and mTor) and p27kip (inhibitor of cyclin-dependent kinases whose expression is reduced by PI3K/Akt through FOXO inhibition).

It is expected that patterns of drug potency in p190 cells can be generalized to other BCR-ABL+ cells. Two additional cell lines are used to confirm this. BaF3-p190 cells are generated by infecting the IL-3-dependent BaF3 pro-B cell line with p190 retrovirus. This renders cells IL-3-independent but completely dependent on BCR-ABL kinase activity. K562 cells are derived from a human patient in Ph+CML blast crisis. Cell cycle and MTS assays of these cell lines in the presence of the inhibitors disclosed herein are used to monitor drug potentcy.

It is expected that the the data generated establish the potency of mTor inhibitor in suppressing BCR-ABL-driven proliferation and survival in three cellular models, including cells expressing WT BCR-ABL or mutants resistant to dasatinib and/or imatinib. The formal synergy studies provide a rigorous comparison of the efficacy of PP242 (or analogue) vs. a mTorC1 inhibitor (rapamycin) or a dual PI3K/mTor inhibitor (BEZ235), when given in combination with a clinically used ABL kinase inhibitor.

Example 29

Comprehensive Survey of Kinase Substrate Phosphorylation of Treated Cells

To obtain a more comprehensive and quantitative survey of cellular protein phosphorylation at different concentrations of PP242, a Typhoon molecular imager is used to analyze immunoblots of treated cells. Using different dyes coupled to antibodies (Abs) raised in different species, specific phosphorylation and total target protein is measured on the same blot. Similarly, immunofluorescent staining with anti-PIP3 monoclonal antibodies allows measurement of inositol phosphorylation. All of the required Abs are available from Cell Signaling Technologies and other vendors. p190 cells are treated with vehicle alone or with different agents for about 2 hr prior to preparation of cell lysates. Each gel typically contain the following samples: vehicle control; rapamycin (about 40 nM=5×$IC_{50}$); PP242 (about 13 nM=$IC_{50}$, 65 nM, 325 nm); BEZ235 (about 5 nM=$IC_{50}$, about 30 nM, about 150 nM); IC (about 10 µM=5×$IC_{50}$); dasatinib (about $IC_{50}$); dasatinib+rapamycin; dasatinib+PP242(about 65 nM); dasatinib+BEZ (30 nM); dasatinib+IC87114.

It is expected that PP242 inhibits Akt phosphorylation at S473, and the "turn motif" in Akt (T450) and PKC isoforms as well as inhibits phosphorylation of Akt substrates such as for example FOXO1/FOXO3 (on residues T24/T32), TSC2 (T1462) and GSK3 (S9/21). It is also expected that the results show diminished phosphorylation of mTor substrates 4EBP1 phosphorylation T37/45 and S65. It is further expected that the results demonstrate enhanced phosphorylation of ERK1/ERK2 (T202/Y204) and its upstream kinase MEK (S217/S221) in treated cells.

A particular goal of this experiment is to define intermediate concentrations of dasatinib and PP242 that synergize to suppress mTor activity and kill p190 cells without strongly diminishing PIP3 production and p Akt-T308. Accordingly, a dasatinib-PP242 combination may have anti-leukemic effects with limited toxicity to normal cells whose signaling is not driven by BCR-ABL.

It is further expected that the status of MAP kinase and JAK/STAT pathways defines potential compensatory changes that occur in response to mTorC1/mTorC2 inhibition. Again, the results of this experiment define drug combinations that achieve cell killing without augmenting other mitogenic signals. Significant changes in flux through other signaling pathways may reflect off-target effects of PP242 rather than compensatory rewiring. In this case, comparison of structural analogs of PP242 may provide a related compound with better selectivity.

Example 30

Effect of Inhibitors on Cellular Metabolism p190 cells are treated for about 6 and about 18 hr with vehicle alone or the following inhibitor treatments: rapamycin (about 40 nM); PP242 (about 65 nM); BEZ235 (about 30 nM); IC (about 10 µM); dasatinib (approximately $IC_{50}$); dasatinib+rapamycin (about 40 nM); dasatinib+PP242 (about 65 nM); dasatinib+BEZ (about 30 nM); dasatinib+IC (about 10 µM). Cells are analyzed by flow cytometry for surface expression of CD98 and CD71 (transferrin receptor), CD19 and B220 as negative controls whose expression should be unaltered. Cell samples are also fixed, permeabilized and stained for immunofluorescence microscopy (IFM) using antibodies to the glucose transporter Glut1 (compared to isotype control Ab). Available antibodies to Glut1 distinguish intracellular vs. surface expression by IFM but are not suitable for flow cytometry. Glucose uptake is measured based on incorporation of 3H-2-deoxyglucose. Glycolytic rate is measured by two assays: conversion of 5-3H-glucose to 3H2O, and lactate accumulation in the media. AMP kinase phosphorylation is assayed by immunoblot.

It is expected that the results of this experiment provide effective concentrations at which cell metabolism is adversely affected in leukemic cells. The results of this experiment and example 30 further help determine which signaling events are disabled at drug concentrations that induce cell cycle arrest and/or apoptosis. It is expected that the anti-proliferative and pro-apoptotic effects of PP242 correlate with reduced p Akt-S473 and stronger suppression of p4EBP1 relative to rapamycin. Alternatively the results may provide that the greater potency of PP242 vs. rapamycin in leukemia cells correlates with differential effects on p Akt-S473.

Another important outcome of examples 30 and 31 is the definition of biomarkers that can be used for pharmacodynamic assays in animal models and in human clinical studies. Phospho-Akt and phospho-S6 are commonly used as biomarkers of PI3K and mTorC1 activity for cancer studies in animals and humans. It is expected that the results of examples 30 and 31 establish a set of phosphorylation sites whose dephosphorylation correlates best with cellular potency of PP242 compared to rapamycin. Having a set of candidate biomarkers facilitates the development of the most sensitive and simple techniques for pharmacodynamic monitoring, for example by FACS instead of immunoblot. It is further expected that p4EBP1 and p Akt-S473 are useful biomarkers, and possibly some other Akt substrates. Studies of metabolic effects might provide other biomarkers such as altered nutrient transport expression (e.g. CD98).

Example 31

Effect of Dasatinib and mTor Inhibitors on Leukemic Cells

The experiments described in example 16, are performed with two important differences. In one set of experiments, dasatinib instead of imatinib as the ABL kinase inhibitor is used. p190 transduced cells are treated with a range of dasatinib concentrations (e.g. 4, 12, 40, 120 nM)+/−PP242 (about 13 nM and about 65 nM) or rapamycin (e.g. at 40 nM) to determine an approximate $IC_{50}$ for dasatinib. These compounds are then tested alone or together in various combinations at a dasatinib concetration of about the $IC_{50}$ and about $5 \times IC_{50}$. It is expected that the results of the experiment provide therapeutic concentrations at which leukemic cell colony formation is inhibited. It is further expected that the combination of dasatinib with mTor inhibitors provide enhanced inhibition of colony formation at lower dasatinib doses. This suggests that combination therapy is an advantageous strategy for treating B-ALL.

Example 32

Ph+B-ALL Colony Formation Assays

Peripheral blood mononuclear cells (PBMC) are obtained from human leukemia patients. Patients who have pathologically confirmed B-ALL or CML with B lymphoid blast crisis (CML-BC) are asked to participate in the study. Consented patients provide up to seven extra tubes containing a total of about 30 ml of blood. Live PBMC are isolated by density gradient centrifugation, resuspended in media (typically IMDM/30% FCS/1× pen-strep) and frozen in approximately 1 ml aliquots of about 5-10×106 cells (typically in 15% DMSO/85% medium). After cytogenetic diagnosis, experiments are performed with Ph+ cells. Ph− cells are saved and studied in further experiments described herein. Colony assays are performed in sets of 3-4 patient samples, using the protocol described for example 17. In each assay, duplicate wells of 48-well plates are seeded with about 5×104 cells (sorted CD19+CD34+) and scored after 12-14 days of growth. Treatment groups are vehicle alone, dasatinib ($IC_{50}$ and $5 \times IC_{50}$), rapamycin (about 40 nM), PP242 (about 13 nM and about 65 nM), dasatinib ($IC_{50}$)+rapamycin (about 40 nM), dasatinib ($IC_{50}$)+PP242 (about 13 nM), dasatinib ($IC_{50}$)+PP242 (about 65 nM). About 9-12 Ph+ALL patient samples are studied. It is expected that the results of the experiment provide therapeutic concentrations at which leukemic cell colony formation is inhibited. It is further expected that the combination of dasatinib with mTor inhibitors provide enhanced inhibition of colony formation at lower dasatinib doses. This suggests that combination therapy is an advantageous strategy for treating B-ALL.

Example 33

Normal Human Progenitor Assays

Normal human CD34+ bone marrow cells (Lonza) are purchased. Cells are plated in Methocult H4434 that contains complete cytokines to support growth of myeloid and erythroid cells. The effects of drugs and combinations, using the same concentrations of dasatinib, rapamycin and PP242 listed in Example 32. After 14-16 days, the number of colonies of different type (CFU-E, BFU-E, CFU-GM, CFU-G, CFU-M and CFU-GEMM) is scored by light microscopy using instructions supplied by the manufacturer (Stem Cell). In these experiments samples treated with BEZ235 or dasatinib+BEZ235 are included to determine if mechanistic differences identified in examples 30 and 31 correlate with differences in toxicity to nonleukemic cells.

Example 34

Colony Assay Using Ph− B-ALL and AML

Human Ph− B-ALL and AML specimens are obtained. Ph− B-ALL and AML are cytogenetically diverse, with diverse therapeutic regimens currently in use depending on patient risk factors. The majority of Ph− B-ALL patients are treated initially with a combination of three drugs: glucocorticoid (e.g. dexamethasone), vincristine, and asparaginase or anthracycline (e.g. daunorubicin). Most AML patients receive an anthracycline only. Pilot experiments with 3 patient samples are conducted to determine concentrations of vincristine (Ph− ALL) or daunorubicin (AML) that partially reduce colony formation in methylcellulose. It is expected that these drugs are effective in the range of 0.1-1 µM (vincristine) and 3-30 nM (daunorubicin). Optionally, the Ph-ALL assays may be supplemented with dexamethasone and/or daunorubicin. 9-12 independent leukemia specimens of each time in colony assays using chemotherapeutic agent alone or together with PP242 (13 nM and 65 nM) or rapamycin (40 nM) are then tested at optimized vincristine or daunorubicin concentrations.

It is expected that PP242 shows greater efficacy than rapamycin in suppressing colony formation, although a considerable degree of variability among patients is anticipated. However, the chosen sample size (9-12) is sufficient to establish whether any trends are statistically significant. It is further expected that mTor inhibitor may have anti-leukemic effects in acute leukemias that are not driven by BCR-ABL (e.g. AML).

Example 35

Murine Bone Marrow Transplant Assay

Female Balb/c recipient mice are lethally irradiated from a γ ray source in two doses about 4 hr apart, at approximately 5Gy each. About 1 hr after the second radiation dose, mice are injected i.v. with about 1×106 leukemic cells from early passage MIG-p190 or MIC-p190 cultures. These cells are administered together with a radioprotective dose of approximately 5×106 normal BM cells from 3-5 wk old donor Balb/c mice. Recipients are given antibiotics in the water and monitored daily. On rare occasions mice become moribund in the first 14 days due to failed engraftment or infection, and are euthanized. Mice who become sick after about 14 days are euthanized and lymphoid organs harvested for FACS analysis and/or magnetic enrichment. Treatment begins on approximately day 10 and continues daily until mice become sick, or after a maximum of about 35 days post-transplant. Drugs are given by oral gavage (p.o.). In a pilot experiment a dose of dasatinib that is not curative but delays leukemia onset by about one week or less is identified; controls are vehicle-treated or treated with imatinib (about 70 mg/kg twice daily), previously shown by us and others to delay but not cure leukemogenesis in this model. For the PP242 experiment groups of about 8 mice per treatment are studied. These groups are: (1) vehicle (2) dasatinib (3) rapamycin, about 7 mg/kg/day i.p. (4-6) PP242 at about 10 mg/kg, about 30 mg/kg, about 60 mg/kg p.o., twice daily (7) dasatinib+rapamycin (8-10) dasatinib+ PP242. For feasibility, the experiment is carried out in two phases, with about 4 mice per group in each phase. For the first phase MIG-p190 cells are used, and postmortem analysis is limited to enumeration of the percentage of leukemic cells in BM, spleen and lymph node (LN) by flow cytometry. In the second phase, MIC-p190 cells are used and the postmortem analysis includes magnetic sorting of hCD4+ cells from spleen followed by immunoblot analysis of key signaling endpoints: p Akt-T308 and S473; pS6 and p4EBP-1. As controls for immunoblot detection, sorted cells are incubated in the presence or absence of pathway inhibitors before lysis. Optionally, "phosflow" is used to detect p Akt-S473 and pS6-S235/236 in hCD4-gated cells without prior sorting. These signaling studies are particularly useful if, for example, drug-treated mice have not developed clinical leukemia at the 35 day time point. Kaplan-Meier plots of survival are generated and statistical analysis done according to methods known in the art. Results from MIG-p190 and MIC-p190 cells are analyzed separated as well as cumulatively.

Samples of peripheral blood (100-200 µl) are obtained weekly from all mice, starting on day 10 immediately prior to commencing treatment. Plasma is used for measuring drug concentrations, and cells are analyzed for leukemia markers (eGFP or hCD4) and signaling biomarkers as described herein.

It is expected that the results of the analysis demonstrate effective therapeutic doses of the biological agents disclosed herein for inhibiting the proliferation of leukemic cells. It is further expected that combination therapy of the mTor inhibitors disclosed herein with other chemotherapeutic agents (e.g. dasatinib) exhibit a greater degree of efficacy or decreased toxicity in comparison to the use of a single chemotherapeutic agent.

Example 36

Murine Xenograft Model

Xenografts of human leukemia cells can expand and cause lethal disease when injected into immunocompromised mice. This provides a useful preclinical system for studying whether in vitro drug delivery can affect the expansion of leukemic cells in human patient material. The NOG mouse strain is used as recipients. NOG mice (available from Jackson labs) are derived from crosses between non-obese diabetic (NOD), severe combined immunodeficient (SCID) and common gamma-chain knockout mice. The strain has more complete ablation of mature T and B cells and NK cell activity compared to NOD-SCID, and is now used commonly for human xenograft studies. These mice are radiation-sensitive due to the SCID mutation, but require only 3Gy of irradiation to create bone marrow space for transplant engraftment. Groups of 2 NOG mice are injected with approximately $1\times10^6$ Ph+B-ALL cells (sorted CD19+CD34+) from at least 5 different patients. Mice are monitored daily for signs of illness, and bled twice weekly (about 50 µl, from tail vein) to monitor the percentage of hCD19+ cells in peripheral blood. It is expected that this experiment, will provide at least 2 human Ph+B-ALL samples that cause progressive leukemia in NOG mice, to use in a drug treatment study as described herein.

Recipient mice are bled twice weekly (about 50 µl, from for example the tail vein) until more than about 5% of peripheral WBC are hCD19+. At that time daily drug treatments are initiated for about 14 days. Blood samples are obtained twice weekly to quantify the % hCD19+ over time. Mice are monitored daily for signs of illness and euthanized if necessary. NOG mice are studied in groups of about 5 animals per human donor cell sample: (1) vehicle (2) dasatinib only (3) rapamycin only (4) PP242 at a dose that shows efficacy in the p190 model (5) dasatinib+rapamycin (6) dasatinib+PP242. At the end of the 14 day treatment period, or when mice become sick, mice are injected i.p. with EdU (BrdU analog with improved detection) 2 hr before sacrifice. Lymphoid organs are harvested and FACS analysis is used to quantify % hCD19+ along with % dividing (EdU+) and % apoptotic (7AAD-/AnnexinV+). p Akt-S473 and pS6 in splenic hCD19+ cells is also assessed, and other biomarkers of signaling and metabolism as developed in example 30.

It is expected that the experiments in examples 35 and 36 provide in-depth and complementary information about the anti-leukemic effects of PP242 in comparison to rapamycin, and in combination with dasatinib. A key aspect of example 35 is the leukemia survival endpoint, it is expected that PP242 can achieve the ultimate goal of delaying or preventing mortality. By comparing different PP242 doses in the p190 system the results disclosed herein define a minimum effective dose while also obtaining useful information about pharmacokinetics (PK) and pharmacodynamics (PD) from blood samples as described. The studies in example 36 have the advantage of assessing efficacy on primary human, rather than mouse, leukemia cells. In addition, the modified treatment and analysis scheme provide information about leukemia cell proliferation and survival to correlate with data on total leukemic burden. In both types of experiment we expect to obtain information about signaling status of leukemia cells postmortem.

Example 37

Non Invasive Sampling

Clinical trials and patient management benefit from non-invasive sampling procedures to determine drug efficacy and distinguish on-target and off-target effects. Aliquots of whole blood (WB) are incubated for 15 min with vehicle or drugs at various concentrations, before addition of stimuli to crosslink the TCR (anti-CD3 with secondary Ab) or the B cell receptor (BCR) using anti-kappa light chain Ab (F(ab')2 fragments). After about 5 and about 15 min, samples are typically fixed with cold 4% paraformaldehyde and used for phosflow. Surface staining is used to distinguish T and B cells, with the nonresponding population as an internal control. The signaling endpoints include p Akt and pS6 along with a control response that is not affected by mTor inhibition (i.e. pSTAT5).

Whole blood assays for mouse lymphocytes are then used to measure pharmacodynamic (PD) activity of selected compounds in mice. As described above, blood samples are obtained weekly from mice in the p190 model. Using 4-color staining, mouse T cells, B cells, leukemia cells (GFP or hCD4) and one intracellular phosphoprotein per sample are distinguished in flow cytometry analysis. At early time points the blood contains too few leukemia cells to quantify signaling, so the signaling response of host T or B cells acts as a surrogate for PD of the drugs.

It is expected that the experiment allows convenient monitoring of signaling states in peripheral lymphocytes and leukemia cells over the course of in vitro drug treatments, providing a powerful tool for correlating therapeutic efficacy with on-target vs. off-target molecular effects. Mice treated with dasatinib (+/−rapamycin or PP242) might exhibit greater suppression of signaling in the leukemia compartment (BCR-ABL-dependent) compared to the normal lymphocytes. On the other hand, both imatinib and dasatinib have been shown to suppress signaling and proliferation of normal lymphocytes due to effects on cellular kinases of the ABL and SRC families. These experiments also provide proof-of-principle and a reference dataset for the incorporation of blood sampling approaches in clinical trials.

Example 38

Non Invasive Imaging

The practice of medicine, and oncology in particular, has been revolutionized by noninvasive imaging approaches. The use of PET scanning with 18fluorodeoxyglucose (18FDG) as a positron emitter is commonly used for cancer detection, based on the high glucose uptake rates of cancer cells originally observed by Warburg. This approach has been used to monitor treatment responses in Ph+CML. Increased glucose uptake is driven in part by elevated PI3K/Akt and mTor signaling in cancer cells. Indeed, rapmycin analogs diminished 18FDG in a glioma model, which correlated with suppression of tumor growth. A miniature version of the PET scanner apparatus ("microPET") can be used to image leukemia development in mice. Thus, microPET is an excellent preclinical tool for monitoring leukemia responses to mTor inhibitors and for establishing protocols that are useful in human clinical trials.

The p190 leukemia model is used to allow stable expression of genetically encoded enzymes for imaging applications. A concentration of mTor inhibitor (e.g. PP242) that augments the anti-leukemic effect of dasatinib and, optionally, has some effect on its own is used. 2 replicate experiments of 2 mice per treatment: (1) vehicle (2) dasatinib (3) rapamycin (4) PP242 (5) dasatinib+rapamycin (6) dasatinib+PP242 are performed. Drug treatments start on day 10 post-transplantation, and mice are imaged on about day 9 and 14, then weekly (e.g. day 21, etc) for surviving healthy animals until about day 35. Mice are fasted overnight, then injected with 18FDG i.v. about 30 min prior to anesthetization (typically with ketamine/xylazine). Serial microPET scans are obtained, and the data normalized and used for 3-dimensional reconstructions using methods known in the art.

It is expected that microPET scanning data correlates with other measures of disease development, with lower 18FDG uptake in animals treated with anti-leukemic drug combinations. One concern with 18FDG is that uptake could be diminished in cancer cells that are nonetheless expanding due to an altered metabolic profile. This is controlled for by analyzing a separate cohort of mice transplanted with leukemia cells expressing a PET reporter gene, e.g. Herpes Simplex Virus Thymidine Kinase (sr39 mutant). This TK mutant has a high affinity for acycloguanosines such as the PET radiotracer 9-(4-[18F]-fluoro-3 hydroxymethylbutyl) guanine (FHBG). Alternatively, imaging is performed via the use of p190 cells superinfected with a virus expressing luciferase to monitor disease progression noninvasively by bioluminescence.

Example 39

Pharmacokinetic and Toxicology Studies of mTor Inhibitors

The present invention provides PP242 ADME properties (adsorption, distribution, metabolism and excretion) and a preliminary toxicity profile. The compound exhibits good drug-like properties: oral bioavailability (F %30-70) with moderate clearance and good volume of distribution; tolerated at 10, 30 or 100 mg/kg in mice and rats (four times or twice daily dosing, p.o.); metabolically stable in microsome and cellular assays; minimal activity in ligand binding receptor profiling screen at 10 μM (CEREP LEAD PROFILINGSCREEN®); highly selective in screen of 220 protein and lipid kinases. PP242 has a clean profile in genetic toxicology (mini-Ames test) and hERG (potassium channel) test.

Prior to toxicology (TOX) studies a PK dose escalation study is performed to prove increasing plasma concentration upon higher dosages by the preferred route of administration (p.o.). Also, a formulation allowing high exposures is tested, optimized and confirmed to be non toxic. Prior to or in parallel to the first rodent in vitro TOX study, a compound metabolite identification across species (mice/rat/dog/pig/non-human primate (monkey) and human) is initiated to select the appropriate non-rodent species for subsequent in vitro TOX. The maximum tolerated dose of PP242 and a biologically active analog is determined, in a rodent species (e.g. rats etc). About 3 rats/sex/group receive one of approximately 5 dose strengths for about 4 days, and are monitored for clinical signs, body weight changes, and gross necropsy findings. Generally, a 10 day repeat-dose experiment using about 5 rats/sex/group, with toxicokinetic monitoring of plasma, and necropsy on day about 11 is then performed. Finally, an approximately 28-day repeat dose with about a 14-day recovery experiment is performed, using about 3 dose strengths plus vehicle control (N=10/sex/dose+5/sex for high-dose recovery). Clinical signs, body weight changes, food consumption, gross necropsy findings, clinical pathology (hematology, coagulation, clinical chemistry, & urinalysis), histopathology (full tissues for high dose and controls), and toxicokinetic monitoring are included. It is expected that the results of this experiment will define the severely toxic dose to 10% of the rodents. Following the rodent studies, a similar progression of 3 TOX protocols is carried out in a non-rodent species (e.g. dog, possibly pig or non-human primate) although with smaller group size (for 4-day and 10-day studies, N=1/sex/dose; for 28-day study, N=3/sex/dose+N=2/sex for high dose recovery). Electrocardiogram and ophthalmological examinations are performed on the large animal species in the 28-day study.

The results of the present experiment are expected to provide pharmacokinetic and pharmacodynamic data on mTor inhibitors (e.g. PP242) and their analogues.

Example 40

Effect of mTor Inhibitors on In Vitro Lymphocyte Function

Balb/c mice (WT), or D011.10 TCR transgenic (specific for ovalbumin (OVA) peptide presented by I-Ad) mice in the Balb/c background are used for all experiments of the example herein. T cells are purified from LN and B cells from spleen by magnetic sorting. For all experiments, cells are preincubated with test compounds (e.g. rapamycin or PP242 in 3-fold dilutions, or vehicle) for about 15 min at 37° C. before plating in wells containing prewarmed stimuli. For proliferation assays, cells generally are labeled with a cell division tracker dye (e.g. CFSE) and stimulated in 96-well plates for about 48 and 72 hr. Supernatants are saved for cytokine measurements, and cell division history determined by FACS. Co-staining with AnnexinV provides a readout for cell death. WT T cells are stimulated with titrations of anti-CD3 alone, or together with anti-CD28. Similar experiments are conducted using human peripheral blood T cells (PBT) stimulated with anti-human CD3+/−CD28. To measure T cell responses to antigen presenting cells (APC) bearing cognate peptide, TCR-Tg T cells are cultured with APC (irradiated syngeneic splenocytes, T-depleted) and a concentration range of OVA peptide. A large panel of cytokines are measured using a Luminex multiplex system (reagents from Millipore). WT B cell proliferation is assessed following stimulation with concentration ranges of anti-IgM, lipopolysaccharide (LPS), or anti-CD40, each +/−IL-4.

Differentiation of activated T and B cells is also assessed. Purified mouse CD4+ T cells are labeled with CFSE before stimulation with syngeneic APC and soluble anti-CD3. Appropriate cytokines and blocking antibodies are included in different samples to skew differentiation towards Th1, Th2, Th17 or induced regulatory T cell (iTreg) subsets. After 3 days, cells are washed and replated in IL-2 for two days, then analyzed by FACS for cell division (CFSE) vs. cytokine production (IFNγ, IL-4, IL-10, IL-17) and/or the Treg marker FoxP3. For B cell differentiation, splenic B cells are labeled with CFSE, and stimulated for 3-5 days with LPS or CD40-ligand, +/−IL-4. Supernatants are collected for measurement of IgM and IgG secretion by ELISA, and cells analyzed by FACS for cell division (CFSE) vs. isotype-switching (IgG1). Plasma cell differentiation is monitored by staining for expression of CD138 and downregulation of B220.

To define signaling defects, T or B cells are treated with drug concentrations that impair functional responses to TCR or BCR engagement, and then stimulated with anti-CD3 or anti-IgM for about 5 min and 15 min. Phosphorylation (p Akt, pS6, p4EBP-1, pFOXO, pERK, pIκB) is measured by phosflow or immunoblot as described. As a readout of PI3K-dependent, mTorC1-independent signaling Ca2+ flux is measured. FACS-based assays include surface staining to distinguish subsets of T (CD4, CD8) and B cells (transitional, follicular, marginal zone).

Rapamycin (Sirolimus) is a clinically approved and widely used immunosuppressive agent. Although the molecular target of rapamycin (mTor) has been known for about 15 years, there is still much to learn about how mTor signaling is wired in different cell types and the possible therapeutic and toxic effects of novel mTor inhibitors in the immune system. PP242 is, a selective and competitive inhibitor of both mTor complexes, and a potent inhibitor of T and B cell proliferation. The results of the present experiment are expected to provide a thorough evaluation of how PP242 (or a structural analog) affects lymphocyte development and function in vitro. This experiment is also expected to provide novel information about mTor function in immunity and methods for therapeutic immunosuppression by mTor inhibition.

Example 41

Synthetic Preparation and Examples for Indolyl Pyrazolopyrimidine mTor Inhibitor Methods The compounds disclosed herein as useful in the methods of the invention, are synthesized as illustrated in the following schemes.

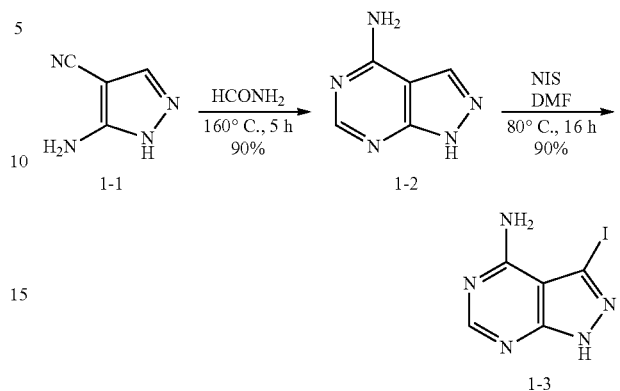

Scheme 1. Synthesis of 2-(4-amino-1H-pyrazolo[3,4-d]pyrimidin-3-yl) iodide (Compound 2-4).

Scheme 1 depicts the synthesis of 2-(4-amino-1H-pyrazolo[3,4-d]pyrimidin-3-yl) iodide. Cyano substituted aminopyrazole 1-1 is heated with formamide at 160° C. for 5 hours to yield 2-(4-amino-1H-pyrazolo[3,4-d]pyrimidine (compound 1-2) in 90% yield. This intermediate is reacted with N-iodosuccinimide in dimethylformamide at 80° C. for 16 hours, to produce 2-(4-amino-1H-pyrazolo[3,4-d]pyrimidin-3-yl) iodide (Cpd. 1-3) in 90% yield.

Synthesis of 2-(4-amino-1-isopropyl-1H-pyrazolo[3,4-d]pyrimidin-3-yl)-1H-indol-5-ol (Compound 2-4)

Compound 2-4 is synthesized as shown in Scheme 2. Compound 1-3 is reacted with isopropyl bromide in dimethylformamide with potassium carbonate at 80° C., to provide the 1-isopropyl pyrazolopyrimidine intermediate, compound 2-1. This intermediate with the protected indolyl boronic acid species 2-2, using tetrakistriphenylphosphine palladium catalysis in DME-water solvent at 80° C. for 4-5 hours, to produce the Suzuki coupling product, compound 2-3. Removal of the protecting groups with acid in dioxane yields the product, 2-(4-amino-1H-pyrazolo[3,4-d]pyrimidin-3-yl) iodide (Cpd. 2-4).

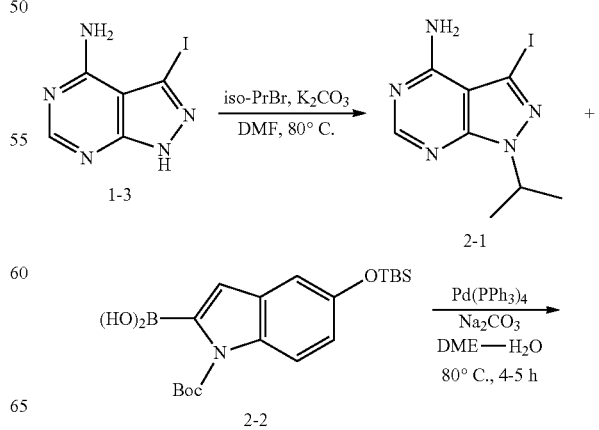

Scheme 2. Synthesis of 2-(4-amino-1-isopropyl-1H-pyrazolo[3,4-d]pyrimidin-3-yl)-1H-indol-5-ol (Compound 2-4).

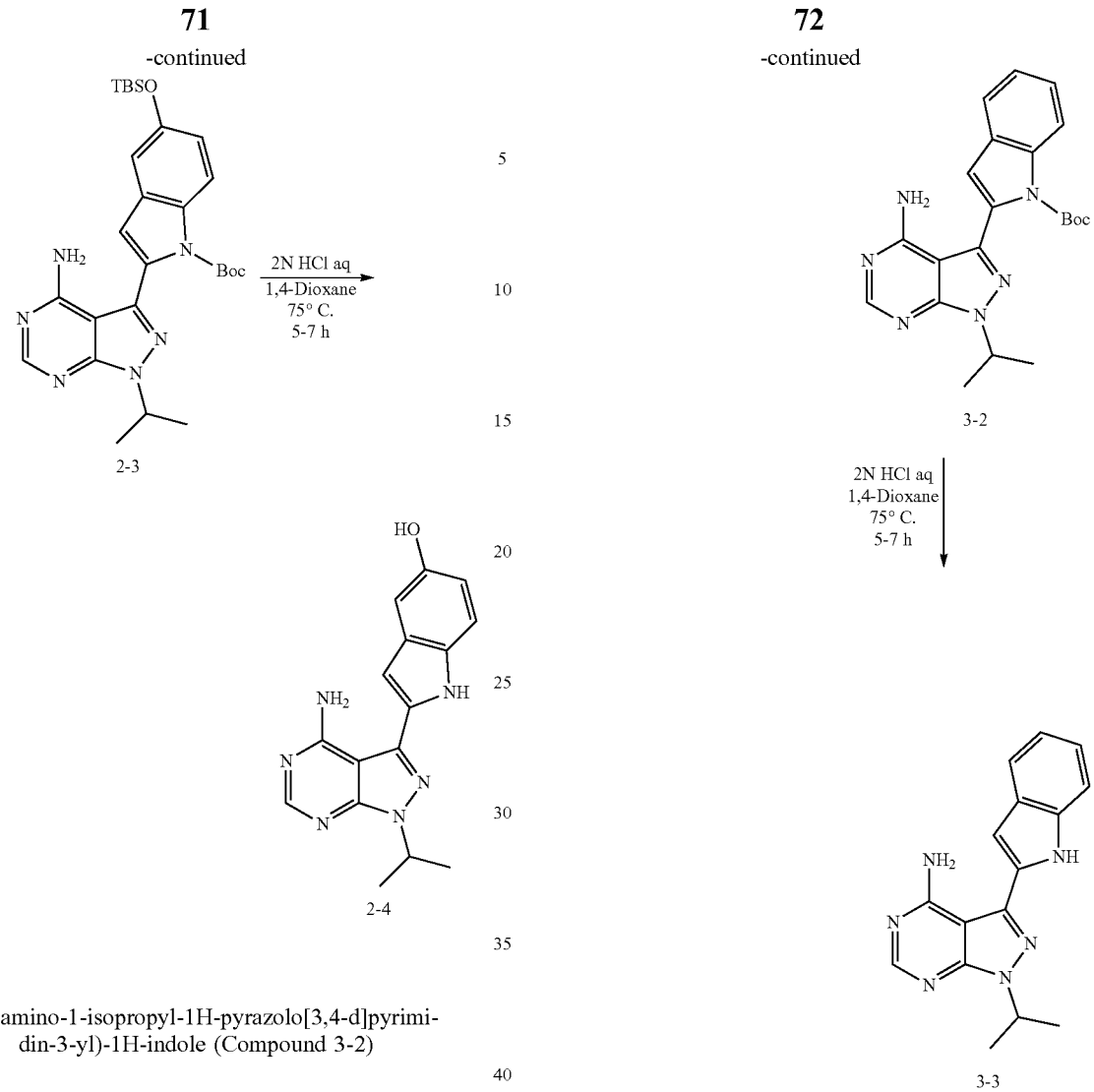

2-(4-amino-1-isopropyl-1H-pyrazolo[3,4-d]pyrimidin-3-yl)-1H-indole (Compound 3-2)

Synthesis of 2-(4-amino-1-isopropyl-1H-pyrazolo[3,4-d]pyrimidin-3-yl)-1H-indole (Compound 3-3) is accomplished via the same reactions except that boronic acid 3-1 is used, as shown in Scheme 3.

Scheme 3. Synthesis of 2-(4-amino-1-isopropyl-1H-pyrazolo[3,4-d]pyrimidin-3-yl)-1H-indole (Compound 3-3).

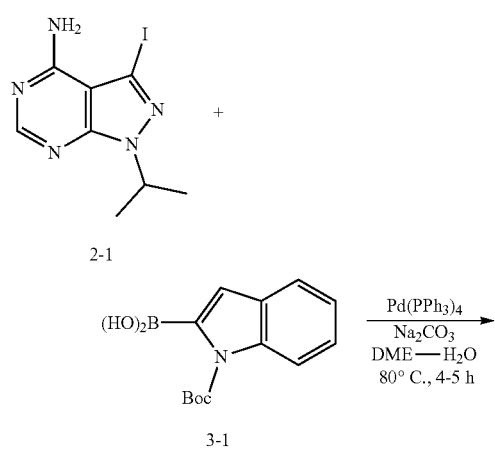

The synthesis of 2-(4-amino-1-isopropyl-1H-pyrazolo[3,4-d]pyrimidin-3-yl)-1H-indol-7-ol (Compound 3-4) is accomplished via the same reactions as in Schemes 1 and 2, using a 7-tert-butyldimethylsilyloxy (TBS) indolyl boronic acid instead of the 5-TBSO indolyl species illustrated. Alternatively, Compound 3-4 is synthesized via methoxy protected intermediates as shown in Scheme 3-B. 5-Methoxy indolyl boronic acid, compound 3-1 is coupled to pyrazolopyrimidine iodide (compound 2-1) using palladium acetate and triphenylphosphine in the presence of sodium carbonate base to provide intermediate 3-6. Along with the desired product, some partially deprotected product is also formed. The crude mixture is taken into the next step for complete Boc deprotection. Deprotection is accomplished with aqueous HCl in ethanol solution and compound 3-7 is isolated as the HCl salt. In the last step, the salt is brought to pH 8 in aqueous potassium carbonate to obtain the free base. This material is treated with boron tribromide to remove the methyl ether protection and yield the final product, Compound 3-4.

Scheme 3-B. Synthesis of 2-(4-amino-1-isopropyl-1H-pyrazolo[3,4-d]pyrimidin-3-yl)-1H-indol-7-ol (Compound 3-4).

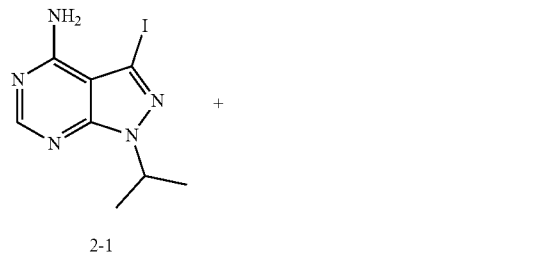

2-1

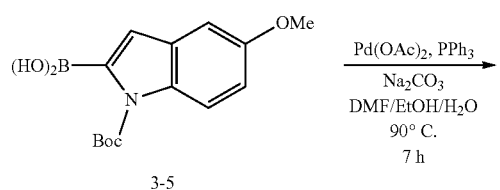

3-5

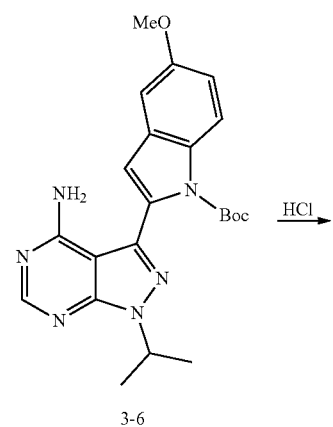

3-6

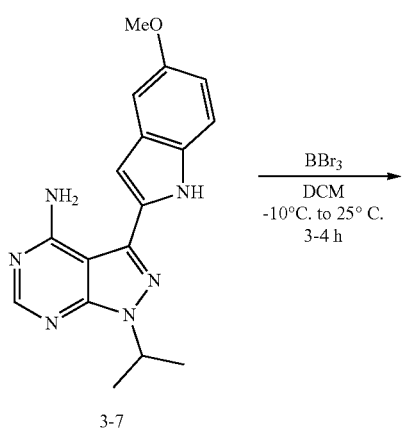

3-7

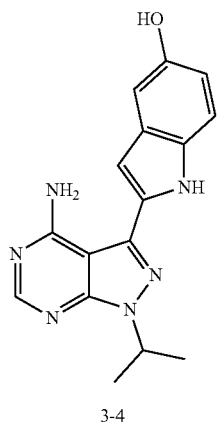

3-4

The synthesis of 2-(4-amino-1-isopropyl-1H-pyrazolo[3,4-d]pyrimidin-3-yl)-1H-indol-6-ol (Compound 3-5) is accomplished via the same reactions as in Schemes 1 and 2, using a 6-tert-butyldimethylsilyloxy (TBS) indolyl boronic acid instead of the 5-TBSO indolyl species illustrated or it is synthesized via reactions as shown in Scheme 3-B, using a 6-methoxy indolyl boronic acid instead of the 5-methoxy indolyl boronic acid illustrated.

Compound 3-5

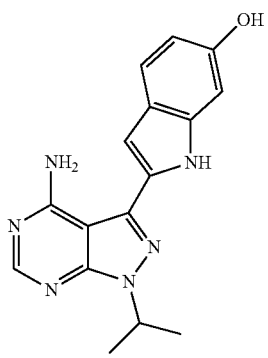 [SMILES: CC(C)n1nc(-c2cc3ccc(O)cc3[nH]2)c2c(N)ncnc21]

The synthesis of PP-30 is shown in Scheme 4.

Scheme 4. The synthesis of PP-30 is accomplished via the same reactions as in Schemes 1 and 2, employing palladium catalyzed Suzuki coupling between the pyrazolopyrimidine intermediate 2-1 and a boronic acid 4-1 to obtain the product, PP-30.

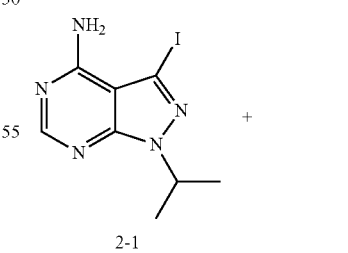

2-1

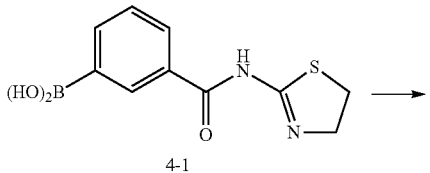

4-1

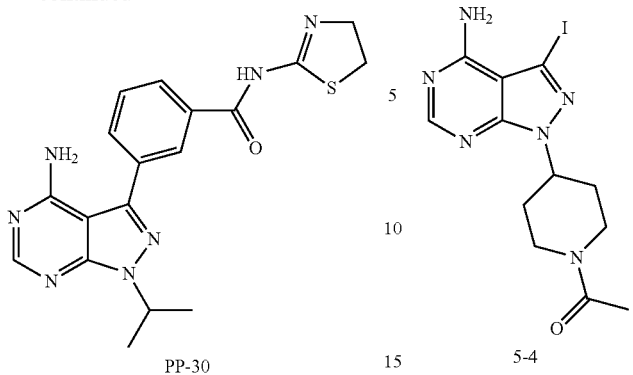

PP-30

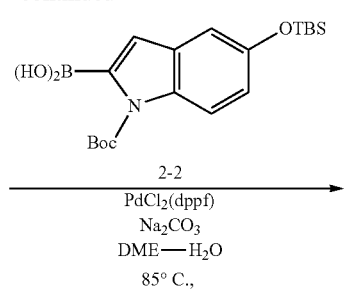

5-4

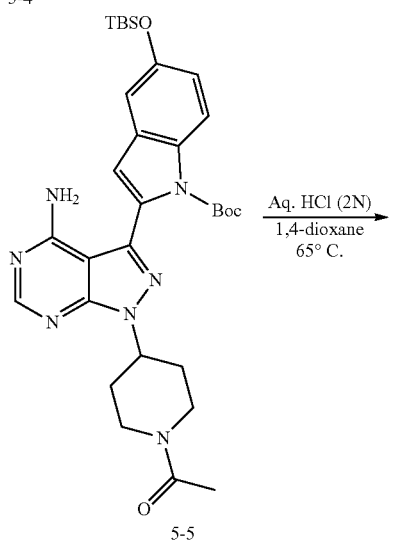

The synthesis of 2-(4-amino-1-(4-N-acetyl-piperidin-1-yl)-1H-pyrazolo[3,4-d]pyrimidin-3-yl)-1H-indol-5-ol (Compound 5-6) is accomplished as illustrated in Scheme 5. Acetic anhydride is used to protect the nitrogen of 4-hydroxy piperidine to obtain compound 5-2. Tosyl chloride, with triethylamine and dimethylaminopyridine (DMAP) in methylene chloride is used to produce the tosylate 5-3. The iodopyrazolopyrimidine intermediate 1-3 is reacted with tosylate 5-3 in dimethylformamide in the presence of cesium carbonate at 80° C. to couple the piperidinyl moiety to the pyrazolopyrimidine molecule, yielding intermediate 5-4. Compound 5-4 is transformed via a Suzuki coupling with boronic acid 2-2 using dichloro[1,1'-bis(diphenylphophino)ferrocene]palladium II (PdCl$_2$(dppf)) in aqueous DME, to obtain compound 5-5, which is deprotected under acidic conditions to yield compound 5-6.

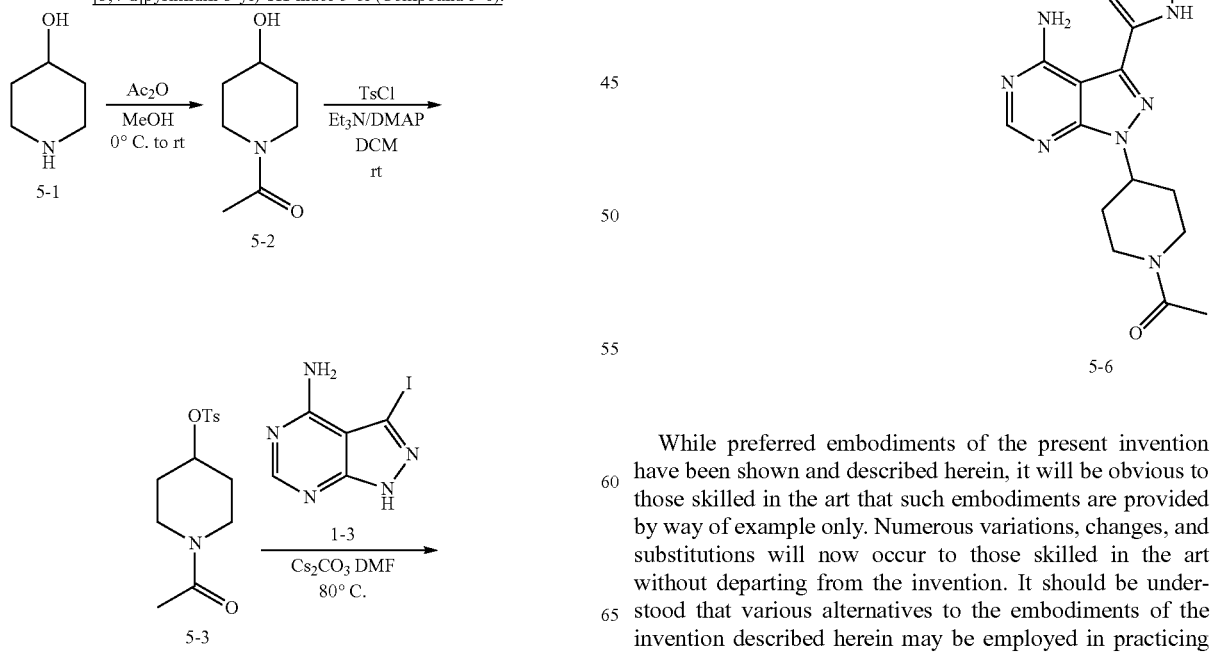

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 42

Figure 26A:
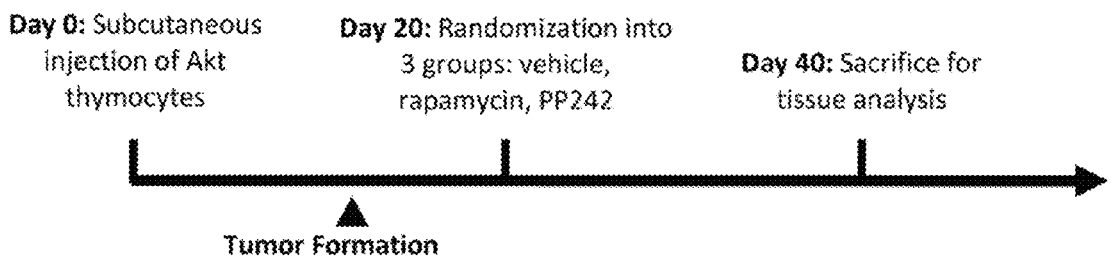
FIGS. 26A-26D illustrate that PP242 is more efficacious than rapamycin in the first in vivo preclinical trial in an Akt-mTOR addicted tumor model.
Figure 26B:
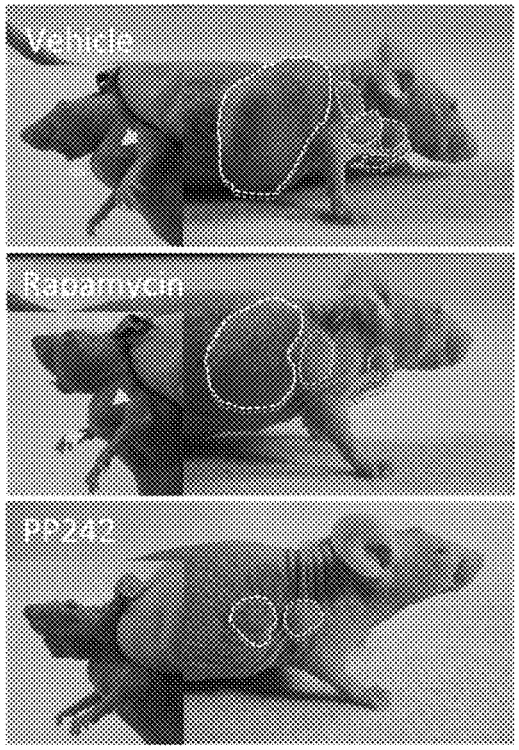
Figure 26C:
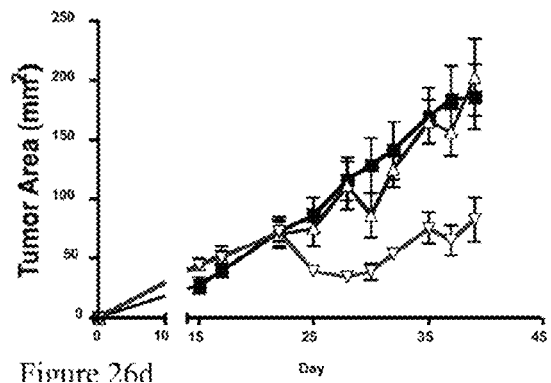
Figure 26D:
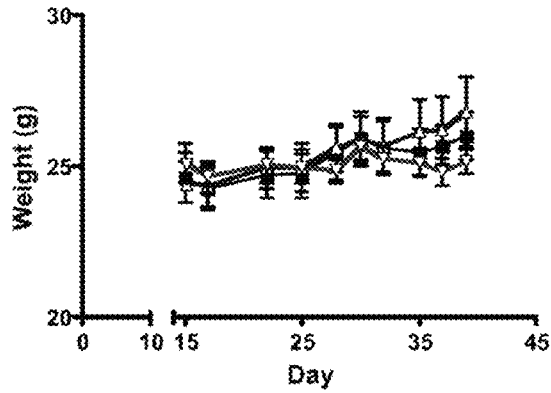
Figure 27A:
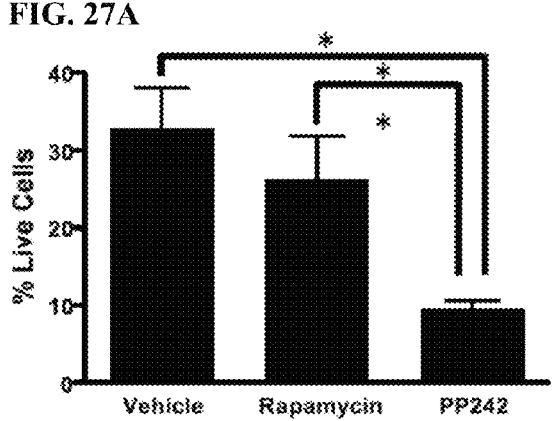
FIGS. 27A-27F illustrate that PP242 in vivo superiority over rapamycin is mediated by incomplete blockade of eIF4E.
Figure 27B:
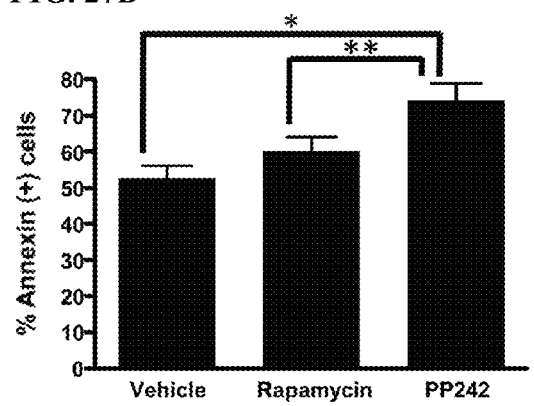
Figure 27C:
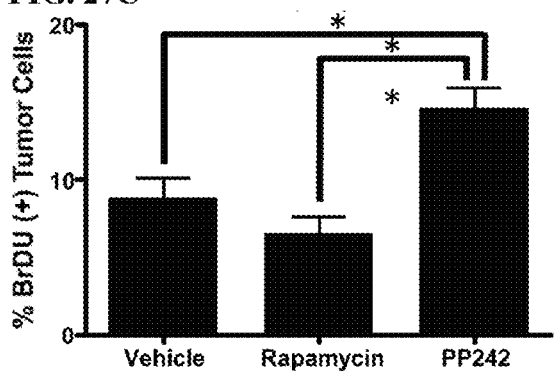
Figure 27D:
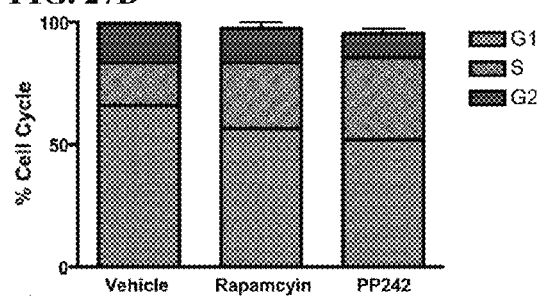
Figure 27E:
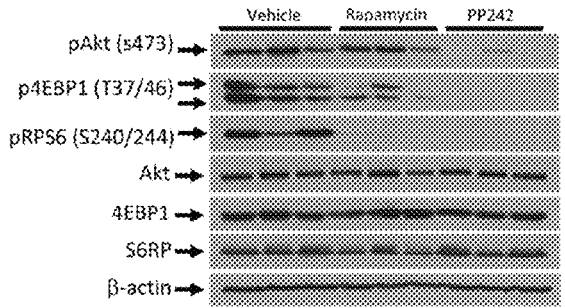
Figure 27F:
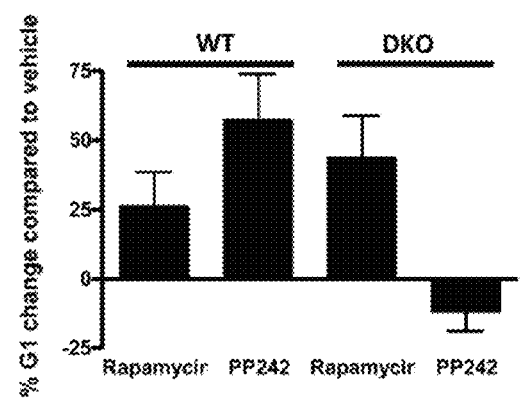

Comparison of Therapeutic Effectiveness of Direct Active-Site mTOR Kinase Inhibition and Rapamycin in Oncogenic Akt-mTOR Driven Tumors The therapeutic efficacy of PP242 in vivo was assessed by conducting a randomized preclinical trial of PP242 in an Akt murine allograft model. See FIGS. 26A-26C. Using a murine allograft model addicted to oncogenic Akt-mTOR signaling, the outstanding question of whether or not more stringent inhibition of mTOR (via PP242) has a significant biological effect on in vivo tumor growth was addressed. Mice were randomized three groups: vehicle control, rapamycin 5 mg/kg and PP242 100 mg/kg. After 20 days of treatment, all groups maintained body weight demonstrating drug tolerability and lack of noticeable toxicity. Out of the three cohorts, only mice treated with PP242 had no tumor growth. Mice treated with rapamycin mirrored the vehicle treated cohort. See FIGS. 27A-27F. This demonstrates for the first time that tumors that arise from oncogenic Akt-mTOR signaling are selectively responsive to PP242, but not rapamycin.

Materials and Methods

Cell line. Immortalized wild type and 4EBP1/2 double knockout mouse embryonic fibroblasts were kindly provided by Dr. Nahum Sonenberg (Department of Biochemistry, McGill University, 3655 Sir William Osler, Montreal, Quebec, Canada, H3G 1Y6). Cells were propagated in DMEM, 10% FBS, 2 mM L-glutamine and penicillin/streptomycin.

Mice and allograft model preparation. Transgenic Lck-Akt2 mice where kindly provided by J. R. Testa (Human Genetics Program, Fox Chase Cancer Center, 7701 Burholme Avenue, Philadelphia, Pa. 19111, USA). Thymi were dissociated in PBS supplemented with 3% fetal bovine serum (PBS-FBS) and filtered through a 40 µm nylon mesh (BD Biosciences). Thymocytes were then washed in PBS-FBS and pelleted at 300×g for 5 min. 8-12 week old NOD/SCID mice were injected with $2 \times 10^6$ total myristolated-Akt transgenic thymocytes mixed in a 1:1 ratio of RPMI and matrigel. A volume was 200 µl of the cell mileu was injected per mouse in the right subscapular region subcutaneously. Tumors were allowed to form for 20 days. Length and width caliper measurements were taken every 2-3 days. UCSF IACUC approval was obtained for all murine experimentation.

Treatment and randomization. 45 allograft mice were generated. 43 of the 45 mice developed tumors and were randomized on day 21 to receive either vehicle, rapamycin (5 mg/kg), or PP242 (100 mg/kg) by gavage 7 days a week.

Tumor preparation. Whole tumor samples were dissociated using a 40 µm nylon cell strainer (BD Biosciences) and resuspended in 3% FBS in PBS.

Western blot analysis. Tumors were removed from euthanized mice on day 45. Single cell suspension was generated a described herein. Cells were pelleted and lysed in protein lysis buffer (150 mM NaCl, 50 mM Tris, 4 mM KCl, 1 mM MgCl2, 1 mM Na3VO4, 10% glycerol, 1% Nonidet P-40, Complete Protease inhibitor (Roche), Phos-stop (Roche) and 20 nM microcysteine (Calbiochem)). Total protein was quantified using the Bradford method (Bio-Rad), resolved on 4-20% gradient SDS-PAGE and transferred onto nitrocellulose membranes (Bio-Rad). Blots were blocked in non-fat dry milk (4% w/v in TBS and 0.1% Tween 20) for 1 hr at room temperature. The following primary antibodies were used according to the manufacturer's instructions: rabbit monoclonal anti-phospho-Akt (Ser473), anti-phospho-rpS6 (Ser240/244), anti-phospho-4EBP1 (Thr37/46), Akt, rpS6 and 4EBP1 (all from Cell Signaling) as well as mouse monoclonal β-actin (Sigma). The appropriate secondary antibodies (Amersham) were used at 1:10,000 (v/v) in TBS+0.1% Tween 20 for 1 hr at room temperature and blots were developed using PICO (Pierce Biotechnology).

Annexin/PI analysis of apoptosis. To characterize in vivo apoptosis, equal numbers of freshly isolated tumor cells were labeled with APC-Cy7-conjugated anti-CD4 (BD Biosciences) and pacific blue-conjugated anti-CD8 (Caltag) in PBS-FBS (all antibodies diluted 1:100 v/v). Apoptotic cells were labeled with Annexin V-FITC (BD Biosciences) as well as propidium iodide, following manufacturer's instructions. Samples ($1 \times 10^6$ cells) were acquired on a BD LSRII flow cytometer. Analysis and quantification were done using FlowJo (version 8.7.1).

In vivo quantification of cell proliferation. Mice were injected with 300 µg of BrDU three hours before tumors were collected. Cells were labeled with APC-Cy7-conjugated anti-CD4 (BD Biosciences) and pacific blue-conjugated anti-CD8 (Caltag) in PBS-FBS (all antibodies diluted 1:100 v/v). Stained cells were washed, fixed and processed for flow cytometry using the FITC BrdU Flow kit (BD Biosciences), following manufacturer's instructions. Cells were analyzed on a BD LSRII flow cytometer and percentage of BrdU positive cells was determined using the FlowJo software (version 8.7.1).

Cell cycle analysis. Tumor cells and mouse embryonic fibroblasts were fixed in 70% ethanol overnight in −20° C. Cells were subsequently washed with PBS twice and treated with 100 µg/mL DNase free RNase (Roche) for 30 minutes at room temperature. Following another PBS wash, the cells were permeabilized and treated with propidium iodide (PI) using a mixture of 10 mg/mL PI, 0.1% Tween, 0.1% sodium citrate. Cell cycle data was acquired using a BD FACS Caliber (BD Biosciences).

Example 43 mTOR Complex-2 Modulation of SGK1 Phosphorylation and ENaC-Dependent Na+Transport Summary The present experiments were designed to investigate which mTOR complex was involved in the phosphorylation of SGK1 and ENaC-dependent Na+ transport in renal epithelial cells. By using a specific inhibitor of mTOR, reduction was observed in SGK1 phosphorylation and amiloride-sensitive Na+ current. In contrast, rapamycin treatment showed minimum effect on the phosphorylation of SGK1 and ENaC-dependent Na+ transport, suggesting involvement of mTORC2. Furthermore, shRNA-mediated knockdown of the expression of rictor inhibited both SGK1 phosphorylation and amiloride-sensitive Na+ current. In contrast, the phosphorylation of SGK1 and ENaC-dependent Na+ transport in renal epithelial cells remained unchanged upon knockdown of the expression of raptor. Finally, SGK1 was found to be associated mainly with mTORC2 and marginally with mTORC1.

Materials and Methods

Cell culture and recombinant plasmid transfection Human Embryonic Kidney (HEK 293) cells were regularly maintained in plastic tissue culture flasks at 37° C. in Dulbecco's Modified Eagle's medium (DMEM) supplemented with 10% fetal bovine serum and 100 units/ml penicillin/streptomycin. Cells were seeded on 10 cm dishes (3×106 cells/dish) and allowed to grow overnight. They were then transfected with 5 μg pMO/Flag/mSGK1 (Flag-epitope at N-terminal of mouse SGK1) or the empty vector using lipofectamine according to manufacturer's instructions (INVITROGEN™, Carlsbad, Calif.). Cells were maintained in serum-free DMEM supplemented with 10% HYCLONE™ CELL BOOST™ 1 supplement (Hyclone, Logan, Utah, USA) for 24 h prior to treatment with 100 nM Insulin for 1 h and then treated with 1 μM PP242, 20 μM LY294002 or 0.1 μM rapamycin for 1 h.

Immunoprecipitation and immunoblotting. Transfected cells were lysed in binding buffer (50 mM Tris-HCl, pH 7.5, 10% glycerol, 1 mM EDTA, 2 mM DTT, 150 mM NaCl, 1% TRITON™ X-100 or 0.3% CHAPS) for 15 min. After centrifugation, the supernatants were collected and incubated with the anti-flag M2 affinity beads (Sigma). The immunoprecipitates were collected by centrifugation, washed three times and boiled for 5 min in 50 μl of cracking buffer (50 mM Tris-HCl, pH 7.0, 10% glycerol, 2% SDS, 2% β-mercaptoethanol). Immunoblotting was carried out by separating the immunoprecipitates on 10% polyacrylamide gels as described using a Bio-Rad minigel apparatus, and transferred electrophoretically to Hybond-C Extra membranes (GE Healthcare) using a Trans-Blot apparatus (Bio-Rad). The membranes were incubated to block non-specific binding in 5% non-fat dry milk in T-PBS (1.5 mM KH2PO4, 8 mM Na2HPO4, 2.7 mM KCl, 130 mM NaCl and 0.1% Tween 20) with gentle agitation for 1 hr at room temperature. Rabbit antisera against rictor, raptor or mTOR were diluted 1:1000 in T-PBS, respectively, and applied to the membranes for overnight. After washing with T-PBS, the membranes were incubated with peroxidase-conjugated goat anti-rabbit IgG in T-PBS for 1 hr, washed three times in T-PBS, and incubated with ECL Plus Western Blotting Detection System working solution (GE Healthcare) according to the manufacturer's instructions.

Generation of recombinant lentiviruses harboring rictor or raptor shRNAs. Synthesized sense and antisense oligos were annealed using a touchdown protocol on a PTC-200 thermal cycler at 950 C for 30 s, 600 C for 10 min, then cooled to 200 C at 1 degree every 15 s. The annealed shRNAs were ligated with the pLentiLox 3.7 vector digested with XhoI/HpaI and treated with calf intestinal alkaline phosphatase. The ligated DNA was transformed into DH5α competent bacterial cells. Ampicillin-resistant colonies were picked and grown in LB broth for 16 hrs. Plasmid DNA was isolated using mini-prep columns (Fermentas). Positive recombinants were identified by restriction enzyme digestion and verified by DNA sequencing. Recombinant lentiviruses were generated by co-transfection of plasmids harboring the shRNAs and a mixture of packaging plasmids into HEK 293T packaging cells. Viral supernatants were harvested 48 hr after transfection. To determine the viral titer, a 10-fold dilution series of viruses was made and used to infect fresh HEK 293T cells. A viral titer of 5×105/ml was routinely observed by visualizing cells for EGFP fluorescence.

Measurement of ENaC-dependent Na+transport. Renal epithelial cells, mpkCCDcl4, were maintained in plastic tissue culture flasks in modified DMEM/Ham's F12 (1:1) medium ("Regular medium") as described previously (Wang et al., 2008, Id.). For electrophysiological measurements, cells were seeded on type VI collagen (Sigma, St. Louis, Mo.) coated filters (TRANSWELL™, pore-size 0.4 μm, Corning Costar) and grown at least 24 h prior to treatment with aldosterone at a concentration of 1 μM in the presence and absence of PP242, LY294002, and rapamycin. Transepithelial resistance and potential difference across the cell monolayer were measured using a mini-volt-ohmmeter (MilliCell ERS, Milipore) at specified time points following treatment. The equivalent short-circuit current was calculated using Ohm's law.

Figure 28A:
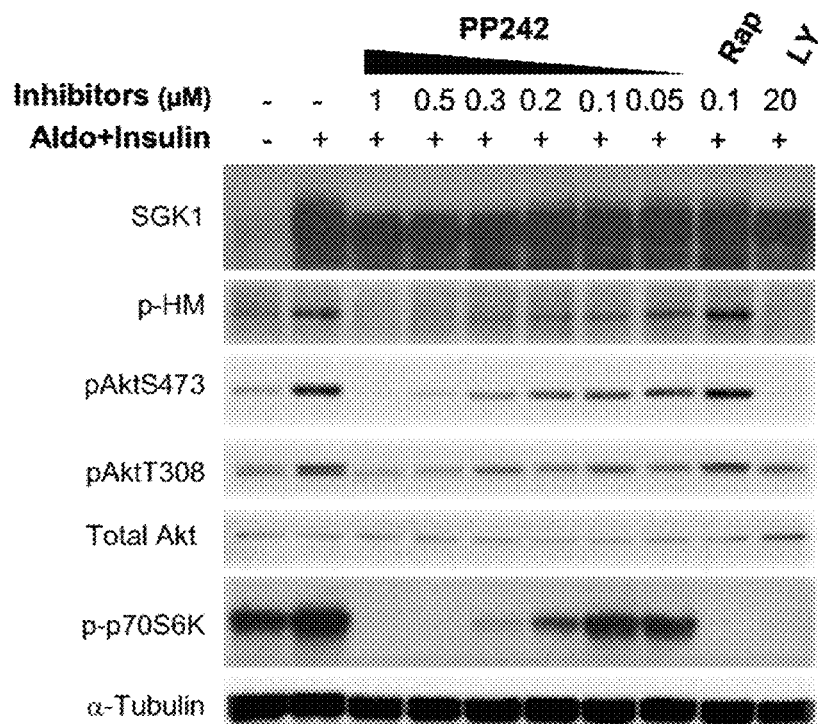
FIGS. 28A-28C illustrate rapamycin-resistant modulation of SGK1 phosphorylation by mTOR.
Figure 28B:
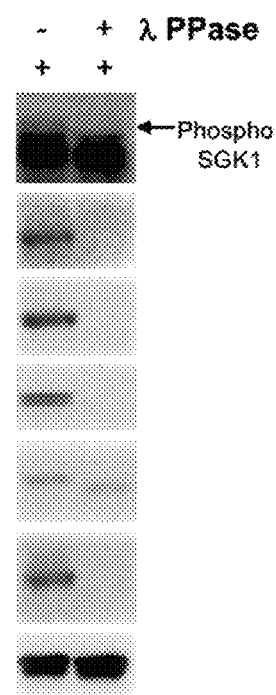

Results mTOR modulates SGK-1 PHOSPHORYLATION in mammalian kidney epithelial cells. By taking advantage of a recently developed, highly selective, ATP-competitive inhibitor of mTOR to acutely inhibit mTOR (Feldman et al., 2009, *PLoS Biol.* 7:e38), it was sought to determine whether SGK1 phosphorylation and its physiologic function are dependent on mTOR activity. Unlike rapamycin, this compound, PP242, binds to the active site of mTOR, irrespective of whether it is associated with components of complex 1 or 2, and specifically inhibits both TORC1 and TORC2 outputs (Feldman et al., 2009, Id) Inhibition occurs at concentrations that do not inhibit 219 other kinases, including PDK1 as well as all isoforms of PI3K, SGK and Akt (Feldman et al., 2009, Id.). We first asked whether mTOR inhibition affects SGK1 phosphorylation in mpkCCD cells, a cell line which is derived from the kidney's cortical collecting duct (CCD) and retains the molecular machinery required for hormone-regulated transepithelial sodium transport, when grown on ion-permeable filters (Bens et al., 1999, *J. Am. Soc. Nephrol.* 10:923-934). In these cells, SGK1 phosphorylation is stimulated by insulin, and its expression is markedly increased by aldosterone, through effects on SGK1 gene transcription (Pearce, 2003, Id.) Attempts to detect HM phosphorylation of endogenous SGK1 using a commercially available antibody (anti-SGK1-pSer422) were unsuccessful, consistent with a previous report (Garcia-Martinez and Alessi, 2008, Id.). Therefore a highly sensitive and specific holo-SGK1 antibody was used, which recognizes both the phosphorylated and unphosphorylated forms of SGK1 (Webster et al., 1993, *Mol. Cell. Biol.* 13:203120-40.; Wang et al., 2001, *Am. J. Physiol.* 280:F303-F313; Wang et al., 2008, Id.), to detect phosphorylated forms of SGK1 by mobility shift. In the presence of aldosterone and insulin, multiple SGK1 bands were detected; the upper bands were eliminated by the pan-PI3K family inhibitor LY294002 (FIG. 28A). Previous work strongly supports the identification of these upper bands as the phosphorylated forms of SGK1, phosphorylated in both the HM and activation loop. Treatment of extracts with lambda phosphatase eliminated the upper bands, further supporting the conclusion that they represent phosphorylated SGK1 (FIG. 28B). Rapamycin, which inhibits mTORC1 but not mTORC2, had no effect on the upper bands (FIG. 28A), while PP242 blocked their appearance at concentrations of 0.2-0.3 μM, which do not inhibit the other relevant kinases, notably PI3K and PDK1 (Feldman et al., 2009, Id.). As confirmation that mTORC1 is expressed in these cells and inhibited by rapamycin, we examined the phosphorylation state of the prototypical mTORC1 substrate, p70S6K. Rapamycin, LY294002 and PP242 all eliminated the band detected by anti-phospho p70S6K antibody, indicative of an mTORC1-mediated effect. Importantly, p70S6K phosphorylation was fully abrogated at a concentration at which rapamycin treatment failed to alter appearance of the phosphorylated forms of SGK1. Together, these data suggest that SGK1 phosphorylation is dependent upon mTORC2, but not mTORC1.

Figure 28C:
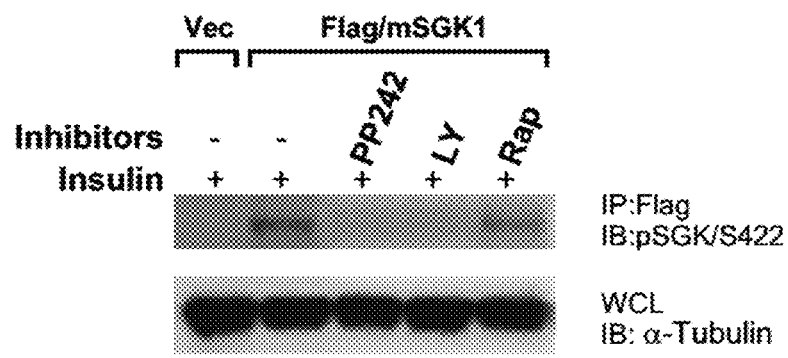
Figure 29A:
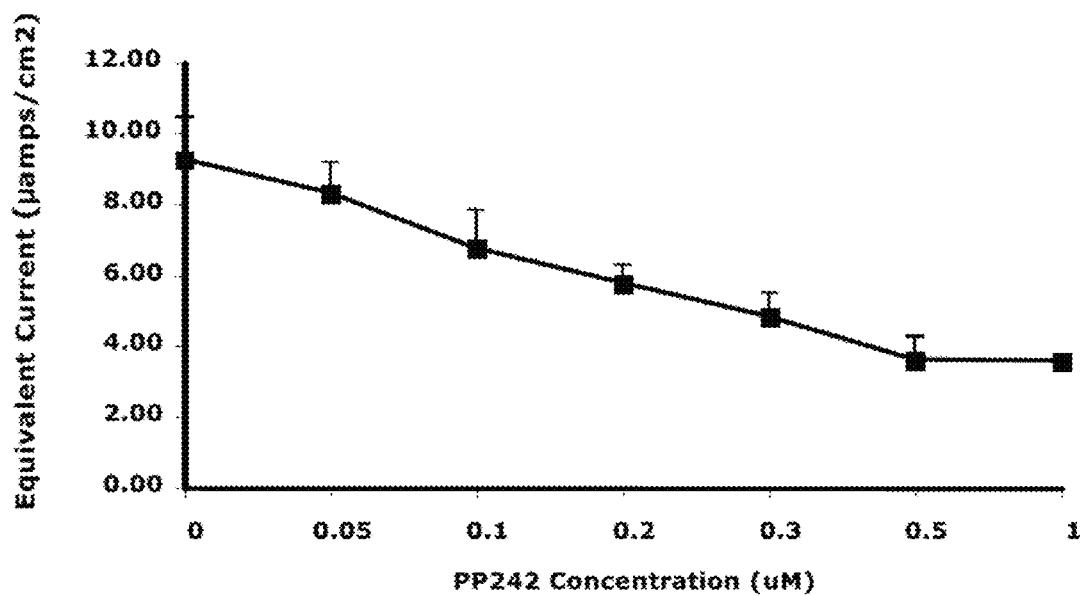
FIGS. 29A-29B illustrate rapamycin-resistant modulation of ENaC-dependent Na+ current by mTOR.
Figure 29B:
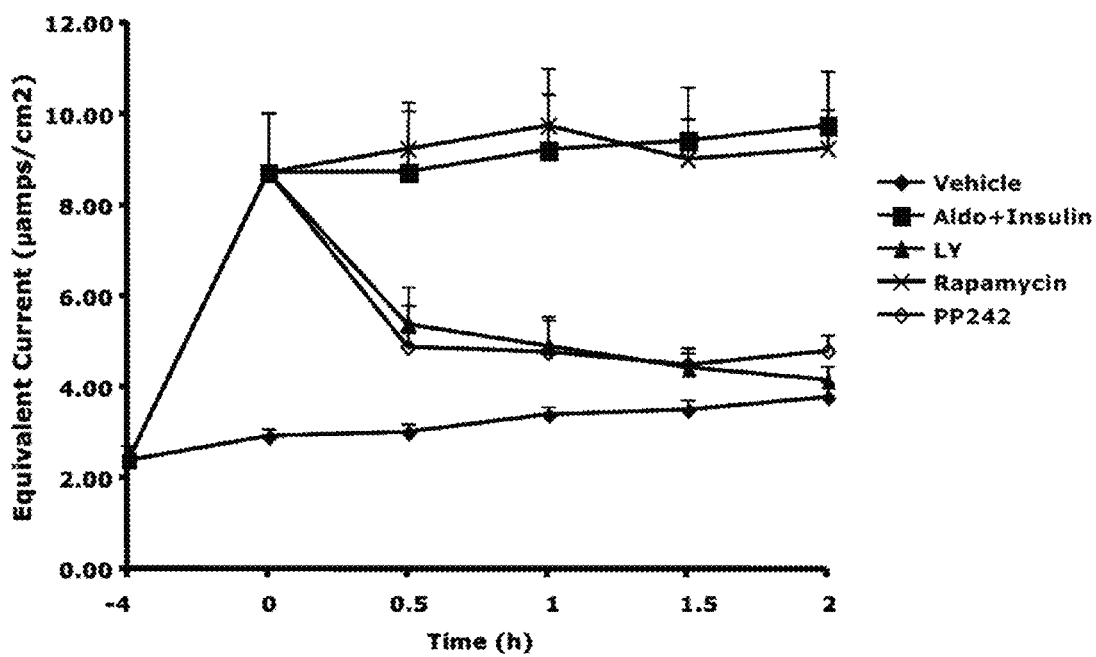

In order to look directly at the role of mTOR in SGK1 HM phosphorylation, conditions were established in which an anti-SGK1 pS422 antibody would give a specific SGK1-pS422-dependent signal. In a previous report, Garcia-Martinez and Alessi (2008, Id.) were unable to detect a specific pS422-SGK1 signal, and that the endogenous species detected with this antibody in murine embryo fibroblasts co-migrated with a species detected by a well characterized antibody recognizing the HM phosphorylated form of p70-S6K. The current data (for example, FIGS. 28A-28C) are consistent with this observation. In contrast, Hong et al. (2008, Id.) reported detecting endogenous HM phosphorylated SGK1 using the same antibody; it is not clear why these findings are not consistent with either the current findings, or those of Garcia-Martinez and Alessi (2008, Id.). The latter were able to detect phospho-SGK1 when it was expressed as a GST-fusion protein in murine embryo fibroblasts and enriched on glutathione beads. A similar strategy was pursued, that is expressing a flag epitope-tagged SGK1 in HEK293 cells, which were treated with insulin followed by PP242, LY294002 or rapamycin. Whole cell lysates were subjected to immunoprecipitation with anti-flag antibody and probed by Western blotting. In immunoblots stained with anti-pS422, a band was detected, which was consistent with pS422-SGK1: it depended on the presence of SGK1 expression vector, and co-migrated precisely with the upper band detected with either anti-holo-SGK1 or anti-flag antibody (not shown). This band was abrogated by PP242 and LY294002 (LY), but not by rapamycin (FIG. 28C). These data support the notion that phosphorylation of transfected SGK1 is mTORC2—and not mTORC1—dependent in HEK293 cells, and further support the identification of the shifted species detected by holo-SGK1 antibody in CCD cell lysates as HM-phosphorylated SGK1 (and not SGK1 phosphorylated only at the activation loop by PDK1). Taken together, these data support the notion that a rapamycin-resistant output of mTOR is required for SGK1 phosphorylation, and that although mTORC1 is expressed in CCD cells, it does not phosphorylate SGK1 at the HM motif site.

mTOR activity is required for Na+transport in mammalian kidney epithelial cells. The best-characterized function of SGK1 in mammals is to mediate aldosterone-induced ENaC-dependent Na+ transport. The fundamental role of SGK1 in ENaC regulation has been demonstrated in numerous different systems, including a variety of cultured cells, Xenopus oocytes, and knockout mice. In order to determine if mTOR activity is important for Na+ transport, we examined the effect of PP242 on Na+ currents in mpkCCD cells grown on TRANSWELL™ filters. As shown in FIGS. 29A-29B, PP242 completely blocked aldosterone-induced current with an IC-50 of approximately 0.2 μM, while rapamycin, at concentrations that fully blocked mTORC1 had no effect (FIG. 29A). Although a precise IC-50 for PP242 inhibition of SGK1 HM phosphorylation could not be determined, it was of the same order of magnitude (compare FIG. 28A and FIG. 29A), and well below the IC-50 for the other relevant kinases, including PI3K (Feldman et al., 2009, Id.). The effect of PP242, like that of LY294002, was rapid (T1/2 of approximately 15 minutes), reversible, and occurred without any significant drop in electrical resistance, a sign of tight junction integrity and cell health (FIG. 29B). It should be noted that prolonged rapamycin treatment (>16 h) does inhibit Na+ current, an effect that has been attributed to blockade of mineralocorticoid receptor function (Edinger et al., 2002, Am. J. Physiol. 283:F254-F261). It also should be noted that prolonged treatment with PP242 or LY294002 (>24 h) diminishes electrical resistance and causes morphological changes (e.g. blebbing) in cells, consistent with a toxic effect. Taken together, these data strongly support the idea that mTORC2 is required for SGK1 HM phosphorylation and acute control of transepithelial sodium current in mammalian kidney collecting duct cells.

Figure 30A:
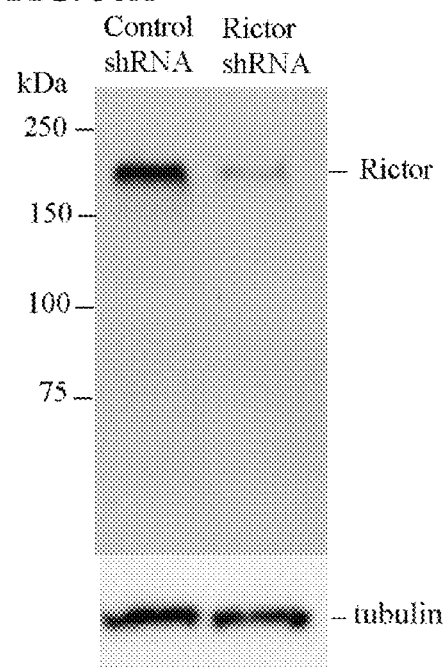
FIGS. 30A-30D illustrate inhibition of SGK1 phosphorylation by knockdown of rictor expression.
Figure 30B:
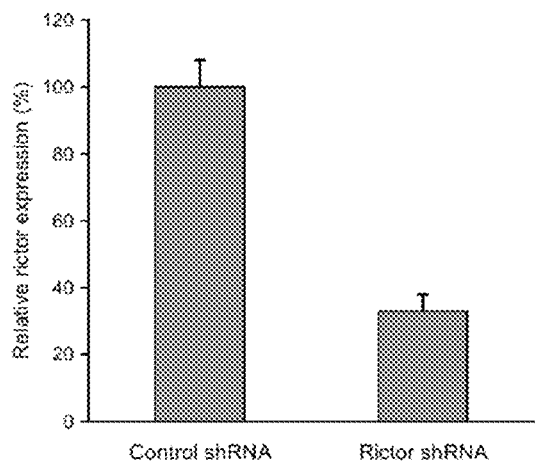
Figure 30C:
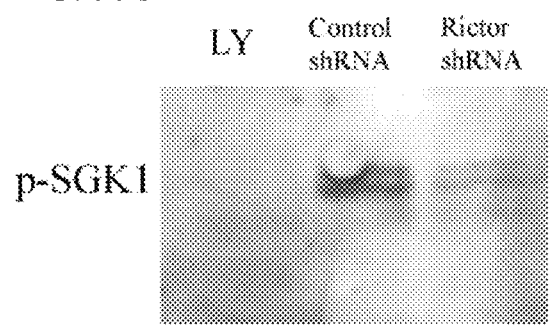
Figure 30D:
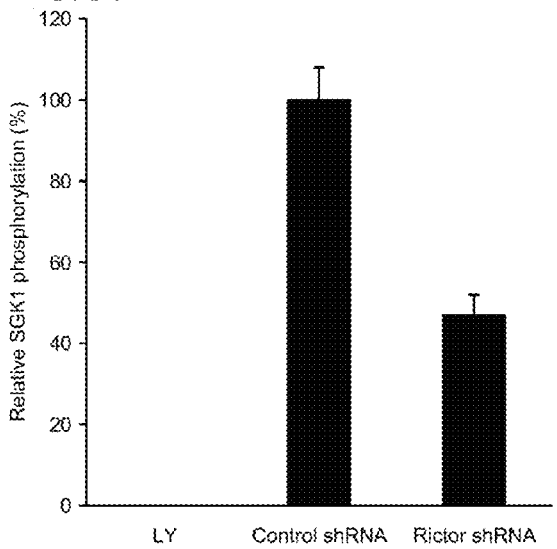

The role of rictor in SGK1 phosphorylation and ENaC-dependent Na+transport. The preceding experiments showed that SGK1 phosphorylation and ENaC-dependent Na+ transport were reduced by PP242 at concentrations that selectively inhibits the activity of mTOR (FIGS. 28A-28C and FIGS. 29A-29B). The inhibition on SGK1 phosphorylation and ENaC-dependent Na+ transport was, however, largely resistant to rapamycin treatment (FIGS. 28A-28C and FIGS. 29A-29B), suggesting involvement of mTORC2, but not mTORC1. To further investigate whether mTORC2 mediates SGK1 phosphorylation and ENaC-dependent Na+ transport, recombinant lentiviruses were generated harboring shRNAs directed at the mTORC2-specific component, rictor. Since the use of transfected HEK293 cells expressing SGK1 allows us to determine direct and unambiguous SGK1 phosphorylation at the HM motif site (FIG. 28C), we used this assay to examine the effect of rictor shRNA on SGK1 phosphorylation. Using lentiviral-mediated transduction, rictor expression was decreased by 67% in HEK293 cells (FIGS. 30A-30B), and HM phosphorylation of flag-tagged SGK1 was reduced by 53% (FIGS. 30-C-30D), whereas control shRNA exerted no discernible effect (FIG. 30C and FIG. 30D).

Figure 31A:
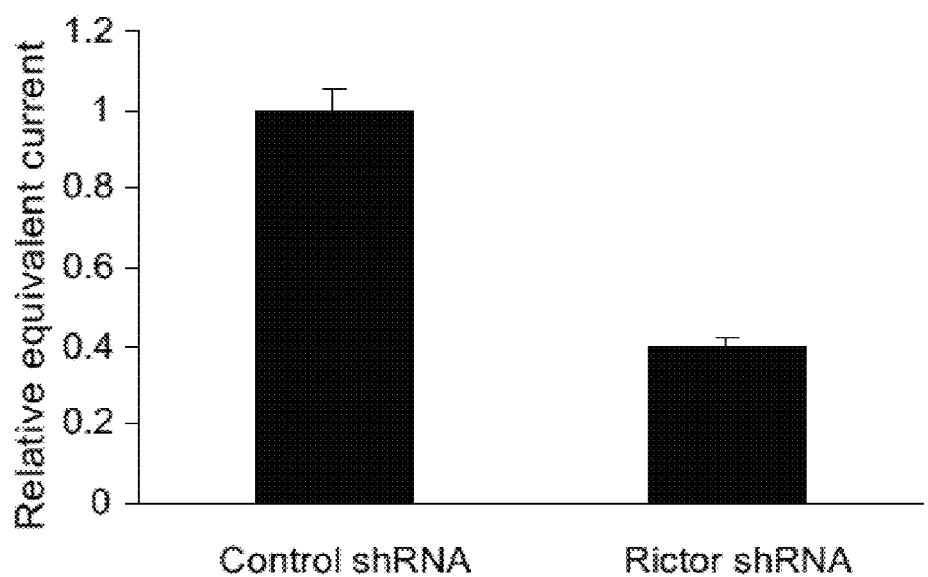
FIGS. 31A-31C illustrate inhibition of ENaC-dependent Na+ current by knockdown of rictor expression.
Figure 31B:
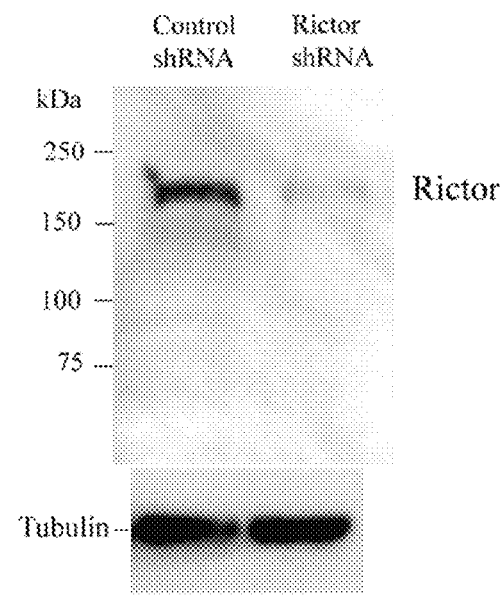
Figure 31C:
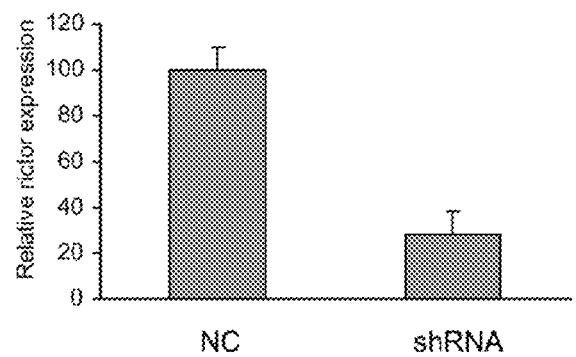

To examine whether knockdown of rictor expression affects ENaC-dependent Na+ transport, we infected mpkCCD cells with lentiviruses harboring the rictor shRNA, seeded the cells on TRANSWELL™ filters, and determined aldosterone-induced Na+ currents (FIGS. 31A-31C). Rictor shRNA reduced Na+ current by approximately 60% (FIG. 31A), which corresponded well to the knockdown in rictor expression (~72%) (FIG. 31B and FIG. 31C). Together with the small molecule inhibitor data, these data provide strong support for the conclusion that mTORC2 mediates SGK1 phosphorylation and ENaC-dependent Na+ transport.

Figure 32A:
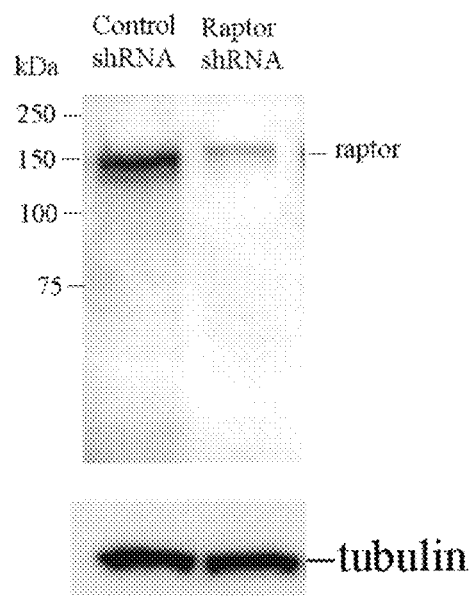
FIGS. 32A-32D illustrate the effect of raptor knockdown on SGK1 phosphorylation.
Figure 32B:
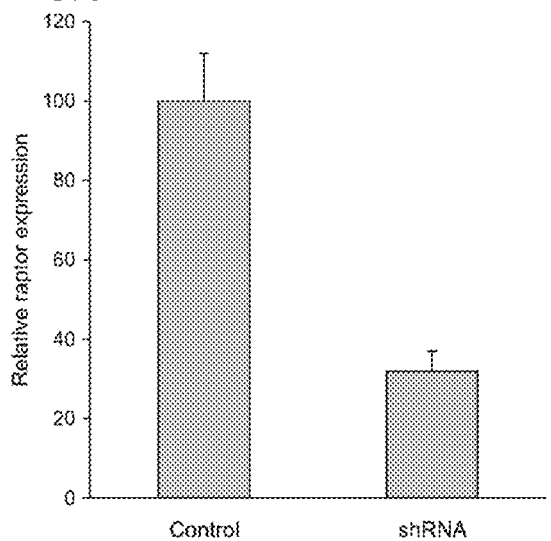
Figure 32C:
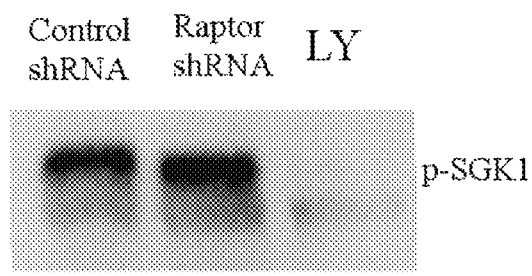
Figure 32D:
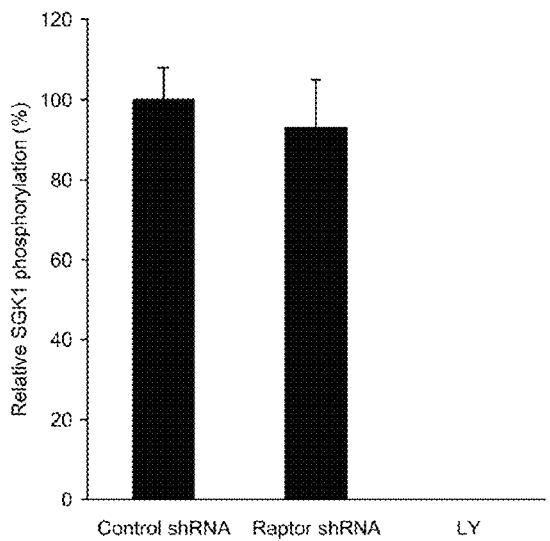
Figure 33A:
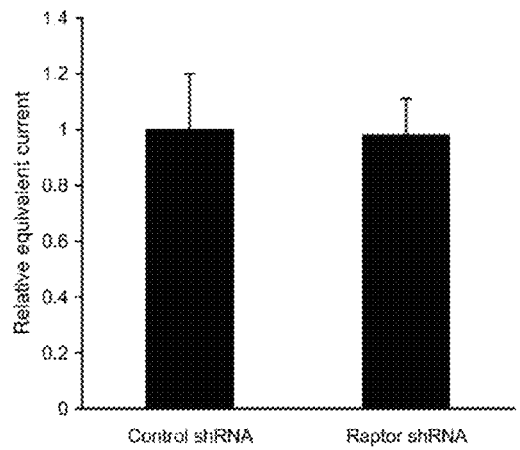
FIGS. 33A-33D illustrate the effect of raptor knockdown on ENaC-dependent Na+ current.
Figure 33B:
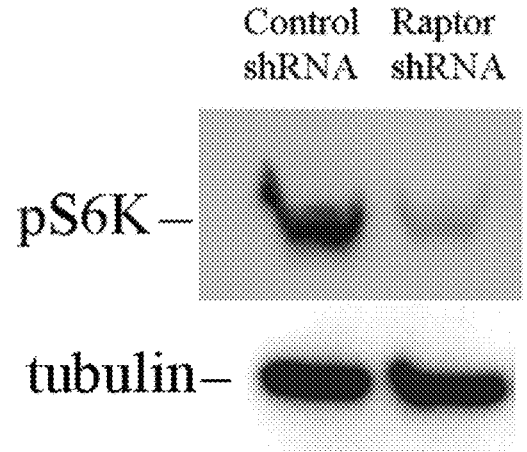
Figure 33C:
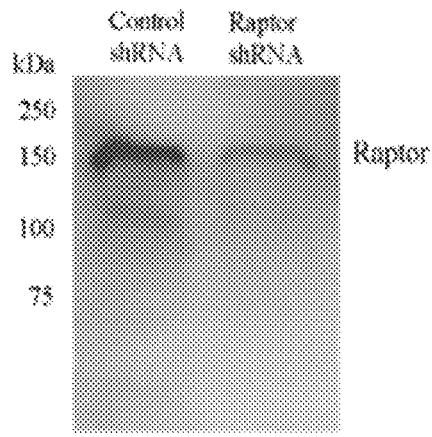
Figure 33D:
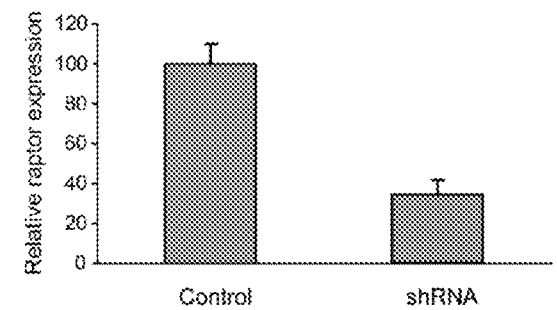

Raptor is not required for SGK1 phosphorylation and ENaC-dependent Na+transport. To further investigate whether mTORC1 is similarly required for SGK1 phosphorylation and ENaC-dependent Na+ transport, lentiviruses were generated harboring raptor shRNA. A knockdown of 68% in raptor expression was observed (FIG. 32B). The reduction in raptor expression, however, showed no effect on SGK1 phosphorylation in transfected HEK293 cells (FIG. 32C, FIG. 32D). When the raptor shRNA was expressed in mpkCCD cells, determination of Na+ transport showed a normal increase in aldosterone-induced currents (FIG. 33A). No inhibitory effect was observed (FIG. 33A), suggesting that mTORC1 is not required for ENaC-dependent Na+ transport. Since S6K is a well-known substrate for mTROC1, the effect of S6K phosphorylation upon knockdown of raptor expression was examined. Reduction in raptor expression resulted in a decrease in S6K phosphorylation in mpkCCD cells (FIG. 33B), demonstrating the effectiveness of the raptor shRNA in disrupting the function of mTORC1.

Figure 34A:
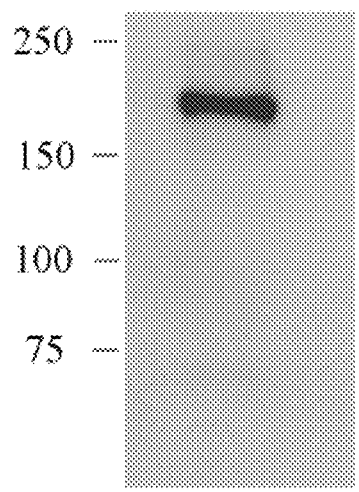
FIGS. 34A-34C illustrate the association of SGK1 with the mTOR complexes.
Figure 34B:
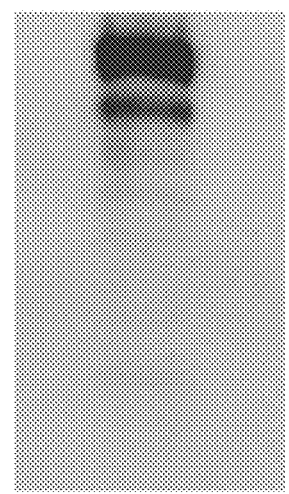
Figure 34C:
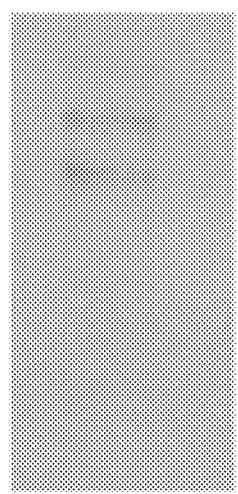

SGK1 physically associates with mTORC2. It was next examined whether the SGK1 protein binds to the mTOR complexes using flag-tagged SGK1. The plasmid was transfected into HEK293 cells. 48 hrs post-transfection, the cells were lysed and immunoprecipitation was carried out using anti-flag antibodies cross-linked to agarose beads. The immunoprecipitates were analyzed by Western blotting using antibodies against mTOR, rictor and raptor, respectively. As shown in FIGS. 34A-34C, strong signals were detected for mTOR and rictor in the SGK1 immunoprecipitates, while only a faint raptor band was detected (<10% of the intensity of the mTOR and rictor signals). These data demonstrate that the majority of SGK1 in the mTOR complexes is associated with mTORC2 and only a minor portion of SGK1 binds to mTORC1.

Discussion

We observed reduction in SGK1 phosphorylation (FIGS. 28A-28C). In contrast, rapamycin treatment showed minimum effect on the phosphorylation of SGK1. This mTOR inhibitor also dramatically reduced amiloride-sensitive Na+ current, whereas rapamycin showed minimum effect on Na+ transport (FIGS. 29A-29B).

To independently confirm a role for mTORC2 in SGK1 phosphorylation, we generated lentiviruses harboring a rictor shRNA. When the shRNA was introduced into HEK293 cells, knockdown of endogenous rictor expression was identified (FIGS. 30A-30D). A decrease in the phosphorylation of SGK1 was also observed (FIGS. 30A-30D). Subsequently, the effect of the rictor shRNA was tested in renal epithelial cells, and a reduction in ENaC-dependent Na+ transport was detected (FIGS. 31A-31C). By using similar experimental approaches, we made lentiviruses harboring a raptor shRNA and examined the effect of raptor expression knockdown. Both SGK1 phosphorylation and ENaC-dependent Na+ transport were found to remain at normal levels (FIGS. 32A-32D and FIGS. 33A-33D).

It is of note that the specific inhibitor of mTOR, PP242, appears to exert strong effects on SGK1 phosphorylation and ENaC-dependent Na+ transport. At a concentration of 0.3 µM, both the phosphorylation of SGK1 and the amiloride-sensitive Na+ current were completely abolished (FIGS. 28A-28C and FIGS. 29A-29B). The extent of inhibition by PP242 is similar to that observed with the PI3K inhibitor, LY294002. On the other hand, the shRNA shows partial inhibition on the expression of rictor (FIGS. 30A-30D and FIGS. 31A-31C). Accordingly, a partial reduction was observed in SGK1 phosphorylation and ENaC-dependent Na+ transport. To obtain direct and unambiguous results on SGK1 phosphorylation at the HM motif site, we developed an assay by transfection of a tagged SGK1 along with lentiviral-mediated infection of shRNA into HEK293 cells. The assay requires immunoprecipitation of SGK1 by an antibody against the flag tag. The enrichment of the SGK1 protein allows detection of its phosphorylation at the HM domain (FIGS. 30A-30D).

In summary, we have carried pharmacological studies and identified a role for mTORC2 in SGK1 phosphorylation and ENaC-dependent Na+ transport in renal epithelial cells (FIGS. 28A-28C and FIGS. 29A-29B). We have subsequently generated recombinant lentiviruses harboring rictor or raptor shRNAs. Knockdown of rictor expression leads to decreases in both SGK1 phosphorylation and amiloride-sensitive Na+ current (FIGS. 30A-30D and FIGS. 31A-31C). In contrast, the phosphorylation of SGK1 and ENaC-dependent Na+ transport appear not to be affected upon knockdown of raptor expression (FIGS. 32A-32D and FIGS. 33A-33D). Taken together, these findings indicate mTORC2-modulates SGK1 phosphorylation and ENaC-dependent Na+ transport in renal epithelial cells. We have shown that SGK1 associates strongly with the rictor-containing mTORC2 (FIGS. 34A-34C).

Example 44 mpkCCD Cell Proliferation in Response to Rapamycin and PP242

Figure 35:
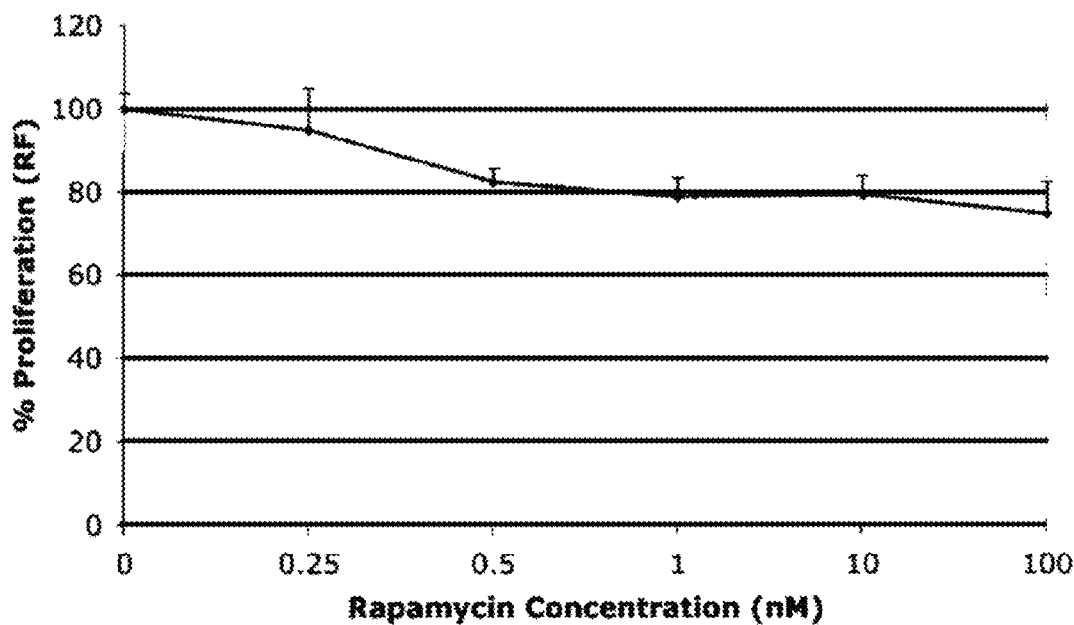
FIG. 35 illustrates the effect of rapamycin concentration on cellular proliferation. The experimental conditions were generally as described in Example 6 (FIG. 7) with the exception that after 28 hours of treatment about 10 µl of approximately 440 µM Resazurin sodium salt (Sigma) was added to each well. Data are presented as %-proliferation, as measured by fluorescence intensity relative to the control having no rapamycin present.
Figure 36:
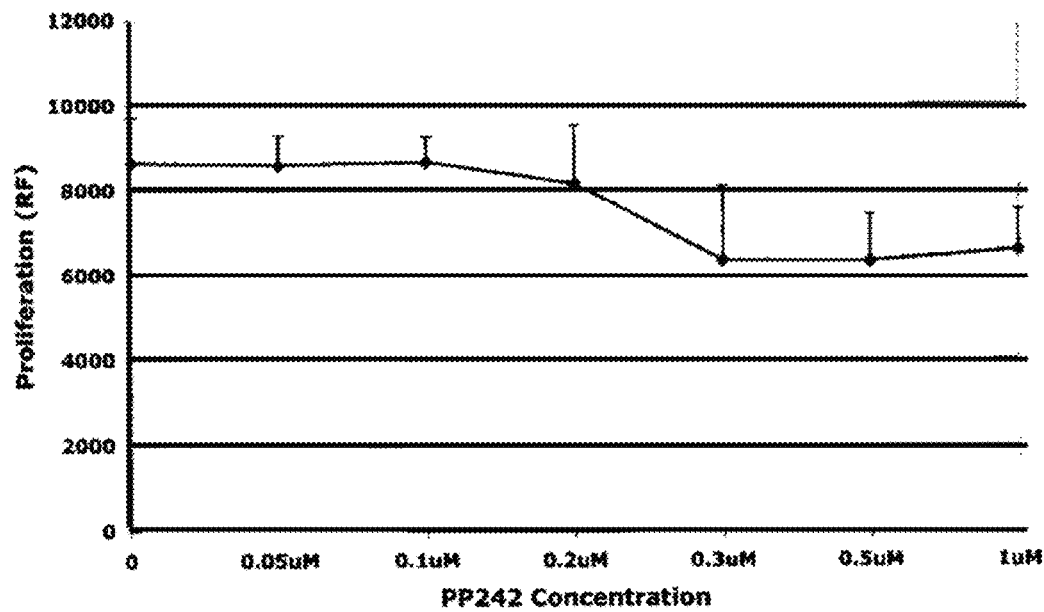
FIG. 36 illustrates the effect of PP242 in a companion experiment to that described for FIG. 35. In the figure, the data for cellular proliferation depict raw fluorescence intensity. PP242 blunts but does not eliminate proliferation in normal collecting duct cells Inhibition is significant at P<0.05 for 0.3 uM and higher concentrations of compound. PP242 had a somewhat greater effect than rapamycin. See FIG. 35.

In order to compare the effect of rapamycin and PP242 on cellular proliferation in mpkCCD cells, the experiment described in FIG. 35 and FIG. 36 was conducted. The experimental procedure followed that described for Example 6, with the exception that treatment lasted 28 hr prior to the introduction of Resazurin. As shown in the figures, PP242 blunts proliferation in normal collecting duct cells, but proliferation is not eliminated Inhibition is significant at P<0.05 for 0.3 uM and higher concentrations of compound. Furthermore, PP242 has a somewhat greater effect than rapamycin, as judged by a comparison of FIG. 35 and FIG. 36.

Example 45

PP242 Induction of Apoptosis

Figure 37A:
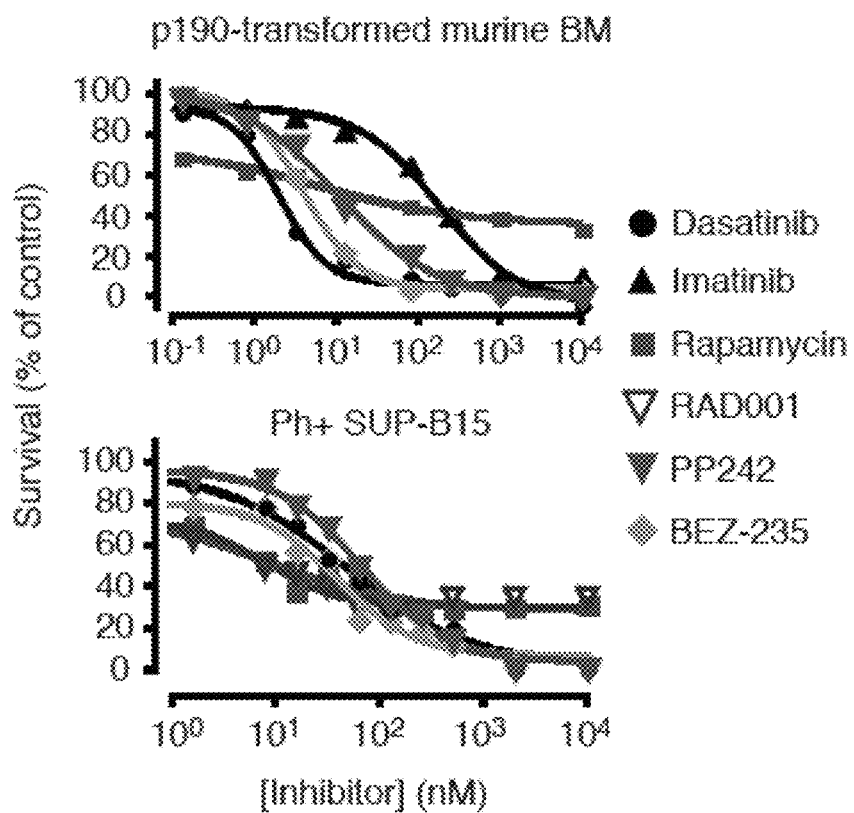
FIGS. 37A-37E illustrate that PP242 induces apoptosis of p190 BCR-ABL-transformed murine hematopoietic progenitors and human Ph+ B-ALL cells in vitro.
Figure 37B:
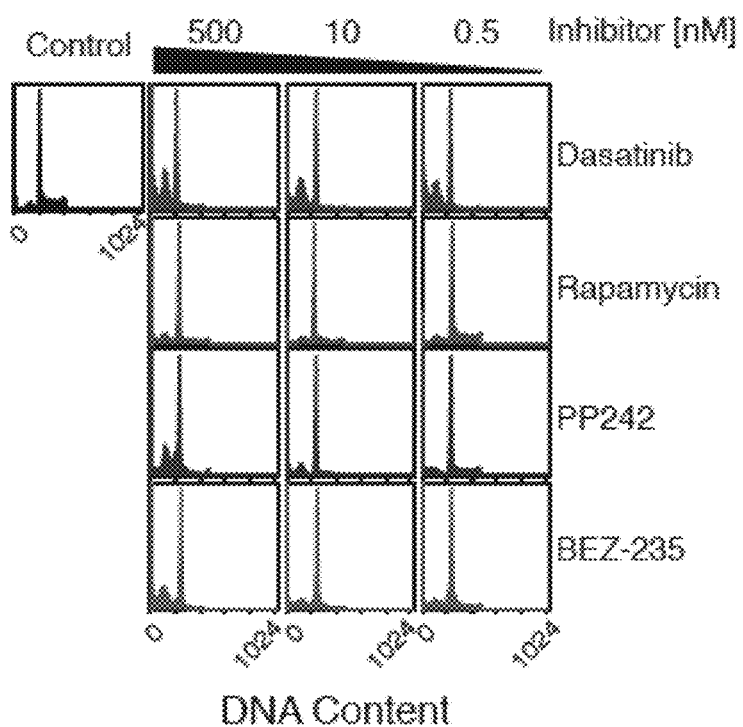
Figure 37C:
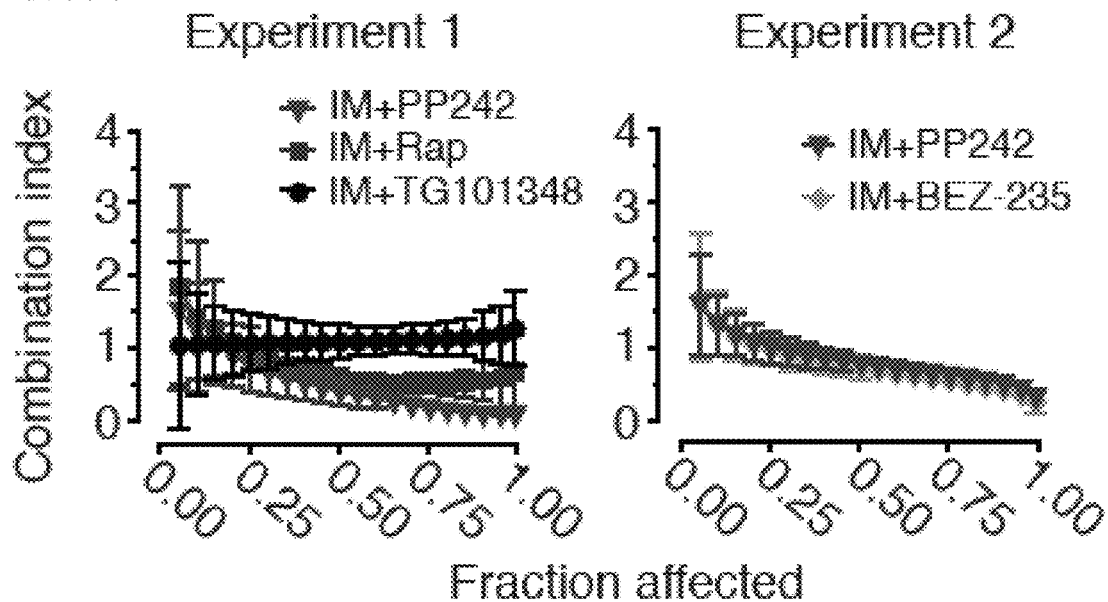
Figure 37D:
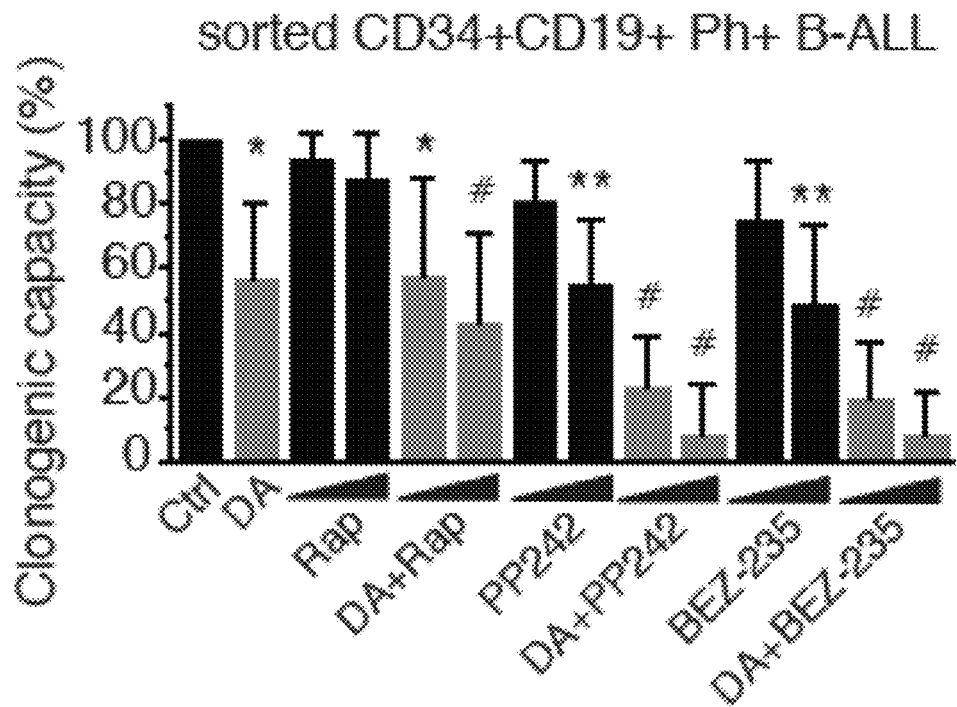
Figure 37E:
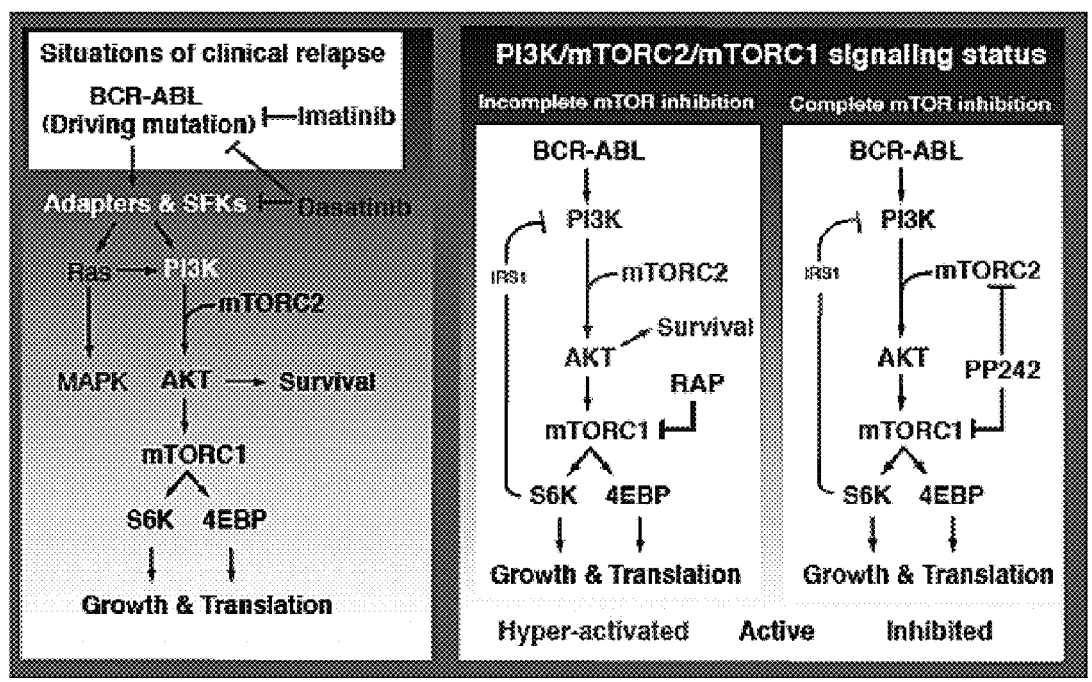

In order to investigate the PP242 induction of apoptosis of p190 BCR-ABL-transformed murine hematopoietic progenitors and human Ph' B-ALL cells in vitro, the following experiment was conducted. With reference to FIG. 37A, Mouse p190 cells (upper) and human SUP-B15 cells (lower) were cultured with inhibitors at the concentrations indicated for 48 hr. The MTS assay, as described herein, was used to quantify viable cell number and the data were expressed as % of control viability in untreated cells. p190 cells were cultured for 24 hr with the inhibitors indicated, then DNA content was measured by flow cytometry, as illustrated in FIG. 37B. p190 cells were cultured for 48 hr with the combinations of compounds indicated in FIG. 37C and assessed for survival using the median effect method, as known in the art. Drug combinations were assessed for synergy by calculating the combination index (CI) using CalcuSyn software, as known in the art. The CI was modeled with Monte Carlo simulation and plotted as a function of the fraction affected by treatment. CI<1, =1, and >1 indicate synergism, additive effect, and antagonism, respectively. The anti-clonogenic effects of PP242 combined with DA in primary Ph+B-ALL. CD19+CD34+ magnetically sorted cells from five different patients were assessed for colony formation potential in cultures with DAD (5 nM) alone or in combination with increasing concentrations [10 or 100 nM] of RAP, PP242, or BEZ-235 (*P<0.05, **P<0.01, #P<0.001. A schematic model (FIG. 37E) of BCR-ABL driven mechanisms of oncogenic survival (left) and a new model of incomplete mTOR inhibition (middle) versus complete mTOR inhibition (right) in B-ALL.

Example 46

PP242 Inhibition of mTORC2/AKT and mTORC1 Signaling

Figure 38A:
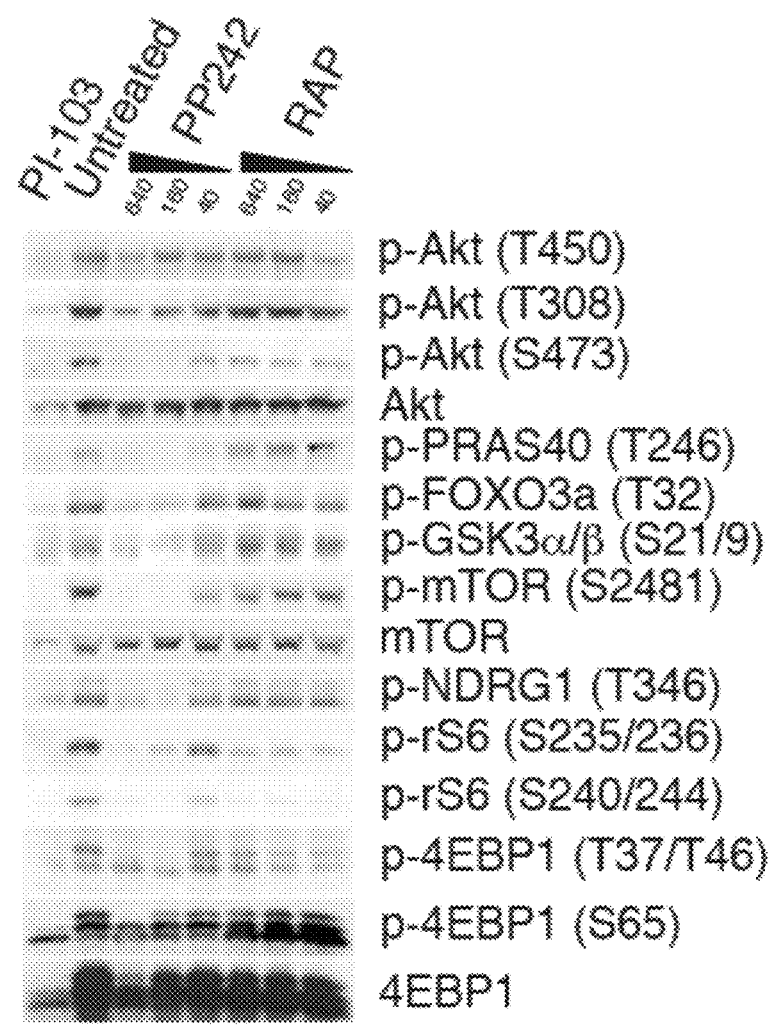
Figure 38B:
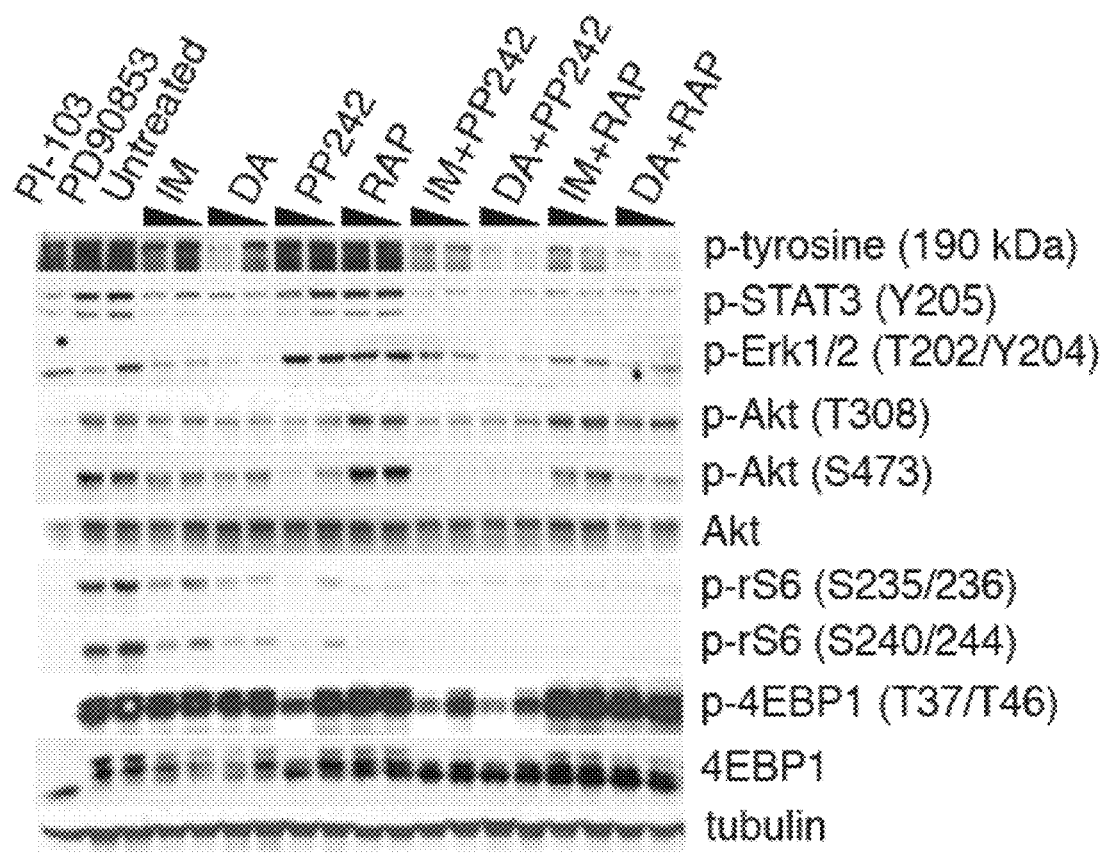
Figure 38C:
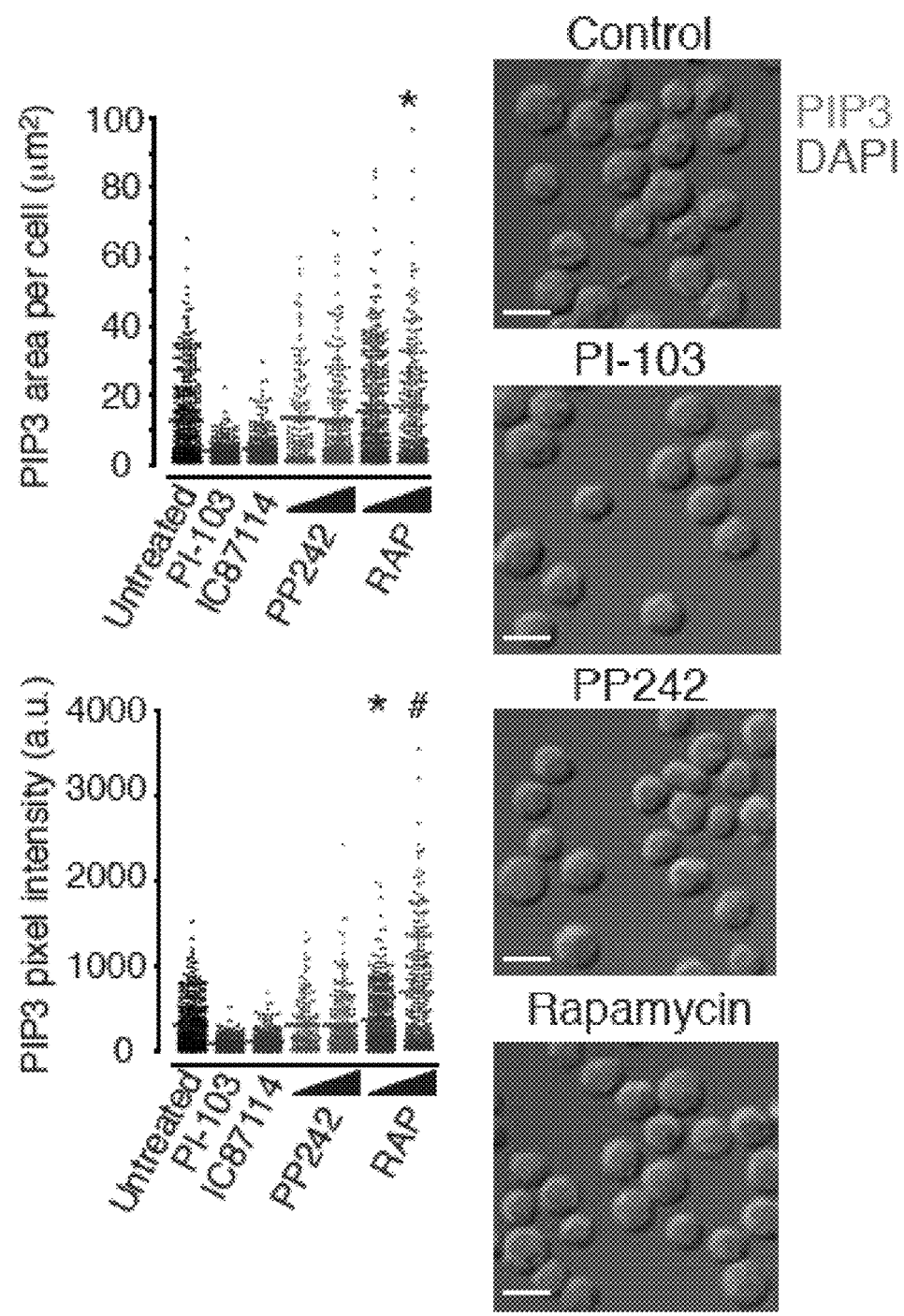
Figure 38D:
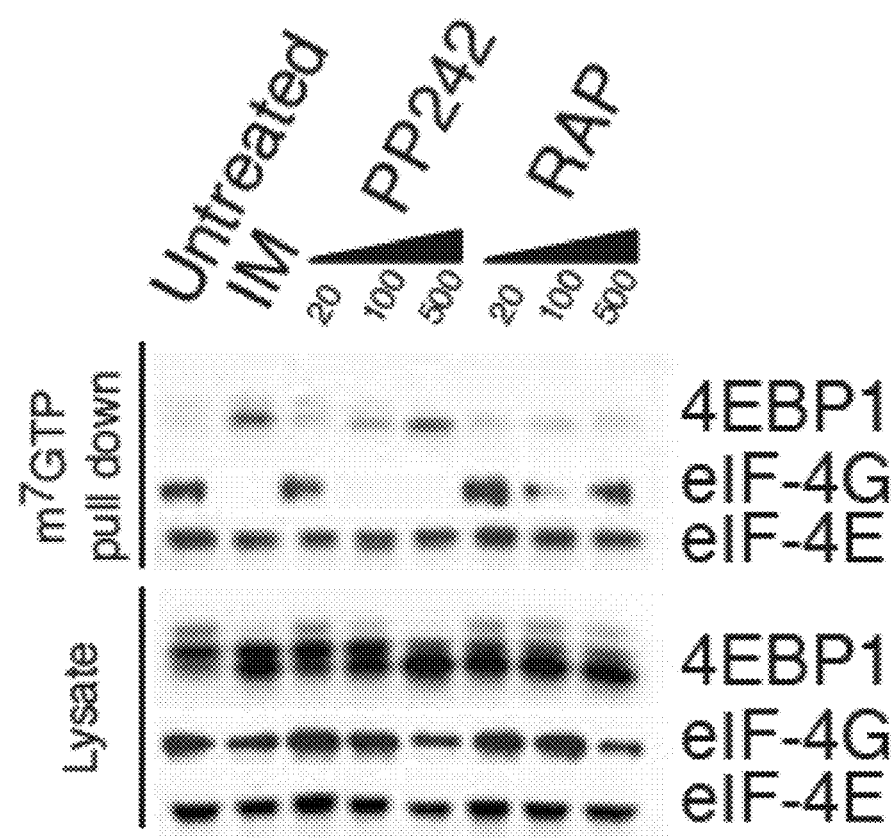

In order to assess the effect of PP242 on mTORC2/AKT and mTORC1 signaling, the experiment illustrated in FIGS. 38A-38E was conducted. In summary, PP242 completely inhibits mTORC2/AKT and mTORC1 signaling in B-ALL whereas rapamycin suppresses mTORC1 driving a PI3K/AKT surge. Western blots of p190 cells treated for 1.5 hr (a)

or 3 hr (b) with indicated inhibitors are depicted in FIG. 38A and FIG. 38B. Cells were treated with IM (0.5 and 1.0 μM), DA (5 and 50 nM), PP242 and RAP (50 and 400 nM). Clinically achievable concentrations of IM (1.0 μM) and DA (100 nM) were used for the combination treatments. See also FIGS. 40A-40B. Activation of PI3K was quantified in cells by signal pixel intensity and localized area of PIP3 accumulation by confocal microscopy, as depicted in FIG. 38C. Cells were cultured for 4 hr with PI-103 (2 μM), IC87114 (10 μM), PP242 (20 and 200 nM), and RAP (20 and 200 nM). A minimum of 250 cells was quantified from 2 separate images. RAP significantly activated PI3K signaling (*P<0.05, #P<0.001) whereas PP242 had no significant effect. Representative images depict PIP3 accumulation, nuclear content (DAPI stain) merged onto DIC images (13.5 μm scale bar). PP242 and high concentrations of IM (5 μM) both inhibit cap-dependent translation whereas RAP does not, as judged by the result depicted in FIG. 38D. Cap-binding proteins in lysates were purified by 7-methyl GTP ($m^7GTP$) affinity and analyzed by western blotting. p190 cells expressing LC3-GFP were cultured for 8 hr in chamber wells with DA (10 nM), PP242 (250 nM), BEZ-235 (250 nM), RAP (250 nM), and pulsed with EdU 1 hr prior to fixation, as shown in FIG. 38E. Autophagy (LC3 puncta accumulation), loss of proliferation (EdU accumulation), and distinct localization patterns of Foxo1 were assessed by confocal microscopy and representative cells were magnified for clarity. Cytoplasmic localization of Foxo1 corresponds to AKT activation, whereas nuclear accumulation signifies AKT inhibition.

Example 47

PP242 Selective Suppression of Leukemic Expansion

Figure 39A:
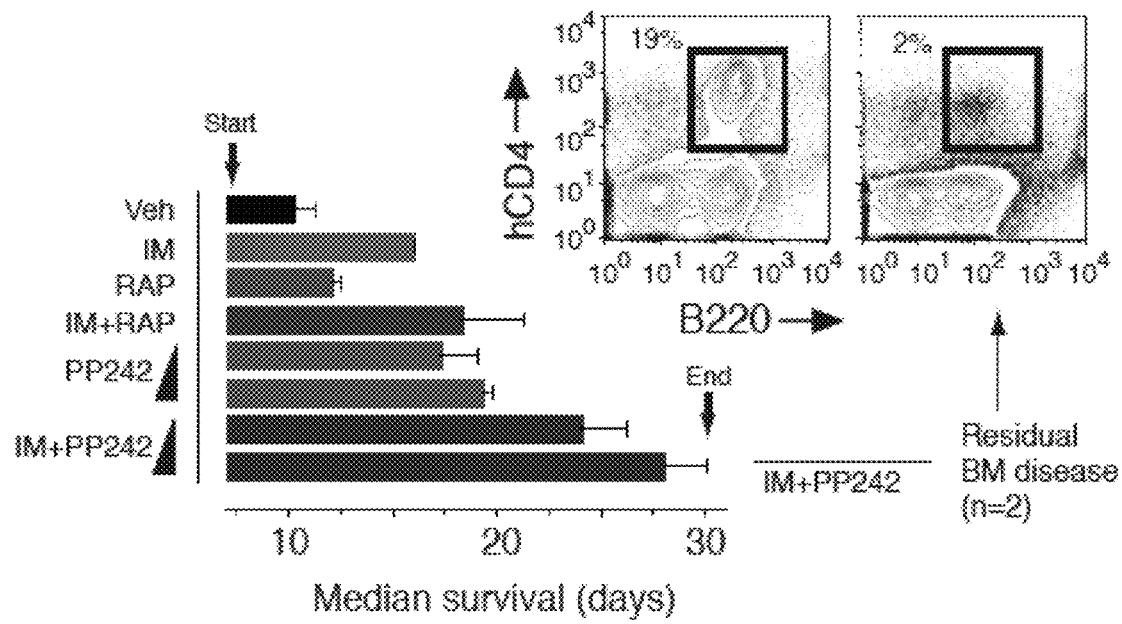
FIGS. 39A-39G illustrate that PP242 selectively suppresses leukemic expansion in vivo.
Figure 39B:
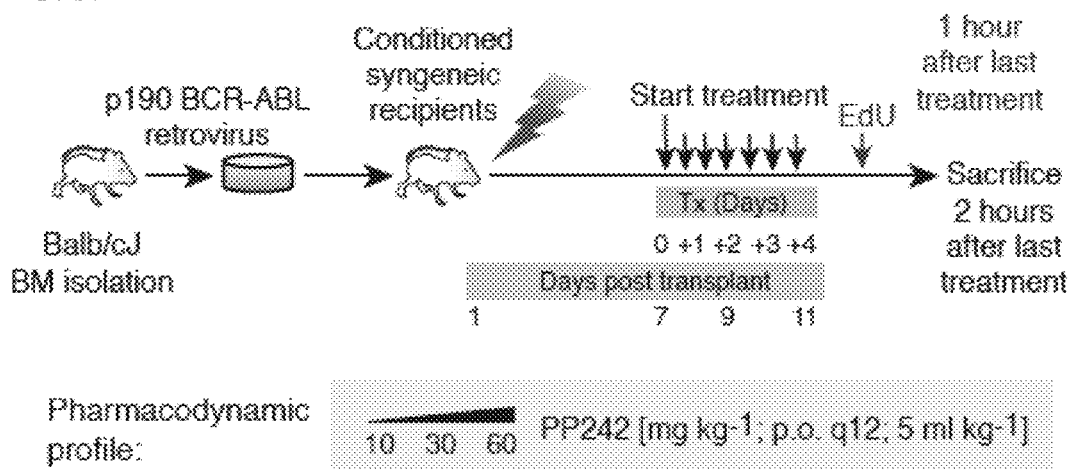
Figure 39C:
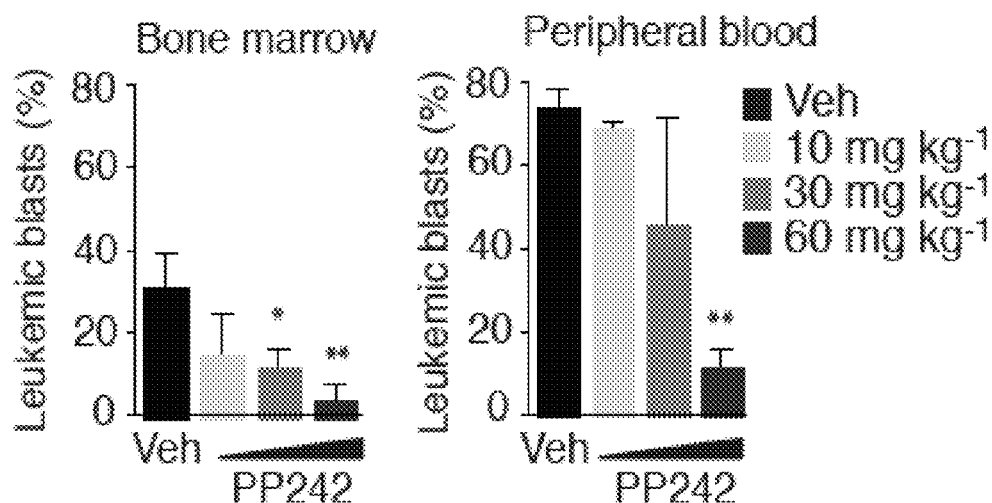
Figure 39D:
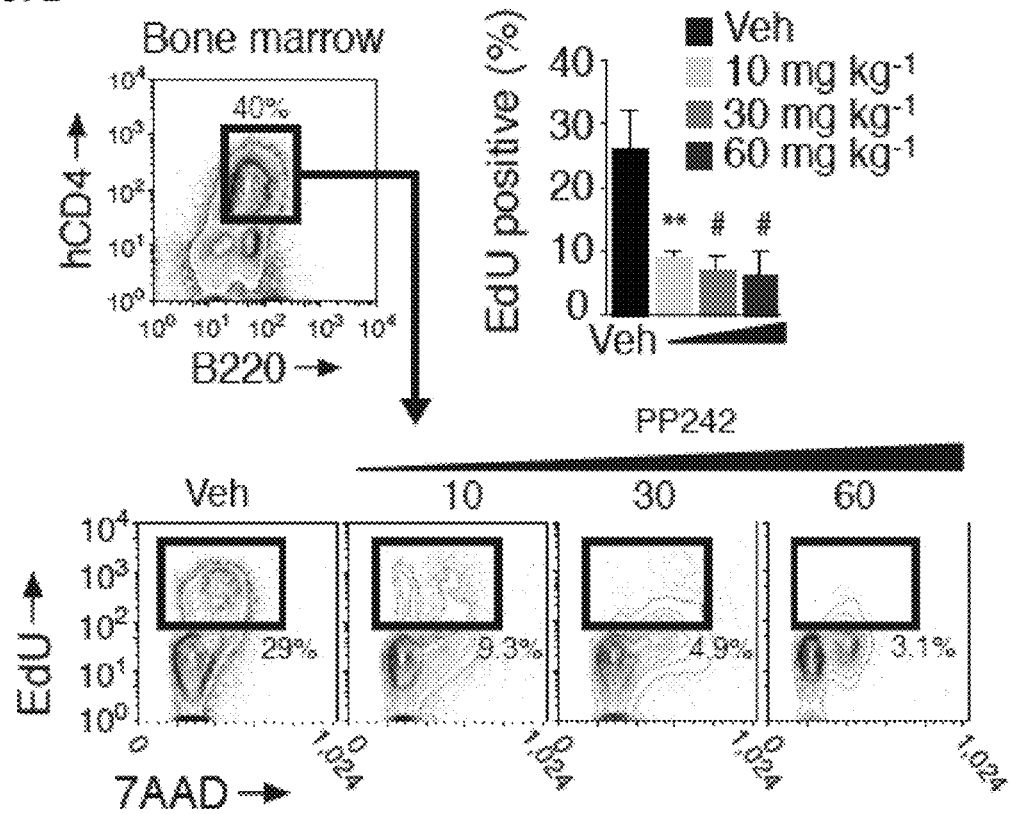
Figure 39E:
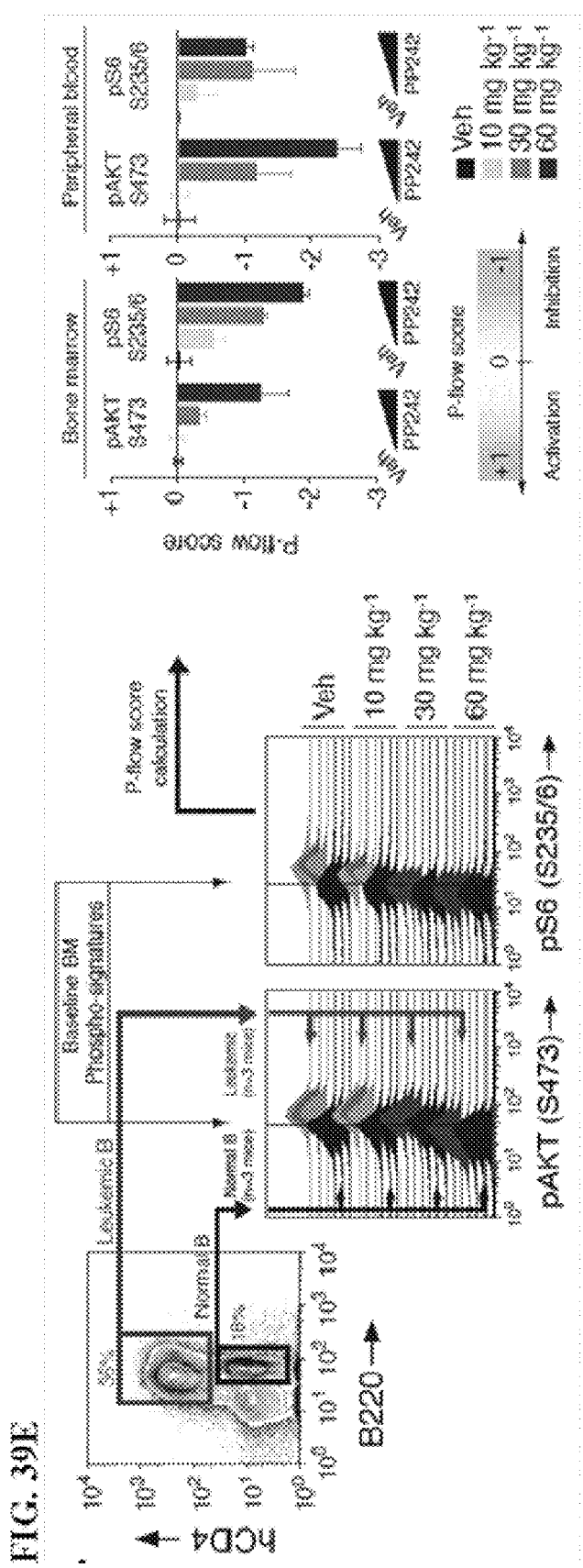
Figure 39F:
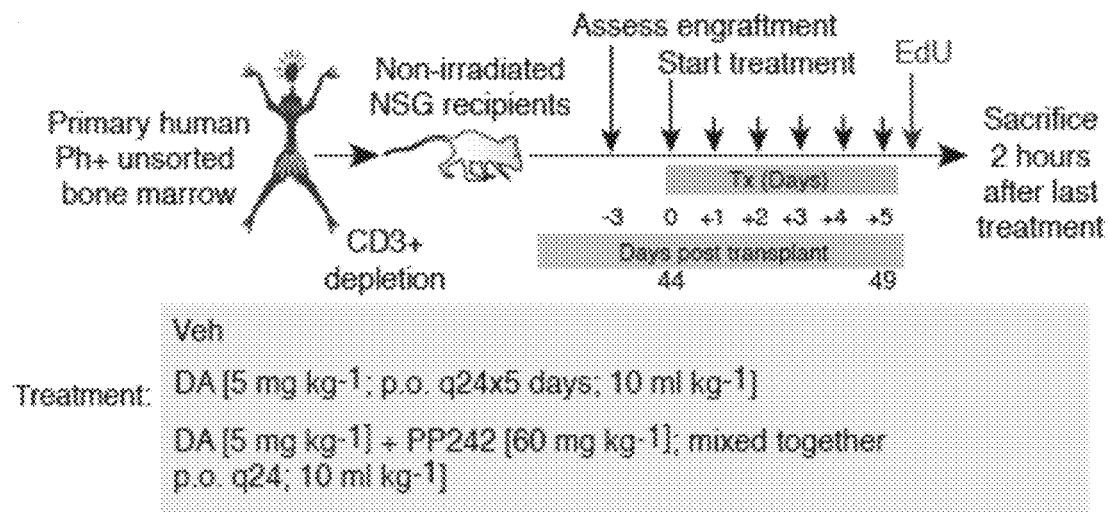
Figure 39G:
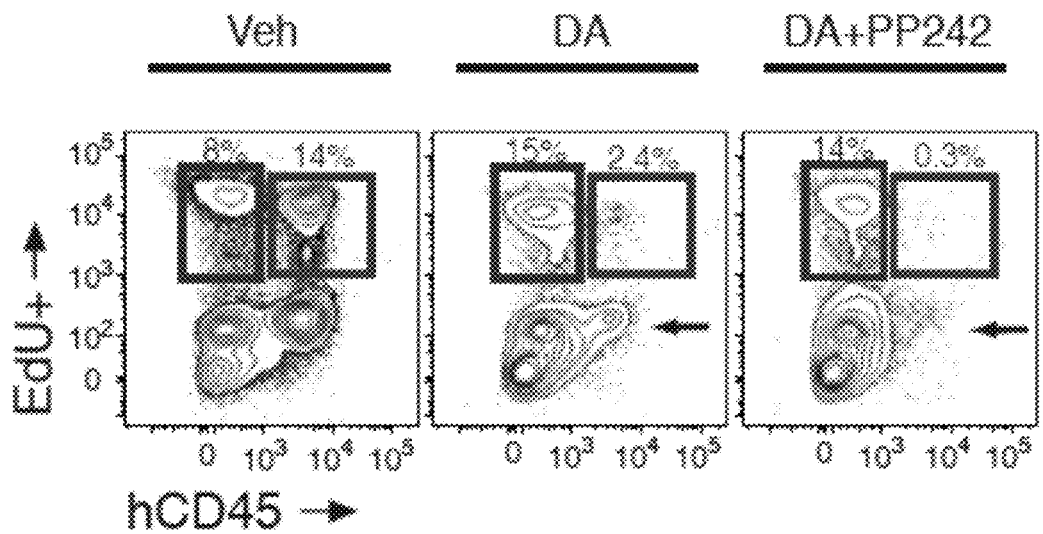

In summary, PP242 selectively suppresses leukemic expansion in vivo. Mice injected with p190 cells (i.v.), were treated daily (q24) starting on D7 post-transplant, as shown in FIG. 39A. Imatinib ("IM," 150 mg $kg^{-1}$, i.p.), rapamycin ("RAP," 7 mg $kg^{-1}$, i.p.) and PP242 (30 and 60 mg $kg^{-1}$, p.o.) were administered to mice as the mice were followed daily for overall survival (median±interquartile range) in groups of 5 mice. Delay in survival was assessed by the log rank test, as known in the art. After 30 days, the surviving 2 mice were analyzed for leukemic burden in the bone marrow (inset) by flow cytometry. FIGS. 39B-39E illustrate short-term pharmacodynamic profile and anti-leukemic efficacy of PP242 in conditioned recipients (450 rad) engrafted with mouse p190 B-ALL. A schematic depiction of the treatment design is provided in FIG. 39B, where groups of 3 mice each were treated twice daily (b.i.d. or q12) starting on day 7 for 4 days (7 treatments), with the indicated doses of PP242 or vehicle (PEG400). 1 hr following the last dose, and 2 hr before sacrifice, mice were injected (i.p.) with EdU to mark cycling cells. Leukemic burden (mean %±s.d.) was assessed by flow cytometry in the corresponding bone marrow and peripheral blood of treated mice, as depicted in FIG. 39C. The abundance of leukemic cells actively cycling (EdU+) following treatment was measured by flow cytometry (mean %±s.d.), as shown in FIG. 39D. FIG. 39E illustrates the pharmacodynamic activity of PP242 using intracellular phospho-staining of bone marrow and peripheral blood cells. Representative gating strategy (left panel) in the bone marrow for phospho-signature determination in leukemic (hCD4+B220+) and normal lymphocyte populations (hCD4-B220+) from each corresponding mouse is displayed. Quantified phospho-signatures are displayed as P-flow scores (right panel). A schematic of treatment design for primary human Ph+B-ALL whole bone marrow xenografts is depicted in FIG. 39F. Groups of 4-5 NSG mice each with equally engrafted disease were treated q24 for 5 days (6 treatments), with the indicated doses of DA, DA combined with PP242, or vehicle. 1 hr following the last dose, and 2 hr before sacrifice, mice were injected (i.p.) with EdU to mark cycling cells. Leukemic burden and cells actively cycling (mean %±s.d.) was assessed by flow cytometry in the corresponding bone marrow of treated mice, as shown in FIG. 39G. Representative residual disease in the bone marrow following treatment is depicted (left panel) and % EdU+ cells were calculated from normal (red gate) and leukemic (blue gate) bone marrow (middle panel). Arrows signify leukemia-specific eradication in non-actively cycling cells. The leukemic burden (% hCD45+) was calculated is depicted (right panel. *P<0.05, **P<0.01, #P<0.001. (1) Plasma concentrations of PP242 following in vivo administration.

Example 48 mTOR Kinase Inhibitor Effects on mTORC1 and TORC2

Figure 40A:
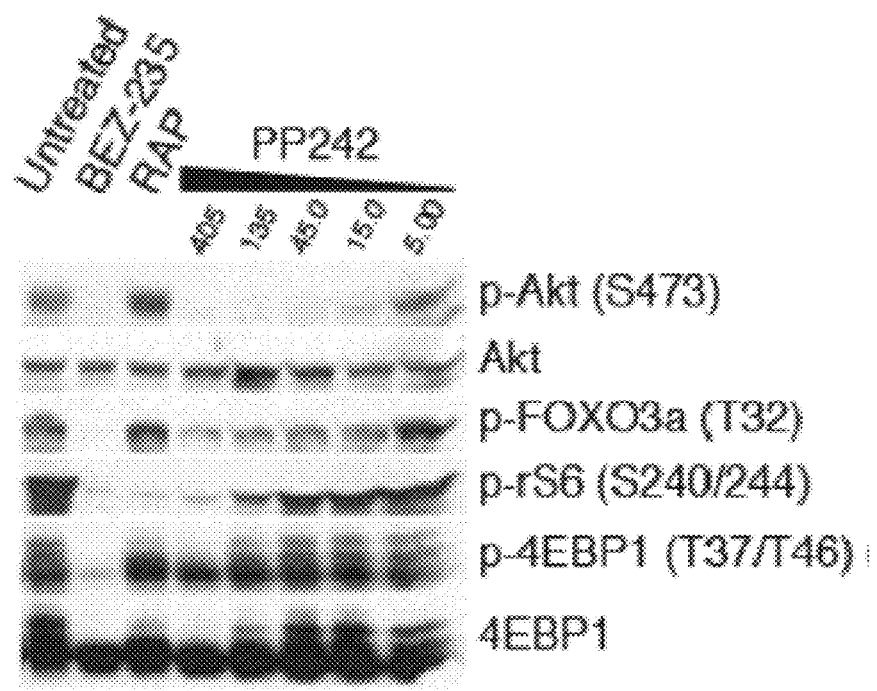
FIGS. 40A-40B illustrate that mTOR kinase inhibitor inhibits mTORC1 and mTORC2 substrates in human Ph+SUP-B15 cells.
Figure 40B:
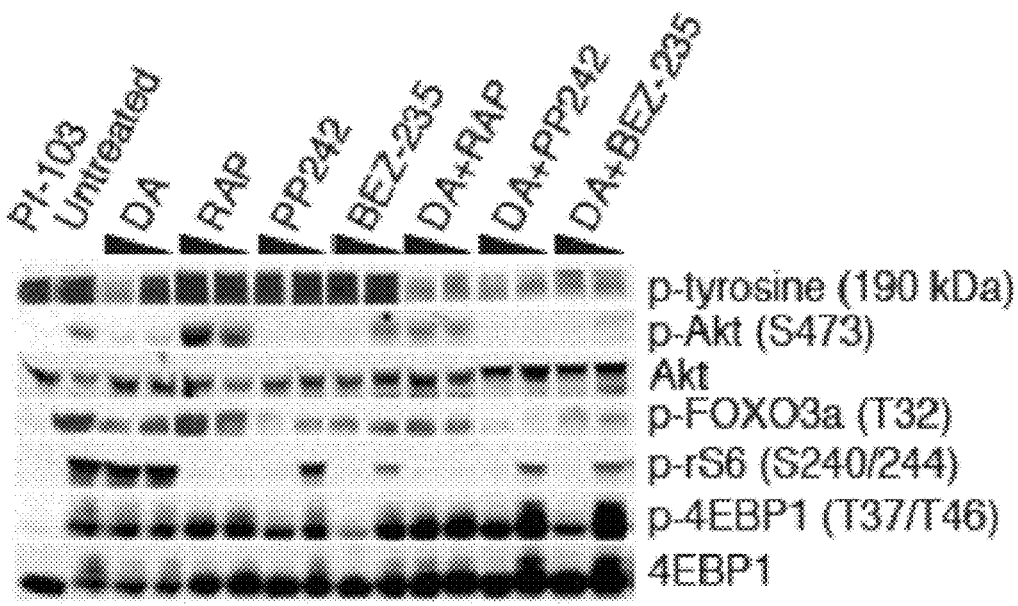

In order to determine the effect of mTOR kinase inhibitor on the inhibition of mTORC1 and mTORC2 substrates in human Ph+SUP-B15 cells, the experiment of FIGS. 40A-40B was conducted. Western blot analysis of SUP-B15 cells treated with the PI3K/mTOR inhibitor BEZ-235 [600 nM], RAP [20 nM], in comparison to a low dose titration of PP242 [5, 15, 45, 135, 405 nM] for 3 hours, as depicted in FIG. 40A. Western blot of SUP-B15 cells treated with PI3K/mTOR inhibitor PI-103 [2000 nM] and the ABL/Src kinase inhibitor dasatinib [DA; 10, 100 nM] alone, or in combination [DA at 100 nM] with RAP [RAP 50, 400 nM], PP242 [50, 400 nM], or BEZ-235 [50, 400 nM] as indicated, is depicted in FIG. 40B.

What is claimed is:
1. A method for inhibiting cell proliferation of a leukemic cell comprising administration of an effective amount of a compound, or a pharmaceutical acceptable salt thereof, to said cell, wherein the compound has the formula:

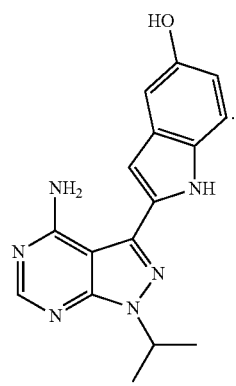 [SMILES: CC(C)n1nc(-c2cc3cc(O)ccc3[nH]2)c2c(N)ncnc21]

* * * * *